US00RE47908E

(19) United States
(12) Reissued Patent
Hoffberg et al.

(10) Patent Number: US RE47,908 E
(45) Date of Reissued Patent: Mar. 17, 2020

(54) ERGONOMIC MAN-MACHINE INTERFACE INCORPORATING ADAPTIVE PATTERN RECOGNITION BASED CONTROL SYSTEM

(71) Applicant: Blanding Hovenweep, LLC, Las Vegas, NV (US)

(72) Inventors: Steven M. Hoffberg, West Harrison, NY (US); Linda I. Hoffberg-Borghesani, Acton, MA (US)

(73) Assignee: Blanding Hovenweep, LLC, Las Vegas, NV (US)

(21) Appl. No.: 15/411,930

(22) Filed: Jan. 20, 2017

Related U.S. Patent Documents

Reissue of:
(64) Patent No.: 7,136,710
Issued: Nov. 14, 2006
Appl. No.: 08/469,589
Filed: Jun. 6, 1995

U.S. Applications:
(63) Continuation-in-part of application No. 07/812,805, filed on Dec. 23, 1991, now Pat. No. 5,903,454, and
(Continued)

(51) Int. Cl.
*G05B 19/42* (2006.01)
*G06K 9/00* (2006.01)
(Continued)

(52) U.S. Cl.
CPC ..... *G06K 9/00369* (2013.01); *G06F 3/00* (2013.01); *G06F 3/0482* (2013.01);
(Continued)

(58) Field of Classification Search
CPC ..... G06Q 30/0266; G06Q 30/0251; G06Q 30/0261; G06F 16/335; G06F 17/30699; H04W 4/23
See application file for complete search history.

(56) References Cited

U.S. PATENT DOCUMENTS 3,560,930 A 2/1971 Howard
4,208,652 A 6/1980 Marshall ..... 382/194
(Continued)

FOREIGN PATENT DOCUMENTS

EP 0401975 A2 * 12/1990
EP 0849948 A2 6/1998
(Continued)

OTHER PUBLICATIONS

Alegiani, J.B., J.L. Buxton, and S.K. Honey "An In-Vehicle Navigation and Information System Utilizing Defined Software Services", Proceedings of the Vehicle Navigation and Information Systems Conference, Sep. 11-13, 1989, pp. A-3 to A-8.*
(Continued)

*Primary Examiner* — Luke S Wassum

(57) ABSTRACT

An adaptive interface for a programmable system, for predicting a desired user function, based on user history, as well as machine internal status and context. The apparatus receives an input from the user and other data. A predicted input is presented for confirmation by the user, and the predictive mechanism is updated based on this feedback. Also provided is a pattern recognition system for a multimedia device, wherein a user input is matched to a video stream on a conceptual basis, allowing inexact programming of a multimedia device. The system analyzes a data stream for correspondence with a data pattern for processing and storage. The data stream is subjected to adaptive pattern recognition to extract features of interest to provide a highly compressed representation which may be efficiently processed to determine correspondence. Applications of the interface and system include a VCR, medical device, vehicle control system, audio device, environmental control system, securities trading terminal, and smart house. The system optionally includes an actuator for effecting the environment
(Continued)

*New* of operation, allowing closed-loop feedback operation and automated learning.

32 Claims, 28 Drawing Sheets

Related U.S. Application Data a continuation of application No. 12/271,602, filed on Nov. 14, 2008, now Pat. No. Re. 46,310, which is an application for the reissue of Pat. No. 7,136,710.

(51) Int. Cl.

| | |
|---|---|
| ***G06Q 30/02*** | (2012.01) |
| ***H04N 7/16*** | (2011.01) |
| ***H04N 21/482*** | (2011.01) |
| ***G06F 3/00*** | (2006.01) |
| ***G06F 3/0482*** | (2013.01) |
| ***H04N 21/25*** | (2011.01) |
| ***H04N 21/45*** | (2011.01) |
| ***H04N 21/466*** | (2011.01) |
| ***H04N 21/422*** | (2011.01) |
| ***H04N 21/442*** | (2011.01) |
| ***H04N 21/454*** | (2011.01) |
| *H04L 29/08* | (2006.01) |
| *G06N 99/00* | (2019.01) |

(52) U.S. Cl.

CPC ..... *G06Q 30/0261* (2013.01); *H04N 7/163* (2013.01); *H04N 21/252* (2013.01); *H04N 21/42201* (2013.01); *H04N 21/44222* (2013.01); *H04N 21/454* (2013.01); *H04N 21/4532* (2013.01); *H04N 21/466* (2013.01); *H04N 21/482* (2013.01); *G06N 99/00* (2013.01); *H04L 67/306* (2013.01)

(56) References Cited

U.S. PATENT DOCUMENTS 4,450,477 A 5/1984 Lovett
4,598,318 A 7/1986 Robbins
4,697,209 A 9/1987 Kiewit et al. ..... 348/1
4,706,121 A 11/1987 Young
4,734,764 A 3/1988 Pocock et al.
4,745,549 A 5/1988 Hashimoto
4,775,935 A * 10/1988 Yourick ..... 395/357
4,789,933 A 12/1988 Chen et al. ..... 382/128
4,829,372 A 5/1989 McCalley et al.
4,841,575 A 6/1989 Welsh et al. ..... 395/2.69
4,870,579 A 9/1989 Hey
4,908,713 A 3/1990 Levine ..... 386/83
4,963,994 A 10/1990 Levine ..... 386/83
4,996,642 A 2/1991 Hey
5,031,228 A 7/1991 Lu ..... 382/227
5,060,277 A 10/1991 Bokser ..... 382/160
5,076,662 A 12/1991 Shih et al. ..... 349/17
5,103,498 A 4/1992 Lanier et al. ..... 395/68
5,123,057 A 6/1992 Verly et al. ..... 382/156
5,123,087 A 6/1992 Newell et al. ..... 395/348
5,136,659 A 8/1992 Kaneko et al. ..... 382/190
5,148,522 A 9/1992 Okazaki ..... 395/358
5,191,410 A 3/1993 McCalley et al.
5,192,999 A 3/1993 Graczyk et al. ..... 348/552
5,195,092 A 3/1993 Wilson et al.
5,208,665 A 5/1993 McCalley et al.
5,223,924 A 6/1993 Strubbe
5,231,494 A 7/1993 Wachob
5,237,499 A * 8/1993 Garback ..... G07B 15/00 705/5
5,255,386 A 10/1993 Prager ..... 395/605
5,280,530 A 1/1994 Trew et al. ..... 382/103
5,283,819 A 2/1994 Glick et al. ..... 379/90
5,327,144 A * 7/1994 Stilp ..... G01S 3/46 342/387
5,333,091 A 7/1994 Iggulden et al.
5,339,239 A * 8/1994 Manabe ..... G06F 3/0489 235/375
5,353,034 A * 10/1994 Sato ..... G01C 21/3611 340/988
5,359,527 A * 10/1994 Takanabe ..... G01C 21/3611 340/990
5,371,551 A 12/1994 Logan et al.
5,390,125 A * 2/1995 Sennott ..... B60K 31/0008 342/357.24
5,390,281 A 2/1995 Luciw et al. ..... 395/12
5,396,546 A 3/1995 Remillard ..... 379/96
5,412,773 A 5/1995 Carlucci et al. ..... 395/327
5,436,653 A 7/1995 Ellis et al. ..... 348/2
5,442,553 A * 8/1995 Parrillo ..... G06F 8/65 455/420
5,446,891 A 8/1995 Kaplan et al.
5,450,490 A 9/1995 Jensen et al. ..... 380/6
5,477,447 A 12/1995 Luciw et al. ..... 395/759
5,487,103 A * 1/1996 Richardson, Jr. ... H04M 3/2281 370/422
5,497,430 A 3/1996 Sadovnik et al.
5,500,920 A 3/1996 Kupiec ..... 395/2.79
5,508,815 A 4/1996 Levine ..... 386/83
5,534,911 A 7/1996 Levitan
5,537,324 A * 7/1996 Nimura ..... G01C 21/3611 340/990
5,544,358 A 8/1996 Capps et al. ..... 395/785
5,550,928 A 8/1996 Lu et al.
5,560,011 A 9/1996 Uyama ..... 395/677
5,572,246 A 11/1996 Ellis et al. ..... 348/2
5,574,573 A 11/1996 Ray et al.
5,579,471 A 11/1996 Barber et al.
5,579,535 A * 11/1996 Orlen ..... H04M 1/72522 340/905
5,583,966 A 12/1996 Nakajima ..... 395/51
5,584,050 A 12/1996 Lyons ..... 455/67.1
5,586,317 A 12/1996 Smith ..... 395/683
5,664,948 A * 9/1997 Dimitriadis ..... G01C 21/26 324/207.26
5,675,663 A 10/1997 Koerner et al.
5,689,648 A * 11/1997 Diaz ..... G06Q 10/10 348/473
5,696,964 A 12/1997 Cox et al.
5,710,833 A 1/1998 Moghaddam et al.
5,724,425 A * 3/1998 Chang ..... G06F 21/125 380/30
5,724,567 A 3/1998 Rose et al.
5,734,444 A 3/1998 Yoshinobu
5,740,274 A 4/1998 Ono et al.
5,748,776 A 5/1998 Yoshida
5,751,286 A 5/1998 Barber et al.
5,754,939 A 5/1998 Herz et al.
5,758,257 A 5/1998 Herz et al.
5,758,332 A * 5/1998 Hirotani ..... G06F 17/30395 707/999.001
5,761,601 A * 6/1998 Nemirofsky ..... H04N 7/165 348/E7.063
5,767,893 A 6/1998 Chen et al.
5,771,307 A 6/1998 Lu et al.
5,774,129 A 6/1998 Poggio et al.
5,774,357 A * 6/1998 Hoffberg ..... G06F 9/453 713/600
5,777,580 A * 7/1998 Janky ..... G01S 1/045 342/457
5,778,135 A 7/1998 Ottesen et al.
5,781,892 A * 7/1998 Hunt ..... G06Q 10/025 705/5
5,781,906 A 7/1998 Aggarwal et al.
5,793,888 A 8/1998 Delanoy
5,798,785 A 8/1998 Hendricks et al.
5,802,208 A 9/1998 Podilchuk et al.
5,802,492 A * 9/1998 DeLorme ..... G01C 21/3476 340/990
5,806,061 A 9/1998 Chaudhuri et al.

(56) References Cited

U.S. PATENT DOCUMENTS 5,819,284 A * 10/1998 Farber ..... G06F 16/335 709/203
5,819,288 A 10/1998 De Bonet
5,832,457 A * 11/1998 O'Brien ..... G06Q 20/20 705/14.13
5,835,061 A * 11/1998 Stewart ..... G06Q 10/107 342/457
5,842,194 A 11/1998 Arbuckle
5,844,573 A 12/1998 Poggio et al.
5,852,823 A 12/1998 De Bonet
RE36,041 E 1/1999 Turk et al.
5,861,881 A 1/1999 Freeman et al.
5,867,118 A 2/1999 McCoy et al.
5,867,205 A 2/1999 Harrison
5,867,226 A 2/1999 Wehmeyer et al.
5,867,386 A * 2/1999 Hoffberg ..... G06F 9/453 700/83
5,867,799 A 2/1999 Lang et al.
5,873,080 A 2/1999 Coden et al.
5,875,108 A * 2/1999 Hoffberg ..... G06F 3/00 700/17
5,875,446 A 2/1999 Brown et al.
5,892,536 A 4/1999 Logan et al.
5,893,095 A 4/1999 Jain et al.
5,893,110 A 4/1999 Weber et al.
5,895,464 A 4/1999 Bhandari et al.
5,899,999 A 5/1999 De Bonet
5,901,244 A 5/1999 Souma et al.
5,901,246 A * 5/1999 Hoffberg ..... G06K 9/00369 382/209
5,903,454 A * 5/1999 Hoffberg ..... G06F 3/0482 700/83
5,907,706 A 5/1999 Brodsky et al.
5,911,139 A 6/1999 Jain et al.
5,913,205 A 6/1999 Jain et al.
5,915,250 A 6/1999 Jain et al.
5,920,477 A * 7/1999 Hoffberg ..... G06F 9/453 382/181
5,920,856 A 7/1999 Syeda-Mahmood
5,922,037 A * 7/1999 Potts ..... G07C 5/0808 701/34.3
5,930,783 A 7/1999 Li et al.
5,933,546 A 8/1999 Stone
5,933,811 A 8/1999 Angles et al.
5,937,392 A 8/1999 Alberts
5,945,988 A 8/1999 Williams et al.
5,948,040 A * 9/1999 DeLorme ..... G01C 21/36 340/990
5,959,577 A * 9/1999 Fan ..... G01S 5/0027 342/357.42
5,963,645 A 10/1999 Kigawa et al.
5,963,670 A 10/1999 Lipson et al.
5,973,683 A 10/1999 Cragun et al.
5,974,162 A * 10/1999 Metz ..... A61B 5/1172 356/71
5,974,188 A 10/1999 Ibenthal
5,974,235 A 10/1999 Nunally et al.
5,974,412 A 10/1999 Hazlehurst et al.
5,977,964 A 11/1999 Williams et al.
5,978,516 A 11/1999 Dickopp et al.
5,982,386 A 11/1999 Fujimoto
5,983,214 A 11/1999 Lang et al.
5,983,218 A 11/1999 Syeda-Mahmood
5,987,459 A 11/1999 Swanson et al.
5,995,094 A 11/1999 Eggen et al.
6,002,406 A 12/1999 Zhao
6,002,794 A 12/1999 Bonneau et al.
6,005,561 A 12/1999 Hawkins et al.
6,005,597 A 12/1999 Barrett et al.
6,006,251 A * 12/1999 Toyouchi ..... G06Q 30/06 707/E17.119
6,011,872 A 1/2000 Qian et al.
6,011,895 A 1/2000 Abecassis
6,012,052 A 1/2000 Altschuler et al.
6,014,638 A 1/2000 Burge et al.
6,016,348 A 1/2000 Blatter et al.
6,020,883 A 2/2000 Herz et al.
6,021,231 A 2/2000 Miyatake et al.
6,023,267 A 2/2000 Chapuis et al.
6,023,530 A 2/2000 Wilson
6,029,045 A 2/2000 Picco et al.
6,029,176 A 2/2000 Cannon
6,029,195 A 2/2000 Herz
6,031,573 A 2/2000 MacCormack et al.
6,031,797 A 2/2000 VanRyzin et al.
6,038,337 A 3/2000 Lawrence et al.
6,038,367 A 3/2000 Abecassis
6,038,591 A 3/2000 Wolfe et al.
6,040,829 A 3/2000 Croy et al.
6,041,147 A 3/2000 Mead
6,044,168 A 3/2000 Tuceryan et al.
6,047,078 A 4/2000 Kang
6,049,333 A 4/2000 LaJoie et al.
6,049,614 A 4/2000 Kim
6,049,777 A 4/2000 Sheena et al.
6,052,676 A 4/2000 Hekmatpour
6,055,314 A 4/2000 Spies et al.
6,055,335 A 4/2000 Ida et al.
6,055,542 A 4/2000 Nielsen et al.
6,058,206 A 5/2000 Kortge
6,064,976 A 5/2000 Tolopka
6,067,107 A 5/2000 Travaille et al.
6,067,369 A 5/2000 Kamei
6,067,401 A 5/2000 Abecassis
6,072,520 A 6/2000 Yuen et al.
6,072,645 A 6/2000 Sprague
6,072,904 A 6/2000 Desai et al.
6,081,750 A * 6/2000 Hoffberg ..... G06F 3/00 700/17
6,084,595 A 7/2000 Bach et al.
6,088,455 A 7/2000 Logan et al.
6,091,886 A 7/2000 Abecassis
6,094,722 A 7/2000 Astola et al.
RE36,801 E 8/2000 Logan et al.
6,108,434 A 8/2000 Cox et al.
6,108,698 A 8/2000 Tenev et al.
6,111,988 A 8/2000 Horowitz et al.
6,115,052 A 9/2000 Freeman et al.
6,115,079 A 9/2000 McRae
6,115,691 A 9/2000 Ulwick
6,118,104 A 9/2000 Berkcan et al.
6,118,450 A 9/2000 Proehl et al.
6,118,493 A 9/2000 Duhault et al.
6,118,886 A 9/2000 Baumgart et al.
6,119,101 A 9/2000 Peckover
6,119,123 A 9/2000 Ellenbaas
6,119,164 A 9/2000 Basche
6,119,229 A 9/2000 Martinez et al.
6,119,946 A 9/2000 Teicher
6,122,628 A 9/2000 Castelli et al.
6,122,634 A 9/2000 Brodsky
6,124,544 A 9/2000 Alexander et al.
6,124,854 A 9/2000 Sartain et al.
6,125,209 A 9/2000 Dorricott
6,128,397 A 10/2000 Baluja et al.
6,128,398 A 10/2000 Kuperstein et al.
6,128,587 A 10/2000 Sjolander
6,128,599 A 10/2000 Walker et al.
6,128,624 A 10/2000 Papierniak et al.
6,128,634 A 10/2000 Golovchinsky et al.
6,128,649 A 10/2000 Smith et al.
6,128,655 A 10/2000 Fields et al.
6,128,663 A 10/2000 Thomas
6,128,668 A 10/2000 Barber et al.
6,129,274 A 10/2000 Suzuki
6,130,726 A 10/2000 Darbee et al.
6,130,898 A 10/2000 Kostreski et al.
6,131,060 A 10/2000 Obradovich et al.
6,133,909 A 10/2000 Schein et al.
6,133,914 A 10/2000 Rogers et al.
6,134,541 A 10/2000 Castelli et al.
6,138,142 A 10/2000 Linsk
6,144,767 A 11/2000 Bottou et al.

(56) References Cited

U.S. PATENT DOCUMENTS 6,151,600 A 11/2000 Dedrick
6,157,413 A 12/2000 Hanafee et al.
6,160,570 A 12/2000 Sitnik
6,163,345 A 12/2000 Noguchi et al.
6,167,136 A 12/2000 Chou
6,167,188 A 12/2000 Young et al.
6,171,109 B1 1/2001 Ohsuga
6,172,674 B1 1/2001 Etheredge
6,173,275 B1 1/2001 Caid et al.
6,175,829 B1 1/2001 Li et al.
6,182,287 B1 1/2001 Schneidewend et al.
6,184,926 B1 2/2001 Khosravi et al.
6,185,337 B1 2/2001 Tsujino et al.
6,188,777 B1 2/2001 Darrell et al.
6,192,340 B1 2/2001 Abecassis
6,192,341 B1 2/2001 Becker et al.
6,195,568 B1 2/2001 Irvin
6,195,651 B1 2/2001 Handel et al.
6,195,692 B1 2/2001 Hsu
6,198,875 B1 3/2001 Edenson et al.
6,199,076 B1 3/2001 Logan et al.
6,199,082 B1 3/2001 Ferrel et al.
6,201,209 B1 3/2001 Llado Abella
6,201,948 B1 3/2001 Cook et al.
6,205,107 B1 3/2001 Burr
6,205,432 B1 3/2001 Gabbard et al.
6,208,758 B1 3/2001 Ono et al.
6,208,989 B1 3/2001 Dockter et al.
6,209,129 B1 3/2001 Carr et al.
6,211,921 B1 4/2001 Cherian et al.
6,212,328 B1 4/2001 Nakamura
6,215,526 B1 4/2001 Barton et al.
6,216,129 B1 4/2001 Eldering
6,216,133 B1 4/2001 Masthoff
6,219,421 B1 4/2001 Backal
6,219,839 B1 4/2001 Sampsell
6,222,932 B1 4/2001 Rao et al.
6,222,939 B1 4/2001 Wiskott et al.
6,225,546 B1 5/2001 Kraft et al.
6,230,111 B1 5/2001 Mizokawa
6,230,199 B1 5/2001 Revashetti et al.
6,230,318 B1 5/2001 Halstead et al.
6,233,389 B1 5/2001 Barton et al.
6,233,682 B1 5/2001 Fritsch
6,236,395 B1 5/2001 Sezan et al.
6,236,975 B1 5/2001 Boe et al.
6,236,978 B1 5/2001 Tuzhilin
6,236,985 B1 5/2001 Aggarwal et al.
6,239,794 B1 5/2001 Yuen et al.
6,240,240 B1 5/2001 Nagano et al.
6,240,555 B1 5/2001 Shoff et al.
6,243,469 B1 6/2001 Kataoka et al.
6,243,492 B1 6/2001 Kamei
6,243,725 B1 6/2001 Hempleman et al.
6,246,441 B1 6/2001 Terakado et al.
6,247,006 B1 6/2001 Tanabe et al.
6,247,130 B1 6/2001 Fritsch
6,249,815 B1 6/2001 Foladare et al.
6,249,914 B1 6/2001 Harrison et al.
6,252,630 B1 6/2001 Kusumi et al.
6,253,237 B1 6/2001 Story et al.
D445,801 S 7/2001 Ma
6,259,405 B1 * 7/2001 Stewart ..... H04M 15/8033 342/457
6,260,192 B1 7/2001 Rosin et al.
6,262,721 B1 7/2001 Tsukidate et al.
6,262,730 B1 7/2001 Horvitz et al.
6,263,309 B1 7/2001 Nguyen et al.
6,263,313 B1 7/2001 Milsted et al.
6,263,501 B1 7/2001 Schein et al.
6,266,060 B1 7/2001 Roth
6,266,644 B1 7/2001 Levine
6,266,649 B1 7/2001 Linden et al.
6,266,814 B1 7/2001 Lemmons et al.
6,268,846 B1 7/2001 Georgiev
6,269,172 B1 7/2001 Rehg et al.
6,269,275 B1 7/2001 Slade
6,272,216 B1 8/2001 Vaios
6,272,231 B1 8/2001 Maurer et al.
6,272,467 B1 8/2001 Durand et al.
6,272,476 B1 8/2001 Shi et al.
6,272,479 B1 8/2001 Farry et al.
6,275,229 B1 8/2001 Weiner et al.
6,275,268 B1 8/2001 Ellis et al.
6,275,648 B1 8/2001 Knudson et al.
6,275,812 B1 8/2001 Haq et al.
6,275,824 B1 8/2001 O'Flaherty et al.
6,285,794 B1 9/2001 Georgiev et al.
6,298,348 B1 10/2001 Eldering
6,301,370 B1 10/2001 Steffens et al.
6,307,139 B1 10/2001 Iwamura
6,308,175 B1 10/2001 Lang et al.
6,310,886 B1 10/2001 Barton
6,314,190 B1 11/2001 Zimmermann
6,314,412 B1 11/2001 Yamaguchi et al.
6,314,420 B1 11/2001 Lang et al.
6,314,568 B1 11/2001 Ochiai et al.
6,314,573 B1 11/2001 Gordon et al.
6,317,722 B1 11/2001 Jacobi et al.
6,317,882 B1 11/2001 Robbins
6,321,208 B1 * 11/2001 Barnett ..... G06Q 20/108 705/14.36
6,321,221 B1 11/2001 Bieganski
6,324,126 B1 11/2001 Nagano
6,327,590 B1 12/2001 Chidlovskii et al.
6,330,499 B1 * 12/2001 Chou ..... G07C 5/008 701/31.4
6,397,040 B1 * 5/2002 Titmuss ..... H04Q 3/0029 455/412.2
6,400,996 B1 6/2002 Hoffberg et al.
6,418,424 B1 7/2002 Hoffberg et al.
6,721,654 B2 * 4/2004 Akiyama ..... G01C 21/362 340/988
7,072,849 B1 * 7/2006 Filepp ..... G06Q 30/02 705/14.66
7,242,988 B1 7/2007 Hoffberg et al.
7,315,823 B2 * 1/2008 Brondrup ..... G06Q 10/02 705/5
7,650,319 B2 1/2010 Hoffberg et al.
8,010,423 B2 * 8/2011 Bodin ..... G06Q 30/0266 705/14.63
RE46,310 E * 2/2017 Hoffberg ..... G06F 3/0482
2001/0000045 A1 3/2001 Yu et al.
2001/0000194 A1 4/2001 Sequeira
2001/0000458 A1 4/2001 Shtivelman et al.
2001/0000540 A1 4/2001 Cooper et al.
2001/0001022 A1 5/2001 Kinghorn
2001/0001024 A1 5/2001 Yanagihara et al.
2001/0001160 A1 5/2001 Shoff et al.
2001/0002224 A1 5/2001 Sasaki et al.
2001/0002852 A1 6/2001 Kwoh
2001/0007147 A1 7/2001 Goldschmidt Iki et al.
2001/0008427 A1 7/2001 Seo
2001/0009034 A1 7/2001 Lee
2001/0009548 A1 7/2001 Morris
2001/0009604 A1 7/2001 Ando et al.
2001/0009605 A1 7/2001 Ando et al.
2001/0010046 A1 7/2001 Muyres et al.
2001/0010094 A1 7/2001 Moir
2001/0010095 A1 7/2001 Ellis et al.
2001/0010523 A1 8/2001 Sezan et al.
2001/0010755 A1 8/2001 Ando et al.
2001/0011264 A1 8/2001 Kawasaki
2001/0011284 A1 8/2001 Humpleman et al.
2001/0011372 A1 8/2001 Lee
2001/0011373 A1 8/2001 Inoue
2001/0011996 A1 8/2001 Terakado et al.
2001/0012323 A1 8/2001 Gaedke et al.
2001/0012440 A1 8/2001 Itoi
2001/0012443 A1 8/2001 Ando et al.
2001/0013123 A1 8/2001 Freeman et al.
2001/0013124 A1 8/2001 Klosterman et al.
2001/0013125 A1 8/2001 Kitsukawa et al.
2001/0013906 A1 8/2001 Thorgeirsson

(56) References Cited

U.S. PATENT DOCUMENTS

| | | | | |
|---|---|---|---|---|
| 2001/0013952 | A1 | 8/2001 | Boon | |
| 2001/0014201 | A1 | 8/2001 | Ando et al. | |
| 2001/0014210 | A1 | 8/2001 | Kang | |
| 2001/0014895 | A1 | 8/2001 | Sappal | |
| 2001/0014974 | A1 | 8/2001 | Asada et al. | |
| 2001/0016944 | A1 | 8/2001 | Terakado et al. | |
| 2001/0016945 | A1 | 8/2001 | Inoue | |
| 2001/0016946 | A1 | 8/2001 | Inoue | |
| 2001/0016947 | A1 | 8/2001 | Nishikawa et al. | |
| 2001/0019367 | A1 | 9/2001 | Walton et al. | |
| 2001/0019658 | A1 | 9/2001 | Barton et al. | |
| 2001/0020297 | A1 | 9/2001 | Inoue | |
| 2001/0021994 | A1 | 9/2001 | Nash | |
| 2001/0021995 | A1 | 9/2001 | Hatano | |
| 2001/0022003 | A1 | 9/2001 | Narushima | |
| 2001/0023401 | A1 | 9/2001 | Weishut et al. | |
| 2001/0023433 | A1 | 9/2001 | Natsubori et al. | |
| 2001/0023498 | A1 | 9/2001 | Cosmao et al. | |
| 2001/0024565 | A1 | 9/2001 | Yui et al. | |
| 2001/0024566 | A1 | 9/2001 | Mankovitz | |
| 2001/0026386 | A1 | 10/2001 | Yamamoto et al. | |
| 2001/0026561 | A1 | 10/2001 | Morris et al. | |
| 2001/0026677 | A1 | 10/2001 | Chen et al. | |
| 2001/0027557 | A1 | 10/2001 | Shinkawa et al. | |
| 2001/0027558 | A1 | 10/2001 | Sasselli et al. | |
| 2001/0029511 | A1 | 10/2001 | Burda et al. | |
| 2001/0029610 | A1 | 10/2001 | Corvin et al. | |
| 2001/0030644 | A1 | 10/2001 | Allport | |
| 2001/0030661 | A1 | 10/2001 | Reichardt | |
| 2001/0030711 | A1 | 10/2001 | Saito | |
| 2001/0032333 | A1 | 10/2001 | Flickinger | |
| 2001/0036224 | A1* | 11/2001 | Demello | H04L 63/30 375/220 |
| 2001/0037238 | A1 | 11/2001 | Gotoh et al. | |
| 2001/0037242 | A1 | 11/2001 | Bataillon et al. | |
| 2001/0037375 | A1 | 11/2001 | Story et al. | |
| 2001/0037462 | A1 | 11/2001 | Bengtson | |
| 2001/0039514 | A1 | 11/2001 | Barenbaum et al. | |
| 2001/0039544 | A1 | 11/2001 | Chakrabarti et al. | |
| 2001/0047357 | A1 | 11/2001 | Vaithilingam et al. | |
| 2001/0047379 | A1 | 11/2001 | Jun et al. | |
| 2001/0048483 | A1 | 12/2001 | Steinberg et al. | |
| 2001/0049820 | A1 | 12/2001 | Barton | |
| 2001/0049822 | A1 | 12/2001 | Yoshida et al. | |
| 2001/0056405 | A1 | 12/2001 | Muyres et al. | |
| 2002/0002488 | A1 | 1/2002 | Muyres et al. | |
| 2002/0004744 | A1 | 1/2002 | Muyres et al. | |
| 2002/0016962 | A1 | 2/2002 | Decarmo | |
| 2002/0019763 | A1 | 2/2002 | Linden et al. | |
| 2002/0019764 | A1 | 2/2002 | Mascarenhas | |
| 2002/0019776 | A1 | 2/2002 | Simpson | |
| 2002/0019855 | A1 | 2/2002 | Sakaguchi et al. | |
| 2002/0049535 | A1* | 4/2002 | Rigo | G01C 21/3629 701/431 |
| 2004/0044605 | A1* | 3/2004 | Kress Bodin | G06Q 30/0266 705/35 |

FOREIGN PATENT DOCUMENTS

| | | | |
|---|---|---|---|
| EP | 0851681 | B1 | 7/1998 |
| EP | 1100063 | A3 | 5/2001 |
| WO | 1997006613 | A3 | 3/1997 |
| WO | 1997014251 | A1 | 4/1997 |
| WO | 1997020279 | A1 | 6/1997 |
| WO | 1997026612 | A1 | 7/1997 |
| WO | 1997027534 | A1 | 7/1997 |
| WO | 1997044767 | A1 | 11/1997 |
| WO | 1997033424 | A3 | 12/1997 |
| WO | 1997047135 | A1 | 12/1997 |
| WO | 1999001984 | A1 | 1/1999 |
| WO | 1999009512 | A1 | 2/1999 |
| WO | 1999012030 | A1 | 3/1999 |
| WO | 1999014678 | A1 | 3/1999 |
| WO | 1999014947 | A1 | 3/1999 |
| WO | 1999022502 | A1 | 5/1999 |
| WO | 1999028877 | A1 | 6/1999 |
| WO | 1999030493 | A1 | 6/1999 |
| WO | 1999038154 | A1 | 7/1999 |
| WO | 1999028835 | A3 | 8/1999 |
| WO | 1999039466 | A1 | 8/1999 |
| WO | 1999043111 | A1 | 8/1999 |
| WO | 1999045701 | A1 | 9/1999 |
| WO | 1999045709 | A1 | 9/1999 |
| WO | 1999046719 | A1 | 9/1999 |
| WO | 1999051031 | A1 | 10/1999 |
| WO | 1999052279 | A1 | 10/1999 |
| WO | 1999055070 | A2 | 10/1999 |
| WO | 1999063458 | A1 | 12/1999 |
| WO | 1999065237 | A1 | 12/1999 |
| WO | 1999065242 | A1 | 12/1999 |
| WO | 1999066427 | A1 | 12/1999 |
| WO | 1999066726 | A1 | 12/1999 |
| WO | 2000007368 | A1 | 2/2000 |
| WO | 2000016336 | A1 | 3/2000 |
| WO | 2000026800 | A1 | 5/2000 |
| WO | 2000026828 | A1 | 5/2000 |
| WO | 2000027117 | A1 | 5/2000 |
| WO | 2000030345 | A1 | 5/2000 |
| WO | 2000030350 | A1 | 5/2000 |
| WO | 2000033224 | A1 | 6/2000 |
| WO | 2000033228 | A1 | 6/2000 |
| WO | 2000033575 | A1 | 6/2000 |
| WO | 2000036775 | A1 | 6/2000 |
| WO | 2000036836 | A1 | 6/2000 |
| WO | 2000039707 | A1 | 7/2000 |
| WO | 2000040017 | A1 | 7/2000 |
| WO | 2000040026 | A1 | 7/2000 |
| WO | 2000044119 | A1 | 7/2000 |
| WO | 2000044171 | A1 | 7/2000 |
| WO | 2000011850 | A9 | 8/2000 |
| WO | 2000045285 | A1 | 8/2000 |
| WO | 2000045319 | A1 | 8/2000 |
| WO | 2000051050 | A1 | 8/2000 |
| WO | 2000055748 | A1 | 9/2000 |
| WO | 2000068756 | A2 | 11/2000 |
| WO | 2000072205 | A1 | 11/2000 |
| WO | 2000045305 | A3 | 12/2000 |
| WO | 2000046988 | A3 | 12/2000 |
| WO | 2000074377 | A1 | 12/2000 |
| WO | 2000018108 | A3 | 1/2001 |
| WO | 2000036539 | A9 | 3/2001 |
| WO | 2000038399 | A3 | 3/2001 |
| WO | 2001022729 | A1 | 3/2001 |
| WO | 2001024027 | A1 | 4/2001 |
| WO | 2001031913 | A1 | 5/2001 |
| WO | 2001046843 | A2 | 6/2001 |
| WO | 2001047238 | A2 | 6/2001 |
| WO | 2001052532 | A1 | 7/2001 |
| WO | 2001054406 | A1 | 7/2001 |
| WO | 2001065762 | A2 | 9/2001 |
| WO | 2001067749 | A2 | 9/2001 |
| WO | 2001069380 | A2 | 9/2001 |
| WO | 2000049801 | A9 | 10/2001 |
| WO | 2000072209 | | 11/2001 |
| WO | 2001037193 | | 11/2001 |
| WO | 2003089222 | A1 | 10/2003 |
| WO | 2001028238 | A3 | 12/2003 |
| WO | 1998044717 | A3 | 6/2004 |

OTHER PUBLICATIONS

Rillings, J.H. and R.J. Betsold "An Advanced Driver Information System for North America", Proceedings of the International Congress on Transportation Electronics, Oct. 1990, pp. 85-94.*

Phail, F. "The Power of Personal Computer for Car Information and Communications Systems", Proceedings of the Vehicle Navigation and Information Systems Conference, Oct. 20-23, 1991, pp. 389-395.*

Muffat, M., P. Geen, and S. Crosnier "European Cooperation on Dual Mode Route Guidance—Perspectives for Advanced Research Partners", Proceedings of the Vehicle Navigation and Information Systems Conference, Oct. 20-23, 1991, pp. 929-935.*

(56) References Cited

OTHER PUBLICATIONS

Zavoli, W., G.L. Latshaw, and J. Rehfeld "Customer Location Services", Proceedings of the 1994 Vehicle Navigation and Information Systems Conference, Aug. 31-Sep. 2, 1994, pp. 613-617.*
Schilit, B.N. and M.M. Theimer "Disseminating Active Map Information to Mobile Hosts", IEEE Network, vol. 8, No. 5, Sep./Oct. 1994, pp. 22-32.*
Pinola, M. "Mobile Computing Devices", www.lifewire.com, downloaded from Internet Archive, Oct. 19, 2016.*
Techopedia "Mobile Device Definition", downloaded from Internet Archive, Jan. 4, 2017.*
Intelity "A Brief Look at the History of Hotel Technology", downloaded from https://intelitycorp.com/main/brief-look-history-hotel-technology, May 16, 2016.*
Sheth, B. and P. Maes, "Evolving Agents for Personalized Information Filtering", Proceedings of the 9th IEEE Conference on Artificial Intelligence for Applications, Mar. 1-5, 1993, pp. 345-352. (Year: 1993).*
Norman, Donald A., "Infuriating by esign", Psychology Today, vol. 22, (Mar. 1988): 52-56.
Pope, et al., "Video Abstraction: Summarizing Video Content for Retrieval and Visualization", In Proc. Thirty-Second Asilomar Conference on Signals, Systems & Computers, 1998, pp. 915-919.
Yoshida, Junko, "EMC.sup.z Pushes Video Rental by Satellite", Electronic Engineering Times (Nov. 2, 1991) 97-98.
Inspec 4671654 B9406-6140C-211 C9406-1250-138 Doc Type: Journal Paper Title: Image coding using fractal parameters of contour lines Authors: Suzuki, Y.; Sumiyoshi, H.; Miyauchi, A. Affiliation: Dept. of Electron. & Commun. Eng. Musashi Inst. of Technol., Tokyo, Japan Journal: Journal of the Institute of Television Engineers of Japan vol. 48 Iss: pp. 69-77 Date: Jan. 1994.
Inspec 4683860 A9414-1230-005 B9407-6140C-104 C9407-1250-076 Doc Type: Journal Paper Title: Fractal error for detecting man-made features in serial images Authors: Cooper, B.E.; Chenoweth, D.L.; Selvage, J.E. Affiliation: Comput. Sci. & Eng. Program, Louisville Univ., KY, USA Journal: Electronics Letters vol. 30 Iss: 7 pp. 554-55 Date: Mar. 31, 1994.
Inspec 4684331 B9407-6140C-107 C94074-1250-078 Doc Type: Journal Paper Title: Uncertainty management for rule-based system with applications to image analysis Authors: Mogre, A.; McLaren, R.; Keller, J.; Krishnapuram, R. Affiliation: LSI Logic Corp., Milpitas, CA, USA Journal: IEEE Transactions on Systems, Man and Cybernetics vol. 24 Iss: 3 pp. 470-481 Date: Mar. 1994.
Inspec 4685821 B9407-6140C-123 C9407-1250-093 Doc Type: Journal Paper Title: Nonorthogonal image expansion related to optimal template matching in complex images Authors: Ragbunath Rao, K.; Ben-Arie, J. Affiliation: Dept. Electr. & Comput. Eng., Illinois Inst. of Technol. Chicago, IL, USA Journal: CVGIP: Graphical Models and Image Processing vol. 56 Iss: 2 pp. 149-160 Date: Mar. 1994.
Inspec 4686006 B9407-6140C-129 C9407-1250-101 Doc Type: Journal Paper Title: Intensity-and distortion-invariant pattern recognition with complex linear morphology Authors: Rahmati, M.; Hasselbrook, L.G. Affiliation: Dept. of Electr. Eng., Kentucky Univ., Lexington, KY, USA Journal: Pattern Recogntion vol. 27 Iss: 4 pp. 549-568 Date: Apr. 1994.
Inspec 4690B59 B9407-6140C-178 C9407-1250-136 Doc Type: Conference Paper Title: Structure from motion: a region based approach using affine tranformations and moment invariants Authors: Lee, C.-Y; Cooper, D.B. Affiliation: Div. of Eng., Brown Univ., Providence, RI, USA Conf. Title: Proceedings IEEE International Conference on Robotics and Automation (Cat. No. 93CH3247-4) pp. 120-127 vol. 3 Publisher. IEEE Comput. Soc. Press Los Alamitos, CA, USA Date: 1993 3 vol. (xviii+1051+xvi+848+xviii+1042 pp.).
Inspec 4691097 B9407-0100-079 C9407-5260B-083 Dog Type: Conference Proceedings Conf. Title: Proceedings of 4th International Workshop on Time-Varying Image Processing and Moving Object Recognition Editors: Cappellini, V. Publisher: Elsevier Amsterdam, Netherlands Date: 1994 xiii+429 pp.
Inspec 4691104 B9407 6140C-184 C9407-1250-144 Dog Type: Conference Paper Title: Study on Gabor expansion and wavelet decomposition for texture analysis Authors: Nemeth, G.; Boroczky, L. Affiliation: KFKI Res. Inst. For Meas. & Comput. Techniques, Budapest, Hungary Conf. Title: Efficient Texture Analysis: Advanced Methods, Applications (KFKI-1994-2/N) pp. 31-41 Editors: Nemeth, G.; Boroczky, L. Publisher: KFKI Res. Instr. Meas. Comput. Tech Budapest, Hungary Date: 1994 94 pp.
Inspec 4691106 B9407-6140C-186 C9407-1250-145 Doc Type: Conference Paper Title: Fractals and multifractals; theory and application to texture recognition Authors: Fioravanni, S.; Giusto, D.D. Affiliation: Dipartimento di Ingegnetic Biofiscia ed Electronica, Genova Univ., Italy Conf. Title: Efficient Texture Analysis: Advanced Methods, Applications (KFKI-1994-2/N) p. 51-9 Editors: Nemeth, G,; Boroczky, L. Publisher: KFKI Res. Inst. Meas. Comput. Tech Budapest, Hungary Date: 1994 94 pp.
Inspec 46931735 C9405-1250-077 Doc Type: Journal Paper Title: Non-analytic object recognition using the Hough transform with machine technique Authors: Set, P.-K.; Siu, W.-C. Affiliation: Dept. of Electron. Eng., Hong Kong Polytech., Hung Hom, Hong Kong Journal: IEE Proceedings—Computers and Digital Techniques vol. 141 Iss: 1 pp. 11-16 Date: Jan. 1994.
Inspec 4695587 B9408-6140C-032 C8408-1250-015 Doc Type: Conference Paper Title: Multi-level fractal block coding in video compression Authors: Lia. J.; Matlow, S.; Murphy, N. A. Affiliation: Sch. of Electron. Eng., Dublin City Univ., Ireland Conf. Title: DSP—The Enabling Technology for Communications. Conference Proceedings (ERA93-0008) pp. 6.4/1-9 Publisher: ERA Technol Leatherhead, UK Date: 1993 iv+284 pp.
Inspec 4697503 B9408-6140C-051 C9408-1250-029 Doc Type: Journal Paper Title: Two-plus-one-dimensional differential geometry Authors: Koenderink, J.J.; Van Doom, A.J. Affiliation: Buys Ballot Lab., Utrecht Biophys. Res. Inst., Netherlands Journal: Pattern Recognition Letters vol. 15 Iss: 5 pp. 439-443 Date: May 1994.
Inspec 4441526 C9308-1250-125 Doc Type: Conference Paper Title: Optoelectronic fractal scanning technique for wavelet transform and neural net pattern classifers Authors: Phuvzn, S.; Oh, T.K.; Caviris, N.; Li, Y.; Szu, H. Affiliation NAVSWC, Silver Spring, MD USA Conf. Title: IJCNN International Joint Conference on Neural Networks (Cat. No. 92CH3114 6) pp. 40 6 vol. Publisher: IEEE New York, NY, USA Date: 1992.
Inspec 4458920 C9309-1250-161 Doc Type: Book Chapter Title: recognition and generation of fractal patterns by using syntactic techniques Authors: Blane-Talon, J. Affiliation: Div. of Inf. Technol., CSSRO, Canberra, Act, Australia Book Title: Complex systems: from biology computation pp. 141-152 Editors: Green, D.G.; Bossomaler, T. Publisher: IOS Press Amsterdam, Netherlands Date: 1993 x+376 pp.
Inspec 4479373 C9310-1250-133 Doc Type: Conference Paper in Journal Title: Bayesian methods for the use of implicit polynomials and algebraic invariants in practical computer vision Authors: Subrahmonia, J.; Keren, D.; Cooper, J.B. Affiliation: Lab. for Eng. Man/Machine Syst., Brown Univ., Providence, RI, USA Journal: Proceedings of the SPIE—The International Society for Optical Engineering vol. 1830 pp. 104-117 Date: 1992.
Inspec 4481437 B9310-6140C-191 C9310-5260B-115 Doc Type: Journal Paper Title: Analysis of snowflake shape by a region and contour approach Authors: Muramoto, K.; Matsuura Shiina, T. Affiliation: Fac. of Technol., Kanazawa Univ., Japan Journal: Transactions of the Institute of Electronics, Information and Communication Engineers D-II vol. 176D-II Iss: 5 pp. 949-958 Date: May 1993.
Inspec 4484044 C9311-1250-007 Doc Type: Conference Paper in Journal Title: Markov iterated function system model of Images Authors: Huiguo Luo: Yaoting Zhu: Guangxi Zhu; Faguan Wan Affiliation: Dept. of Electr. & Inf. Eng. Hunrhong Univ. of Sci. & Technol., Wohen China Journal: Proceedings of the SPIE—The Internaional Society for Optical Engineering vol. 1 71 pp. 598-604 Date: 1993.
Inspec 4492170 A9321-0365-052 B9311-6140C-084 C9311-1250-052 Doc Type: Journal Paper Title: Two ways to incorporate scale in the Heisenberg group with an interviewing operator Authors:

(56) References Cited

OTHER PUBLICATIONS

Segman, I.; Schempp, W. Affiliation: Div. of Appl. Sci. Harvard Univ., Cambridge, MA, USA Journal of Mathematical Imaging and Vision vol. 3 Iss: pp. 79-94 Date: Mar. 1993.
Inspec 4495112 B9311-6140C-120 C9311-1260-075 Doc Type: Conference Paper in Journal Title: Affine models for motion and shape recovery Authors: Fuh, C.-S.; Maragos, P. Affiliation: Div of Apol. Scil., Harvard Univ., Cambridge, MA, USA Journal: Proceedings of the SPIE—The Internaional Society for Optical Engineering vol. 1388 Iss: pt.1 pp. 120-134 Date: 1992.
Inspec 44990066 B9311-6140C-213 C9311-1250-151 Doc Type: Conference Paper Title: Color image compression based on fractal geometry Authors: Hong Yan; Fillippoff; G. Affiliation: Dept. of Electr. Eng. Sydney Univ., NSW, Australia Conf. Title: ICIP 92. Proceedings of the 2nd Singapore International Conference on Image Processing pp. 3-5 Editors: Srinivasa, V.; Ong Sim Heng; Ang Yew Hock Publisher: World Scitentific Singapore Date: 1992 xxii+734 pp.
Inspec 4499009 B9311-6140C-216 C9311-1250-153 Doc Type: Conference Paper Title: A new image compression method based on fractals and human visual system Authors: Li. Ding-Bing; Chang Yi-Lin; Hu Zheng Affiliation: Dept. 1. Xidian Univ., X1 'an, China Conf. Title: ICIP 92. Proceedings of the 2nd Singapore International Conference on Image Processing pp. 16-20 Editors Srinivasa, V.; Ong Sim Heng; Ang Yew Hock Publisher: World Scientific Singapore Date; 1992 xxii +734 pp.
Inspec 4508271 B9312-6140C-058 C9312-1250-0520 Doc Type: Journal Paper Title: Object recognition using alegrabraic and differential invariants Authors: Reiss, T.H. Affiliation: Commun. Signal Processing Lab., Cambridge Univ., UK Journal: Signal Processing vol. 32 Iss: 3 pp. 367-395 Date: Jun. 1993.
Inspec 4518350 B9312-6140C-C9312-1260-138 Doc Type: Conference Paper Title: Natural scene segmentation using fractal based autocorrelation Authors: Luo, R.C; Potlapalli, FL; Hislop, D.w. Affiliation; Dept of Electr. & Comput. Eng., North Carolina State Univ., Raleigh, NC, USA Conf. Title: Proceedings of the 1992 International Conference on industrial Electronics, Control, Instrumentation, and Automation. Power Electronics and Motion Control (Cat. No. D2CH3137-7) pp. 700-705 vol. 2 Publisher: IEEE New York, NY, USA Date: 1992 3 vol. 1649 pp.
Inspec 4544295 C9401-5260B-140 Doc Type: Journal Paper Title: Trackability as a cue for potential obstacle identification and 3-D description Authors: Sawhney, H.S.; Hanson, A.R. Affiliation: Dept. of Comput. Sci., Massachusetts Univ., Amherst, MA, USA Journal: International Journal of Computer Vision vol. II Iss: 237-265 Date: Dec. 1993.
Inspec 45490140 B9401-6140C-307 C9401-1250-222 Doc Type: Journal Paper Title: Determining the fractal dimension of scenes and digital signals using Roseta and other novel approaches Authors: Jaznisch, H.M.; Barton, P. E.; Carruth, R.T. Affiliation: Nichols Res. Corp., Huntsville, AL, USA Journal: Proceedings of the SPIE—The International Society for Optical Engineering vol. 1995 pp. 298-315 Date: 1993.
Inspec 4561907 B9402-6140C-053 C9402-1250-037 Doc Type: Journal Paper Title: Improved fractal geometry based texture segmentation technique Authors: Chaudhuri, B.D.; Satkar, N.; Kundu, P. Affiliation: Electron. & Commun. Sci. Unit Indian Stat. Inst., Calcutta, India Journal: IEEE Proceedings E [Computers and Digital Techniques] vol. 140 Iss: 5 pp. 233-241 Date: Sep. 1993.
Inspec 4572079 B9402 6140C-117 C9402-1250-083 Doc Type: Journal Paper Title: Image data matching for affine transformed pictures—reduction of calculation Authors: Ujifaku, S,; Normura, Y.; Fujii, S. Affiliation: Fac. of Eng., Nagoya Univ., Japan Journal: Transactions of the Institute of Electronics, Information and Communications Engineers D-II vol. 176D-II Iss: 8 pp. 1581-1586 Date: Aug. 1993.
INSPEC 458378 C9403-5260B-028 Doc Type: Conference Paper Title: Frame-to-frame image motion estimation with fuzzy logic system Authors: Lipp, J. I. Affiliation: Dept. of Electr. Eng., Michigan Technol. Univ. Houghton, MI, USA Conf. Title: Proceedings of the 35.sup.th Midwest Symposium on Circuits and Systems (Cat. No. 92 CH3099-9) p. 987-90-7 vol. 2 Publisher: IEEE New York, NY, USA Date 1992 2 vol. xxvii+1584 pp.
INSPEC 4584412 B9403-6140C-070 C9403-1250-053 Title: Application of the EM technique to estimation of affine modeled image motion Authors: Shaltaf, S.; Namazi, N.M. Affiliation: Dept. of Electr. Eng., Michigan Technol. Univ. Houghton, MI, USA Cont. Title: Proceedings of the 35.sup.th Midwest Symposium on Circuits and Systems (Cat. No. 92CH3099-9) p. 1324-7 Publisher: IEEE New York, NY, USA Date 1992 2 vol. xxvii+1584 pp.
Inspec 4589423 B9403-1295-008 C9403-5190-007 Doc Type: Journal Paper Title: Generalization ability of extended cascaded artificial neural network architecture Authors: Kamruzzaman J.; Kumagai, Y., Hikita, H. Affiliation: Dept. of Electr. & Electron. Eng., Bangladesh Univ. of Eng. & Technol, Dhaks, Bangladesh Journal: IEICE Transactions on Fundamentals of Electronics, Communications and Computer Sciences vol. E76-A Iss: 10 pp. 1877-1883 Date: Oct. 1993.
Inspec 4595560 B9403-7230G-035 C9403-3240E-002 Doc Type: Conference Paper Title: A CMOS silicon VLSI optical sensor Authors: Camp. W.O., Jr.; Van der Speigel, J. Affiliation: IBM Federal Syst. Co., Owego, NY, USA Conf. Title: 1992 International Conference on Systems, Man and Cybernetics (Cat. No. 92CH3176-5) pp. 25-30 vol. 1 Publisher: IEEE New York, NY, USA Date: 1992 2 vol. xviii+1735 pp.
Inspec 4595662 C9403-1250-200 Doc Type: Conference Paper Title: Comments on the evaluation of a certain pattern method as an intellectual information processing Authors: Munakata, T.; Okashita, K.; Nakahara, T. Affiliation: Dept. of Mech. Eng., Hiroshima—Denki Inst. of Technol., Hiroshima-city, Japan Conf. Title: 1992 IEEE International Conference on Systems, Man and Cybernetics (Cat. No. 92CH3176-5) pp. 611-616 vol. 1 Publisher IEEE New York, NY, USA Date: 1992 2 vol. xviii+1735 pp.
Inspec 4596010 B9403-6140C-282 C9403-1250-215 Doc Type: Conference Paper Title: An efficient image compression algorithm based on filter bank analysis and fractal theory Authors: Temerinac, M.; Kozzrev, A.; Tipovski, Z.; Simsic, B. Affiliation: Fac. of Tech. Sci., Novi Sad univ., Yugoslavia Conf. Title: Signal Processing VI—Theories and Applications Proceedings of EUSIPCO-92, Sixth European Signal Processing Conference pp. 1373-1376 vol. 3 Editors: Vandewalie, J.; Boite, R.; Moonen, M.; Oosterlinck, A. Publisher: Elsevier Amsterdam, Netherlands, Date:
Inspec 4596362 C9403-1230D-112 Doc Type: Conference Paper Title: Invariant object recognition using Fahiman and Lebiere's learning algorithm Authors: Ito. K.; Hamamoto, M.; Kamruzzaman, J.; Kumagai, Y. Affiliation: Dept. of Comput. Sci., Mutoran Inst. of Technol., Japan Conf. Title: New Trends in Neural Computation. International Workshop on Artificial Neural Networks. Iwann '93 Proceedings pp. 237-242 Editors: Mira J.; Cabestany, J.; Prieto, A. Publishers: Springer-Verlag Berlin, Germany Date: 1993 746 pp.
Inspec 4603677 C9404-1230D-003 Doc Type: Conference Paper in Journal Title: Differential theory of learning for efficient neural network pattern recognition authors: Hampshire, J.B., II; Vijaya Kumar, B.V.K. Affiliation: Dept. of Electr. & Comput. Eng. Carnegie Mellon Univ., Pittsburgh, PA, USA Journal: Proceedings for Optical Engineering vol. 1965 pp. 76-95 Date: 1993.
Inspec 4606815 C9404-5290 004 Dog Type: Journal Paper Title: The use of neural networks in pattern recognition and control Authors: Windsor, C.,G. Affiliation Nat. Nondestructive Test. Centre, Harwell Lab., UK Journal: Systems Science vol. 19 Iss: 3 pp. 31-41 Date: 1993.
Inspec 4607872 B9404-6140C-074 C9404-1250-045 Doc Type: Conference Paper Title: Characterization of clutter in IR images using maximum likelihood adaptive neural system Authors: Perlovsky, L.II; Jaskolski, J.J.; Chernick, J. Affiliation : Nicholas Res. Corp., Wakefield, MA, USA Conf. Title: Conference Record of the Twenty-Sixth Asilomar Conference on Signals, Systems and Computers (Cat. No. 92CH3245-8) pp. 1076-1080 vol. 2 Editors: Singh, A. Publisher: IEEE Comput. Soc. Press Los Alamitos, CA, USA Date: 1992 2 vol. (xviii+xix+1156 pp.).
Inspec 4609098 B9404-6140C-114 C9404-1250-055 Doc Type: Conference Paper in Journal Title: Feature competition and domain of attraction in artificial-perceptron pattern-recognizer Authors: Mu,

(56) References Cited

OTHER PUBLICATIONS

C.I,.J. Affiliation: Dept. of Electr. Eng. Southern Illinois Univ., Carbondale, IL, USA Journal: Proceedings of the SPIE—The International Society for Optical Engineering vol. 2032 pp. 87-90 Date: 1993.
Inspec 4620036 C9404-1730-048 Doc Type: Conference Proceedings in Journal Conf. Title: Adaptive and Learning Systems II Journal: Proceedings of the SPIE-13 The International Society for Optical Engineering vol. 1962 Date: 1953.
Dialog No. 03773367 EI Monthly No. EIP94011166696 Title: Texture classification by wavelet packet signatures Author: Laine, Andrew; Fan, Nan Corporate Source: Univ of Florida, Gainesville, FL., USA Source: IEEE Transactions on Pattern Analysis and Machine Intelligence v 15 n. 11 Nov. 1993. pp. 1186-1191 Publication Year 1993.
Dialog No. 03771133 EI Monthly No. EIP93121160707 Title: Proceedings of the Graphics Interface Author Anen (Ed.) Conference Title: Proceedings of the Graphics Interface Conference Location: Toronto, Ont, Can Source: Proceedings—Graphics Interface 1993. Publ by Canadian Information Processing Soc, Toronto, Ont, Can. 263p. Publication Year: 1993.
Atkinson, Terryy, "VCR Programming: Making Life Easier Using Bar Codes", The Globe, date unknown.
Bindra, Ashok et al, "Ti Leads Five-Firm Parallel-Processing Effort", Electronics Engineering Times, (Dec. 2, 1991): 21-22.
Booney, Paula, "New World for Windows to Tap 'Smart' Features" PC WEEK, vol. 10: 1&14 (Mar. 22, 1993).
Dialog No. 0310278 EI Monthly No. EIP94021217664 Title: From global to local, a continuum of shape models with fractal priors Author: Vemuri, B.C.; Radisavljevic, A. Corporate Source: Univ of Florida, Gainesville, FL, USA Conference Title: Proceedings of the 1993 IEEE Computer Society on Computer Vision and Pattern Recognition Conference Location: New York, NY, USA Conference Sponsor: IEEE Source: IEEE Computer Vision and Pattern Recognition Proc 1993 IEEE Comput Soc Conf Comput Vision Pattern Recognit 1993. Publ by IEEE, IEEE Service.
Dialog No. 03750577 EI Monthly No. EIP93111131815 Title: Fractal precision models of lathe-type turning matchines Author: Turner, Irem Y.; Srinlvasen, R.L.; Wood, Kristin L.; Busch-Vishniac, Ilene Corporate Source: Univ of Texas, Austin, TX, USA Conference Title: Proceedings of the 19th Annual ASME Design Automation Conference. part 2 (of 2) Conference Location: Albuquerque, NM, USA Conference Sponsor: ASME, The Design Engineering Division Source: Advances in Design Automation American Society of Mechanical Engineers, Design Engineering Division (Publication).
Dialog No. 03751707 EI Monthly No. EIP9311134256 Title: Computer art representing the behavior of the Newton-Raphson method Author: Walter, David John Corporate Source: Nanyang Technological Univ, Singapore, Source: Computers & Graphics (Pergamon) v 17 n 4 Jul.-Aug. 1993. pp. 487-488 Publication Year: 1991.
Dialog No. 03758542 EI Monthly No. EIP93121144140 Title: Implications of the user's informatoin processing strategy on the design of decision aids for complex systems Author: Matthews, Michael L.; McFadden, Sharon M. Corporate Source: Univ of Guelph. Ont. Can Conference Title: Proceedings of the 37th Annual Meeting the Human Factors and Ergonomics Society Conference Location: Seattle, WA, USA Source: Designing for Diversity Proceedgins of the Human Factors and Ergonomics Society v 1 1993. publ by Human Factors and Ergonomics Society, Inc., Santa.
Dialog No. 03765361 EI Monthly No. EIP93071030657 Title: Investigating facial verification systems using back-propagation neural networks Author: Payne, Tanya L.; Solheim, Inger, Castain, Ralph Corporate Source: Los Alamos Natl Lab, Los Alamos, NM, USA Conference Title: Proceedings of the 3rd Workshop on Neural Networks: Academic/Industrial/NASA/Defense Conference Location: Alabama, AL, USA Conference Sponsor: Auburn University Space Power Institute; Center for Commercial Development of Space Power and Advanced Electronics; NASA Headquarter.
Dialog No. 03765362 EI Monthly No. EIP93071030658 Title: Neural net based 2D-vision system for real-time applications Author: Reddy, O.N.; Valthilingham, S.; Bean, W.C. Corporate Source: Lamar Univ, Beaumont, TX, USA Conference Title: Proceedings of the 3rd Workshop on Neural Networks: Academic/Industrial/NASA/Defense Conference Location: Alabama, AL, USA Conference Sponsor: Auburn University Space Power Institute; Center for Commercial Development of Space Power and Advanced Electronics; NASA Headquarters Source: Proceedings of.
Dialog No. 03765834 EI Monthly No. EIP930111599 Title: Improved electro-optical target detection in a natural fractal environment Author: Cohen, G.; Reina, G.; Tidhar, Gil; Rotman, Stanley R. Corporate Source: Ben-Gurion Univ. of the Negev, Beer-Sheva, Isr Conference Title: 8th Meeting on Optical Engineering in Israel: Optical Engineering and Remote Sensing Conference Location: Tel Aviv, Isr Conference Sponsor: SPIE—International Soc for Opt Engineering, Bellingham, WA USA; Int Commission for Optics; European Optical Soc; Optical Soc of America: Asia-Pacific Optics.
Inspec 4620259 B9404-6140C-368 C9404-526B-217 Doc Type: Conference Paper in Journal Title: Automatic target recognition with intensity-and distortion-invariant hybrid composite filters Authors: Rahmati. M.; Hassebrook, L.G.; Vijaya Kumar, B.V.K. Affiliation: Dept. of Electr. Engl. Kentucky Univ., Lexington, KY, USA Journal: Proceedings of the SPIE—The International Society for Optical Engineering vol. 1959 pp. 133-145 Date: 1993.
Inspec 4620265 A9408-4230-017 B9404-6140C-374 C904-1250-233 Doc Type: Conference Paper in Journal Title: Distortion invariant optical pattern recognition using composite binary filters Authors: Roe, M.G.; Sebehrer, K.L.; Dobson, R.; Schirber, L. Affiliation: Rocketdyne Div., Rockwell Int. Corp., Canoga Park, CA, USA Journal: Proceedings of the SPIE—The Internationl Society for Optical Engineering vol. 1959 pp. 203-213 Date: 1993.
Inspec 4626676 B940-025 C9405-1250-031 Doc Type: Conference Paper in Journal Title: Discriminant analysis in aerial images using fractal based features Authors: Priebe, C.E.; Soika, J.L.; Rogers. G.W. Affiliation: Syst. Res. & Technol. Dept., Advanced Computation Technol. Dahlgren, VA, USA Journal: Proceedings of the SPIE—The International Society for Optical Engineering vol. 1962 pp. 196-208 Date: 1993.
Inspec 4626677 B9405-6140C-026 C94054-1250-032 Doc Type: Conference Paper in Journal Title: A probabilistic approach to fractal based texture discrimination Authors: Soika, J.L.; Priebe, C.E.; Rogers, G.W. Affiliation: Dept. of Syst. Res. & Technol., Naval Surface Warfare Center, Dahlgren, VA, USA Journal: Proceedings of the SPIE—The International Society for Optical Engineering vol. 1962 pp. 209-218 Date: 1993.
Inspec 4626678 B9405-6140C-207 C9405-5260B-006 Doc Type: Conference Paper in Journal Title: Parallel computation of fractal dimesion Authors: Hayes, H.I.; Solka, J.LI. Priebe, C.E. Affiliation: Syst. Res. & Technol. Dept. Naval Surface Warfare Center, Dahlgren, VA, USA Journal: Proceedings of the SPIE—The International Society for Optical Engineering vol. 1962 pp. 219-230 Date: 1993.
Inspec 4626939 C9405-1250-068 Doc Type: Conference Paper in Journal Title: Searching geometric libraries using generalized epsilon-congruence Authors: Phillips, P.J. Affiliation: Rutor, Rutgers Univ., New Brunswick, NJ USA Journal: Proceedings of the SPIE—The International Society for Optical Engineering vol. 2060, pp. 225-235 Date: 1993.
Inspec 462891 B9405-6140C-079 C9405-5260B-039 Doc Type: Conference Paper in Journal Title: Object tracking through adaptive correlation Authors: Montera, D.A.; Rogers, S.K.; Ruck, D.W. Oxley, M.E. Affiliation: Dept. of Elect. & Comput. Eng., Air Force Inst. of Technol., Wright-Patterson AFB, OH, USA Journal: Proceedings of the SPIE—The International Society for Optical Emgineering vol. 1959 pp. 314-321 Date: 1993.
Inspec 4632198 B9405-4180-003 C9405-5270-002 Doc Type: Conference Paper in Journal Title: Shift invariant optical neural network with holographic bipolar synapses Authors: Chao, T. H. Affiliation: Jet Propulsion Lab., California Inst. of Technol., Pasadena, CA, USA Journal: Proceedings of the SPIE—The International Soociety for Optical Engineering vol. 1959 pp. 422-430 Date: 1993.
Inspec 4632199 B9405-4120-003 C9405-5320K-006 Doc Type: Conference Paper in Journal Title: A content-addressable polychromatic

(56) References Cited

OTHER PUBLICATIONS neural net using a specially doped LiNbO/sub 3/ photorefractive crystal Authors: Yu, F, F.T.S.; Yin. S.; Uang, C.-M. Affiliation: Dept. of Electr. & Comput. Eng., Pennsylvania Journal: Proceedings of the SPIE—The International Society for Optical Engineering vol. 1959 431-441 Date: 1993.
Inspec 4637540 B9405-6140C-152 C9405-1250-103 Doc Type: Journal Paper Title: Classified vector quantisation with variable block-size DCT models Authors: Lee, M.H.; Crebbin, G. Affiliation: Dept. of Electr. & Electron. Eng., Western Australia Univ., Nedland, WA Australia Journal: IEE Proceedings-Vision, Image and Signal Processing vol. 141 ISS: 1 pp. 39-48 Date: Feb. 1994.
Inspec 4639978 B9405-6140C-159 C9405-1250-112 Doc Type: Journal Paper Title: A method to estimate position and orientation of 3-D object from 2-D projection Authors: Nomura, Y.; Sae-Han, D.; Fujii, S. Affiliation: Fac. of Eng., Nagoya Univ., Japan Journal: Transactions of the Institute of Electronics, Information and Communication Engineers D-II vol. 177D-II Iss: 1 pp. 101-107 Date: Jan. 1994.
Inspec 4656976 C9406-2590-006 Doc Type: Conference Paper in Journal Title: An incremental neutral classifer on a MIMD parallel computer Authors: Azcarraga, A., Paugarn-Moisy, H.; Puzzenat, D. Affiliation: Lifia Imag Inpg, Grenoble, France Journal: Ifip Transactions A [Computer Science and Technology] vol. A-44 pp. 13-22 Date: 1994.
Inspec 4657256 C9406-5260B-031 Doc Type: Journal Paper Title: An experimental study of an object recognition system that learns Authors: Chung-Mong Lee: Ting-Chuen Pang; Slagle, J.R.; Esterline, A. Affiliation: Dept. of Comput. Sci., Hong Kong Univ. of Sci. & Technol., Hong Kong Journal: Pattern Recognition vol. 27 Iss: 1 pp. 65-89 Date: Jan. 1994.
Inspec 4657258 B9406-6140C-063 C9406-1250-044 Doc Type: Journal Paper Title: The canonical coordinates method for pattern recognition. II. Isomorphisms with affine tranformations Authors: Blatt, N.; Rubinstein, S. Affiliation: Dept. of Math., Technion—Israel Inst. of Technol, Haifa, Israel Journal: Pattern Recognition vol. 27 Iss: pp. 99-107 Date: Jan. 1994.
Inspec 4666384 C9406-7490-009 Doc Type: Conference Paper in Journal Title: Pattern classification of RGB colour images using a BP neural network classifer Authors: Iia, J. Affiliation: Sch. of Electr. & Electron. Eng., Nanyang Technological Univ. Singapore Journal: Proceedings of the SPIE—The International Society for Optical Engineering vol. 1989 pp. 248-256 Date: 1993.
Inspec 4666490 B9406-6140C-154 C9406-1250-109 Doc Type: Journal Paper Title: Efficacy of fractal features in segementing images of natural textures Authors: Dubuisson, M.-P.; Dubes, R.C. Affiliation: Dept. of Comput. Sci., Michigan State Univ., East Lansing, MI, USA Journal: Pattern Recognition Letters vol. 15 Iss: 4 pp. 419-431 Date: Apr. 1994.
Dialog No. 03769393 EI Monthly No. EIP3121154226 Title: Outdoor landmark recognition using fractal based vision and neural networks Author Luo, Ren C.; Porlapalli, Harsh, Hislop, David W. Corporate Source: North Carolina State Univ, Raleigh, NC, USA Conference Title: Proceedings of the IEEE/RSJ International Conference on Intelligent Robots and Systems Conference Location: Yokohama, JPN Conference Sponsor IEEE Industrial Electronics Society; IEEE Robotics and Automation Society; Robotics Society of Japan (RSJ); Society of Instrument and Control Engineers.
Dialog No. 03769393 EI Monthly No. EIP93121154226 Title: Outdoor landmark recognition using fractal based vision and neural networks Author Luo, Ren C.; Potlapalli, Harsh; Hislop, David W. Corporate Source: North Carolina State Univ, Raleigh, NC, USA Conference Title: Proceedings of the IEEE/RSJ International Conference on Intelligent Robots and Systems Conference Location: Yokchama, JPN Conference Sponsor: IEEE Industrial Electronics Society, IEEE Robotics and Automation Society; Robotics Society of Japan (RSJ); Society of Instrument and Control Engineer.
Dialog No. 03770270 EI Monthly No. EIP93121161716 Title: Recognition and inspection of manufactured parts using line moments of their boundaries Author: Wen, Wei; Lozzi, Andrei Corporate Source: Univ of Sydney, Sydney Aust Source: Pattern Recognition v 26 n 10 Oct. 1991 pp. 1461-1471 Publication Year: 1993.
Dialog No. 03780159 EI Monthly No. EIP9401117143 Title: Sensperceptor: Image based evidence formation model as a logical sensor for robot hand preshaping Author Nazlibilek, L.; Erkmen, A.; Erkmen, I. Corporate Source: Middle East Technical Univ, Ankara, Turk Conference Title: Proceedings of the 1993 IEEE International Symposium on Intelligent Control Conference Location: Chicago, IL, USA Conference Sponsor IEEE Control Systems Society Source: Proc 1993 IEEEE Int Symp Intell Control 1993. Publ by IEEE, IEEE Service Center, Piscataway, NJ, USA.
Dialog No. 03780174 EI Monthly No. EIP94011171758 Title: Barnet: A new approach to behavior arbitration Author: Yavnai Corporate Source: Rafael, Haifa, Isr Conference Title: Proceedings of the 1993 IEEE International Symposium on Intelligent Control Conference Location: Chicago, IL, USA Conference Sponsor: IEEE Control Systems Society Source: Proc 1993 IEEE Int Symp Intel Control 1993. Publ by IEEE, IEEE Service Center, Piscataway, NJ, USA, (IEEE cat n 93CH3278-9). pp. 417-422 Publication Year: 1993.
Dialog No. 03795505 EI Monthly No. EIP9402120064 Title: Fractal image coding: a review Author: Jacquin, Arnand E. Corporate Source: AT&T Bell Lab, Murray Hill, NJ USA Source: Proceedings of the IEEE v 81 n 10 Oct. 1991 pp. 1451-1465 Publication Year: 1993.
Dialog No. 03803851 EI Monthly No. EIP94021215641 Title: Fractal modeling techniques for spatial data Author: Gregorski, Mark E.; Jensen, Olivia Corporate Source: Univ of Waterloo, Waterloo, Ont, Can Source: IEEE Transactions on Geoscience and Remote Sensing v 31 n 5 Sep. 1991 pp. 980-988. Publication Year: 1993.
Dialog No. 03810250 EI Monthly No. EIP94021217636 Title: Efficient recognition of rotationally symmetric surfaces and straight homogeneous generalized cylinders Authors: Liu, Jane; Mundy, Joe; Forsyth, David; Zisserman, Andrew; Rothwell, Charlie Corporate Source: GE Cent for Research and evelopment, Schenectady, NY, USA Conference Title: Proceedings of the 1993 IEEE Computer Society Conference on Computer Vision and Pattern Recognition conference Location Proc 1993 IEEE Comput Soc Conf Comput Vision Pattern Recognit 1993. Publ by IEEE, IEEE.
Dialog No. 03810264 EI Monthly No. EIP94021217650 Title: On the recognition of occluded shapes and generic faces using multiple-template expansion matching Author: Ben-Arie, Jezekjel; Rao, K. Raghunath Corporate Source: Illinois Inst of Technology, Chicago, IL, USA Conference Title: Proceedings of the 1993 IEEE Computer Society Conference on Computer Vision and Pattern Recognition Conference Location: New York, NY, USA Conference Sponsor: IEEE Source: IEEE Computer Vision and Pattern Recognition Proc 1993 IEEE Comput Soc Conf Vision Pattern Recognit.
Dialog No. 03810291 EI Monthly No. EIP94021217677 Title: Robust affine invariant matching with application to line features Author: Tsai, Frank C.D. Corporate Source: New York Univ, New York, NY, USA Conference Title: Proceedings of the 1993 IEEE Computer Society Conference on Computer Vision and Pattern Recognition Conference Location: New York, NY, USA Conference Sponsor: IEEE Source: IEEE Computer Vision and Recognition Proc 1993 IEEE COmput Soc Conf Comput Vision Pattern Recognit 1993. Publ by IEEE, IEEE Service Center, Piscataway, NJ.
Dialog No. 03819787 EI Monthly No. EIP93121145108 Title: Object tracking through adaptive correlation Author: Montera, Dennis A.; Rogers, Steven, K.; Ruck, Dennis W.; Oxley, Mark E. Corporate Source: Air Force Inst. of Technology, Wright-Patterson AFB, OH, USA Conference Title: Optical Pattern Recognition IV Conference Location: Orlando, FL, USA Conference Sponsor: SPIE—Int Soc for Opt Engineering, Bellingham, WA USA Source: Proceedings of SPIE—The International Society for Optical Engineering v 1959 1993. Publ by Society of Photo-Optical.
Dialog No. 03839591 EI Monthly No. EIP94041264411 Title: Fractal characteristics of mesofractures in compressed rock specimens Author: Zhao, Yonghong; Huang, Jiefan; Wang, Ren Corporate Source: Peking Univ, Beijing, China conference Title: Proceedings of the 34th U.S. Symposium on Rock Mechanics Conference Location: Madison, WI, USA Source: International Journal of Rock

(56) References Cited

OTHER PUBLICATIONS

Mechanics and Mining Science & Mechanics Geomechanics Abstracts v 30 n Dec. 7, 1991 pp. 877-882 Publication Year: 1993.
Dialog No. 03854639 EI Monthly No. EIP940501281744 Title: Competitive neural network for affine invariant pattern recognition Author: Kurogi, Shuichi Corporate Source: Kyushu Inst of Technology, Kitakyushu, Jpn Conference Title: Proceedings of 1993 International Joint Conference on Neural Networks. Part 1 (of 3) Conference Location: Nagoya, Jpn Conference Sponsor: ENNS; INNS; IEEE; SCIE; IEICE; et al Source: Proceedings of the International Joint conference on Neural Networks v 1993. Publ by IEEE, IEEE Service Center, Piscataway, NJ, USA 93CH3353-0. pp.
Dialog No. 03854641 EI Monthly No. EIP94051281746 Title: Segmentation method of texture image by using neural network Author: Oe, Shunichiro; Hashida, Masaharu; Shinohara, Yasunori Corporate Source: Univ of Tokushima, Tokushima, Jpn Conference Title: Proceedings of 1993 International Joint Conference on Neural Networks. Part 1 (of 3) Conference Location: Nagoya, JPN Conference Sponsor: ENNS; INNS; IEEE; SICE; IEICE; et al Source: Proceedings of the International Joint Conference on Neural Networks v 1 1993. Publ by IEEE, IEEE Service Center.
Dialog No. 03854872 EI Monthly No. EIP94051281977 Title: Network model for invariant object recognition and rotation angle estimation Author: You, Shingchem, D.; Ford, Gary E. Corporate Source: Univ of California, Davis, CA, USA Conference Title: Proceedings of 1993 International Joint Conferenceon Neural Networks. Part 3 (of 3) Conference Location: Nagoya, Jpn Conferenc Sponsor: ENNS; INNS; IEEE; SICE; IEICE; et al Source: Proceedings of the International Joint Conference on Neural Networks v 3 1993. Publ by IEEE, IEEE Service Center, Piscataway, NJ.
Dialog No. 03854884 EI Monthly No. EIP94051281989 Title: Texture classitication using a two-stage neural network approach Author: Raghu, P.P.; Poongodi, R.; Yegnanarayana, B. Corporate Source: Italian Inst of Technology, Madras, India Conference Title: Proceedings of 1993 International Joint Conference on Neural Networks. Part 3 (of 3) conference Location: Nagoya, Jpn Conference Sponsor: ENNS; INNS; IEEE; SICE; IEICE; et al Source: Proceedings of the International Joint Conference on Neural Networks v 3 1993. Publ by IEEE, IEEE Service Center, Piscataway.
Dialog No. 03855007 EI Monthly No. EIP94051282111 Title: Waveform recognition and classification using an unsupervised network Author: Lee, C.K.; Yeung, K.F. Corporate Source: Hong Kong Polytechnic, Hung Hom, Hong Kong Conference Title: Proceedings of 1993 International Joint Conference on Neural Networks. Part 3 (of 3) conference Location: Nagoya, Jpn Conference Sponsor: ENNS; INNS; IEEE; IEICE; et al Source: Proceedings of the International Joint Conference on Neural Networks v 3 1993. Publ by IEEE, IEEE Service Center, Piscataway, NJ.
Dialog No. 03855870 EI Monthly No. EIP94051282331 Title: Correlation effects of fractal compression Author: Sirgany, Wajie N.; Mazel, David S. Corporate Source: IBM Federal Systems Co, Manaesas, VA, USA Conference Title: proceedings of the 27th Asilomar Conference on Signals, System & Computers Conference Location: Pacific Grove, CA, USA Conference Sponsor: IEEE Computer Society Press; Naval Postgraduate School; San Jose State university Source: Conference Record of the Asilomar Conference on Signals, Systems & Computers v 2 1993. Publ by IEEE.
Inspec 4441256 B9308-6140C-136 C9308-5260B-086 Doc Type: Journal Paper Title: Advances in digital image processing Authors: Anuradha, M. Affiliation: Rakshnpuram Colony, Hyderabad, India Journal: Students' Journal of the Institution of Electronics & Telecommunications Engineers vol. 33 Iss: 3 pp. 197-208 Date: Jul.-Sep. 1992.
Hoffberg, Linda I, Thesis "*An Improved Human Factored Interface For Programmable Devices: A Case Study Of The VCR*", Tufts University Master of Sciences in Engineering Design (Nov. 1990).
Netrologic, Inc. "*Image Compression Using Fractals and Wavelets*" Final Report for the Phase II Contract Sponsored by the Office of Naval Research Contract No. N00014-91-C-0117, (Jun. 2, 1993): Index 62.
Micromint, "*The Catalog of Embedded Controllers*", (Winter 1991):1-28.
Didier LeGall, "*MPEG: A Video Compression Standard for Multimedia Applications", Communications of the ACM* (Apr., 1991).
Carter, Robert S. Jr, "The Business of Technology", *EET,* (Apr. 20, 1992): 22.
Booney, Paula, "New Word for Windows to Tap 'Smart' Features" *PC WEEK,* vol. 10: 1&14 (Mar. 22, 1993).
Bryant, Adam, "For The Lowly Radio, New Tricks Are In Store", *The New York Times,* (Feb. 17, 1993): D2L.
Kolbert, Elizabeth, "With 500 Channels, How Could Anyone Learn What's On", *The New York Times,* (Jan. 4, 1993): 1.
Bursky, Dave, "Improved DSP ICS Eye New Horizons", *Electronic Design,* (Nov. 11, 1993): 69-82.
"Never Miss Anything Again", *Starsight Brochure,* (1994).
Comaford, Christine, "User-Responsive Software Must Anticipate Our Needs", *PC WEEK,* (May 24, 1993).
Shepard, Jeffrey D, "Tapping The Potential Of Data Compression", *Military & Aerospace Electronics* (May 17, 1993): 25-28.
Optical Computing "Trained Neural Network Recognizes Faces," *Laser Focus World,* (Jun. 1993): 26-28.
Cohen, Raines, "Full Pixel Search Helps Users Locate Graphics", *MacWeek,* (Aug. 23, 1993).
Baran, Nicholas, "Fractal Compression Goes On-Line", *BYTE* , (Sep. 1993): 40.
Anson, Louisa F, "Fractal Image Compression," *BYTE,* (Oct. 1993): 195-202.
Lu, Cary, "State Of The Art—Publish It Electronically", *BYTE,* (Sep. 1993): 94-109.
Bagley, Hal & Sloan, Jeff, "In Pursuit Of Perfection", *Photonics Spectra,* (Aug. 1993): 101-106.
Yoshida, Junko, "The Video-On-Demand Demand", *Electronic Engineering Times,* (Mar. 15, 1993): 71-72.
Green, Lee, "ThermoTech", *Popular Mechanics,* (Oct. 1985): 155-160.
Sperling, Barbra & Tullis, Thomas, "Are You A Better "Mouser" or "Trackballer"? A Comparison Of Cursor Positioning Performance", *McDonnell Douglas Astronautics Company :* 1-4, date unknown.
Abedini, Kamran, "An Ergonomically-Improved Control Unit Design", *Proceedings Of Interface 87,* (1987): 375-380.
Schmitt, Lee & Olson, Dean, "Let's Discuss Programmable Controllers" *Modern Machine Shop,* (May 1987): 90-99.
Carlson, Mark A., "Design Goals For An Effective User Interface", *Human Interfacing With Instruments,* pp. 1-4, date unknown.
Wilke, William, "Easy Operation Of Instruments By Both Man And Machine", *Human Interfacing With Instruments :* pp. 1-4, date unknown.
Kreifeldt, John, "Human Factors Approach To Medical Instrument Design" *Human Interfacing With Instruments :* pp. 1-6, date unknown.
Atkinson, Terry, "VCR Programming: Making Life Easier Using Bar Codes", *The Globe,* date unknown.
Abedini, Kamran, "Guidelines For Designing Better VCRs", *California State Polytechnic University, Pomona,* Report No IME 462, (Feb. 4, 1987).
Card, Stuart, "A Method For Calculating Performance Times For Users Of Interactive Computing Systems", *IEEE* CH 1424, (Jan., 1979): 653-658.
Meads, Jon, "Friendly or Frivolous?", *Hardware Gimmicks and Software,* (Jan., 1988): 95-100.
Kreifeldt, J.G., "A Methodology For Consumer Product Safety Analysis," *Dept of Engineering Design-Tufts University,*: pp. 175-184, date unknown.
Carroll, Paul, "High Tech Gear Draws Ones Of" Uncle, *Wall Street Journal,* (Apr. 27, 1988): 29.
Kolson, Ann, "Computer Wimps Drown In A Raging Sea Of Technology", *Globe,* (May 24, 1989).
Wiedenbeck, Susan, et al, "Using Protocol Analysis To Study The User Interface", *Bulletin Of The American Society For Information Science,* (Jul. 1989): 25-26.
"The Highs and Lows of Nielsen Home Video Index," *Marketing & Media Decisions,* (Nov. 1985): 84-86.
Tello, Ernest R, "Between Man And Machine", *BYTE,* (Sep. 1988) : 288-293.

(56) References Cited

OTHER PUBLICATIONS

"Voice Recognition: Understanding The Master's Voice", *PC Magazine,* (Oct. 27, 1987): 261-308.
Hawkins, William J., "Super Remotes", *Popular Science,* (Feb. 1989): 76-77.
Norman, Donald A., "Infuriating By Design", *Psychology Today,* vol. 22, (Mar. 1988): 52-56.
The Quest For 'User Friendly', *US News & World Report,* (Jun. 13, 1988): 54-56.
Trachtenberg, Jeffrey, "How Do We Confuse Thee? Let Us Count The Ways", *Forbes,* (Mar. 21, 1988): 155-160.
Sharpe, Lora, "Teen Havens", *The Globe,* : 12.
Cobb, Nathan, "I Dont Get It", *The Globe Magazine,* (Mar. 25, 1990): 22-29.
Weiss, Ray, "32-Bit Floating Point DSP Processors", *EDN,* (Nov. 7, 1997):128-146.
Hoffberg, Linda I, "Designing A Programmable Interface For A Video Cassette Recorder (VCR) To Meet The User's Needs", *Interface '91*:346-351.
Hoffberg, Linda I, "Designing User Interface Guidelines For Time-Shift Programming On A Video Cassette Recorder(VCR)": pp. 501-504 (1991).
Hoban, Phoebe, "Stacking The Decks", *New York v* 20: p. 14 (Feb. 16, 1987).
Platte, Hans-Joachim et al "A New Intelligent Remote Control Unit For Consumer Electronic Devices", *IEEE,* (1985): 59-68.
Zeisel, Gunter et al, "An Interactive Menu-Driven Remote Control Unit For TV-Receivers And VC-Recorders", *IEEE,* (1988):814-818.
Bensch, U, "VPV—Videotext Programs VideoRecorder", *IEEE,* (1988): 788-792.
Moore, . T.G. & Dartnall, A., "Human Factors Of A Microelectronic Product. The Central Heating Timer/Programmer", *Applied Ergonomics,* (1982), 13.1:15-23.
Kraiss, K.F, "Alternative Input Devices For Human Computer Interaction", Preprint, date unknown.
Verplank, William, "Graphics In Human-Computer Communication: Principles Of Graphical User-Interface Design", Preprint, date unknown.
Doherty, Richard, "Digital Compression Hikes Cable Capacity", *Electronic Engineering,* (Dec. 2, 1991): 1-16.
Moser, Karen D., "Rexx/Windows Shortens GUI Design Time", *PC Week,* (1991).
Davis, Frederic E, "A Scripting Language For The Mac: One Man's Odyssey", *PC Week,* (Nov. 11, 1991):142.
McNamara, George, "Multimedia The Rainbow Pot—or Pothole?" *Computer Technology,* (1991).
Costlow, Terry, "IBM' Points A New Way", *Electronic Engineering Times,* (Oct. 28, 1991):62.
Casasent, David, "Optical Pattern Recognition: For Inspection, Image Enhancement", *Photonics Spectra,* (1991) : 130-140.
"Microway," *AD,* 1991.
"Scene Locator", *New Media,* Nov./Dec. (Nov. 12, 1991).
Donovan, John W., "Intel/IBM's Audio-Video Kernel", *BYTE,* (Dec. 1991): 177-202.
Kim, Yongmin, "Chips Deliver Multimedia", *BYTE,* (Dec. 1991) : 163-173.
"Frame Grabber/Imager Has TM534020 IC", date unknown.
Bindra, Ashok et al, "Ti Leads Five-Firm Parallel-Processing Effort", *Electronic Engineering Times,* (Dec. 2, 1991): 21-22.
"Compression ICs Target Digital.Cameras", *EDN,* (Nov. 28, 1991).
Yoshida, Junko, "Battle Brewing Over Digital-Video Formats", *Electronic Engineering Times,* (Dec. 2, 1991): 20-21.
"Fractal Geometry Compresses Video Images That Have Independent Resolution", *EDN,* (Nov. 7, 1991):122-123.
Mera, Narciso, "DSP And Open Real Time OS Target Multimedia Applications", *Computer Technology Review,* (Fall 1991):14-17.
Guglielmo, Connie, "MPEG Standard Aims To Squeeze Digital Video Into Mainstream", *MacWeek* (Dec. 3, 1991 vol. 5, No. 41): 31-32.
Doherty, Richard, "MPEG Group Reveals Audiovisual Code Data", *Electronic Engineering Times 1991,* (Dec. 2, 1991): 97.
Quinnel, Richard A, "Gyroscope Allows 3-D Motion Sensing For Robotics And Desktop Computers", *EDN,* (Nov. 7, 1991):120.
Zook, Chris, "8mm Incorporates Arithmetic Encoding For Data Compression", *Computer Technology Review,* (Fall 1991):81-85.
Conway, William "New Modem Standards Challenge Integrators With Multiple Choices", *Computer Technology Review,* (Fall 1991) 23-28.
NBC TV News "Radio TV Reports" (Jul. 17, 1990) 1-37.
"The "Smart" House: Human Factors In Home Automation", *Human Factors In Practice* (Dec. 1990) 3-36.
LaGale, Didier, "MPEG:A Video Compression Standard For Multimedia Applications", *Communications Of The ACM* (Apr. 1991/ vol. 34, No. 4) 47-58.
Yoshida, Junko, "EMC Pushes Video Rental By Satellite", *Electronic Engineering Times* (Nov. 2, 1991) 97-98.
Quinnell, Richard, "Image Compression, Part 3", EDN, May 13, 1993, pp. 114-120.
Erickson, Thomas and Salomon, Gitta "Designing a Desktop Information System: Observation and Issues", *CHI '91 Proceedings.* (1991) ACM 0-89791-383-3/91/0004/0049, pp. 49-54.
Shepard, Jeffrey, "Tapping the Potenial of Data Compression", Military & Aerospace Electronics, May 17, 1993, pp. 25-28.
Cypher, Allen, "Video Presentation Eager: Programming Repetitive Tasks by Example", *CHI '91 Proceedings,* (1991), pp. 445-446.
Ueda, Hirotada et al, "Impact: An Interactive Natural-Motion-Picture Dedicated Multimedia Authoring System", *CHI '91 Proceedings:* (1991) ACM 0-89791-383-3/91/0004/0343, pp. 343-350.
Cypher, Allen, "Eager: Programming Repetitive Tasks by Example", *CHI '91 Proceedings,* (1991), ACM 0-89791-383-3/91/0004/0033. pp. 33-39.
Siohi, Antonio C. and Hix. Deborah, "A Study of Computer-Supported User Interface Evaluation Using Maximal Repeating Pattern Analysis", *CHI '91 Proceedings,* (1991), ACM 0-89791-383-3/91/0004/0301,pp. 301-304.
Smith, Sidney L. and Mosier, Jane N., "Guidelines for Designing User Interface Software", ESD-TR-86-278, MTR 10090, Mitre Corporation, Bedford, Massachusetts, (Aug. 1986), (pp. 1-10, 401-418 provided) NTIS AD A177 198.
Fox, Jeffrey, A. and Smith, Sydney L., "Dynamic Rules for User Interface Design" (Druid), M89-22, Mitre Corporation, Bedford, Massachusetts, (May 1989), (pp. 1-2, 40-42 provided).
Inspec 4678814 A9413 4230-029 B9407-6140C-038 C9407-1250-025 Doc Type: Conference Paper in Journal Title: Optical synergetic computers for pattern recognition Authors: Haken, H. Affiliation: Inst. for Theor. Phys. & Synergetics, Stutigart, Germany Journal: Proceedings of the SPIE—The International Society for Optical Engineering vol. 2039 pp. 270-281 Date: 1993.
Inspec 4678793 A9413-4230-025 B9407-6140C-035 C9407-1250-023 Doc Type: Conference Paper in Journal Title: Performance of the optical wavelet matched filter Authors: Roherge, D.; Sheng, Y. Affiliaoon: Dept de Phys., Laval Univ., Ste-Foy, Canada Journal. Proceedings of the SPIE—The International Society for Optical Engineering vol. 2026 pp. 150-160. Date: 1993.
Inspec 4677845 C9407-5260B-019 Doc Type: Conference Paper Title: Distortion-invariant object recognition using adaptive resonance theory Authors: Kadiran, S., Patnaik, L.M. Affiliation: Tao Consultancy Services, Bombay, India Conf. Title: Proceedings 1993 The First New Zealand International Two-Stream Conference on Artificial Neural Networks and Expert Systems p. 341-344 Editors: Kasabov, N.K. Publisher: IEEE Comput. Soc. Press Los Alamitos, CA, USA Date: 1993 xiii+346 pp.
Inspec 4670688 C9406-5260B-164 Doc Type: Conference Paper in Journal Title: Knowledge based object recognition and model generation Authors: Paulus, D.W.R.; Winzen, A.; Niemann, H. Affiliation: Lehrstuld fur Musterezkennang, Univ. Erlangen-Nurnberg, Germany Journal: Proceedings of the SPIE—The International Society for Optical Engineering vol. 1989 pp. 382-393 Date: 1993.
Inspec 4669185 C9406-1230-068 Doc Type: Journal Paper Title: Rule-base structure identification in an adaptive-network-based fuzzy inference system Authors: Chen-Tsai Sun Affiliation: Dept. of

(56) References Cited

OTHER PUBLICATIONS

Comput. & Inf. Sci., Nat. Chiao Tung Univ., Hsinchu, Taiwan Journal: IEEE Transactions on Fuzzy Systems vol. 2 Iss: 1 pp. 64-73 Date: Feb. 1994.
Inspec 4668515 A9412 4230-005 B9406-4180-028 C9406-1250-121 Doc Type: Journal Paper Title: Adaptive-optical neural network for classifying patterns on structured backgrounds Authors: Pavlov, A. V. Affiliation: Vavilov (S.I.) State Opt. Inst., Saint Petersburg, Russia Journal: Optics and Spectroscopy vol. 75 Iss: 3 pp. 391-394 Date: Sep. 1993.
Inspec 4666461 A9412-8780-003 B9406-2230-005 Doc Type: Journal Paper Title: Mutated bacteriorhodopsins-versatile media in optical image processing Authors: Hampp, N.; Zeisel, D. Affiliation: Inst. for Phys. Chem., Munich Univ., Germany Journal: IEEE Engineering in Medicine and Biology Magazine vol. 13 Iss: 1 pp. 67-74 Date: Feb.-Mar. 1994.
Inspec 4686357 A9414-1230-016 B9407-6140C-135 C9407-1250-106 Doc Type: Journal Paper Title: Pattern recognition by optical neural network based on the optical correlator Authors: Pavlov, A. V.; Shubnikow, E.I. Affiliation: Lab. of Opt. Pattern Recognition & Neural Networks, Vavilov (S.I.) State Opt. Inst., Saint Petersburg, Russia Journal: Optical Memory & Neural Networks vol. 2 Iss: 4 pp. 245-250 Date: 1993.
Inspec 468356 A9414-1230-015 C9407-1230D-066 Doc Type: Journal Paper Title: Multiple dynamic neural network for pattern time sequence processing Authors: Kotov, V.B. Affiliation: Inst. of Opt. Neural Technol., Acad. of Sci., Moscow, Russia Journal: Optical Memory & Neural Networks vol. 2 Iss: 4 pp. 235-243 Date: 1993.
Inspec 4686009 A9414-4230-012 B9407-6140C-132 C9407-1250-104 Doc Type: Journal Paper Title: Optical pattern recognition using Bayesian classification Affiliation: Dept. of Electr. & Comput. Engl., New Mexico State Univ., Las Cruces, NM, USA Journal: Pattern Recognition vol. 27 Iss: 4 pp. 587-606 Date: Apr. 1994.
Inspec 4686006 B9407-6140C-129 C9407-1250-101 Doc Type: Journal Paper Title: Intensity-and distortion-invariant pattern recognition with complex linear morphology Authors: Rahmati, M.; Hasselbrook, L.G. Affiliation: Dept. of Electr. Eng., Kentucky Univ., Lexington, KY, USA Journal: Pattern Recognition vol. 27 Iss: 4 pp. 549-568 Date: Apr. 1994.
Inspec 4685821 B9407-6140C-123 C9407-1250-093 Doc Type: Journal Paper Title: Nonorthogonal image expansion related to optimal template matching in complex images Authors: Ragbunath Rao, K.; Ben-Arie, J. Affiliation: Dept. of Electr. & Comput. Eng., Illinois Inst. of Technol. Chicago, IL, USA Journal: CVGIP: Graphical Models and Image Processing vol. 56 Iss: 2 pp. 149-160 Date: Mar. 1994.
Inspec 4684331 B9407-6140C-107 C9407-1250-078 Doc Type: Journal Paper Title: Uncertainty management for rule-based system with applications to image analysis Authors: Mogre, A.; McLaren, R.; Keller, J.; Krishnapuram, R. Affiliation: LSI Logic Corp., Milpitas, CA, USA Journal: IEEE Transactions on Systems, Man and Cybernetics vol. 24 Iss: 3 pp. 470-481 Date: Mar. 1994.
Inspec 4681576 C9407-1230-025 Doc Type: Conference Proceedings Conf. Title: Proceedings of IEEE 2nd International Fuzzy Systems Conference Publisher: IEEE New York, NY, USA Date: 1993 2 vol. (xviii+xx+1430 pp.).
Inspec 4666384 C9406-7490-009 Doc Type: Conference Paper in Journal Title: Pattern classification of RGB colour images using a BP neural network classifier Authors: Iia, J. Affiliation: Sch. of Electr. & Electron. Eng., Nanyang Technological Univ. Singapore Journal: Proceedings of the SPIE—The International Society for Optical Engineering vol. 1989 pp. 248-256 Date: 1993.
Inspec 4666379 C9406-5260B-115 Doc Type: Conference Paper in Journal Title: A study of Fourier descriptors statistical features Authors: Darwish, A.M.; Mohamed, E.E.H. Affiliation: Dept. of Electron. Eng., Cairo Univ., Giza, Egypt Journal: Proceedings of the SPIE—The International Society for Optical Engineering vol. 1989 pp. 195-204 Date: 1993.
Inspec 4658298 C9406-5260B-046 Doc Type: Conference Paper Title: Robustness and evolution in an adaptive system applications on classification task Authors: Biodi, J. Affiliation: Univ. of Nice-Sophia Antipolis, Yalbonne, France Conf. Title: Artificial Neural Nets and Genetic Algorithms. Proceedings of the International Conference pp. 463-470 Editors: Albrecht, R.F.; Reeves, C.R.; Steele, N.C. Publisher: Springer-Verlag Berlin, Germany Date: 1993 xiii+737 pp.
Inspec 4657799 B9406-6140C-077 C9406-5260B-039 Doc Type: Journal Paper Title: An analysis of different area from shadow mask using morphological operations Authors: Okada, Y. Affiliation: Ryukoku Univ., Ohtsu, Japan Journal: Transactions of the Institute of Electrical Engineers of Japan, Part C vol. 113-C Iss: 12 pp. 1056-1061 Date: Dec. 1993.
Inspec 4657264 B9406-6140C 067 C9406-5260B-034 Doc Type: Journal Paper Title: Variations on the evidence-based object recognition theme Authors: Caelli, T.; Dreier, A. Affiliation: Dept. of Comput. Sci., Curtin Univ. of Technol., Perth, WA, Australia Journal: Pattern Recognition vol. 27 Iss: 2 pp. 185-204 Date: Feb. 1994.
Inspec 4657256 C9406-5260B-031 Doc Type: Journal Paper Title: An experimental study of an object recognition system that learns Authors: Chung-Mong Lee: Ting-Chuen Pong; Slagle, J.R.; Esterline, A. Affiliation: Dept. of Comput. Sci., Hong Kong Univ. of Sci. & Technol., Hong Kong Journal: Pattern Recognition vol. 27 Iss. 1 pp. 65-89 Date: Jan. 1994.
Inspec 4656976 C9406-2590-006 Doc Type: Conference Paper in Journal Title: An incremental neutral classifier on a MIMD parallel computer Authors: Azcarraga, A.; Paugarn-Moisy, H.; Puzzenat, D. Affiliation: Lifia Imag Inpg, Grenoble, France Journal: Ifip Transactions A [Computer Science and Technology] vol. A-44 pp. 13-22 Date: 1994.
Inspec 4656179 B9406-6140C-040 C9406-1250-030 Doc Type: Journal Paper Title: Necognitron with dual C-cell layers Authors: Fakushima, K.; Okada, M.; Hiroshige, K. Affiliation: Dept. of Biophys. Eng., Osaka Univ., Japan Journal: Neural Networks vol. 7 Iss: 1 pp. 41-47 Date: 1994.
Inspec 4654377 B9406-6140C-026 C9406-1250-020 Doc Type: Conference Paper in Journal Title: A fuzzy logic approach to object recognition Authors: Trung Tat Pham; Guanrong Chen Affiliation: McDonnell Douglas Aerosp., Adv. Software Technol. Group. Houston, TX, USA Journal: Proceedings of the SPIE—The International Society for Optical Engineering vol. 2061 pp. 547-556 Date: 1993.
Inspec 4644903 B9405-6140C-196 C9405-5260B-180 Doc Type: Journal Paper Title: RPCT algorithm and its VLSI implementation Authors: Tang, Y.Y.; Suen, C.Y. Affiliation: Centre for Pattern Recognition & Machine Intelligence, Concordia Univ., Montreal, Que., Canada Journal: IEEE Transactions on Systems, Man and Cybernetics vol. 24 Iss 1 pp. 87-99 Date: Jan. 1994.
Inspec 460339 B9410-1230-017 B9405-6410C-162 C9405-1250-113 Doc Type: Journal Paper Title: Recognition of partially occluded objects by correlation methods Authors: Campos. J.; Styczynski, K.,; Yzuei, M.J.; Chalasinska-Macukow, K. Affiliation: Dept. of Phys., Barcelona Univ., Spain Journal: Optics Communications vol. 106 Iss: 1-3 pp. 45-51 Date: Mar. 1, 1994.
Inspec 4639978 B9405-6140C-159 C9405-1250-112 Doc Type: Journal Paper Title: A method to estimate position and orientation of 3-D object from 2-D projection Authors: Nomura, Y.; Sae-Han, D.; Fujii, S. Affiliation: Fac. of Eng., Nagoya Univ., Japan Journal: Transactions of the Institute of Electronics, Information and Communicaton Engineers D-II vol. 177D-II Iss: 1 pp. 101-107 Date: Jan. 1994.
Inspec 4637540 B9405-6140C-152 C9405-1250-103 Doc Type: Journal Paper Title: Classified vector quantisation with variable block-size DCT models Authors: Lee, M.H.; Crebbin, G. Affiliation: Dept. of Electr. & Electron. Eng., Western Australia Univ., Nedlands, WA Australia Journal: IEE Proceedings-Vision, Image and Signal Processing vol.: 141 Iss: 1 pp. 39-48 Date: Feb. 1994.
Inspec 4634402 B9405-6140C-115 C9405-5260B-098 Doc Type: Journal Paper Title: Associative structures for vision Authors: Anguita, D.: Parodi, G,; Zunino, R. Affiliation: Dept. of Biophys. & Electron. Eng., Genoa Univ., Italy Journal: Multidimensional Systems and Signal Processing vol. 5 Iss: 1 pp. 75-96 Date: Jan. 1994.
Inspec 4632200 B9405-4180-004 C9405-5270-003 Doc Type: Conference Paper in Journal Title: Three-dimensional pattern recogni-

(56) References Cited

OTHER PUBLICATIONS tion using an opto-electronic inner product complex neural network Authors: Awwal, A.A.S.; Power, G.J. Affiliation: Dept. of Comput. Sci. & Eng., Wright State Univ., Dayton, OH, USA Journal: Proceedings of the SPIE—The International Society for Optical Engineering vol. 1959 pp. 442-451 Date: 1993.
Inspec 4632199 B9405-4120-003 C9405-5320K-006 Doc Type: Conference Paper in Journal Title: A content-addressable polychromatic neural net using a specially doped LiNbO/sub 3/ photorefractive crystal Authors: Yu, F.T.S.; Yin. S.; Uang, C.-M. Affiliation: Dept. of Electr. & Comput. Eng., Pennsylvania State Univ., University Park, PA, USA Journal: Proceedings of the SPIE—The International Society for Optical Engineering vol. 1959 pp. 431-441 Date: 1993.
Inspec 4632198 B9405-4180-003 C9405-5270-002 Doc Type: Conference Paper in Journal Title: Shift invariant optical neural network with holographic bipolar synapses Authors: Chao, T. H. Affiliation: Jet Propulsion Lab., California Inst. of Technol., Pasadena, CA, USA Journal: Proceedings of the SPIE—The International Society for Optical Engineering vol. 1959 pp. 422-430 Date: 1993.
Inspec 4632197 A9409-4280B-002 B9405-4170-003 Doc Type: Conference Paper in Journal Title: Spatial-spectral optical pattern recognition using an acousto-optic runable filter preprocessor Authors: Chao, T.-H.; Reyes, O.; Hegblom, E.; Cheog. L.J. Affiliation: Jet Propulsion Lab., California Inst. of Technol., Pasadena, CA, USA Journal: Proceedings of the SPIE—The International Society for Optical Engineering vol. 1959 pp. 410-420 Date: 1993.
Inspec 4632058 B9405-0100-016 C9405-5260B-092 Doc Type: Conference Proceedings in Journal Conf. Title: Intelligent Robots and Computer Vision XI: Biological, Neural Net and 3-D Methods Journal: Proceedings of the SPIE—The International Society for Optical Engineering vol. 1826 Date: 1992.
Inspe 4631735 C9405-1250-077 Doc Type: Journal Paper Title: Non-analytic object recognition using the Hough transform with the machine technique Authors: Set, P.-K.; Siu, W.-C. Affiliation: Dept. of Electron. Eng., Hong Kong Polytech., Hung Hom, Hong Kong Journal: IEE Proceedings—Computers and Digital Techniques vol. 141 Iss: 1 pp. 11-16 Date: Jan. 1994.
Inspec 4626939 C9405-1250-068 Doc Type: Conference Paper in Journal Title: Searching geometric libraries using generalized epsilon-congruence Authors: Phillips, P.J. Affiliation: Rutor, Rutgers Univ., New Brunswick, NJ, USA Journal: Proceedings of the SPIE—The International Society for Optical Engineering vol. 2060 pp. 225-236 Date: 1993.
Inspec 4626933 C9405-5260B-049 Doc Type: Conference Paper in Journal Title: Projected morion group for vision Authors: Tanalm, M. Affiliation: Electrotech. Lab., Tsukuba, Japan Journal: Proceedings of the SPIE—The International Society for Optical Engineering vol. 2060 pp. 161-168 Date: 1993.
Inspec 4626929 B9405-6140C-087 C9405-5260B-047 Doc Type: Conference Paper in Journal Title: Continuous-tone image recognition using fractal theory Authors: Ying Liu Affiliation: Dept. of Math. & Comput. Sci., Savannah State Coll., GA, USA Journal: Proceedings of the SPIE—The International Society for Optical Engineering vol. 2060 pp. 112-124 Date: 1993.
Inspec 4626891 B9405-6140C-079 C9405-5260B-039 Doc Type: Conference Paper in Journal Title: Object tracking through adaptive correlation Authors: Montera, D.A.; Rogers, S.K.; Ruck, D.W.; Oxley, M.E. Affiliation: Dept. of Electr. & Comput. Eng., Air Force Inst. of Technol., Wright-Patterson AFB, OH, USA Journal: Proceedings of the SPIE—The International Society for Optical Engineering vol. 1959 pp. 314-321 Date: 1993.
Inspec 4626634 B9405-6140C-008 C9405-1250-009 Doc Type: Conference Paper in Journal Title: Invariant pattern recognition using higher-order neural networks Authors: Sunthankar, S.; Jaravine, V.A. Affiliation: Kingston Univ., UK Journal: Proceedings of the SPIE—The International Society for Optical Engineering vol. 1826 pp. 160-167 Date: 1992.
Inspec 4625222 C9404-5530-010 Doc Type: Conference Paper Title: Extending conventional template matching to include color, rotation, and scale Authors: McGarry, F.J. Conf. Title: Proceedings of the International Robots and Vision Automation Conference P. 4/5 Publisher: Robotic Ind Assoc Ann Arbor, MI, USA Date 1993 xxv+889 pp.
Inspec 4624108 C9404-6130B-051 Doc Type: Journal Paper Title: Coloring of a landscape by fuzzy logic Authors: Terano, T.; Masui, S.; Terada, T.; Watanabe, H. Journal: Japanese Journal of Fuzzy Theory and Systems vol.: 5 Iss: 2 pp. 209-221 Date: 1993.
Inspec 4620268 B9404-8520B-006 C9404-5260B-220 Doc Type: Conference Paper in Journal Title: Optical roadsign recognition to improve active safety features Authors: Guibert, L.: Keryer, G.; Attia, M. Affiliation: Groupe Optique et Syst. de Commun., Telecom Bretagne, Brest, France Journal: Proceedings of the SPIE—The International Society for Optical Engineering vol. 1959 pp. 230-234 Date: 1993.
Inspec 4620266 A9408-1230-018 B9404-6140C-375 C9404-1250-234 Doc Type: Conference Paper in Journal Title: Design of distortion-invariant correlation filters using supervised learning Authors: Kozaitis, S.P.; Coter, R.H.; Foot, W.E. Affiliation: Dept. of Electr. & Comput. Eng., Florida Inst. of Technol., Melbourne, FL, USA Journal: Proceedings of the SPIE—The International Society for Optical Engineering vol. 1959 pp. 214-219 Date: 1993.
Inspec 4620265 A9408-4230-017 B9404-6140C-374 C9404-1250-233 Doc Type: Conference Paper in Journal Title: Distortion invariant optical pattern recognition using composite binary filters Authors: Roe, M.G.; Sebehrer, K.L.; Dobson, R.; Schirber, L. Affiliation: Rocketdyne Div., Rockwell Int. Corp., Canoga Park, CA, USA Journal: Proceedings of the SPIE—The International Society for Optical Engineering vol. 1959 pp. 203-213 Date: 1993.
Inspec 4620259 B9404-6140C-368 C9404-5260B-217 Doc Type: Conference Paper in Journal Title: Automatic target recognition with intensity-and distortion-invariant hybrid composite filters Authors: Rahmati. M.; Hassebrook, L.G.; Vijaya Kumar, B.V.K. Affiliation: Dept. of Electr. Engl., Kentucky Univ., Lexington, KY, USA Journal: Proceedings of the SPIE—The International Society for Optical Engineering vol. 1959 pp. 133-145 Date: 1993.
Inspec 4; Eewing, T.K., Serati, R.A.; Johnson, K.M.; Simon, D.M. Affiliation: Boulder Nonlinear Syst. Inc., Boulder, CO, USA Journal: Proceedings of the SPIE—The International Society for Optical Engineering vol. 1959 pp. 55-68 Date: 1993.
Inspec 4620247 A9408-4230-008 B9404-6140C-359 C9404-1250-224 Doc Type: Conference Paper in Journal Title: Sequential and fused optical filters for clutter reduction and detection Authors: Casasent, D. Affiliation: Dept. of Electr. & Comput. Eng., Carnegie Mellon Univ., Pittsburgh, PA, USA Journal: Proceedings of the SPIE—The International Society for Optical Engineering vol. 1959 pp. 2-11 Date: 1993.
Inspec 4620036 C9404-1230-048 Doc Type: Conference Paper in Journal Conf. Title: Adaptive and Learning Systems II Journal: Proceedings of the SPIE—The International Society for Optical Engineering vol. 1962 Date: 1993.
Inspec 4619943 C9404-7480-093 Doc Type: Conference Paper in Journal Title: Recognition of containers using a multidimensional pattern classifier Authors: Magee, M.; Weniger, R.; Wenzel, D.; Pirasteh, R. Affiliation: Dept. of Comput. Sci., Wyoming Univ., Laramie, WY, USA Journal: Proceedings of the SPIE—The International Society for Optical Engineering vol. 1825 pp. 33-45 Date: 1992.
Inspec 4617407 A9408-4240-004 B9404-4180-027 C9404-5270-022 Doc Type: Journal Paper Title: Holographic implementation of interpattern association (IPA) neural network Authors: Taiwei Lu; Lin. F. Affiliation: Physical Opt. Corp., Torrance, CA, USA Journal: Optical Memory & Neural Networks vol. 2 Iss: 3 pp. 157-166 Date: 1993.
Inspec 4617406 A9408-4230-005 B9404-6140C-251 C9404-1250-152 Doc Type: Journal Paper Title: Optoelectronically implemented three-layer neural network with 100.RTM.100 input for pattern recognition Authors: Gao-Guang, Stu: Yang Sun: Yanxin Zhang; Xangpeng Yang Affiliation: Inst. of Modern Opt., Nankai Univ., Tianjin, China Journal: Optical Memory & Neural Networks vol. 2 Iss: 3 pp. 151-155 Date: 1993.
Inspec 4614533 B9404-0100-043 C9404-1250-113 Doc Type: Conference Proceedings in Journal Conf. Title: Visual Communications

(56) References Cited

OTHER PUBLICATIONS and Image Processing '93 Journal: Proceedings of the SPIE—The International Society for Optical Engineering vol. 2094 Iss: pt. 1 Date: 1993.
Inspec 4614474 A9408-0130C-007 B9404-0100-039 C9404-7330-067 Doc Type: Conference Proceedings in Journal Conf. Title: Medical Imaging 1993: Image Processing Journal: Proceedings of the SPIE—The International Society for Optical Engineering vol. 1898 Date: 1993.
Inspec 4609098 B9404-6140C-122 C9404-1250-061 Doc Type: Conference Paper in Journal Title: Evolving neural network pattern classifiers Authors: McDonnell, J.R.; Waagen, D.E.; Page, W.C. Affiliation: NCCOSC, RDT&E Div., San Diego, CA, USA Journal: Proceedings of the SPIE—The International Society for Optical Engineering vol. 2032 pp. 176-187 Date: 1993.
Inspec 4609095 B9404-6140C-120 C9404-1250-059 Doc Type: Conference Paper in Journal Title: Spatio-temporal pattern recognition using hidden Markov models Authors: Fielding, K.H.; Ruck, D.W.; Fogers, S.K.; Welsh, B.M.; Oxely, M.E. Affiliation: Air Force Inst. of Technol., Dept. of Electr. & Comput. Eng., Wright-Patterson AFB, OH, USA Journal: Proceedings of the SPIE—The International Society for Optical Engineering vol. 2032 pp. 144-154 Date: 1993.
Inspec 4609092 B9404-6140C-117 C9404-1250-057 Doc Type: Conference Paper in Journal Title: Storing temporal sequences of patterns in neural networks Authors: Krishzswamy, D.; Mehrotra, K.; Mohan, C.K.; Ranka, S. Affiliation: Sch. of Comput. & Inf. Sci., Syracuse Univ. NY, USA Journal: Proceedings of the SPIE—The International Society for Optical Engineering vol. 2032 pp. 120-126 Date: 1993.
Inspec 4609089 B9404-6140C-114 C9404-1250-055 Doc Type: Conference Paper in Journal Title: Feature competition and domain of attraction in artificial-perceptron pattern-recognizer Authors: Mu, C.I,.J. Affiliation: Dept. of Electr. Eng., Southern Illinois Univ., Carbondale, IL, USA Journal: Proceedings of the SPIE—The International Society for Optical Engineering vol. 2032 pp. 87-90 Date: 1993.
Inspec 4607872 B9404-6140C-074 C9404-1250-045 Doc Type: Conference Paper Title: Characterization of clutter in IR images using maximum likelihood adaptive neural system Authors: Perlovsky, L.Il; Jaskolski, J.J.; Chernick, J. Affiliation: Nicholas Res. Corp., Wakefield, MA, USA Conf. Title: Conference Record of the Twenty-Sixth Asilomar Conference on Signals, Systems and Computers (Cat. No. 92CH3245-8) pp. 1076-1080 vol. 2 Editors: Singh, A. Publisher: IEEE Comput. Soc. Press Los Alamitos, CA, USA Date: 1992 2 vol. (xviii+xix+1156 pp.).
Inspec 4607867 B9404-6310-009 C9404-7410-010 Doc Type: Conference Paper Title: High resolution radar target identification Authors: Novak, L.M.; Irving, W.W.; Verbout, S.M.; Owirka, G.J. Affiliation: MIT Lincoln Lab., Lexington, MA, USA Conf. Title: Conference Record at the Twenty-Sixth Asilomar Conference on Signals, Systems and Computers (Cat. No. 92CH3245-8) p. 1048-1057 vol. 2 Editors: Singh, A. Publisher: IEEE Comput. Soc. Press Los Alamitos, CA, USA Date: 1992 2 vol. (xviii+xix+1156 pp.).
Inspec 460782 B9404-6140C-067 C9404-1250-040 Doc Type: Conference Paper Title: Gabor wavelet transform and application to problems in early vision Authors: Mahjunath, B.S. Affilication: Dept. of Electr. & Comput. Eng., California Univ., Santa Barbara, CA, USA Conf. Title: Conference Record at the Twenty-Sixth Asilomar Conference on Signals, Systems and Computers (Cat. No. 92CH3245-8) pp. 796-800 vol. 2. Editors: Singh, A. Publisher: IEEE Comput. Soc. Press Los Alamitos, CA, USA Date: 1992 2 vol. (xviii+xix+1156 pp.).
Inspec 4606815 C9404-5290 004 Doc Type: Journal Paper Title: The use of neural networks in pattern recognition and control Authors: Windsor, C.,G. Affiliation: Nat. Nondestructive Test. Centre, Harwell Lab., UK Journal: Systems Science vol. 19 Iss: 3 pp. 31-41 Date: 1993.
Inspec 4604007 C9404-5260B-015 Doc Type: Journal Paper Title: Fuzzy control systems for image Identification Authors: Xaldert, J.; Kerber, J.V. Journal: Elektronik vol. 42 Iss: 24 pp. 84, 89-91 Date Nov. 30, 1993.
Inspec 4603677 C9404-1230D-003 Doc Type: Conference Paper in Journal Title: Differential theory of learning for efficient neural network pattern recognition Authors: Hampshire, J.B., II; Vijaya Kumar, B.V.K. Affiliation: Dept. of Electr. & Comput. Eng., Carnegie Mellon Univ., Pittsburgh, PA USA Journal: Proceedings of the SPIE—The International Society for Optical Engineering vol. 1965 pp. 76-95 Date: 1993.
Inspec 4597772 A9406-1230-014 B9403-4120-043 Doc Type: Conference Paper in Journal Title: Optical processing and storage with bacteriorbodopsin Authors: Brauchle, C.; Hampp. N.; Oesterhelt, D. Affiliation: Inst. for Phys. Chem., Munchen Univ., Germany Journal: Proceedings of the SPIE—The International Society for Optical Engineering vol. 1852 pp. 238-242 Date: 1993.
Inspec 4596362 C9403-1230D-112 Doc Type: Conference Paper Title: Invariant object recognition using Fahiman and Lebiere's learning algorithm Authors: Ito, K.; Hamamoto, M.; Kamruzzaman, J.; Kumagal, Y. Affiliation: Dept. of Comput. Sci., Mutoran Inst. of Technol., Japan Conf. Title: New Trends in Neural Computation. International Workshop on Artifcial Neural Networks. Iwann '93 Proceedings pp. 237-242 Editors: Mira J.; Cabestany, J.; Prieto, A. Publishers: Springer-Verlag Berlin, Germany Date: 1993 746 pp.
Inspec 4595662 C9403-1250-200 Doc Type: Conference Paper Title: Comments on the evaluation of a certain pattern classification method as an intellectual information processing Authors: Munakata, T.; Okashita, K.; Nakahara, T. Affiliation: Dept. of Mech. Eng., Hiroshima-Denki Inst. of Technol., Hiroshima-city, Japan Conf. Title: 1992 IEEE International Conference on Systems, Man and Cybernetics (Cat. No. 92CH3176-5) pp. 611-616 vol. 1 Publisher: IEEE New York, NY, USA Date: 1992 2 vol. xviii+1735 pp.
Inspec 4595625 B9403-6140C-264 C9403-1250-198 Doc Type: Conference Paper Title: Vector contour representation for object recognition in neural networks Authors: Starzyk, J.A.; Chai, S. Affiliation: Dept. of Electr. & Comput. Eng., Ohio Univ., Athena, OH, USA. Conf. Title: 1992 IEEE International Conference on Systems, Man and Cybernetics (Cat. No.92CH3176-5) pp. 299-404 vol. 1 Publisher: IEEE New York, NY, USA Date: 1992 2 vol. xviii+1735 pp.
Inspec 4595560 B9403-7230G-035 C9403-3240F-002 Doc Type: Conference Paper Title: A CMOS silicon VLSI optical sensor Authors: Carnp. W.O., Jr.; Van der Speigel, J. Affiliation: IBM Federal Syst. Co., Owego, NY, USA Conf. Title: 1992 IEEE International Conference on Systems, Man and Cybernetics (Cat. No.92CH3176-5) pp. 25-30 vol. 1 Publisher: IEEE New York, NY, USA Date: 1992 2 vol. xviii+1735 pp.
Inspec 4593819 B9403-6140C-226 C9403-1250-178 Doc Type: Journal Paper Title: Invariant object recognition based on a neural network of cascaded RCE nets Authors: Li, W.; Nasrabadi, N.M. Affiliation: Dept. of Electr. & Comput. Eng., State Univ. of New York, Buffalo, NY, USA Journal: International Journal of Pattern Recognition and Artificial Intelligence vol. 7 Iss: 4 pp. 815-829 Date: Aug. 1993.
Inspec 4593814 B9403-6140C-224 C9403-1250-176 Doc Type: Journal Paper Title: Multi-modular neural network architectures: applications in optical character and human face recognition Authors: Soulic, F.F.; Viennet, E.; Lamy, B. Affiliation: Lab. de Recherche en Inf., Univ. de Paris-Sod, Orsay, France Journal: International Journal of Pattern Recognition and Artificial Intelligence vol. 7 Iss: 4 pp. 721-755 Date: Aug. 1993.
Inspec 4592282 B9403-6140C-217 C9403-1250-172 Doc Type: Journal Paper Title: Introducing rotation invariance into the neocognitron model for target recognition Authors: Chihwen Li; Chwan-Hwa Wu Affiliation: Dept. of Electr. Eng., Auburn Univ., AL, USA Journal: Pattern Recognition Letters vol. 14 Iss: 12 pp. 985-995 Date: 1993.
Inspec 4592280 B9403-6140C-215 C9403-1250-170 Doc Type: Journal Paper Title: Shape analysis using genetic algorithms Authors: Bala, J.; Wechsler, H. Affiliation: Dept. of Comput. Sci., George Mason Univ., Fairfax, VA, USA Journal: Pattern Recognition Letters vol. 14 Iss: 12 pp. 965-973 Date: Dec. 1993.

(56) References Cited

OTHER PUBLICATIONS

Inspec 4592004 B9403-6140C-208 C9403-1250-163 Doc Type: Conference Paper in Journal Title: Optical Hart wavelet transform for image features extraction Authors: Guofan Jin; Yinbai Yan; Wenlu Wang; Zhiqing Wen; Minxian Wu Affiliation: Dept. of Precision Instrum, Tsinghua Univ., Beijing, China Journal: Proceedings of the SPIE—The International Society for Optical Engineering vol. 2034 pp. 371-380 Date: 1993.
Inspec 4591752 C9403-6160S-018 Doc Type: Conference Paper in Journal Title: Self-aligning and compressed autosophy video databases Authors: Holtz, K. Affiliation: Omni Dimensional Networks, San Francisco, CA, USA Journal: Proceedings of SPIE—The International Society for Optical Engineering vol. 1908 pp. 37-48 Date: 1993.
Inspec 4589423 B9403-1295-008 C9403-5190-007 Doc Type: Journal Paper Title: Generalization ability of extended cascaded artificial neural network architecture Authors: Kamruzzaman, J.; Kumagal, Y.; Hikita, H. Affiliation: Dept. of Electr. & Electron. Eng., Bangladesh Univ. of Eng. & Technol., Dhaks, Bangladesh Journal: IEICE Transactions on Fundamentals of Electronics, Communications and Computer Sciences vol. E76-A Iss: 10 pp. 1877-1883 Date: Oct. 1993.
Inspec 4584709 B9403-6140C-079 C9403-1250-063 Doc Type: Conference Paper Title: Classification of texture by an association between a self-organizing feature map Authors: Maillard, E.; Zeir, D.; Merckle, J. Affiliation: IRP, Mulhouse, France Conf. Title: Signal Processing VI—Theories and Applications, Proceedings of Eusipco 92, Sixth European Signal Processing Conference pp. 1173-1176 vol. 2 Editors: Vandewaile, J.; Doite, R.; Moonen, M.; Oosterlinck, A. Publishers: Elsevier Amsterdam, Netherlands Date: 1992 3 vol. ivii+1844 pp.
Inspec 4706675 B9408-6140C-186 C9408-1250-106 Doc Type: Conference Paper Title: Analysis of texture images using robust fractal description Authors: Avadhanam, N.; Mitra, S. Affiliation: Dept. of Electr. & Comput. Eng., California Univ., Davis, CA, USA Conf. Title: Proceedings of the IEEE Southwest Symposium on Image Analysis and Interpretation p. 1-6 Publisher: IEEE Comput. Soc. Press Los Alamitos, CA, USA Date: 1994 viii+167 pp.
Inspec 4697251 A9415-1230-038 B9408-6140C-048 C9408-1250-022 Doc Type: Conference Paper in Journal Title: Fractal dimension estimation for optical image segmentation Authors: Andrews, H.G., II; Getbehead, M.A.; Kozaitis. S.P. Affiliation: Rome Lab. Photonics Center, Griffiss AFB, NY, USA Journal: Proceedings of the SPIE—The International Society for Optical Engineering vol. 2026 pp. 361-370 Date: 1993.
Inspec 4695587 B9408-6140C-032 C9408-1250-015 Doc Type: Conference Paper Title: Multi-level fractal block coding in video compression Authors: Lia, J.; Matlow, S.; Murphy, N.A. Affiliation: Sch. of Electron. Eng., Dublin City Univ., Ireland Conf. Title: DSP—The Enabling Technology for Communications. Conference Proceedings (ERA 93-0008) pp. 6.4/1-9 Publisher: ERA Technol Leatherhead, UK Date: 1993 iv+284 pp.
Inspec 4691106 B9407-6140C-186 C9407-1250-145 Doc Type: Conference Paper Title: Fractals and multifractals; theory and application to texture recognition Authors: Fioravanni, S.; Giusto, D.D. Affiliation: Dipartimento di Ingegnetic Biofisica ed Electronica, Genova Univ., Italy Conf. Title: Efficient Texture Analysis: Advanced Methods, Applications (KFKI-1994-2/N) p. 51-9 Editors: Nemeth, G.; Boroczky, L. Publisher: KFKI Res. Inst. Meas. Comput. Tech Budapest, Hungary Date: 1994 94 pp.
Inspec 4690B59 B9407-6140C-178 C9407-1250-136 Doc Type: Conference Paper Title: Structure from motion: a region based approach using affine transformations and moment invariants Authors: Lee, C.-Y; Cooper, D.B. Affiliation: Div. of Eng., Brown Univ., Providence, RI, USA Conf. Title: Proceedings IEEE International Conference on Robotics and Automation (Cat. No. 93CH3247-4) pp. 120-127 vol. 3 Publisher: IEEE Comput. Soc. Press Los Alamitos, CA, USA Date: 1993 3 vol. (xviii+1051+xvi+848+xviii+1042 pp.).
Inspec 4572079 B9402 6140C-117 C9402-1250-083 Doc Type: Journal Paper Title: Image data matching for affine transformed pictures—reduction of calculation Authors: Ujifaku, S.; Normura, Y.; Fujii, S. Affiliation: Fac. of Eng., Nagoya Univ., Japan Journal: Transactions of the Institute of Electronics, Information and Communication Engineers D-II vol. 176D-II ISS: 8 pp. 1581-1586 Date: Aug. 1993.
Inspec 4561907 B9402-6140C-053 C9402-1250-037 Doc Type: Journal Paper Title: Improved fractal geometry based texture segmentation technique Authors: Chaudhuri, B.D.; Satkar, N.; Kundu, P. Affiliation: Electron. & Commun. Sci. Unit. Indian Stat. Inst., Calcutta, India Journal: IEE Proceedings E [Computers and Digital Techniques] vol. 140 ISS: 5 pp. 233-241 Date: Sep. 1993.
Inspec 4555192 B9402-6140C-006 C9401-1250-003 Doc Type: Journal Paper Title: Contractivity of fractal transforms for image coding Authors: Hungen, B. Affiliation: Inst. of Commun. Eng., Azchen Univ. of Technol., Germany Journal: Electronics Letters vol. 29 Iss: 20 pp. 1749-1750 Date: Sep. 30, 1993.
Inspec 4550663 B9401-6140C-331 C9401-1250-237 Doc Type: Journal Paper Title: A 3-D vision system model for automatic object surface sensing Authors: Theodoracatos, V.E.; Calkins, D.E. Affiliation: Sch. of Aerosp. & Mech. Eng., Oklahoma Univ., Norman, OK, USA Journal: International Journal of Computer Vision vol. II Iss: 1 pp. 75-99 Date; Aug. 1993.
Inspec 4549014 B9401-6140C-307 C9401-1250-222 Doc Type: Journal Paper Title: Determining the fractal dimension of scenes and digital signals using Roseta and other novel approaches Authors: Jaznisch, H.M.; Barton, P.E.; Carruth, R.T. Affiliation: Nichols Res. Corp., Huntsville, AL, USA Journal: Proceedings of the SPIE—The International Society for Optical Engineering vol. 1995 pp. 298-315 Date: 1993.
Inspec 4549004 B9401-6140C-300 C9401-1250-215 Doc Type: Journal Paper Title: Modeling of deterministic chaotic noise to improve target recognition Authors: McAulay, P.D.; Saruhan, K. Affiliation: Dept. of Electr. Eng. & Comput. Sci., Lehigh Univ., Bethlehem, PA, USA Journal: Proceedings of the SPIE—The International Society for Optical Engineering vol. 1955 pp. 210-217 Date: 1993.
Inspec 4548815 B9401-6140C-277 C9401-1250-198 Doc Type: Conference Paper in Journal Title: Image-data-based matching for affine transformed pictures Authors: Nomura, Y.; Harada. Y.; Fujii, S. Affiliation: Dept. of Inf. Eng., Nagoya Univ., Japan Journal: Proceedings of the SPIE--The International Society for Optical Engineering vol. 1827 pp. 97-104 Date: 1993.
Inspec 4547439 C9401-5260B-163 Doc Type: Conference Paper Title: A geometric invariant for visual recognition and 3D reconstruction from two perspective/orthographic views Authors: Shashua, A. Affiliation: Dept. of Brain & Cognitive Sci., MIT, Cambridge, MA, USA Conf. Title: Proceedings of IEEE Workshop on Qualitative Vision (Cat. No. 93TH0521-5) pp. 107-117 Publisher: IEEE Comput. Soc. Press Los Alamitos, CA, USA Date: 1993 vi+151 pp.
Inspec 4547438 C9401-5260B-162 Doc Type: Conference Paper Title: A hierarchy of invariant representations of 3D shape Authors: Weinshall, D. Affiliation: Inst. of Comput. Sci., Hebrew univ. of Jerusalem, Israel Conf. Title: Proceedings of IEEE Workshop Qualitative Vision (Cat. No. 93TH0521-5) pp. 97-106 Publisher: IEEE Comput. Soc. Press Los Alamitos, CA, USA Date: 1993, evi+151 pp.
Inspec 4544295 C9401-5260B-140 Doc Type: Journal Paper Title: Trackability as a cue for potential obstacle identification and 3-D description Authors: Sawhney, H.S.; Hanson, A.R. Affiliation: Dept. of Comput. Sci., Massachusetts Univ., Amherst, MA, USA Journal: International Journal of Computer Vision vol. II Iss: 3 pp. 237-265 Date: Dec. 1993.
Inspec 4535866 B9401-6140C-121 C9401-1250-084 Doc Type: Conference Paper in Journal Title: Fractal equations and their solutions Authors: Liu, Y. Affiliation: Dept. of Math. & Comput. Sci., Savannah State Coll., GA, USA Journal: Proceedings of the SPIE—The International Society for Optical Engineering vol. 1904 pp. 52-68 Date: 1993.
Inspec 4532589 B9401-6140C-091 C9401-1250-060 Doc Type: Journal Paper Title: Fractal image compression Authors: Goojun Lu Affiliation: Dept. of Syst. & Comput. Sci., Nat. Univ. of Singapore,

(56) References Cited

OTHER PUBLICATIONS

Singapore Journal: Signal Processing: Image Communication vol. 5 Iss: 4 pp. 327-343 Date: Oct. 1993.
Inspec 4529437 B9401-6140C-065 C9401-1250-043 Doc Type: Conference Paper Title: Generalized fractal transforms; complexity issues Authors: Monro, D.M. Affiliation: Sch. of Electron. & Electr. Eng., Bath Univ., UK Conf. Title: DCC '93, Data Compression Conference (Cat. No. 93TH10536-3) pp. 254-261 Editors: Storer, J.A.; Cohn, M. Publisher: IEEE Comput. Soc. Press Los Alamitos, CA, USA Date: 1993 xiii+505 pp.
Inspec 4529436 B9401-6140C-064 C9401-5260B-035 Doc Type: Conference Paper Title: Fractal based image compression with affine transformations Authors: Raittinen, H.; Kaski, K. Affiliation: Dept. of Electr. Eng., Tampere Univ. of Technol., Finland Conf. Title: DCC '93. Data Compression Conference (Cat. No. 93TH0536-3) pp. 244-253 Editors: Storer, J.A.; Cohn, M. Publisher: IEEE Comput. Soc. Press Los Alamitos, CA, USA Date: 1993 xiii+505 pp.
Inspec 4529435 B9401-6140C-063 C9401-1250-042 Doc Type: Conference Paper Title: Efficient compression of wavelet coefficients for smooth and fractal like data Authors: Culik, K., H; Dube, S.; Rajcani. P. Affiliation: Dept. of Comput. Sci., South Carolina Univ., Columbia, SC, USA Conf. Title: DCC '93. Data Compression Conference (Cat. No.93TH0536-3) pp. 234-243 Editors: Storer, J.A.; Cohn, M. Publisher: IEEE Comput. Soc. Press Los Alamitos, CA, USA Date: 1993 xiii+505 pp.
Inspec 4529410 B9401-0100-005 C9401-1260-018 Doc Type: Conference Paper Conf. Title: DCC '93. Data Compression Conference (Cat. No.93TH0536-3) Editors: Storer, J.A.; Cohn, M. Publisher: IEEE Comput. Soc. Press Los Alamitos, CA, USA Date: 1993 xiii+505 pp.
Inspec 4528335 B9401-6140C-036 C9401-5260B-013 Doc Type: Journal Paper Title: Recognition and Inspection of manufactured parts using line moments of their boundaries Authors: Wei Wen; Lozzi, A. Affiliation: Dept. of Mech. Eng., Sydney Univ., NSW, Australian Journal: Pattern Recognition vol. 26 Iss: 10 pp. 1461-1471 Date: Oct. 1993.
Inspec 4527608 B9401-6140C-022 C9401-1250-016 Doc Type: Journal Paper Title: Extraction of symmetry properties using correlation with rotated and reflected images Authors: Masuda, T.; Yamamoto, K.; Yamada, H. Affiliation: Electrotech. Lab., Tsukuba, Japan Journal: Electronics and Communications in Japan, Part 3 (Fundamental Electronic Science) vol. 76 Iss: 1 pp. 8-19 Date: Jan. 1993.
Inspec 4519462 A9324-9575-007 C9312-1250-166 Doc Type: Journal Paper Title: Neural network and wavelet transform for scale-invariant data classification Authors; Szu, H.H.; Yang, X.-Y.; Telfer, B.A.; Sheng, Y. Affiliation: Naval Surface Warfare Center, Dahlgren Division Code R44, Silver Spring, MD, USA Journal: Physical Review E (Statistical Physics, Plasmas, Fluids, and Related Interdisciplinary Topics) vol. 48 Iss: 2 pp. 1497-1501 Date: Aug. 1991.
Inspec 4518350 B9312-6140C-C9312-1260-138 Doc Type: Conference Paper Title: Natural scene segmentation using fractal based autocorrelation Authors: Luo, R.C; Potlapalli, H.; Hislop, D.W. Affiliation; Dept. of Electr. & Comput. Eng., North Carolina State Univ., Raleigh, NC, USA Conf. Title: Proceedings of the 1992 International Conference on Industrial Electronics, Control, Instrumentation, and Automation. Power Electronics and Motion Control (Cat. No.92CH3137-7) pp. 700-705 vol. 2 Publisher: IEEE New York, NY, USA Date: 1992 3 vol. 1649 pp.
Inspec 4509986 B9312-6140C-105 C9312-1250-076 Doc Type: Journal Paper Title: The geometric transformation of the discrete images Authors: Margant, L. Affiliation: Polytech. Inst. of Bucharest, Romania Journal: IPB Bulehn Scientific, polytechnic Institute of Bucharest Scientific, Bulletin, Electrical Engineering vol. 53 Iss: 1-2 pp. 117-127 Date: 1991.
Inspec 4508845 B9312-6140C-073 C9312-1250-057 Doc Type: Conference Paper Title: Directed spreading activation in multiple layers for low-level feature extraction Authors: Arul Valan. A.; Yegnanarayana, B. Affiliation: Dept. of Comput. Sci. & Eng., Indian Inst. of Technol., Madras, Indian Inst. of Technol., Madras, India Conf. Title: Communications on the Move. Singapore. ICCS/ISITA '92 (Cat. No.92TH0179-6) pp. 563-567 vol. 2 Editors: Ng. C.S.; Yeo, T.S.; Yeo, S.P. Publisher: IEEE New York, NY, USA Date: 1990 3 vol. (xxvii+1422 pp.).
Inspec 4508271 B9312-6140C-058 C9312-1250-052 Doc Type: Journal Paper Title: Object recognition using alegbraic and differential invariants Authors: Reiss, T.H. Affiliation: Commun. Signal Processing Lab., Cambridge Univ., UK Journal: Signal Processing vol. 32 Iss: 3 pp. 367-395 Date: Jun. 1993.
Inspec 4504546 B9312-6140C-002 C9312-1250-002 Doc Type: Conference Paper in Journal Title: Image classification and segmentation using multichannel fractal modelling Authors: Kaloyeras, D.K.; Kollias, S.D. Affiliation: Dept. of Electr. & Comp. Eng., Nat. Tech. Univ. of Athens, Greece Journal: Proceedings of the SPIE—The International Society for Optical Engineering vol. 1818 Iss: pt. 3 pp. 950-957 Date: 1992.
Inspec 4504545 B9312-6140C-001 C9312-1250-001 Doc Type: Conference Paper in Journal Title: Fast algorithm to select maps in an iterated function system fractal model Authors: Vines, G.; Hayes, M.H., III Affiliation: Sch. of Electr. Eng., Georgia Inst. of Technol., Atlanta, GA, USA Journal: Proceedings of the SPIE—The International Society for Optical Engineering vol. 1818 Iss: pt.3 pp. 944-949 Date: 1992.
Inspec 4502313 B9311-6140C-330 C9311-1250-245 Doc Type: Journal Paper Title: Fractal-based image sequence compression science Authors: Haibo Li, Novak, M.; Forchheimer, R. Affiliation: Dept. of Electr. Eng., Linkoping Univ., Sweden Journal: Optical Engineering vol. 32 Iss: 7 pp. 1588-1595, Date: Jul. 1993.
Inspec 4499057 B9311-6140C-252 C9311-1250-182 Doc Type: Conference Paper Title: Fractal dimension estimation: some methods and their reliability Authors: Lim Hock; Lxi Choy Heng; Oh Geok Lian Affiliation: Dept. of Phys., Nat. Univ. of Singapore, Singapore Conf. Title: ICIP 92, Proceedings of the 2nd Singapore International Conference on Image Processing pp. 380-384 Editors: Srinivasa, V.; Ong Sim Heng; Ang Yew Hock Publisher: World Scientific Singapore Date: 1992 xxii+734 pp.
Inspec 4499022 B9311-6140C-226 C9311-1250-157 Doc Type: Conference Paper Title: Affine and projective image invariants based on algebraic invariants Authors: Reiss, T.H. Affiliation: Dept. of Eng., Cambridge Univ., UK Conf. Title: ICIP 92. Proceedings of the 2nd Singapore International Conference on Image Processing pp. 80-84 Editors: Srinivasa, V.; Ong Sim Heng: Ang Yew Hock Publisher: World Scientific Singapore Date: 1992 xxii+734 pp.
Inspec 4499009 B9311-6140C-216 C9311-1250-153 Doc Type: Conference Paper Title: A new image compression method based on fractals and human visual system Authors: Li. Ding-Bing; Chang Yi-Lin; Hu Zheng Affiliation: Dept. 1. Xidian Univ., Xl 'an, China Conf. Title: ICIP 92. Proceedings of the 2nd Singapore International Conference on Image Processing pp. 16-20 Editors: Srinivasa, V.; Ong Sim Heng; Ang Yew Hock Publisher: World Scientific Singapore Date: 1992 xxll +734 pp.
Inspec 44990066 B9311-6140C-213 C9311-1250-151 Doc Type: Conference Paper Title: Color image compression based on fractal geometry Authors: Hong Yan; Fillippoff; G. Affiliation: Dept. of Electr. Eng., Sydney Univ., NSW, Australia Conf. Title: ICIP 92. Proceedings of the 2nd Singapore International Conference on Image Processing pp. 3-5 Editors: Srinivasa, V.; Ong Sim Heng; Ang Yew Hock Publisher: World Scientific Singapore Date: 1992 xxii+734 pp.
Inspec 4495283 B9311-0250-010 C9311-1160-037 Doc Type: Journal Paper Title: On the most robust affine basis Authors: Gottman, C. Affiliation: Dept. of Comput. Sci. Technlou, Haifa, Israel Journal: Pattern Recognition Letters vol. 14 Iss: pp. 647-650 Date: Aug. 1993.
Inspec 4495112 B9311-6140C-120 C9311-1260-075 Doc Type: Conference Paper in Journal Title: Affine models for motion and shape recovery Authors: Fuh, C.-S.; Maragos, P. Affiliation: Div of Apol. Scil., Harvard Univ., Cambridge, MA, USA Journal: Proceedings of the SPIE—The International Society for Optical Engineering vol. 1388 Iss: pt.1 pp. 120-134 Date: 1992.
Inspec 4492170 A9321-0365-052 B9311-6140C-084 C9311-1250-052 Doc Type: Journal Paper Title: Two ways to incorporate scale

(56) References Cited

OTHER PUBLICATIONS in the Helsenberg group with an interviewing operator Authors: Segman, I.; Schempp, W. Affiliation: Div. of Appl. Sci., Harvard Univ., Cambridge, MA, USA Journal of Mathematical Imaging and Vision vol. 3 Iss: 1 pp. 79-94 Date: Mar. 1993.
Inspec 4484044 C9311-1250-007 Doc Type: Conference Paper in Journal Title: Markov iterated function system model of Images Authors: Huiguo Luo: Yaoting Zhu: Guangxi Zhu; Faguan Wan Affiliation: Dept. of Electr. & Inf. Eng., Hunrhong Univ. of Sci. & Technol., Wohen, China Journal: Proceedings of the SPIE—The International Society for Optical Engineering vol. 1 71 pp. 598-604 Date: 1993.
Inspec 4481437 B9310-6140C-191 C9310-5260B-115 Doc Type: Journal Paper Title: Analysis of snowflake shape by a region and contour approach Authors: Muramoto, K.; Matsuura, K.; Shiina, T. Affiliation: Fac. of Technol., Kanazawa Univ., Japan Journal: Transactions of the Institute of Electronics, Information and Communication Engineers D-II vol. 176D-II Iss: 5 pp. 949-958 Date: May 1993.
Inspec 4479373 C9310-1250-133 Doc Type: Conference Paper in Journal Title: Bayesian methods for the use of implicit polynomials and algebraic invariants in practical computer vision Authors: Subrahmonia, J.; Keren, D.; Cooper, D.B. Affiliation: Lab. for Eng. Man/Machine Syst., Brown Univ., Providence, RI, USA Journal: Proceedings of the SPIE—The International Society for Optical Engineering vol. 1830 pp. 104-117 Date: 1992.
Inspec 4476336 B9310-6140C-168 C9310-5260B-089 Doc Type: Journal Paper Title: Motion segmentation and qualitative dynamic scene analysis from an image sequence Authors: Bouthemy, P.; Francois, E.Affiliation: IRISA/INRIA, Reanes, France Journal: International Journal of Computer Vision vol. 10 Iss: 2 pp. 157-182 Date Apr. 1993.
Inspec 4471520 B9310-6140C-105 C9310-1250-068 Doc Type: Conference Paper Title: Multiresolutional texture analysis based on morphological techniques Authors: Popov, A.T., Hall, A.G. Affiliation: Fac. of Math. & Inf., St. Kilment Ohrikiski Univ. of Sofia, Bulgaria Conf. Title: IEE Colloquim on Morphological and Nonlinear Image Processing Techniques (Digest No.1993/145) pp. 4/1-6 Publisher: IEE London, UK Date: 1993 51 pp.
Inspec 4471518 B9310-6140C-103 C9310-1250-066 Doc Type: Conference Paper Title: Wavelet multiscale representation and morphological filtering for texture segmentation Authors: Xie, Z.Y.; Brady, M. Affiliation: Dept. of Eng. Sci., Oxford Univ., UK Conf. Title: IEE Colloquim on 'Morphological and Nonlinear Image Processing Techniques' (Digest No.1993/145) pp. 2/1-8 Publisher: IEE London, UK Date: 1193 51 pp.
Inspec 4471319 B9310-6140C-098 C9310-1250-061 Doc Type: Conference Paper Title: Fractal image compression using iterative transforms: applications to DTED Authors: Jacobs, E.W.; Boss, R.D. Affiliation: NCCOSC RDT&E Div., San Diego, CA, USA Conf. Title: MILCOM '92—Communications—Fusing Command, Control and Intelligent—Conference Record (Cat. No. 92CH 3131-0) pp. 0-1122-1128 vol. 3 Publisher: IEEE New York, NY, USA Date: 1992.
Inspec 4468930 B9310-6140C-081 C9310-5260B-053 Doc Type: Conference Paper in Journal Title: A fractal model for digital image texture analysis Authors: Penolkas, M.G.; Mitra, S. Affiliation: Dept. of Electr. Eng., Texas Tech. Univ., Lubbock, TX, USA Journal: Proceedings of the SPIE—The International Society for Optical Engineering vol. 1771 pp. 292-298 Date: 1993.
Inspec 4465220 B9310-6140C-008 C9310-1250-004 Doc Type: Journal Paper Title: 3-D motion estimation in model-based facial image coding Authors: Li, H.; Roivainen, P.; Forcheimer, R. Affiliation: Dept. of Electr. Eng., Linkoping Univ., Sweden Journal: IEEE Transactions on Pattern Analysis and Machine Intelligence vol. 15 Iss: 6 pp. 545-555 Date: Jun. 1993.
Inspec 4464625 A9319-4230-003 B9310-6140C-006 C9310-1250-003 Doc Type: Conference Paper in Journal Title: Optical image analysis using fractal techniques Authors: Kozaius, S.P.: Andrews, H.G.; Foor, W.E. Affiliation: Dept. of Eelctr. & Comput. Eng., Florida Inst. of Technol., Melbourne, FL, USA Journal: Proceedings of tha SPIE—The International Society for Optical Engineering vol.1790 pp. 117-124 Date: 1993.
Inspec 4459657 B9309-6140C-202 C9309-169 Doc Type: Conference Paper Title: Inverse problem for two-dimensional fractal sets using the wavelet transform and the moment method Authors: Rinaldo, R.; Zakhor, A. Affiliation: Dept. of Electr. Eng. & Comput. Sci, California Univ., Berkeley, CA USA Conf. Title ICASSP-92: 1992 IEEE International Conference on Acoustics, Speech and Signal Processing (Cat. No.92C3103-9) pp. 665-668 vol. 4 Publisher: IEEE New York, NY, USA Date: 1992 5 vol. 3219 pp.
Inspec 4458920 C9309-1250-161 Doc Type: Book Chapter Title: Recognition and generation of fractal patterns by using syntactic techniques Authors: Blane-Talon, J. Affiliation: Div. of Inf. Technol., CSSRO, Canberra, Act, Australia Book Title: Complex systems: from biology computation pp. 141-152 Editors: Green, D.G.; Bossomaler, T. Publisher: IOS Press Amsterdam, Netherlands Date: 1993 x+376 pp.
Inspec 4454556 B9309-6140C-127 C9309-1250-112 Doc Type: Conference Paper Title: Recursive estimation of facial expression and movement Authors: Li, H.; Roivinen, P.; Forchheimer, R. Affiliation: Dept. of Electr. Eng., Linkoping Univ., Sweden Conf. Title: Icassp 92: 1992 IEEE International Conference on Acoustics. Speech and Signal Processing (Cat. No.92CH3103-9) pp. 391-396 vol. 3 Publisher: IEEE New York, NY, USA Date: 1992 5 vol. 3219 pp.
Inspec 4454529 B9309-6140C-103 C9309-1250-099 Doc Type: Conference Paper Title: Fractal approximation add data: Sch. of Electron. & Electr. Eng., Bath Univ., UK Conf. Title: ICASSP-92 IEEE International Conference on Acoustics, Speech and Signal Processing (Cat. No.92CH3103-9) pp. 485-488 vol. 3 Publisher: IEEE New York, NY, USA Date: 1992 5 vol. 3219 pp.
Inspec 4441526 C9308-1250-125 Doc Type: Conference Paper Title: Optoelectronic fractal scanning technique for wavelet transform and neural net pattern classifiers Authors: Phuvzn, S.; Oh, T.K.; Caviris, N.; Li, Y.; Szu, H. Affiliation NAVSWC, Silver Spring, MD USA Conf. Title: IJCNN International Joint Conference on Neural Networks (Cat. No.92CH3114 6) pp. 40 6 vol. 1 Publisher: IEEE New York, NY, USA Date: 1992.
Inspec 4441256 B9308-6140C-136 C9308-5260B-086 Doc Type: Journal Paper Title: Advances in digital image processing Authors: Anuradha, M. Affiliation: Rakshnpuram Colony, Hyderabad, India Journal: Students'Journal of the Institution of Electronics & Telecommunication Engineers vol. 33 Iss: 3 pp. 197-208 Date: Jul.-Sep. 1992.
Inspec 4431389 B9308-6140C-029 C9308-5260B-014 Doc Type: Journal Paper Title: A parallel image generation by an IFS and an adaptive IFS estimation of the gray scale image Authors: Sonehara, N.; Nakane, K. Journal: Journal of the Institute of Image Electronics Engineers of Japan vol. 21 Iss: 5 pp. 486-493 Date: Oct. 1992.
Inspec 4426937 B9307-0170L-017 C9307-5260B-120 Doc Type: Conference Paper Title: A fractal dimension feature extraction technique for detecting flaws in silicon wafers Authors: Stubbendieck. G.T.; Oldham, W.J.B. Affiliation: Dept. of Comput. Sci., Texas Tech. Univ., Lubbock, TX, USA Conf. Title: IJCCN International Joint Conference on Neural Networks (Cat. No.92CH3114-6) pp. 717-723 vol.3 Publisher: IEEE New York, NY, USA Date: 1992.
Inspec 4422802 B9307-6140C-189 C9307-1250-145 Doc Type: Conference Paper Title: Efficient compression of wavelet coefficients for smooth and fractal-like data Authors: Culik, K., II; Dube, S. Affiliation: Dept. of Comput. Sci., South Carolina, Columbia, SC, USA Conf. Title: STACS 93. 10th Annual Symposium on Theoretical Aspects of Computer Science pp. 343-353 Editors: Enjalbert, P.; Finkel, A.; Wagner, K.W. Publisher: Spring-Verlag Berlin, Germany Date: 1993 xiv+723 pp.
Inspec 4422202 C9307-5260B-085 Doc Type: Conference Paper Title: Sensitivity of Alias to small variations in the dimension of fractal images Authors: Bock, P.; Kocinski, C.J.; Schmidt, H.; Klinnert, R.; Kober, R.; Rovner, R. Affiliation: Res. Inst. for Appl. Knowledge Process., Ulm, Germany Conf. Title: IJCNN Interna-

(56) References Cited

OTHER PUBLICATIONS tional Joint Conference on Neural Networks (Cat. No. 92CH3114-6) pp. 339-353 vol. 4 Publisher: IEEE New York, NY, USA Date: 1992.
Inspec 4697503 B9408-6140C-051 C9408-1250-029 Doc Type: Journal Paper Title: Two-plus-one-dimensional differential geometry Authors: Koenderink, J.J.; Van Doorn, A.J. Affiliation: Buys Ballot Lab., Utrecht Biophys. Res. Inst., Netherlands Journal: Pattern Recognition Letters vol. 15 Iss: 5 pp. 439-443 Date: May 1994.
Inspec 4699458 B9408-6140C-025 C9408-5260B-006 Doc Type: Journal Paper Title: Model-based multiresolution motion estimation in noisy images Authors: Wool Boon Gob; Martin, O.R. Affiliation: Sch. of Appl. Sci., Nanyang Technol. Inst., Singapore Journal: CVGIP: Image Understanding vol. 59 Iss: 3 pp. 307-319 Date: May 1994.
Inspec 4683860 A9414-230-005 B9407-6140C-104 C9407-1250-076 Doc Type: Journal Paper Title: Fractal error for detecting man-made features in serial images Authors: Cooper, B.E.; Chenoweth, D.L.; Selvage, J.E. Affiliation: Comput. Sci. & Eng. Program, Louisville Univ., KY, USA Journal: Electronics Letters vol. 30 Iss: 7 pp. 554-555 Date: Mar. 31, 1994.
Inspec 4671654 B9406-6140C-211 C9406-1250-138 Doc Type: Journal Paper Title: Image coding using fractal parameters of contour lines Authors: Suzuki, Y.; Sumiyoshi, H.; Miyauchi, A. Affiliation: Dept. of Electron. & Commun. Eng., Musashi Inst. of Technol., Tokyo, Japan Journal: Journal of the Institute of Television Engineers of Japan vol. 48 Iss: 1 pp. 69-77 Date: Jan. 1994.
Inspec 4666757 B9406-6140-128 C9406-1260-077 Doc Type: Journal Paper Title: Multiscale recursive estimation, data fusion, and regularization Authors: Chan, K.C.; Willsky, A.S.; Benvenisce, A. Affiliation: SRI Int., Menlo Park, CA, USA Journal: IEEE Transactions on Automatic Control vol. 39 Iss: 3 pp. 464-478 Date: Mar. 1994.
Inspec 4666490 B9406-6140C-154 C9406-1250-109 Doc Type: Journal Paper Title: Efficacy of fractal features in segmenting images of natural textures Authors: Dubuisson, M.-P.; Dubes, R.C. Affiliation: Dept. of Comput. Sci., Michigan State Univ., East Lansing, MI, USA Journal: Pattern Recognition Letters vol. 15 Iss: 4 pp. 419-431 Date: Apr. 1994.
Inspec 4666580 B9406-6140C-147 C9406-1250-102 Doc Type: Journal Paper Title: Affine point matching Authors: Sprinzak, J.; Werman, M. Affiliation: Dept. of Comput. Sci., Hebrew Univ., Jerusalem, Israel Journal: Pattern Recognition Letters vol. 15 Iss: 4 pp. 337-339 Date: Apr. 1994.
Inspec 4657258 B9406-6140C-063 C9406-1250-044 Doc Type: Journal Paper Title: The canonical coordinates method for pattern recognition. II. Isomorphisms with affine transformations Authors: Blatt, N.; Rubinstein, S. Affiliation: Dept. of Math., Technion-Israel Inst. of Technol., Haifa, Israel Journal: Pattern Recognition vol. 27 Iss: 1 pp. 99-107 Date: Jan. 1994.
Inspec 4648042-B9405-6140C-249 C9405-1250-179 Doc Type; Conference paper Title: A feature space for derivatives of deformations Authors: Bookstein, F.L.; Green, W.D.K. Affiliation: Center for Human Growth & Dev., Michigan Univ., Ann Arbor, MI, USA Conf. Title: Information Processing in Medical Imaging. 13th International Conference, IPMI '93 Proceedings pp. 1-16 Editors: Barrett, H.H.; Gmitro, A.F. Publisher: Springer-Verlag Berlin, Germany Date: 1993 xvi+567 pp.
Inspec 4645049 B9405-6140C-203 C9405-1250-141 Doc Type: Journal Paper Title: Part I: Modeling image curves using invariant 3-D object curve models-a path to 3-D recognition and shape estimation from image contours Authors: Cohen, F.S.; Jin-Yinn Wang Affiliation: Dept. of Electr. & Comput. Eng., Drexel Univ., Philadelphia, PA, USA Journal: IEEE Transactions on Pattern Analysis and Machine Intelligence vol. 16 Iss: 1 pp. 1-12 Date: Jan. 1994.
Inspec 4644907 B9405-6140C-198 C9405-1250-137 Doc Type: Journal Paper Title: An efficient differential box-counting approach to compute fractal dimension of image Authors: Sarkar, N.; Chaudhuri, B.B. Affiliation: Electron. & Commun. Sci. Unit, Indian Stat. Inst., Inst., Calcutta, India Journal: IEEE Transactions on Systems, Man and Cybernetics vol. 24 Iss: 1 pp. 115-120 Date: Jan. 1994.
Inspec 4644141 B9405-6140C-192 C9405-1250-133 Doc Type: Journal Paper Title: Space and frequency variant image enhancement based on a Gabor representation Authors: Castobal, G.; Navarro, R. Affiliation: Inst. de Opt. CSIC, Madrid, Spain Journal: Pattern Recognition Letters vol. 15 Iss: 3 pp. 273-277 Date: Mar. 1994.
Inspec 4638188 C94505-3390-079 Doc Type: Journal Paper Title: Uncalibrated stereo hand-eye coordination Authors: Hollinghurst, N.; Cipolla, R. Affiliation: Dept. of Eng., Cambridge Univ., UK Journal: Image and Vision Computing vol. 12 Iss: 3 pp. 187-192 Date: Apr. 1994.
Inspec 4637182 B9405-6140C-145 C9405-1250-096 Doc Type: Journal Paper Title: Bessel sequences and affine frames Authors: Chui, C.K.; Xianliang Shi Affiliation: Center for Approx. Theory, Texas A&M Univ., College Station, TX, USA Journal: Applied and Computational Harmonic Analysis vol. 1 Iss: 1 pp. 29-49 Date: Dec. 1993.
Inspec 4626788 B9405-6140C-043 C9405-1250-043 Doc Type: Conference Paper in Journal Title: Structural limitations of self-affine and partially self-affine fractal compression Authors: Domaszewicz, J.: Vaishampayan, V.A. Affiliation: Dept. fo Electr. Eng., Texas A&M Univ., College Station, TX, USA Journal: Proceedings of the SPIE—The International Society for Optical Engineering vol. 2094 Iss: pt.3 pp. 1498-1507 Date: 1993.
Inspec 4626678 B9405-6140C-207 C9405-5260B-006 Doc Type: Conference Paper in Journal Title: Parallel computation of fractal dimension Authors: Hayes, H.I.; Solka, J.Ll. Priebe, C.E. Affiliation: Syst. Res. & Technol. Dept., Naval Surface Warfare Center, Dahlgren, VA, USA Journal: Proceedings of the SPIE—The International Society for Optical Engineering vol. 1962 pp. 219-230 Date: 1993.
Inspec 4626677 B9405-6140C-026 C9405-1250-032 Doc Type: Conference Paper in Journal Title: A probabilistic approach to fractal based texture discrimination Authors: Soika, J.L.; Priebe, C.E.; Rogers, G.W. Affiliation: Dept. of Syst. Res. & Technol., Naval Surface Warfare Center, Dahlgren, VA, USA Journal: Proceedings of the SPIE—The International Society for Optical Engineering vol. 1962 pp. 209-218 Date: 1993.
Inspec 4626676 B940-6140C-025 C9405-1250-031 Doc Type: Conference Paper in Journal Title: Discriminant analysis in aerial images using fractal based features Authors: Priebe, C.E.; Soika, J.L.; Rogers, G.W. Affiliation: Syst. Res. & Technol. Dept., Advanced Computation Technol. Dahlgren, VA, USA Journal: Proceedings of the SPIE—The International Society for Optical Engineering vol. 1962 pp. 196-208 Date: 1993.
Inspec 4626670 B9405-6140C-021 C9405-1250-027 Doc Type: Conference Paper in Journal Title: Search Space reductions in deriving a fractal set for an arbitrary shape Authors: Neuleton, D.J.; Garigliano, R. Affiliation: Sch. of Eng. & Comput. Sci., Durham Univ., UK Journal: Proceedings of the SPIE—The International Society for Optical Engineering vol. 1962 pp. 137-145 Date: 1993.
Inspec 4626658 C9405-1250-021 Doc Type: Conference Paper in Journal Title: Computing part hierarchies of 3D object shape from metric and nonmetric surface representations Authors: Zlateva, S. Affiliation: Dept. of Comput. Sci., Boston Univ., MA, USA Journal: Proceedings of the SPIE—The International Society for Optical Engineering vol. 1826 pp. 419-427 Date: 1992.
Inspec 4620235 B9404-6140C-354 C9404-1250-220 Doc Type: Conference Paper in Journal Title: Fractal-based image coding with polyphase decomposition Authors: Kwn-lyt Wong; Ching-Han Hsu; Jay Kuo, C.-C. Affiliation: Dept. of Electr. Eng. Syst., univ. of Southern California, Los Angeles, CA, USA Journal: Proceedings of the SPIE—The International Society for Optical Engineering vol. 2094 Iss: pt.3 pp. 1207-1218 Date: 1993.
Inspec 4620225 B9404-6140C-346 C9404-1250-215 Doc Type: Conference Paper in Journal Title: A pyramid AR model to generate fractal Brownian random (FBR) field Authors: Bingcheng Li; Song Do Ma Affiliation: Inst. of Autom., Chinese Acad. of Sci., Beijing, China Journal: Proceedings of the SPIE—The International Society for Optical Engineering vol. 2094 Iss: pt.3 pp. 1094-1102 Date: 1993.

(56) References Cited

OTHER PUBLICATIONS

Inspec 4620036 C9404-1730-048 Doc Type: Conference Proceedings in Journal Conf. Title: Adaptive and Learning Systems II Journal: Proceedings of the SPIE—The International Society for Optical Engineering vol. 1962 Date: 1993.
Inspec 4619946 B9404-6140C-271 C9404-1250-164 Doc Type: Conference Paper in Journal Title: Pattern recognition using Hilbert space Authors: Lin, Y. Affiliation: Dept. of Math. and Comput. Sci., Savannah State Coll., GA, USA Journal: Proceedings of the SPIE—The International Society for Optical Engineering vol. 1825 pp. 63-77 Date: 1992.
Inspec 461456 B9404-6140C-197 C9404-1250-119 Doc Type: Conference Paper in Journal Title: Sequence coding based on the fractal theory of iterated transformations systems Authors: Reusens, E. Affiliation: Signal Process. Lab., Swiss Federal Inst. of Technol., Lausanno, Switzerland Journal: Proceedings of the SPIE—The International Society for Optical Engineering vol. 2094 Iss: pt.1 pp. 132-140 Date: 1993.
Inspec 4614545 B9404-6140C-196 C9404-1250-118 Doc Type: Conference Paper in Journal Title: Fractal approach to low rate video coding Authors: Hurtgen, B.; Burtgen, P. Affiliation: Inst. for Commun. Eng., Aachen Univ. of Technol., Germany Journal: Proceedings of the SPIE—The International Society for Optical Engineering vol. 2094 Iss: pt.1 pp. 120-131 Date: 1993.
Inspec 4614452 B9404-6140C-184 C9404-1250-107 Doc Type: Conference Paper in Journal Title: Extensions of fractal theory Authors: Liu, Y. Affiliation: Dept. of Math. & Comput. Sci., Savannah State Coll., GA, USA Journal: Proceedings of the SPIE—The International Society for Optical Engineering vol. 1966 pp. 255-268 Date: 1993.
Inspec 4612850 B9404-6140C-173 C9404-1250-096 Doc Type: Conference Paper Title: A fractal block coding technique employing frequency sensitive competitive learning Authors: Wall, L.; Kinsner, W. Affiliation: Dept. of Electr. & Comput. Eng., Manitoba Univ., Winnipeg, Man., Canada Conf. Title: IEEE WESCANEX 93. Communications, Computers and Power in the Modern Environment Conference Proceedings (Cat. No.93CH3317-5) pp. 320-329 Publisher: IEEE New York, NY, USA Date: 1993 ix+415 pp.
Inspec 4609104 B9404-6140C-127 C9404-1250-064 Doc Type: Conference Paper In Journal Title: Robust fractal characterization of 1-D and 2-D signals Authors: Avadhanam, N.; Mitra, S. Affiliation: Dept. of Electr. Eng., Texas Tech. Univ., Lubbock, TX, USA Journal: Proceedings of the SPIE—The International Society for Optical Engineering vol. 2032 pp. 232-244 Date: 1993.
Inspec 4603689 B9404-6140C-029 C9404-1250-021 Doc Type: Conference Paper in Journal Title: Evaluation of the fractal dimension as a pattern recognition feature using neutral networks Authors: DaPonte, J.; Parikh, J.A.; Decker, J.; Vitale, J. Affiliation: Southern Connecticut State Univ., New Haven, CT USA Journal: Proceedings of the SPIE—The International Society for Optical Engineering vol. 1965 pp. 221-231 Date: 1993.
Inspec 4597653 B9403-6140C-294 C9403-1250-229 Doc Type: Conference Paper In Journal Title: Affine-invariant moments and B-splines for object recognition from image curves Authors: Huang, Z.; Cohen, F.S. Affiliation: Dept. of Electr. & Comput. Eng., Drexel Univ., Philadelphia, PA, USA Journal: Proceedings of the SPIE—The International Society for Optical Engineering vol. 1964 pp. 2-12 Date: 1993.
Inspec 4596010 B9403-6140C-282 C9403-1250-215 Doc Type: Conference Paper Title: An efficient image compression algorithm based on filter bank analysis and fractal theory Authors: Temerinac, M.; Kozzrev, A.; Tipovski, Z.; Simsic, B. Affiliation: Fac. of Tech. Sci., Novi Sad univ., Yugoslavia Conf. Title: Signal Processing VI—Theories and Applications Proceedings of EUSIPCO-92, Sixth European Signal Processing Conference pp. 1373-1376 vol. 3 Editors: Vandewalie, J.; Boite, R.; Moonen, M.; Oosterlinck, A. Publisher: Elsevier Amsterdam, Netherlands, Date: 1992 3 vol. 1vii+1844 pp.
Inspec 4572079 B9402-6140C-117 C9402-1250-083 Doc Type: Journal paper Title: Image data matching for affine transformed pictures-reduction of calculation Authors: Ujifuko, S.; Nomure, Y.; Fujii, S. Affiliation: Fac. of Eng., Nagoya Univ., Japan Journal: Transactions of the Institute of Electronics, Information and Communication Engineers D-II vol. J76D-II Iss: 8 pp. 1581-1586 Date: Aug. 1993.
Inspec 4571131 C9402-5260B-064 Doc Type: Journal Paper Title: A framework for spatiotemporal control in the tracking of visual contours Authors: Blake, A.; Curwen, R.; Zisserman, A. Affiliation: Dept. of Eng. Sci., Oxford Univ., UK Journal: International Journal of Computer Vision vol. II Iss: 2 pp. 127-145 Date: Oct. 1993.
Inspec 4567756 B9402 6140C-035 C9402-1250-060 Doc Type: Journal Paper Title: Moment-based edge detection in anisotropic image data Authors; Xie Xiaoua, Luo Limin; Wei Yu Affiliation: Dept. of Biol. & Med. Eng., Southeast Univ., Nanjing, China Journal: Acta Electronica Sinica vol. 21 Iss: 10 pp. 14-21 Date: Oct. 1993.
Dialog No.: 03854641 EI Monthly No.: EIP94051281746 Title: Segmentation method of texture image by using neural network Author: Oe, Shunichiro; Hashida, Masaharu; Shinohara, Yasunori Corporate Source: Univ of Tokushima, Tokushima, Jpn Conference Title: Proceedings of 1993 International Joint Conference on Neural Networks. Part 1 (of 3) Conference Location: Nagoya, Jpn Conference Sponsor: ENNS; INNS; IEEE; SICE; IEICE; et al Source: Proceedings of the International Joint Conference on Neural Networks v 1 1993. Publ by IEEE, IEEE Service Center, Piscataway, NJ, USA,93CH3353-0. pp. 189-192 Publication Year: 1993.
Dialog No.: 03854639 EI Monthly No.: EIP94051281744 Title: Competitive neural network for affine invariant pattern recognition Author: Kurogi, Shuichi Corporate Source: Kyushu Inst of Technology, Kitakyushu, Jpn Conference Title: Proceedings of 1993 International Joint Conference on Neural Networks. Part 1 (of 3) Conference Location: Nagoya, Jpn Conference Sponsor: ENNS; INNS; IEEE; SCIE; IEICE; et al Source: Proceedings of the International Joint Conference on Neural Networks v 1993. Publ by IEEE, IEEE Service Center, Piscataway, NJ, USA 93CH3353-0. pp. 181-184. Publication Year: 1993.
Dialog No.: 03847362 EI Monthly No.: EIP94041265976 Title: Systemized serendipity for producing computer art Author: Walter, David Corporate Source: Imperial Coll of Science, Technology and Medicine, London, UK Source: Computers & Graphics (Pergamon) v 17 n 6 Nov.-Dec. 1993. pp. 699-700 Publication Year: 1993.
Dialog No.: 03839591 EI Monthly No.: EIP94041264411 Title: Fractal characteristics of mesofractures in compressed rock specimens Author: Zhao, Yonghong; Huang, Jiefan; Wang, Ren Corporate Source: Peking Univ, Beijing, China Conference Title: Proceedings of the 34th U.S. Symposium on Rock Mechanics Conference Location: Madison, WI, USA Source: International Journal of Rock Mechanics and Mining Science & Mechanics Geomechanics Abstracts v 30 n Dec. 7. 1993. pp. 877-882 Publication Year: 1993.
Dialog No.: 03810291 EI Monthly No.: EIP94021217677 Title: Robust affine invariant matching with application to line features Author: Tsai, Frank C.D. Corporate Source: New York Univ, New York, NY, USA Conference Title: Proceedings of the 1993 IEEE Computer Society Conference on Computer Vision and Pattern Recognition Conference Location: New York, NY, USA Conference Sponsor: IEEE Source: IEEE Computer Vision and Recognition Proc 1993 IEEE COmput Soc Conf Comput Vision Pattern Recognit 1993. Publ by IEEE, IEEE Service Center, Piscataway, NJ, USA, (IEEE cat n 93CH3309-2). pp. 393-399 Publication Year: 1993.
Dialog No.: 0310278 EI Monthly No.: EIP94021217664 Title: From global to local, a continuum of shape models with fractal priors Author: Vemuri, B.C.; Radisavljevic, A. Corporate Source: Univ of Florida, Gainesville, FL, USA Conference Title: Proceedings of the 1993 IEEE Computer Society on Computer Vision and Pattern Recognition Conference Location: New York, NY, USA Conference Sponsor: IEEE Source: IEEE Computer Vision and Pattern Recognition Proc 1993 IEEE Comput Soc Conf Comput Vision Pattern Recognit 1993. Publ by IEEE, IEEE Service Center, Piscataway, NJ, USA, (IEEE cat n 93CH3309-2). pp. 307-313 Publication Year: 1993.
Dialog No.: 03810250 EI Monthly No.: EIP94021217636 Title: Efficient recognition of rotationally symmetric surfaces and straight homogeneous generalized cylinders Authors: Liu, Jane; Mundy,

(56) References Cited

OTHER PUBLICATIONS

Joe; Forsyth, David; Zisserman, Andrew; Rothwell, Charlie Corporate Source: GE Cent for Research and Development, Schenectady, NY, USA Conference Title: Proceedings of the 1993 IEEE Computer Society Conference on Computer Vision and Pattern Recognition Conference Location Proc 1993 IEEE Comput Soc Conf Comput Vision Pattern Recognit 1993. Publ by IEEE, IEEE Service Center, Piscataway, NJ, USA, (IEEE cat n 93CH3309-2). pp. 123-128 Publication Year: 1993.

Dialog No.: 03807554 EI Monthly No.: EIP94021216087 Title: VLSI architecture for polygon recognition Author: Sastry, Raghu; Ranganthan, N.; Bunka, Horst Corporate Source: Univ. of South Florida, Tampa, FL, USA Source: IEEE Transactions on Very Large Scale Integration (VLSI) Systems v 1 n 4 Dec. 1993. pp. 398-407 Publication Year: 1993.

Dialog No.: 03798198 EI Monthly No.: EIP94021198639 Title: Magnetization reversal in CoPt magnetoopic recording alloys Author: Klenefeld, T.; Kim, W.S.; Valentin, J.; Weller, D. Corporate Source: Univ Duisburg, Duisburg Ger Conference Title: Proceedings of the 1993 MRS Spring Meeting on Magnetic Ultrathin Films Conference Location: San Francisco, CA, USA Source: Multilayers and Surfaces Materialse Research Society Symposium Proceedings v 313 1993. Publ by Materials Rsearch Society, Pittsburgh, PA, USA. pp. 315-319 Publication Year 1993.

Dialog No.: 03782823 EI Monthly No.: EIP94011185543 Title: Fractal analysis of fracture patterns using the standard box-counting technique: valid and invalid methodologies Author: Walsh, J.J.; Waterson, J. Corporate Source: Univ of Liverpool, Liverpool, Engl Source: Journal of Structural Geology v 15 n 12 Dec. 1993. pp. 1509-1512 Publication Year: 1993.

Dialog No.: 03780159 EI Monthly No.: EIP94011171743 Title: Sensperceptor: Image based evidence formation model as a logical sensor for robot hand preshaping Author: Nazlibilek, L.; Erkmen, A.; Erkmen, I. Corporate Source: Middle East Technical Univ, Ankara, Turk Conference Title: Proceedings of the 1993 IEEE International Symposium on Intelligent Control Conference Location: Chicago, IL, USA Conference Sponsor: IEEE Control Systems Society Source: Proc 1993 IEEEE Int Symp Intell Control 1993. Publ by IEEE, IEEE Service Center, Piscataway, NJ, USA (IEEE cat n 93CH3278-9). pp. 326-331 Publication Year: 1993.

Dialog No.: 03770294 EI Monthly No.: EIP93121161740 Title: New linear systolic arrays for the string comparison algorithm Author: Gosev, Marjan; Evans, David J. Corporate Source: Univ. ?Kiril i Meiodij of Skopje, Skopje, Macedonia Source: Parallel Computing v 19 n 10 Oct. 1993, pp. 1177-1193 Publication Year: 1993.

Dialog No.: 03730066 EI Monthly No.: EIP93121161511 Title: Multi-target tracking in dense threat environments Author: Toomarian, Nikzad Corporate Source: California Inst of Technology, Pasadena, CA, USA Source: Computer & Electrical Engineering v 19 n 6 Nov. 1993. pp. 469-479 Publication Year: 1993.

Dialog No.: 03770270 EI Monthly No.: EIP93121161716 Title: Recognition and inspection of manufactured parts using line moments of their boundaries Author: Wen, Wei; Lozzi, Andrei Corporate Source: Univ of Sydney, Sydney Aust Source: Pattern Recognition v 26 n 10 Oct. 1993. pp. 1461-1471 Publication Year: 1993.

Dialog No.: 03769393 EI Monthly No.: EIP93121154226 Title: Outdoor landmark recognition using fractal based vision and neural networks Author: Luo, Ren C.; Potlapalli, Harsh; Hislop, David W. Corporate Source: North Carolina State Univ, Raleigh, NC, USA Conference Title: Proceedings of the IEEE/RSJ International Conference on Intelligent Robots and Systems Conference Location: Yokchama, Jpn Conference Sponsor: IEEE Industrial Electronics Society, IEEE Robotics and Automation Society; Robotics Society of Japan (RSJ); Society of Instrument and Control Engineer (SICE); New Technology Foundation Source: 1993 International Conference on Intelligent Robots and Systems 1993. Publ by IEEE, IEEE Service Center, Piscataway, NJ, USA, (IEEE cat n 93CH3213-6). pp. 612-618 Publication Year: 1993.

Dialog No.: 037681138 EI Monthly No.: EIP3121154399 Title: 2 plus 3 model; fractal processes for knowledge-based engineering design Author: Chen, Q. Corporate Source: Dalian Univ of Technology, Dalian, China Source: Cybernetics and Systems v 24 n 5 Sep.-Oct. 1993. pp. 419-440 Publication Year: 1993.

Dialog No.: 03750577 EI Monthly No.: EIP93111131815 Title: Fractal precision models of lathe-type turning matchines Author: Tumer, Irem Y.; Srinlvasen, R.L.; Wood, Kristin L.; Busch-Vishniac, Ilene Corporate Source: Univ of Texas, Austin, TX, USA Conference Title: Proceedings of the 19th Annual ASME Design Automation Conference. part 2 (of 2) Conference Location: Albuquerque, NM, USA Conference Sponsor: ASME, The Design Engineering Division Source: Advances in Design Automation American Society of Mechanical Engineers, Design Engineering Division (Publication) DE v 65 pt 2 1993. Publ by ASME, New York, NY, USA. pp. 501-513 Publication Year, 1993.

Dialog No.: 03747408 EI Monthly No.: EIP93111125364 Title: Fractal neutron optics multilayers in cantor ternary set pattern Author: Maaza, M.; Pardo, B.; Megademini, T. Corporate Source: Commissaria; a l'Energie Atomique-Centre National de la Recherche Scientifique, Gif-sur-Yvente, Fr Source: Journal of Applied Crystallography v 26 pt 4 Aug. 1, 1993. pp. 519-524 Publication Year: 1993.

Dialog No.: 03855870 EI Monthly No.: EIP94051282331 Title: Correlation effects of fractal compression Author: Sirgany, Wajie N.; Mazel, David S. Corporate Source: IBM Federal Systems Co, Manaesas, VA, USA Conference Title: Proceedings of the 27th Asilomar Conference on Signals, System & Computers Conference Location: Pacific Grove, CA, USA Conference Sponsor: IEEE Computer Society Press; Naval Postgraduate School; San Jose State university Source: Conference Record of the Asilomar Conference on Signals, Systems & Computers v 2 1993. Publ by IEEE, Computer Society Press, Los Alamitos, CA, USA. pp. 1524-1528 Publication Year: 1993.

Dialog No.: 03803851 EI Monthly No.: EIP94021215641 Title: Fractal modeling techniques for spatial data Author: Gregorski, Mark E.; Jensen, Olivia Corporate Source: Univ of Waterloo, Waterloo, Ont, Can Source: IEEE Transactions on Geoscience and Remote Sensing v 31 n 5 Sep. 1993. pp. 980-988. Publication Year: 1993.

Dialog No.: 03795505 EI Monthly No.: EIP9402120064 Title: Fractal image coding: a review Author: Jacquin, Arnand E. Corporate Source: AT&T Bell Lab, Murray Hill, NJ USA Source: Proceedings of the IEEE v 81 n 10 Oct. 1993. pp. 1451-1465 Publication Year: 1993.

Dialog No.: 03780174 EI Monthly No.: EIP94011171758 Title: Barnet: A new approach to behavior arbitration Author: Yavnai Corporate Source: Rafael, Haifa, Isr Conference Title: Proceedings of the 1993 IEEE International Symposium on Intelligent Control Conference Location: Chicago, IL, USA Conference Sponsor: IEEE Control Systems Society Source: Proc 1993 IEEE Int Symp Intell Control 1993. Publ by IEEE, IEEE Service Center, Piscataway, NJ, USA, (IEEE cat n 93CH3278-9). pp. 417-422 Publication Year: 1993.

Dialog No.: 0378009 EI Monthly No.: EIP93121138971 Title: Metal/coating electrolyte interfacial impedance and its global fractal model Author: Hubrecht, J.; Entbrechts, M.; Bogserts, W. Corporate Source: Katholieke Univ Leuven, Heverlee, Belg Conference Title: Proceedings of the Second International Symposium on Electrochemical Impedance Spectroscopy Conference Location: Berling, Ger Source: Electrochimica Acta v 38 n 14 Oct. 1993, pp. 1867-1875 Publication Year: 1993.

6 of 11 Complete Record Dialog No.: 03771133 EI Monthly No.: EIP93121160707 Title: Proceedings of the Graphics Interface Author: Anen (Ed.) Conference Title: Proceedings of the Graphics Interface Conference Location: Toronto, Ont, Can Source: Proceedings--Graphics Interface 1993. Publ by Canadian Information Processing Soc, Toronto, Ont, Can. 263p. Publication Year: 1993.

Dialog No.: 03769393 EI Monthly No.:EIP3121154226 Title: Outdoor landmark recognition using fractal based vision and neural networks Author: Luo, Ren C.; Porlapalli, Harsh, Hislop, David W. Corporate Source: North Carolina State Univ, Raleigh, NC, USA Conference Title: Proceedings of the IEEE/RSJ International Con-

(56) References Cited

OTHER PUBLICATIONS ference on Intelligent Robots and Systems Conference Location: Yokohama, Jpn Conference Sponsor: IEEE Industrial Electronics Society; IEEE Robotics and Automation Society; Robotics Society of Japan (RSJ); Society of Instrument and Control Engineers (SICE); New Technology Foundation Source: 1993 International Conference on Intelligent Robots and Systems 1993. Publ by IEEE, IEEE Service Center, Piscataway, NJ, USA, (IEEE cat n 93CH3213-6). pp. 612-618 Publication Year: 1993.

Dialog No.: 03765834 EI Monthly No.: EIP93101115999 Title: Improved electro-optical target detection in a natural fractal environment Author: Cohen, G.; Reina, G.; Tidhar, Gil; Rotman, Stanley R. Corporate Source: Ben-Gurion Univ. of the Negev, Beer-Sheva, Isr Conference Title: 8th Meeting on Optical Engineering in Israel: Optical Engineering and Remote Sensing Conference Location: Tel Aviv, Isr Conference Sponsor: SPIE—International Soc for Opt Engineering, Bellingham, WA USA; Int Commission for Optics; European Optical Soc; Optical Soc of America: Asia-Pacific Optics Federation Source: Proceedings of SPIE—The International Society for Optical Engineering v 1971 1993. Publ by Society of Photo-Optical Instrumentation Engineers, Bellingham, WA, USA, pp. 78-92 Publication Year: 1993.

Dialog No.: 03759087 EI Monthly No.: EIP93111136171 Title: Chaos and fractal algorithms applied to signal processing and analysis Author: Handley, J.W.; Jaerusch, H.M.; Bjork, C.A.; Richardson, L.T.; Carruth, R.T. Corporate Source: Univ of Alabama in Huntsville, Huntsville, AL, USA Source: Simulation v 60 n 4 Apr. 1993. pp. 261-279 Publication Year: 1993.

Dialog No.: 03755356 EI Monthly No.: EIP93121139068 Title: Realistic phase distributions derived from the Wigner function Author: Bandiilla, A.; Ritze, H.H. Corporate Source: Univ Berlin, Berlin, Ger Source: Journal of the European Optical Society Part B: Quantum Optics v 5 n 4 Aug. 1993. pp. 213-222 Publication Year: 1993.

Dialog No.: 03751707 EI Monthly No.: EIP9311134256 Title: Computer art representing the behavior of the Newton-Raphson method Author: Walter, David John Corporate Source: Nanyang Technological Univ, Singapore, Source: Computers & Graphics (Pergamon) v 17 n 4 Jul.-Aug. 1993. pp. 487-488 Publication Year: 1993.

Dialog No.: 03758542 EI Monthly No.: EIP93121144140 Title: Implications of the user's informatoin processing strategy on the design of decision aids for complex systems Author: Matthews, Michael L.; McFadden, Sharon M. Corporate Source: Univ of Guelph. Ont. Can Conference Title: Proceedings of the 37th Annual Meeting the Human Factors and Ergonomics Society Conference Location: Seattle, WA, USA Source: Designing for Diversity Proceedgins of the Human Factors and Ergonomics Society v 1 1993. publ by Human Factors and Ergonomics Society, Inc., Santa Monica, CA, USA. pp. 358-362 Publication Year: 1993.

Dialog No.: 03855007 EI Monthly No.: EIP94051282111 Title: Waveform recognition and classification using an unsupervised network Author: Lee, C.K.; Yeung, K.F. Corporate Source: Hong Kong Polytechnic, Hung Hom, Hong Kong Conference Title: Proceedings of 1993 International Joint Conference on Neural Networks. Part 3 (of 3) Conference Location: Nagoya, Jpn Conference Sponsor: ENNS; INNS; IEEE; IEICE; et al Source: Proceedings of the International Joint Conference on Neural Networks v 3 1993. Publ by IEEE, IEEE Service Center, Piscataway, NJ, USA. 93CH3353-0. pp. 2710-2713 Publication Year: 1993.

Dialog No.: 03854884 EI Monthly No: EIP94051281989 Title: Texture classification using a two-stage neural network approach Author: Raghu, P.P.; Poongodi, R.; Yegnanarayana, B. Corporate Source: Italian Inst of Technology, Madras, India Conference Title: Proceedings of 1993 International Joint Conference on Neural Networks. Part 3 (of 3) Conference Location: Nagoya, Jpn Conference Sponsor: ENNS; INNS; IEEE; SICE; IEICE; et al Source: Proceedings of the International Joint Conference on Neural Networks v 3 1993. Publ by IEEE, IEEE Service Center, Piscataway, NJ, USA.93CH3353-0. pp. 2195-2198 Publication Year: 1993.

Dialog No.: 03773364 EI Monthly No.: EIP94011166633 Title: High confidence visual recognition of persons by a test of statistical independence Author: Daugman, John G. Corporate Source: Cambridge Univ. Cambridge, Engl Source: IEEE Transactions on Pattern Analysis and Machine Intellignece v 15 n 11 Nov. 1993. pp. 1148-1161 Publication Year: 1993.

Dialog No.: 03817787 EI Monthly No.: EIP94031234613 Title: Lalpacian and orthogonal wavelet pyramid decompositions in coarse-to-fine registration Author: Allen, Ronald L.; Kamangar, Farhad, A.; Stokely, Ernest M. Corporate Source: Univ of Texas at Arlington, TX, USA Source: IEEE Transactions on Signal Processing v41 n 12 Dec. 1993. pp. 3536-3541 Publication Year: 1993.

573 of 727 Complete Record Dialog No.: 03773367 EI Monthly No.: EIP94011166696 Title: Texture classification by wavelet packet signatures Author: Laine, Andrew; Fan, Nan Corporate Source: Univ of Florida, Gainesville, FL., USA Source: IEEE Transactions on Pattern Analysis and Machine Intelligence v 15 n 11 Nov. 1993. pp. 1186-1191 Publication Year: 1993.

Dialog No.: 03854872 EI Monthly No.: EIP94051281977 Title: Network model for invariant object recognition and rotation angle estimation Author: You, Shingchern, D.; Ford, Gary E. Corporate Source: Univ of California, Davis, CA, USA Conference Title: Proceedings of 1993 International Joint Conferenceon Neural Networks. Part 3 (of 3) Conference Location: Nagoya, Jpn Conferenc Sponsor: ENNS; INNS; IEEE; SICE; IEICE; et al Source: Proceedings of the International Joint Conference on Neural Networks v 3 1993. Publ by IEEE, IEEE Service Center, Piscataway, NJ, USA. 93CH3353-0. pp. 2145-2148 Publication Year: 1993.

Dialog No.: 03819787 EI Monthly No. EIP93121145108 Title: Object tracking through adaptive correlation Author: Montera, Dennis A.; Rogers, Steven, K.; Ruck, Dennis W.; Oxley, Mark E. Corporate Source: Air Force Inst. of Technology, Wright-Patterson AFB, OH, USA Conference Title: Optical Pattern Recognition IV Conference Location: Orlando, FL, USA Conference Sponsor: SPIE—Int Soc for Opt Engineering, Bellingham, WA USA Source: Proceedings Of SPIE—The International Society for Optical Engineering v 1959 1993. Publ by Society of Photo-Optical Instrumentation Engineers, Bellingham, WA, USA. pp. 314-321. Publication Year: 1993.

Dialog No.: 03810264 EI Monthly No.: EIP94021217650 Title: On the recognition of occluded shapes and generic faces using multiple-template expansion matching Author: Ben-Arie, Jezekjel; Rao, K. Raghunath Corporate Source: Illinois Inst of Technology, Chicago, IL, USA Conference Title: Proceedings of the 1993 IEEE Computer Society Conference on Computer Vision and Pattern Recognition Conference Location: New York, NY, USA Conference Sponsor: IEEE Source: IEEE Computer Vision and Pattern Recognition Proc 1993 IEEE Comput Soc Conf Vision Pattern Recognit 1993. Publ by IEEE, IEEE Service Center, Piscataway, NJ, USA, (IEEE cat n 93CH3309-2). pp. 214-219 Publication Year: 1993.

Dialog No.: 03810232 EI Monthly No.: EIP94021217618 Title: IEEE Computer Vision and Pattern Recognition Author: Anon(Ed.) Conference Title: Proceedings of the 1993 IEEE Computer Society Conference on Computer Vision and Pattern Recognition Conference Location: New York, NY, USA, Conference Sponsor: IEEE Source: IEEE Computer Vision and Pattern Recognition Proc 1993 IEEE Comput Soc Conf Comput Vision Pattern Recognit 1993. Publ by IEEE, IEEE Service Center, Piscataway, NJ, USA, (IEEE cat n 93CH3309-2) 801p. Publication Year: 1993.

Dialog No.: 03765362 EI Monthly No.: EIP93071030658 Title: Neural net based 2D-vision system for real-time applications Author: Reddy, O.N.; Valthilingham, S.; Bean, W.C. Corporate Source: Lamar Univ, Beaumont, TX, USA Conference Title: Proceedings of the 3rd Workshop on Neural Networks: Academic/Industrial/NASA/Defense Conference Location: Alabama, AL, USA Conference Sponsor: Auburn University Space Power Institute; Center for Commercial Development of Space Power and Advanced Electronics; NASA Headquarters Source: Proceedings of SPIE—The International Society for Optical Engineering v 1721 1993. Publ by Society of Photo-Optical Instrumentation Engineers, Bellingham, WA, USA. pp. 345-348 Publication Year: 1993.

Dialog No.: 03765361 EI Monthly No.: EIP93071030657 Title: Investigating facial verification systems using backpropagation neu-

(56) References Cited

OTHER PUBLICATIONS ral networks Author: Payne, Tanya L.; Solheim, Inger, Castain, Ralph Corporate Source: Los Alamos Natl Lab, Los Alamos, NM, USA Conference Title: Proceedings of the 3rd Workshop on Neural Networks: Academic/Industrial/NASA/Defense Conference Location: Alabama, AL, USA Conference Sponsor: Auburn University Space Power Institute; Center for Commercial Development of Space Power and Advanced Electronics; NASA Headquarter Source: Proceedings of SPIE—The International Society for Optical Engineering v 1721 1993. Publ by Society of Photo-Optical Instrumentation Engineers, Bellingham, WA, USA. pp. 340-344 Publication Year: 1993.

Dialog No.: 03763234 EI Monthly No.: EIP93121145940 Title: Pattern recognition properties of various feature spaces for high order neural networks Author: Schmidt, William A. C.; Davis, John P. Corporate Source: Naval Air Development Cent Mission and Avionics Technology Dep, Warminster, PA, USA Source: IEEE Transactions on Pattern Anaysis and Machine Intelligence v 15 n 8 Aug. 1993. pp. 795-801 Publication Year: 1993.

Dialog No.: 03759968 EI Monthly No.: EIP93111136890 Title: Face recognition: Features versus templates Author: Brunelli, Roberto; Poggio, Tomaso Corporate Source: Instituito per la Ricerez Scientifica e Tecnologica, Trento, Italy Source: IEEE Transactions on Pattern Analysis and Machine Intelligence v 15 n 10 Oct. 1993. pp. 1042-1052 Publication Year: 1993.

Inspec :699540 B9408-6140C 083 C9408-5260B-046 Doc Type: Journal Paper Title: A new modern compensation method for image sequence coding using hierarchical grid interpolation Authors: Chuag-Ian Huang; Chao-Yuen Hsu Affiliation: Inst. of Electr. Eng., Nat. Tsing Hua Univ., Hsinchu, Taiwan Journal: IEEE Transactions on Circuits and Systems for Video Technology vol. 4 Iss: 1 pp. 42-52 Date: Feb. 1994.

Inspec 470: 135 B9408-6140-085 C9408-1250-063 Doc Type: Conference Paper Title: Pattern theory in algorithm design Authors: Axtell, M.; Ross, T.; Noviskey, M. Conf. Title: Proceedings of the IEEE 1993 National Aerospace and Electronics Conference NAECON 1993 (Cat. No.93CH3506-8) pp. 920-925 vol.2 Publisher: IEEE New York, NY, USA Date: 1993 2 vol. xii+1171 pp.

Inspec 4702077 B9408-4180-022 C9408-5270-017 Doc Type: Conference Paper in Journal Title: Optoelectronically implemented neural network with a wavelet preprocessor Authors: Chao, T.-H.; Hegbloni, E.; Lae, B.; Stone, W.W.; Michdi, W.I. Affiliation: Jet Propulsion Lab., California Inst. of Technol., Pasadena, C.A. USA Journal: Proceedings of the SPIE—The International Society for Optical Engineering vol. 2026 pp. 472-283 Date: 1993.

Title: A fractal detection algorithm for a Ladar Sensor Authors: Schweiker, K.S. Affiliation: Hercules Defense Electron. Syst. Inc., Clearwater, FL, USA Journal: Proceedings of the SPIE—The International Society for Optical Engineering vol. 1960 pp. 33-38 Date: 1993.

Inspec 4579882 B9403-6140C-011 C9403-5260B-007 Doc Type: Conference Paper in Journal Title: Experiments in the use of fractal in computer pattern recognition Authors: Sadjadi, F. Affiliation: Mach. Intelligence Co., Los Angeles, CA, USA Journal: Proceedings of the SPIE—The International Society for Optical Engineering vol. 1960 pp. 214-222 Date: 1993.

Inspec 4628608 C9405-5260B-064 Doc Type: Journal Paper Title: Adaptive edge detection with fractal dimension Authors: Cheong, C.K.; Aizawa, K.; Salio, T.; Hatori, M. Affiliation: Fac. of Eng., Tokyo Univ., Japan Journal: Transactions of the Institute of Electronics. Information and Communication Engineers D-II vol. J176D-II Iss: 11 pp. 2459-2463 Date: Nov. 1993.

Inspec 4666480 B9406-6140C-147 C9406-1250-192 Doc Type: Journal Paper Title: Affine point matching Authors: Sprinzak, J.; Werman, M. Affiliation: Dept. of Comput. Sci., Hebrew Univ., Jerusalem, Israel Journal: Pattern Recognition, Jetters vol. 15 Iss: 4 pp. 337-339 Date: Apr. 1994.

Inspec 4619976 C9404-5260B-168 Doc Type: Conference Paper in Journal Title: Algorithm for dynamic object tracking Authors: Datcu, M.; Folta, F.; Toma, C. Affiliation: Polytechnic Inst. of Bucharest, Romania Journal: Proceedings of the SPIE--The International Society for Optical Engineering vol. 1825 pp. 389-394 Date: 1992.

Inspec 4706074 B9408-6310-021 Doc Type: Conference Paper Title: The Concept of kinematical image and its practical use in radar target studies Authors; Bertrand, J.; Bertrand, P.; Vignaud, L. Affiliation: CNRS, Paris VII Univ., France Conf. Title: Time-Varying Image Processing and Moving Object Recognition, 3. Proceedings of the 4th International Workshop pp. 217-224 Editors: Cappellini, V. Publisher: Elsevier Amsterdam, Netherlands Date: 1994 xiii+429 pp.

Inspec 4706056 B9408-6140C-143 C9408-1250-088 Doc Type: Conference Paper Title: Spotting recognition of human gestures from motion images Authors: Takahash. K.; Schl. S.; Oka, R. Affiliation: Tsukube Res. Center, Ibaraki, Japan Conf. Title: Time-Varying Image Processing and Moving Object Recognition. 3. Proceedings of the 4th International Workshop pp. 65-72 Editors: Cappellini, V. Publisher: Elsevier Amsterdam, Netherland Date: 1994 xiii+429 pp.

Inspec 4704763 C9408-7150-019 Doc Type: Journal Paper Title: Design and implementation of map database systems (MDS) Authors: Tan Guozben, Huang Qingming; Gao Wen; Zhang Tianwon; Zhu Zhiying Affiliation: Dept. of Comput. Sci. & Eng., Dalian Univ. of Technol., China Journal: Journal of Dalian University of Technology vol. 34 Iss: 2 pp. 180-184 Date: Apr. 1994.

Inspec 4701197 B9408-0100-026 C9408-1250-066 Doc Type: Conference Proceedings Conf. Title: Proceedings of the IEEE Southwest Symposium on Image Analysis and Interpretation Publisher: IEEE Comput. Soc. Press Los Alamitos, CA, USA Date: 1994 viii+167 pp.

Inspec 4699527 B9408-6140C-076 C9408-52608-5260B-043 Doc Type: Journal Paper Title: A probabilistic matching algorithm for computer vision Authors: Camps, O.I.; Shapiro, L.G.; Haralick, R.M. Affiliation: Dept. of Electr. Eng., Pennsylvania State Univ., University Park, PA, USA Journal: Annals of Mathematics and Artifical Intelligence vol. 10 Iss: 1-2 pp. 85-124 Date: May 1994. Doc Type: Journal Paper Title: Road recognition with a neural networks Authors: MacKeown, W.P.J.; Greenway, P.; Thomas, B.T.; Wright, W.A. Affiliation: Adv. Comput. Res. Centre, Bristol Univ., UK Journal Engineering Applications of Artifical Intelligence vol. 7 Iss: 2 pp. 169-176 Date: Apr. 1994.

Inspec 4697282 C9408-5260B-031 Doc Type: Conference Paper in Journal Title: Hybrid pyramid/neural network object recognition Authors: Ansidan, P.; Burt, P.J.; Pearson, J.C.; Spence, C.D. Affiliation: David Semoff Res. Center, Princeton, NJ, USA Journal: Proceedings of the SPIE—The International Society for Optical Engineering vol. 2103 pp. 92-97 Date: 1994.

Inspec 4697256 A9415-4230-041 B9408-4180-010 C9408-1250-025 Doc Type: Conference Paper in Journal Title: Large-scale neural network model for multi-class pattern recognition Authors: Phys. Optics Corp., Torrance, CA, USA Affiliation: Lu, T.; Lin, F.; Chou, H.; Kostrzewski, A.; Chen, J. Journal: Proceedings of the SPIE—The International Society for Optical Engineering vol. 2026 pp. 403-414 Date: 1993.

Inspec 46977248 A9415-4230-036 B9408-6140C-046 C9408-1250-021 Doc Type: Conference Paper in Journal Title: Spatially multiplexed composite filters for optical pattern recognition Authors: Abushagur, M.A.G. Affiliation: Dept. of Electr. & Comput. Eng., Alabama Univ., Huntsville, AL, USA Journal: Proceedings of the SPIE—The International Society for Optical Engineering vol. 2026 pp. 338-343 Date: 1993.

Inspec 4696291 A9415-4230-031 B9408-6140C-041 C9408-1250-018 Doc Type: Journal Paper Title: Invariant optical pattern recognition based on a contour bank Authors: Shoude Chang; Arsenault, H.H.; Dahe Liu Affiliation: Dept. de Phys., Laval Univ., Que., Canada Journal: Applied Optics vol. 33 Iss: 14 pp. 3076-3085 Date: May 10, 1994.

Inspec 4696290 A9415-4230-030 B9408-6140C-040 Doc Type: Journal Paper Title: Controlled-intensity detection peaks in a binary joint transform correlator Authors: Carnicer, A.; Moneo, I.R. de F. Affiliation: Dept. de Fisica Aplicada I Electron., Barcelona Univ., Spain Journal: Applied Optics vol. 33 Iss: 14 pp. 3070-3075 Date: May 10, 1994.

(56) References Cited

OTHER PUBLICATIONS

Inspec 4695429 B9408-6140C-031 C9408-5260B-013 Doc Type: Conference Paper Title: Vector quantization based target cueing Authors: Call, R.W.; Puisipher, D.C. Affiliation: Paramas Syst. Corp., Salt Lake City, UT, USA Conf. Title: Proceedings of the IEEE 1993 National Aerospace and Electronics Conference. NAECON 1993 (Cat. No.93CH3306-8) pp. 240-244 vol. 1 Publisher: IEEE New York, NY, USA Date: 1993 2 vol. xvii+1171 pp.
Inspec 4695175 C9408-5260B-011 Doc Type: Journal Paper Title: Generated Moment invariant features by cascaded neural network for pattern classification Authors: Raveendran, P.; Omaru, S. Affiliation: Dept. of Electr. Eng., Malaya Univ., Kuala Lumput, Malaysia Journal: Transactions of the Information Processing Society of Japan vol. 35 Iss: 2 pp. 291-300 Date: Feb. 1994.
Inspec 4694463 B9408-6140C-028 C948-5260B-008 Doc Type: Journal Paper Title: Image analysis and computer vision: 1993 Authors: Rosenfeld, A. Affiliation: Center for Aurorn. Res., Maryland Univ., College Park, MD, USA Journal: CVGIP: Image Understanding vol. 59 Iss: 3 pp. 367-396 Date: May 1994.
Inspec 4691104 B9407 6140C-184 C9407-1250-144 Doc Type: Conference Paper Title: Study on Gabor expansion and wavelet decomposition for texture analysis Authors: Nemeth, G.; Boroczky, L. Affiliation: KFKI Res. Inst. for Meas. & Comput. Techniques, Budapest, Hungary Conf. Title: Efficient Texture Analysis: Advanced Methods, Applications (KFKI-1994-2/N) pp. 31-41 Editors: Nemeth, G.; Boroczky, L. Publisher: KFKI Res. Instr. Meas. Comput. Tech Budapest, Hungary Date: 1994 94 pp.
Inspec 4691097 B9407-0100-079 C9407-5260B-083 Doc Type: Conference Proceedings Conf. Title: Proceedings of 4th International Workshop on Time-Varying Image Processing and Moving Object Recognition Editors: Cappellini, V. Publisher: Elsevier Amsterdam, Netherlands Date: 1994 xiii+429 pp.
Inspec 4689867 A9414-4230-026 B9407-6140C-167 C9407-1250-134 Doc Type: Journal Paper Title: Edge enhancement techniques for improving the performance of binary phase-only filter pattern recognition devices Authors: Khoury, J.; Gianino, P.D.; Kane, J.S.; Woods, C.L. Affiliation: Tufts Univ., Medford, MA, USA Journal: Optical Engineering vol. 33 Iss: 3 pp. 856-864 Date: Mar. 1994.
Inspec 4686995 B9407-6140C-139 C9407-1250-110 Doc Type: Conference Paper Title: A new class of fuzzy operators for image processing: design and implementation Authors: Russo, F. Affiliation: Dipartimento di Elettrotecnica Elettronica Inf., Trieste Univ., Italy Conf. Title: Second IEEE International Conference on Fuzzy Systems (Cat. No.93CH3136-9) pp. 815-820 vol. 2 Publisher: IEEE New York, NY, USA Date: 1993 vol. 2 (xviii+xx+1430 pp.).
Erickson, Thomas and Salomon, Gitta "Designing a Desktop Information System: Observations and Issues", CHI '91 Proceedings. (1991) ACM 0-89791-383-3/91/0004/0049,pp. 49-54.
Shepard, Jeffrey, "Tapping the Potential of Data Compression", Military & Aerospace Electronics, May 17, 1993, pp. 25-28.
Meda, Hirotada et al, "Impact: An Interactive Natural-Motion-Picture Dedicated Multimedia Authoring System", CHI '91 Proceedings(1991) ACM 0-889791-383-3/91/0004/0343,pp. 343-350.
Siochi, Antonio C. and Hix, Deborah, "A Study of Computer-Supported User Interface Evaluation Using Maximal Repeating Pattern Analysis", CHI '91 Proceedings(1991). (1991), ACM 0-89791-383-3/91/0004/0301,pp. 301-304.
NSPEC 4596005 B9403-6140C-279 C9403-1250-213 Doc Type: Conference Paper Title: Reducing the complexity of a fractal-based image coder Authors: Oien. G.E.; Leposy, S.; Ramstad, T.A. Affiliation: Inst. for Teleteknikk, Norges Tekniska Hogskola Trondheim Norway Conf. Title: Signal Processing VI, Theories And Applications, Proceedings of EUSIPCO-92, Sixth European Signal Processing Conference p. 1353-6 vol. 3 Editors: Vandewalle J.; Bolte, R.; Moonen, M.; Oosterlinck, A. Publisher: Elsevier Amsterdam, Netherlands Date: 1992 3 vol. |vi| 1844 pp.
INSPEC 4588458 B9403-6140C-121 C9403-1250-100 Doc Type: Journal Paper Title: Viewpoint independent representation and recognition of polygonal faces in 3-D Authors: Bunke, H.; Glauser, T. Affiliation: Bern Univ, Switzerland Journal: IEEE Transactions on Robotics and Automation vol. 9 Iss. 4 p.457-63. Date: Aug. 1993.
INSPEC 4584412 B9403-6140C-070 C9403-1250-053 Title: Application of the EM technique to estimation of affine modeled image motion Authors: Shaltaf, S.; Namazi, N.M. Affiliation: Dept. of Electr. Eng., Michigan Technol. Univ. Houghton, MI, USA Conf. Title: Proceedings of the 35.sup.th Midwest Symposium on Circuits and Systems (Cat. No. 92CH3099-9) p. 1324-7 Publisher: IEEE New York, NY, USA Date 1992 2 vol. xxvii+1584 pp.
INSPEC 458378 C9403-5260B-028 Doc Type: Conference Paper Title: Frame-to-frame image motion estimation with fuzzy logic system Authors: Lipp, J. I. Affiliation: Dept. of Electr. Eng., Michigan Technol. Univ. Houghton, MI, USA Conf. Title: Proceedings of the 35$^{th}$ Midwest Symposium on Circuits and Systems (Cat. No. 92 CH3099-9) p. 987-90-7 vol. 2 Publisher: IEEE New York, NY, USA Date 1992 2 vol. xxvii+1584 pp.
INSPEC 4582942 C9403-4260-006 Doc Type: Journal Paper Title: Recognition of affine transformed planar curves by external geometric properties Authors: Gotsman, C.; Werman, M. Affiliation: Dept. of Comput. Sci., Technion, Israel Inst. of Technol., Haifa, Israel Journal: International Journal of Computational Geometry & Applications vol. 3 Iss: 2 p. 183-202 Date: Jun. 1993.
INSPEC 4580742 B9403-6140C-033 C9403-1250-022 Doc Type: Journal Paper Title: On the calculation of Fractal features from images Authors: Chen, S.S.; Keller, J.M.; Crownover, R. M. Affiliation: Allied Bendix/King Radio Corp., Olathe, KS, USA Journal: IEEE Transactions on Pattern Analysis and Machine Intelligence vol. 15 Iss: 10 p. 1087-90 Date: Oct. 1993.

* cited by examiner

Existing Interface

New Interface

*New*

ERGONOMIC MAN-MACHINE INTERFACE INCORPORATING ADAPTIVE PATTERN RECOGNITION BASED CONTROL SYSTEM

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

The present application is a *continuation of U.S. patent application Ser. No. 12/271,602, filed Nov. 14, 2008, which is a reissue application of U.S. Pat. No. 7,136,710, which granted on Nov. 14, 2006 from U.S. patent application Ser. No. 08/469,589, filed on Jun. 6, 1995, which is a* continuation-in-part of U.S. patent application Ser. No. 07/812,805, filed Dec. 23, 1991, now U.S. Pat. No. 5,903,454. *This application is also a reissue application of the above-mentioned U.S. Pat. No. 7,136,710. This application is therefore a continuation reissue. U.S. patent application Ser. No. 15/411,939, filed on the same date as this application, is also a reissue application of the above-mentioned U.S. Pat. No. 7,136,710.*

A portion of the disclosure of this patent document and appendices contain material which is subject to copyright protection. The copyright owner has no objection to the facsimile reproduction by anyone of this patent document or the patent disclosure, as it appears in the U.S. Patent and Trademark Office patent file or records, but otherwise reserves all copyright rights whatsoever.

FIELD OF THE INVENTION

The present invention relates to the field of programmable man-machine interfaces, for general or special purpose computing or sequencing devices. The present interface system is ergonomically adapted to provide an optimized environment for human interaction with the device. The present system preferably employs a graphical direct-manipulation style interface. The present invention provides an enhanced interface for facilitating human input of a desired information and for modifying information previously entered information.

BACKGROUND OF THE INVENTION

Significant difficulties are experienced by users when complex programmable devices having multiple commands which are infrequently used or programmed by those users. Further, when a user attempts to use an uncommon or rarely used function of these devices, which may be, for example video cassette recorders (hereinafter "VCRs") difficulties are also encountered. For example, studies have concluded that 80% of users cannot correctly program their VCRs. This has been due, in part, to the fact that manufacturers continue to add more features to existing devices, without simplifying those which already exist. Another problem has been the failure of manufacturers to design products in which the control interface adapts to the behavior of the user or to allow a system to be adaptive to the behaviors of a plurality of users.

People learn most efficiently through the interactive experiences of doing, thinking, and knowing. Learning may often be facilitated by observing an experienced teacher. For ease-of-use, efficiency, and lack of frustration of the user, utilizing the device should be intuitive. Users should be able to operate the device without referring to an instruction manual. Often, actual working examples are helpful. Well-designed products should contain visual clues which prompt and convey their meanings, however, prior art devices do not always live up to this ideal. This problem of insufficient perceptual clues to cue the user as to the identity and nature of available choices is accentuated by various manufacturers and designers who focus on the production and design of feature-rich systems, rather than on ones which are also "User Friendly" and thus easier to use. Therefore, many products are extremely complex and thus difficult to use, thereby preventing all but the most technically advanced people from using them. Other products are simple to use for a low level of functionality, but make it extremely difficult to transcend an arbitrary barrier set by the interface designer.

Some display systems have a higher available resolution than others, and the interface is preferably arranged to optimize the intended display for the resolution limits and display format of the intended or available display device. Further, even with sufficient resolution, certain displays are of small size, and thus the visibility of the information may also be optimized by taking into consideration the size, resolution, contrast, brightness of the display, ambient conditions, characteristics of the human visual system, factors specific for a known user, and the available options of the apparatus. Thus, the interface may employ a number of methods to optimize the visibility of the information for a variety of display devices, storage formats and transmission standards. Known display standards and types include: National Television Standards Committee (NTSC), Phase Alternate Line (PAL), Sequential Coleur à Memoire (SECAM), Comité Consultatif International des Radio-communications (International Radio Consultative Committee, Geneva, Switzerland) (CCIR) standard 601 (encoding parameters for digital television); High Definition Television (HDTV), Multiple Sideband Encoding (MUSE), Improved Definition Television (IDTV), Video Home System (VHS), Super-Video Home System (S-VHS), Beta, SuperBeta, 8 mm, Hi-8 mm, videotel or picturephone (Px64), International Telecommunication Union (ITU) standard H.261, Motion Picture Experts Group (MPEG) 1, MPEG-2, Joint Photographic Experts Group (JPEG), computer display standards (Color Graphics Adapter (CGA), Hercules Graphic Card (HGC), Enhanced Graphics Adapter (EGA), Video Graphics Array (VGA), Super Video Graphics Array (SVGA), extended Graphics Array (XGA), Macintosh®, 8514/A (IBM high resolution video standard), Private Eye® (a small reflection scanned light emitting diode (LED line array for projecting a virtual image in front of the eye, available from Reflection Technology, Inc.), Liquid Crystal Display (LCD), etc., each of which may have a number of size ranges, e.g. about 1 $cm^2$ to about 10 $m^2$, with a resolution range including displays having about 16 dot matrix characters or more or about 16 by 64 pixels to about 2,048 by 2,048 pixels. Techniques such as antialiasing, font substitution, hinting, precompensating for expected distortion, etc., are all known employed to improve the readability of the display under various circumstances.

PRIOR ART

The prior art details a number of components of the present invention, and in fact, in a number of areas the present invention builds upon the prior art by adding novel aspects disclosed herein to result in improvements. Therefore, as set forth below, and in the attached appendix of references (including abstracts), incorporated herein by reference, a significant number of references detail fundamental technologies which may be improved according to the present invention. To the extent necessary, these technologies are disclosed and are expressly incorporated herein by reference to avoid duplication of prior art teachings. Recitation hereinbelow of these teachings or reference to these teachings is not meant to imply that the inventors hereof were necessarily in any way involved in these references, nor that the particular improvements recited herein were made or conceived after the publication of these references. Thus, prior art cited herein is intended to (1) disclose information related to the application published before the filing hereof; (2) define the problem in the art to which the present invention is directed, (3) define prior art methods of solving various problems also addressed by the present invention; (4) define the state of the art with respect to methods disclosed or referenced herein; and/or (5) detail technologies used to implement methods or apparatus in accordance with the present invention.

Human Interface

One aspect of the present invention relates to a programmable device that comprises a menu-driven interface in which the user enters information using a direct manipulation input device. Such a type of interface scheme is disclosed in Verplank, William L., "Graphics in Human-Computer Communication: Principles of Graphical User-Interface Design", Xerox Office Systems, which is incorporated herein by reference; the references cited therein: Foley, J. D., Wallace, V. L., Chan, P., "The Human Factor of Computer Graphics Interaction Techniques", IEEE CG&A, November 1984, pp. 1348; Koch, H., "Ergonomische Betrachtung von Schreibtastaturen", Humane Production, 1, pp. 12-15 (1985); Norman, D. A., Fisher, D., "Why Alphabetic Keyboards Are Not Easy To Use: Keyboard Layout Doesn't Much Matter", Human Factors 24(5), pp. 509-519 (1982); Perspectives: High Technology 2, 1985; Knowlton, K., "Virtual Pushbuttons as a Means of Person-Machine Interaction", Proc of Conf. Computer Graphics, Pattern Recognition and Data Structure, Beverly Hills, Calif., May 1975, pp. 350-352; "Machine Now Reads, enters Information 25 Times Faster Than Human Keyboard Operators", Information Display 9, p. 18 (1981); "Scanner Converts Materials to Electronic Files for PCs", IEEE CG&A, December 1984, p. 76; "New Beetle Cursor Director Escapes All Surface Constraints", Information Display 10, p. 12, 1984; Lu, C., "Computer Pointing Devices: Living With Mice", High Technology, January 1984, pp. 61-65; "Finger Painting", Information Display 12, p. 18, 1981; Kraiss, K. F., "Neuere Methoden der Interaktion an der Schnittstelle Mensch-Maschine", Z. F. Arbeitswissenschaft, 2, pp. 65-70, 1978; Hirzinger, G., Landzettel, K., "Sensory Feedback Structures for Robots with Supervised Learning", IEEE Conf. on Robotics and Automation, St. Louis, March 1985; Horgan, H., "Medical Electronics", IEEE Spectrum, January 1984, pp. 90-93, are also incorporated herein by reference.

The following references, expressly incorporated herein by reference, are relevant to the interface aspects of the present invention, certain of which are incorporated by reference in U.S. patent application Ser. No. 07/812,805, incorporated herein by reference:

Hoffberg, Linda I, "AN IMPROVED HUMAN FACTORED INTERFACE FOR PROGRAMMABLE DEVICES: A CASE STUDY OF THE VCR" Master's Thesis, Tufts University (Master of Sciences in Engineering Design, November, 1990).

"Bar Code Programs VCR", Design News, Feb. 1, 1988, 26.

"The Highs and Lows of Nielsen Homevideo Index", Marketing & Media Decisions, November 1985, 84-86+.

"The Quest for 'User Friendly'", U.S. News & World Report, Jun. 13, 1988. 54-56.

"The Smart House: Human Factors in Home Automation", Human Factors in Practice, December 1990, 1-36.

"VCR, Camcorder Trends", Television Digest, Vol. 29:16 (Mar. 20, 1989).

Abedini, Kamran, "An Ergonomically-improved Remote Control Unit Design", Interface '87 Proceedings, 375-380.

Abedini, Kamran, and Hadad, George, "Guidelines For Designing Better VCRs", Report No. IME 462, Feb. 4, 1987.

Bensch, U., "VPV—VIDEOTEXT PROGRAMS VIDEORECORDER", IEEE Transactions on Consumer Electronics, 34(3):788-792.

Berger, Ivan, "Secrets of the Universals", Video, February 1989, 4547+.

Beringer, D. B., "A Comparative Evaluation of Calculator Watch Data Entry Technologies: Keyboards to Chalkboards", Applied Ergonomics, December 1985, 275-278.

Bishop, Edward W., and Guinness, G. Victor Jr., "Human Factors Interaction with Industrial Design", Human Factors, 8(4):279-289 (August 1966).

Brown, Edward, "Human Factors Concepts For Management", Proceedings of the Human Factors Society, 1973, 372-375.

Bulkeley, Debra, "The Smartest House in America", Design News, Oct. 19, 1987, 56-61.

Card, Stuart K., "A Method for Calculating Performance times for Users of Interactive Computing Systems", IEEE, 1979, 653-658.

Carlson, Mark A., "Design Goals for an Effective User Interface", Electro/82 Proceedings, 3/1/1-3/1/4.

Carlson, Mark A., "Design Goals for an Effective User Interface", Human Interfacing with Instruments, Session 3.

Carroll, Paul B., "High Tech Gear Draws Cries of "Uncle", Wall Street Journal, Apr. 27, 1988, 29.

Cobb, Nathan, "I don't get it", Boston Sunday Globe Magazine, Mar. 25, 1990, 23-29.

Davis, Fred, "The Great Look-and-Feel Debate", A+, 5:9-11 (July 1987).

Dehning, Waltraud, Essig Heidrun, and Maass, Susanne, The Adaptation of Virtual Man-Computer Interfaces to User Requirements in Dialogs, Germany: Springer-Verlag, 1981.

Ehrenreich, S. L., "Computer Abbreviations—Evidence and Synthesis", Human Factors, 27(2):143-155 (April 1985).

Friedman, M. B., "An Eye Gaze Controlled Keyboard", Proceedings of the 2nd International Conference on Rehabilitation Engineering, 1984, 446-447.

Gilfoil, D., and Mauro, C. L., "Integrating Human Factors and Design: Matching Human Factors Methods up to Product Development", C. L. Mauro Assoc., Inc., 1-7.

Gould, John D., Boies, Stephen J., Meluson, Antonia, Rasammy, Marwan, and Vosburgh, Ann Marie, "Entry and Selection Methods For Specifying Dates". Human Factors, 32(2):199-214 (April 1989).

Green, Lee, "Thermo Tech: Here's a common sense guide to the new thinking thermostats", Popular Mechanics, October 1985, 155-159.

Grudin, Jonathan, "The Case Against User Interface Consistency", MCC Technical Report Number ACA-HI-002-89, January 1989.

Harvey, Michael G., and Rothe, James T., "VideoCassette Recorders: Their Impact on Viewers and Advertisers", Journal of Advertising, 25:19-29 (December/January 1985).

Hawkins, William J., "Super Remotes", Popular Science, February 1989, 76-77.

Henke, Lucy L., and Donohue, Thomas R., "Functional Displacement of Traditional TV Viewing by VCR Owners", Journal of Advertising Research, 29:18-24 (April-May 1989).

Hoban, Phoebe, "Stacking the Decks", New York, Feb. 16, 1987, 20:14. "How to find the best value in VCRs", Consumer Reports, March 1988, 135-141.

Howard, Bill, "Point and Shoot Devices", PC Magazine, 6:95-97 (August 1987).

Jane Pauley Special, NBC TV News Transcript, Jul. 17, 1990, 10:00 PM.

Kolson, Ann, "Computer wimps drown in a raging sea of technology", The Hartford Courant, May 24, 1989, B1.

Kreifeldt, J. G., "A Methodology For Consumer Product Safety Analysis", The 3rd National Symposium on Human Factors in Industrial Design in Consumer Products, August 1982, 175-184.

Kreifeldt, John, "Human Factors Approach to Medical Instrument Design", Electro/82 Proceedings, 3/3/1-3/3/6.

Kuocheng, Andy Poing, and Ellingstad, Vernon S., "Touch Tablet and Touch Input", Interface '87, 327.

Ledgard, Henry, Singer, Andrew, and Whiteside, John, Directions in Human Factors for Interactive Systems, New York, Springer-Verlag, 1981.

Lee, Eric, and MacGregor, James, "Miniming User Search Time Menu Retrieval Systems", Human Factors, 27(2): 157-162 (April 1986).

Leon, Carol Boyd, "Selling Through the VCR", American Demographics, December 1987, 4043.

Long, John, "The Effect of Display Format on the Direct Entry of Numerical Information by Pointing", Human Factors, 26(1):3-17 (February 1984). "Low-Cost VCRs: More For Less", Consumer Reports, March 1990, 168-172.

Mantei, Marilyn M., and Teorey, Toby J., "Cost/Benefit Analysis for Incorporating Human Factors in the Software Lifecycle", Association for Computing Machinery, 1988.

Meads, Jon A., "Friendly or Frivolous", Datamation, Apr. 1, 1988, 98-100.

Moore, T. G. and Dartnall, "Human Factors of a Microelectronic Product: The Central Heating Timer/Programmer", Applied Ergonomics, 1983, 13(1):15-23.

"Nielsen Views VCRs", Television Digest, Jun. 23, 1988, 15.

Norman, Donald A., "Infuriating By Design", Psychology Today, 22(3):52-56 (March 1988).

Norman, Donald A., The Psychology of Everyday Things, New York, Basic Book, Inc. 1988.

Platte, Hans-Joachim, Oberjatzas, Gunter, and Voessing, Walter, "A New Intelligent Remote Control Unit for Consumer Electronic Device", IEEE Transactions on Consumer Electronics, Vol. CE-31(1):59-68 (February 1985).

Rogus, John G. and Armstrong, Richard, "Use of Human Engineering Standards in Design", Human Factors, 19(1):15-23 (February 1977).

Rosch, Winn L., "Voice Recognition: Understanding the Master's Voice", PC Magazine, Oct. 27, 1987, 261-308.

Sarver, Carleton, "A Perfect Friendship", High Fidelity, 39:4249 (May 1989).

Schmitt, Lee, "Let's Discuss Programmable Controllers", Modem Machine Shop, May 1987, 90-99.

Schniederman, Ben, Designing the User Interface: Strategies for Effective Human-Computer Interaction, Reading, Mass., Addison-Wesley, 1987.

Smith, Sidney J., and Mosier, Jane N., Guidelines for Designing User Interface Software, Bedford, Mass., MITRE, 1986.

Sperling, Barbara Bied, Tullis Thomas S., "Are You a Better 'Mouser' or 'Trackballer'? A Comparison of Cursor—Positioning Performance", An Interactive/Poster Session at the CHI+GI'87 Graphics Interface and Human Factors in Computing Systems Conference.

Streeter, L. A., Ackroff, J. M., and Taylor, G. A. "On Abbreviating Command Names", The Bell System Technical Journal, 62(6):1807-1826 (July/August 1983).

Swanson, David, and Klopfenstein, Bruce, "How to Forecast VCR Penetration", American Demographic, December 1987, 4445.

Tello, Ernest R., "Between Man And Machine", Byte, September 1988, 288-293.

Thomas, John, C., and Schneider, Michael L., Human Factors in Computer Systems, New Jersey, Ablex Publ. Co., 1984.

Trachtenberg, Jeffrey A., "How do we confusse thee? Let us count the ways", Forbes, Mar. 21, 1988, 159-160.

Tyldesley, D. A., "Employing Usability Engineering in the Development of Office Products", The Computer Journal", 31(5):431-436 (1988). "VCR's: A Look At The Top Of The Line", Consumer Reports, March 1989, 167-170.

Verplank, William L., "Graphics in Human-Computer Communication: Principles of Graphical User-Interface Design", Xerox Office Systems. "VHS Videocassette Recorders", Consumer Guide, 1990, 17-20.

Voyt, Carlton F., "PLC's Learn New Languages", Design News, Jan. 2, 1989, 78.

Whitefield, A. "Human Factors Aspects of Pointing as an Input Technique in Interactive Computer Systems", Applied Ergonomics, June 1986, 97-104.

Wiedenbeck, Susan, Lambert, Robin, and Scholtz, Jean, "Using Protocol Analysis to Study the User Interface", Bulletin of the American Society for Information Science, June/July 1989, 25-26.

Wilke, William, "Easy Operation of Instruments by Both Man and Machine". Electro/82 Proceedings, 3/2/1-3/2/4.

Yoder, Stephen Kreider, "U.S. Inventors Thrive at Electronics Show", The Wall Street Journal, Jan. 10, 1990, B1.

Zeisel, Gunter, Tomas, Philippe, Tomaszewski, Peter, "An Interactive Menu-Driven Remote Control Unit for TV-Receivers and VC-Recorders", IEEE Transactions on Consumer Electronics, 34(3):814-818.

A menu based remote control-contained display device is disclosed in Platte, Oberjatzas, and Voessing, "A New Intelligent Remote Control Unit for Consumer Electronic Device", IEEE Transactions on Consumer Electronics, Vol. CE-31, No. 1, February 1985, 59-68, incorporated herein by reference. This system does not incorporate on-screen programming, nor various aspects of the display of the present invention.

A directional or direct manipulation-type sensor based infrared remote control is disclosed in Zeisel, Tomas, Tomaszewski, "An Interactive Menu-Driven Remote Control Unit for TV-Receivers and VC-Recorders", IEEE Transactions on Consumer Electronics, Vol. 34, No. 3, 814-818 (1988), incorporated herein by reference, which relates to a control for programming with the West German Videotext system. This is a different implementation of the Videotext programming system than described in Bensch, U., "VPV—VIDEOTEXT PROGRAMS VIDEORECORDER", IEEE Transactions on Consumer Electronics, Vol. 34, No. 3, 788-792 (1988), incorporated herein by reference, which describes the system of Video Program System Signal Transmitters, in which the VCR is programmed by entering a code for the Video Program System signal, which is emitted by television stations in West Germany. Each separate program has a unique identifier code, transmitted at the beginning of the program, so that a user need only enter the code for the program, and the VCR will monitor the channel for the code transmission, and begin recording when the code is received, regardless of schedule changes. The Videotext Programs Recorder (VPV) disclosed does not intelligently interpret the transmission, rather the system reads the transmitted code as a literal label, without any analysis or determination of a classification of the program type.

Known manual input devices include the trackball, mouse, and joystick. In addition, other devices are known, including the so-called "J-cursor" or "mousekey" which embeds a two (x,y) or three (x,y,p) axis pressure sensor in a button conformed to a finger, present in a general purpose keyboard; a keyboard joystick of the type described in Electronic Engineering Times, Oct. 28, 1991, p. 62, "IBM Points a New Way"; a so-called "isobar" which provides a two axis input by optical sensors (θ,x), a two and one half axis (x,y,digital input) input device, such as a mouse or a "felix" device, infrared, acoustic, etc.; position sensors for determining the position of a finger or pointer on a display screen (touch-screen input) or on a touch surface, e.g., "GlidePoint" (ALPS/Cirque); goniometer input (angle position, such as human joint position detector), etc. Many of such suitable devices are summarized in Kraiss, K. F., "Alternative Input Devices For Human Computer Interaction", Forschunginstitut Fur Anthropotecahnik, Werthhoven, F. R. Germany, incorporated herein by reference. A new device, which may also be suitable is the GyroPoint, available from Gyration Inc., which provides 2-D or 3-D input information in up to six axes of motion: height, length, depth, roll, pitch and yaw. While such a device is generally considered too complex and costly for use with a VCR, and is therefore not most preferred for a VCR embodiment, the many degrees of freedom available may provide suitable input for other types of controllers, such as those based on "Virtual Reality" or which track a moving object, where many degrees of freedom and a high degree of input accuracy is required. The Hallpot, a device which pivots a magnet about a Hall effect sensor to produce angular orientation information, a pair of which may be used to provide information about two axes of displacement, available from Elweco, Inc, Willoughby, Ohio, may also be employed as an input device.

These input devices may be broken down into a number of categories: direct inputs, i.e. touch-screen and light pen; indirect inputs, i.e. trackball, joystick, mouse, touch-tablet, bar code scanner (see, e.g., Atkinson, Terry, "VCR Programming: Making Life Easier Using Bar Codes"), keyboard, and multi-function keys; and interactive input, i.e. Voice activation/instructions (see, e.g., Rosch, Winn L., "Voice Recognition: Understanding the Master's Voice", PC Magazine, Oct. 27, 1987, 261-308); and eye tracker and data suit/data glove (see, e.g. Tello, Ernest R., "Between Man And Machine", Byte, September 1988, 288-293; products of EXOS, Inc; Data Glove).

Each of the aforementioned input devices has advantages and disadvantages, which are summarized in the table below.

TABLE

| DEVICE | ADVANTAGES | DISADVANTAGES |
|---|---|---|
| Touch-Screen: a device which allows users to point directly to the screen to enter their choices. | accurate. fast. "natural" pointing device. Hand obscures view. Difficult with curved screens. | Doesn't show location of the cursor on screen. Requires overlay. Requires frequent cleaning. Expensive. Must be within reach envelope. |
| Light Pen: a pen shaped device with which the users touch the screen to select their choices. | Points to the screen. | Inexpensive. Inaccurate. Awkward to use. Pen needs a storage location. Must be within reach envelope. |
| Trackball: a ball mounted on a stationary object; the ball's rolling motion controls the cursor. | Can be mounted and used anywhere. Does not require a horizontal surface. Quick to use. | |
| Joystick: a stick mounted on a object; the stick's movement controls the cursor. | Can be mounted and used anywhere. Does not require a horizontal surface. | Clumsy for cursor control. |
| Mouse: a ball mounted on the bottom of a movable object, which is rolled on a horizontal surface to control the cursor. | Most effective for pointing and selecting objects on the screen. Popular. | Requires a horizontal surface area. |
| Touch-Tablet: a pad which sits on a horizontal surface on which selections are made by using a finger or stylus. | Activated with fingers or stylus. | Small interface. Remote from display. |
| Keyboard: a device which lies on horizontal surface and has alphanumeric keys on which to type information. | | Requires a horizontal surface. Large. Many keys. |
| Multi-Function Keys: buttons which serve more than one function. | Inexpensive. Space efficient. | Confusing. |
| Bar Code Scanner: a wand which must be wiped over a bar code to type enter information. Pressing a button then signals the controlling device. | Quick if Barcode is present in TV directory. | May require several tries to send data. Tedious if Barcode is not available in the TV directory. |
| Voice: the use of the human voice to give speech prompts or to accept commands. | Frees hands. Enables disabled persons to use the device. | Requires training. Affected by surrounding noises. Low accuracy. Expensive. Limited vocabulary. sensitive to differences in languages, accents, and speech patterns. |
| Eye Tracker: an optical scanner which is activated by the human eye. | Frees hands. Enables disabled persons to use the device. | Expensive. Inaccurate. |
| Data Suit/Data Glove: a Suit or glove which is controlled by manipulation of an on-screen "Virtual Image". It is controlled by optical | Reacts to hand and body gestures. Gives a 3-D image. | Expensive. Computer intensive. |

TABLE-continued

| DEVICE | ADVANTAGES | DISADVANTAGES |
|---|---|---|
| fibers which measure the degree of bending. | | |

Recent studies suggest that a "direct manipulation" style of interface has advantages for menu selection tasks. This type of interface provides visual objects on the screen which can be manipulated by "pointing" and "clicking" on the them. For example, the popular Graphical User Interfaces ("GUIs"), known in the art, use a direct manipulation style interface. A device such as a touch-screen, with a more natural selection technique, is technically preferable to the direct manipulation method. However, its low accuracy and high cost make other inputs more commercially practical. In addition, the user must be within arms' length of the touch-screen display. In a cursor positioning task, Albert (1982) found the trackball to be the most accurate pointing device and the touch-screen to be the least accurate when compared with other input devices such as the light pen, joystick, data tablet, trackball, and keyboard. Epps (1986) found both the mouse and trackball to be somewhat faster than both the touch-pad and joystick, but he concluded that there were no significant performance differences between the mouse and trackball as compared with the touch-pad and joystick.

It is noted that many present devices, intended for use in computers having graphic interfaces, would advantageously make use of an input device which is accessible, without the necessity of moving the user's hands from the keyboard. Thus, for example, Electronic Engineering Times (EET), Oct. 28, 1991, p. 62, incorporated herein by reference, discloses a miniature joystick incorporated into the functional area of the keyboard. This technique does not employ any minimization of the number of keys.

In a study of menu selection tasks comparing the mouse and the trackball, the accuracy data showed no significant difference between the two. The key finding shows that both mouse users and trackball users performed better with the trackball on the menu selection task. It should be noted that this was not the case for all tasks. The definition of the menu selection task used by Sperling, Bied, Tullis, in "Are You a Better 'Mouser' or 'Trackballer'? A Comparison of Cursor—Positioning Performance", Interactive/Poster Session at the CHI+GI'87 Graphics Interface and Human Factors in Computing Systems Conference, incorporated herein by reference, involves moving the cursor through a list of items and making a selection.

Pattern Recognition

The following cited patents and publications are relevant to pattern recognition and control aspects of the present invention, and are herein expressly incorporated by reference:

U.S. Pat. No. 5,067,163, incorporated herein by reference, discloses a method for determining a desired image signal range from an image having a single background, in particular a radiation image such as a medical X-ray. This reference teaches basic image enhancement techniques.

U.S. Pat. No. 5,068,664, incorporated herein by reference, discloses a method and device for recognizing a target among a plurality of known targets, by using a probability based recognition system. This patent document cites a number of other references, each incorporated herein by reference, which are relevant to the problem of image recognition:

Vannicola et al, "Applications of Knowledge based Systems to Surveillance", Proceedings of the 1988 IEEE National Radar Conference, 20-21 April 1988, pp. 157-164;

Ksienski et al., "Low Frequency Approach to Target Identification", Proc. of the IEEE, 63(12):1651-1660 (December 1975);

Appriou, A., "Interet des theories de l'incertain en fusion de donnees", Colloque International sur le Radar Paris, 24-28 avril 1989;

Appriou, A., "Procedure d'aide a la decision multi-informateurs. Applications a la classification multiapteurs de cibles", Symposiumn de l'Avionics Panel (AGARD) Turquie, 25-29 avril 1988;

Arrow, K. J., "Social choice and individual valves", John Wiley and Sons Inc. (1963);

Blair, D., R. Pollack, "La logique du choix collectif" Pour la Science (1983);

Scharlic, A., "Decider sur plusieurs criteres. Panorama de l'aide a la decision multicritere" Presses Polytechniques Romandes (1985);

Keeney, R. L., B. Raiffa, "Decisions with multiple objectives: Preferences and value tradeoffs", John Wiley and Sons, New York (1976);

Jeffrey, R. J., "The logic of decision", The University of Chicago Press, Ltd., London (1983)(2nd Ed.);

Roy, B., "Classements et choix en presence de points de vue multiples", R.I.R.O.-2eme annee-no. 8, pp. 57-75 (1968);

Roy, B., "Electre III: un algorithme de classements fonde sur une representation floue des preferences en presence de criteres multiples", Cahiers du CERO, 20(1): 3-24 (1978);

Duda, R. O., P. E. Hart, M. J. Nilsson, "Subjective Bayesian methods for rule-based inference systems", Technical Note 124-Artificial Intelligence Center-SRI International;

Bhatnagar, R. K., L. N. Kamal, "Handling uncertain information: a review of numeric and non-numeric methods", Uncertainty in Artificial Intelligence, L. N. Kamal and J. F. Lenuner, Eds. (1986);

Dempster, A. P., "Upper and lower probabilities induced by a multivalued mapping", Annals of mathematical Statistics, no. 38 (1967);

Dempster, A. P., "A generalization of Bayesian inference", Journal of the Royal Statistical Society, Vol. 30, Series B (1968);

Shafer, G., "A mathematical theory of evidence", Princeton University Press, Princeton, New Jersey (1976);

Dubois, D., N. Prade, "Combination of uncertainty with belief functions: a reexamination", Proceedings 9th International Joint Conference on Artificial Intelligence, Los Angeles (1985);

Kyburg, H. E., "Bayesian and non Bayesian evidential updating", Artificial Intelligence 31:271-293 (1987);

Fua, P. V., "Using probability density functions in the framework of evidential reasoning Uncertainty in knowledge based systems", B. Bouchon, R. R. Yager, Eds. Springer Verlag (1987);

Chao, J. J., E. Drakopoulos, C. C. Lee, "An evidential reasoning approach to distributed multiple hypothesis detection", Proceedings of the 20th Conference on decision and control, Los Angeles, Calif., December 1987;

Yager, R. R., "Entropy and specificity in a mathematical theory of Evidence", Int. J. General Systems, 9:249-260 (1983);

Ishizuka, M., "Inference methods based on extended Dempster and Shafer's theory for problems with uncertainty/fuzziness", New Generation Computing, 1: 159-168 (1983), Ohmsha, Ltd, and Springer Verlag;

Zadeh, L. A., "Fuzzy sets", Information and Control, 8:338-353 (1965);

Zadeh, L. A., "Probability measures of fuzzy events", Journal of Mathematical Analysis and Applications, 23:421427 (1968);

Kaufmann, A., "Introduction a la theorie des sousensembles flous", Vol. 1, 2 et 3-Masson-Paris (1975);

Sugeno, M., "Theory of fuzzy integrals and its applications", Tokyo Institute of Technology (1974);

Bellman, R. E., L. A. Zadeh, "Decision making in a fuzzy environment", Management Science, 17(4) (December 1970);

Dubois, D., N. Prade, "Fuzzy sets and systems-Theory and applications", Academic Press, New York (1980);

Zadeh, L. A., "Fuzzy sets as a basis for a theory of possibility", Fuzzy sets and Systems 1:3-28 (1978);

Dubois, D., "Modeles mathematiques de l'imprecis et de l'incertain en vue d'applications aux techniques d'aide a la decision", Doctoral Thesis, University of Grenoble (1983);

Dubois, D., N. Prade, "Theorie des possibilites: application a la representation des connaissances en informatique", Masson, Paris (1985).

U.S. Pat. No. 5,067,161, incorporated herein by reference, relates to a video image pattern recognition system, which recognizes objects in near real time.

U.S. Pat. Nos. 4,817,176and 4,802,230, both incorporated herein by reference, relate to harmonic transform methods of pattern matching of an undetermined pattern to known patterns, and are useful in the pattern recognition method of the present invention. U.S. Pat. No. 4,998,286, incorporated herein by reference, relates to a harmonic transform method for comparing multidimensional images, such as color images, and is useful in the present pattern recognition methods.

U.S. Pat. No. 5,067,166, incorporated herein by reference, relates to a pattern recognition system, in which a local optimum match between subsets of candidate reference label sequences and candidate templates. It is clear that this method is useful in the pattern recognition aspects of the present invention. It is also clear that the interface and control system of the present invention are useful adjuncts to the method disclosed in U.S. Pat. No. 5,067,166.

U.S. Pat. No. 5,048,095, incorporated herein by reference, relates to the use of a genetic learning algorithm to adaptively segment images, which is an initial stage in image recognition. This patent has a software listing for this method. It is clear that this method is useful in the pattern recognition aspects of the present invention. It is also clear that the interface and control system of the present invention are useful adjuncts to the method disclosed in U.S. Pat. No. 5,048,095.

Fractal-Based Image Processing

U.S. Pat. Nos. 5,065,447, and 4,941,193, both incorporated herein by reference, relate to the compression of image data by using fractal transforms. These are discussed in detail below. U.S. Pat. No. 5,065,447 cites a number of references, all incorporated herein by reference, relevant to the use of fractals in image processing:

U.S. Pat. No. 4,831,659;

Barnsley et al., "Hidden Variable Fractal Interpolation Functions", School of Mathematics, Georgia Institute of Technology, Atlanta, Ga. 30332, July, 1986;

Barnsley, M. F., and Demko, S., "Iterated Function Systems and The Global Construction of Fractals", Proc. R. Soc. Lond., A399:243-275 (1985);

Barnsley, M. F., Ervin, V., Hardin, D., Lancaster, J., "Solution of an Inverse Problem for Fractals and Other Sets", Proc. Natl. Acad. Sci. U.S.A., 83:1975-1977 (April 1986);

"A New Class of Markov Processes for Image Encoding", School of Mathematics, Georgia Inst. of Technology (1988), pp. 14-32;

"Fractal Modelling of Biological Structures", Perspectives in Biological Dynamics and Theoretical Medicine, Koslow, Mandell, Shlesinger, eds., Annals of New York Academy of Sciences, vol. 504, 179-194 (date unknown);

Elton, J., "An Ergodic Theorem for Iterated Maps", Journal of Ergodic Theory and Dynamical Systems, 7 (1987);

"Construction of Fractal Objects with Iterated Function Systems", Siggraph '85 Proceedings, 19(3):271-278 (1985);

"Fractal Modelling of Real World Images, Lecture Notes for Fractals: Introduction, Basics and Perspectives", Siggraph (1987);

Peterson, Ivars, "Packing It In-Fractals . . . ", Science News, 131(18):283-285 (May 2, 1987);

"Fractal Geometry-Understanding Chaos", Georgia Tech Alumni Magazine, p. 16 (Spring 1986);

"Fractals-A Geometry of Nature", Georgia Institute of Technology Research Horizons, p. 9 (Spring 1986);

Fractal Modelling of Biological Structures, School of Mathematics, Georgia Institute of Technology (date unknown);

Barnsley et al., "A Better Way to Compress Images", Byte Magazine, January 1988, pp. 213-225;

Derra, Skip, "Researchers Use Fractal Geometry, . . . ", Research and Development Magazine, March 1988;

"Data Compression: Pntng by Numbrs", The Economist, May 21, 1988;

Baldwin, William, "Just the Bare Facts, Please", Forbes Magazine, Dec. 12, 1988;

Barnsley et al., "Harnessing Chaos For Images Synthesis", Computer Graphics, 22(4):131-140 (August, 1988);

Barnsley et al., "Chaotic Compression", Computer Graphics World, November 1987;

Gleick, James, "Making a New Science", pp. 215, 239, date unknown.

Byte Magazine, January 1988, supra, cites:

Mandelbrot, B., "The Fractal Geometry of Nature", W.H. Freeman & Co., San Francisco, Calif., 1982, 1977; and Barnsley, M. F., "Fractals Everywhere", Academic Press, Boston, Mass., 1988, both of which are also incorporated herein by reference.

U.S. Pat. No. 5,347,600, incorporated herein by reference, relates to a method and apparatus for compression and decompression of digital image data, using fractal methods. According to this method, digital image data is automatically processed by dividing stored image data into domain blocks and range blocks. The range blocks are subjected to processes such as a shrinking process to obtain mapped range blocks. The range blocks or domain blocks may also be processed by processes such as amine transforms. Then, for each domain block, the mapped range block which is most similar to the domain block is determined, and the address of that range block and the processes the blocks were subjected to are combined as an identifier which is appended to a list of identifiers for other domain blocks. The list of identifiers for all domain blocks is called a fractal transform and constitutes a compressed representation of the input image. To decompress the fractal transform and recover the input image, an arbitrary input image is formed into range blocks and the range blocks processed in a manner specified by the identifiers to form a representation of the original input image.

"Image Compression Using Fractals and Wavelets", Final Report for the Phase II Contract Sponsored by the Office of Naval Research, Contract No. N00014-91-C0117, Netrologic Inc., San Diego, Calif. (Jun. 2, 1993), expressly incorporated herein by reference, and attached hereto as an appendix, relates to various methods of compressing image data, including fractals and wavelets. This method may also be applicable in pattern recognition applications. This reference provides theory and comparative analysis of compression schemes.

A fractal-processing method based image extraction method is described in Kim, D. H.; Caulfield, H. J.; Jannson, T.; Kostrzewski, A.; Savant, G, "Optical fractal image processor for noise-embedded targets detection", Proceedings of the SPIE—The International Society for Optical Engineering, Vol: 2026 p. 144-9 (1993) (SPIE Conf: Photonics for Processors, Neural Networks, and Memories 12-15 July 1993, San Diego, Calif., USA), expressly incorporated herein by reference. According to this paper, a fractal dimensionality measurement and analysis-based automatic target recognition (ATR) is described. The ATR is a multi-step procedure, based on fractal image processing, and can simultaneously perform preprocessing, interest locating, segmenting, feature extracting, and classifying. See also, Cheong, C. K.; Aizawa, K.; Saito, T.; Hatori, M., "Adaptive edge detection with fractal dimension", Transactions of the Institute of Electronics. Information and Communication Engineers D-II, J76D-II(11):2459-63 (1993); Hayes, H. I.; Solka, J. L.; Priebe, C. E.; "Parallel computation of fractal dimension", Proceedings of the SPIE—The International Society for Optical Engineering, 1962:219-30 (1993); Priebe, C. E.; Solka, J. L.; Rogers, G. W., "Discriminant analysis in aerial images using fractal based features", Proceedings of the SPIE—The International Society for Optical Engineering, 1962:196-208(1993). See also, Anson, L., "Fracal Image Compression", Byte, October 1993, pp. 195-202; "Fractal Compression Goes On-Line", Byte, September 1993.

Methods employing other than fractal-based algorithms may also be used. See, e.g., Liu, Y., "Pattern recognition using Hilbert space", Proceedings of the SPIE—The International Society for Optical Engineering, 1825:63-77 (1992), which describes a learning approach, the Hilbert learning. This approach is similar to Fractal learning, but the Fractal part is replaced by Hilbert space. Like the Fractal learning, the first stage is to encode an image to a small vector in the internal space of a learning system. The next stage is to quantize the internal parameter space. The internal space of a Hilbert learning system is defined as follows: a pattern can be interpreted as a representation of a vector in a Hilbert space; Any vectors in a Hilbert space can be expanded. If a vector happens to be in a subspace of a Hilbert space where the dimension L of the subspace is low (order of 10), the vector can be specified by its norm, an L-vector, and the Hermitian operator which spans the Hilbert space, establishing a mapping from an image space to the internal space P. This mapping converts an input image to a 4-tuple: t in P=(Norm, T, N, L-vector), where T is an operator parameter space, N is a set of integers which specifies the boundary condition. The encoding is implemented by mapping an input pattern into a point in its internal space. The system uses local search algorithm, i.e., the system adjusts its internal data locally. The search is first conducted for an operator in a parameter space of operators, then an error function delta (t) is computed. The algorithm stops at a local minimum of delta (t). Finally, the input training set divides the internal space by a quantization procedure. See also, Liu, Y., "Extensions of fractal theory", Proceedings of the SPIE—The International Society for Optical Engineering, 1966:255-68(1993).

Fractal methods may be used for pattern recognition. See, Sadjadi, F., "Experiments in the use of fractal in computer pattern recognition", Proceedings of the SPIE—The International Society for Optical Engineering, 1960:214-22 (1993). According to this reference, man-made objects in infrared and millimeter wave (MMW) radar imagery may be recognized using fractal-based methods. The technique is based on estimation of the fractal dimensions of sequential blocks of an image of a scene and slicing of the histogram of the fractal dimensions computed by Fourier regression. The technique is shown to be effective for the detection of tactical military vehicles in IR, and of airport attributes in MMW radar imagery.

In addition to spatial self similarity, temporal self-similarity may also be analyzed using fractal methods. See, Reusens, E., "Sequence coding based on the fractal theory of iterated transformations systems", Proceedings of the SPIE—The International Society for Optical Engineering, 2094(pt. 1): 132-40(1993), incorporated herein by reference. This reference describes a scheme based on the iterated functions systems theory which relies on a 3D approach in which the sequence is adaptively partitioned. Each partition block can be coded either by using the spatial self similarities or by exploiting temporal redundancies.

Fractal compression methods may be used for video data for transmission. See, Hurtgen, B.; Buttgen, P., "Fractal approach to low rate video coding", Proceedings of the SPIE— The International Society for Optical Engineering, 2094(pt.1):120-31(1993). This reference relates to a method for fast encoding and decoding of image sequences on the basis of fractal coding theory and the hybrid coding concept. The differential pulse code modulation (DPCM) loop accounts for statistical dependencies of natural image sequences in the temporal direction. Those regions of the original image where the prediction, i.e. motion estimation and compensation, fails are encoded using an advanced fractal coding scheme, suitable for still images, and whose introduction instead of the commonly used DCT-based coding is advantageous especially at very low bit rates (8-64 kbit/s). In order to increase reconstruction quality, encoding speed and compression ratio, some additional features such as hierarchical codebook search and multilevel block segmentation may be employed. This hybrid technique may be used in conjunction with the present adaptive interface or other features of the present invention.

Fractal methods may be used to segment an image into objects having various surface textures. See, Zhi-Yan Xie; Brady, M., "Fractal dimension image for texture segmentation", ICARCV '92. Second International Conference on Automation, Robotics and Computer Vision, p. CV4.3/1-5 vol.1, (1992). According to this reference, the fractal dimension and its change over boundaries of different homogeneous textured regions is analyzed and used to segment textures in infrared aerial images. Based on the fractal dimension, different textures map into different fractal dimension image features, such that there is smooth variation within a single homogeneous texture but sharp variation at texture boundaries. Since the fractal dimension remains unchanged under linear transformation, this method is robust for dismissing effects caused by lighting and other extrinsic factors. Morphology is the only tool used in the implementation of the whole process: texture feature extraction, texture segmentation and boundary detection. This makes possible parallel implementations of each stage of the process.

Rahmati, M.; Hassebrook, L. G., "Intensity- and distortion-invariant pattern recognition with complex linear morphology", Pattern Recognition, 27 (4):549-68(1994) relates to a unified model based pattern recognition approach is introduced which can be formulated into a variety of techniques to be used for a variety of applications. In this approach, complex phasor addition and cancellation are incorporated into the design of filter(s) to perform implicit logical operations using linear correlation operators. These implicit logical operations are suitable to implement high level gray scale morphological transformations of input images. In this way non-linear decision boundaries are effectively projected into the input signal space yet the mathematical simplicity of linear filter designs is maintained. This approach is applied to the automatic distortion- and intensity-invariant object recognition problem. A set of shape operators or complex filters is introduced which are logically structured into a filter bank architecture to accomplish the distortion and intensity-invariant system. This synthesized complex filter bank is optimally sensitive to fractal noise representing natural scenery. The sensitivity is optimized for a specific fractal parameter range using the Fisher discriminant. The output responses of the proposed system are shown for target, clutter, and pseudo-target inputs to represent its discrimination and generalization capability in the presence of distortion and intensity variations. Its performance is demonstrated with realistic scenery as well as synthesized inputs.

Sprinzak, J.; Werman, M., "Affine point matching", Pattern Recognition Letters, 15(4):337-9(1994), relates to a pattern recognition method. A fundamental problem of pattern recognition, in general, is recognizing and locating objects within a given scene. The image of an object may have been distorted by different geometric transformations such as translation, rotation, scaling, general affine transformation or perspective projection. The recognition task involves finding a transformation that superimposes the model on its instance in the image. This reference proposes an improved method of superimposing the model.

Temporal Image Analysis

U.S. Pat. No. 5,280,530, incorporated herein by reference, relates to a method and apparatus for tracking a moving object in a scene, for example the face of a person in videophone applications, comprises forming an initial template of the face, extracting a mask outlining the face, dividing the template into a plurality (for example sixteen) sub-templates, searching the next frame to find a match with the template, searching the next frame to find a match with each of the sub-templates, determining the displacements of each of the sub-templates with respect to the template, using the displacements to determine affine transform coefficients and performing an affine transform to produce an updated template and updated mask.

U.S. Pat. No. 5,214,504 relates to a moving video image estimation system, based on an original video image of time n and time n+1, the centroid, the principal axis of inertia, the moment about the principal axis of inertia and the moment about the axis perpendicular to the principal axis of inertia are obtained. By using this information, an affine transformation for transforming the original video image at time n to the original video image at time n+1 is obtained. Based on the infinitesimal transformation $e^{At}$, and $e^{A(t-1)}$ obtained by making the affine transformation continuous with regard to time is executed on the original video image at time n and time n+1. The results are synthesized to perform an interpolation between the frames. $e^{A(t-1)}$ is applied to the original video system time n+1. The video image after time n+1 is thereby protected.

U.S. Pat. No. 5,063,603, incorporated herein by reference, relates to a dynamic method for recognizing objects and image processing system therefor. This reference discloses a method of distinguishing between different members of a class of images, such as human beings. A time series of successive relatively high-resolution frames of image data, any frame of which may or may not include a graphical representation of one or more predetermined specific members (e.g., particular known persons) of a given generic class (e.g. human beings), is examined in order to recognize the identity of a specific member; if that member's image is included in the time series. The frames of image data may be examined in real time at various resolutions, starting with a relatively low resolution, to detect whether some earlier-occurring frame includes any of a group of image features possessed by an image of a member of the given class. The image location of a detected image feature is stored and then used in a later-occurring, higher resolution frame to direct the examination only to the image region of the stored location in order to (1) verify the detection of the aforesaid image feature, and (2) detect one or more other of the group of image features, if any is present in that image region of the frame being examined. By repeating this type of examination for later and later occurring frames, the accumulated detected features can first reliably recognize the detected image region to be an image of a generic object of the given class, and later can reliably recognize the detected image region to be an image of a certain specific member of the given class. Thus, the personae recognition feature of the present invention may be implemented in this manner. Further, it is clear that this recognition feature may form an integral part of certain embodiments of the present invention. It is also clear that the various features of the present invention would be applicable as an adjunct to the various elements of the system disclosed in U.S. Pat. No. 5,063,603.

U.S. Pat. No. 5,067,160, incorporated herein by reference, relates to a motion-pattern recognition apparatus, having adaptive capabilities. The apparatus recognizes a motion of an object which is moving and is hidden in an image signal, and discriminates the object from the background within the signal. The apparatus has an image forming unit comprising non-linear oscillators, which forms an image of the motion of the object in accordance with an adjacent-mutual-interference-rule, on the basis of the image signal. A memory unit, comprising non-linear oscillators, stores conceptualized meanings of several motions. A retrieval unit retrieves a conceptualized meaning close to the motion image of the object. An altering unit alters the rule, on the basis of the conceptualized meaning. The image forming unit, memory unit, retrieval unit and altering unit form a holonic-loop. Successive alterations of the rules by the altering unit within the holonic loop change an ambiguous image formed in the image forming unit into a distinct image. U.S. Pat. No. 5,067,160 cites the following references, incorporated herein by reference, which are relevant to the task of discriminating a moving object in a background:

U.S. Pat. No. 4,710,964;

Shimizu et al, "Principle of Holonic Computer and Holovision", Journal of the Institute of Electronics, Information and Communication, 70(9):921-930 (1987);

Omata et al, "Holonic Model of Motion Perception", IEICE Technical Reports, Mar. 26,1988, pp. 339-346;

Ohsuga et al, "Entrainment of Two Coupled van der Pol Oscillators by an External Oscillation", Biological Cybernetics, 51:225-239 (1985).

U.S. Pat. No. 5,065,440, incorporated herein by reference, relates to a pattern recognition apparatus, which compensates for, and is thus insensitive to pattern shifting, thus being useful for decomposing an image or sequence of images, into various structural features and recognizing the features. U.S. Pat. No. 5,065,440 cites the following references, incorporated herein by reference, which are also relevant to the present invention: U.S. Pat. Nos. 4,543,660, 4,630,308, 4,677,680, 4,809,341, 4,864,629, 4,872,024 and 4,905,296.

Biometric Analysis

U.S. Pat. No. 5,055,658, incorporated herein by reference, relates to a security system employing digitized personal characteristics, such as voice. The following cited references are incorporated herein by reference:

Naik et al., "High Performance Speaker Verification . . . ", ICASSP 86, Tokyo, CH22434/86/0000-0881, IEEE 1986, pp. 881-884;

"Voice Recognition and Speech Processing", Elektor Electronics, September 1985, pp. 56-57;

Shinan et al., "The Effects of Voice Disguise . . . ", ICASSP 86, Tokyo, CH22434/86/0000-0885, IEEE 1986, pp. 885-888.

Parts of this system relating to speaker recognition may be used to implement a voice recognition system of the present invention for determining an actor or performer in a broadcast.

Neural Networks

U.S. Pat. No. 5,067,164, incorporated herein by reference, relates to a hierarchical constrained automatic learning neural network for character recognition, and thus represents an example of a trainable neural network for pattern recognition, which discloses methods which are useful for the present invention. This Patent cites various references of interest, which are incorporated herein by reference:

U.S. Pat. Nos. 4,760,604, 4,774,677 and 4,897,811;

Rumelhart, D. E., et al., Parallel Distr. Proc.: Explorations in Microstructure of Cognition, vol. 1, 1986, "Learning Internal Representations by Error Propagation", pp. 318-362;

Lippmann, R. P., "An Introduction to Computing with Neural Nets", IEEE ASSP Magazine, 4(2):4-22 (April 1987);

LeCun, Y., Connectionism in Perspective, R. Pfeifer, Z. Schreter, F. Fogelman, L. Steels, (Eds.), 1989, "Generalization and Network Design Strategies", pp. 143-55;

LeCun, Y., et al., "Handwritten Digit Recognition: Applications of Neural . . . ", IEEE Comm. Magazine, pp. 41-46 (November 1989).

U.S. Pat. Nos. 5,048,100, 5,063,601 and 5,060,278, all incorporated herein by reference, also relate to neural network adaptive pattern recognition methods and apparatuses. It is clear that the methods of 5,048,100, 5,060,278 and 5,063,601 may be used to perform the adaptive pattern recognition functions of the present invention. More general neural networks are disclosed in U.S. Pat. Nos. 5,040,134 and 5,058,184, both incorporated herein be reference, which provide background on the use of neural networks. In particular, U.S. Pat. No. 5,058,184 relates to the use of the apparatus in information processing and feature detection applications.

U.S. Pat. No. 5,058,180, incorporated herein by reference, relates to neural network apparatus and method for pattern recognition, and is thus relevant to the intelligent pattern recognition functions of the present invention. This patent cites the following documents of interest, which are incorporated herein by reference:

U.S. Pat. Nos. 4,876,731 and 4,914,708;

Computer Visions, Graphics, and Image Processing 1987, 37:54-115;

Jackel, L. D., H. P. Graf, J. S. Denker, D. Henderson and I. Guyon, "An Application of Neural Net Chips: Handwritten Digit Recognition," ICNN Proceeding, 1988, pp. II-1107-15;

Carpenter, G. A., S. Grossberg, "The Art of Adaptive Pattern Recognition by a Self-Organizing Neural Network," IEEE Computer, March 1988, pp. 77-88;

Pawlicki, T. F., D. S. Lee, J. J. Hull and S. N. Srihari, "Neural Network Models and their Application to Handwritten Digit Recognition," ICNN Proceeding, 1988, pp. 163-70;

Gullichsen E., E. Chang, "Pattern Classification by Neural Network: An Experiment System for Icon Recognition," ICNN Proceeding on Neural Networks, March 1987, pp. IV-725-32;

Grossberg, S., G. Carpenter, "A Massively Parallel Architecture for a Self-Organizing Neural Pattern Recognition Machine," Computer Vision, Graphics, and Image Processing (1987, 37, 54-115), pp. 252-315;

Lippman, R. P., "An Introduction to Computing with Neural Nets," IEEE ASSP Magazine, April 1987, pp. 4-22.

Chao, T.-H.; Hegblom, E.; Lau, B.; Stoner, W. W.; Miceli, W. J., "Optoelectronically implemented neural network with a wavelet preprocessor", Proceedings of the SPIE—The International Society for Optical Engineering, 2026:472-82(1993), relates to an optoelectronic neural network based upon the Neocognitron paradigm has been implemented and successfully demonstrated for automatic target recognition for both focal plane array imageries and range-Doppler radar signatures. A particular feature of this neural network architectural design is the use of a shift-invariant multichannel Fourier optical correlation as a building block for iterative multilayer processing. A bipolar neural weights holographic synthesis technique was utilized to implement both the excitatory and inhibitory neural functions and increase its discrimination capability. In order to further increase the optoelectronic Neocognitron's self-organization processing ability, a wavelet preprocessor was employed for feature extraction preprocessing (orientation, size, location, etc.). A multichannel optoelectronic wavelet processor using an e-beam complex-valued wavelet filter is also described.

Optical Pattern Recognition

U.S. Pat. No. 5,060,282, incorporated herein by reference, relates to an optical pattern recognition architecture implementing the mean-square error correlation algorithm. This method allows an optical computing function to perform pattern recognition functions. U.S. Pat. No. 5,060,282 cites the following references, incorporated herein by reference, which are relevant to optical pattern recognition:

Psaltis, D., "Incoherent Electro-Optic Image Correlator", Optical Engineering, 23(1):12-15 (January/February 1984);

Kellman, P., "Time Integrating Optical Signal Processing", Ph. D. Dissertation, Stanford University, 1979, pp. 51-55;

Molley, P., "Implementing the Difference-Squared Error Algorithm Using An Acousto-Optic Processor", SPIE, 1098:232-239, (1989);

Rhodes, W., "Acousto-Optic Signal Processing: Convolution and Correlation", Proc. of the IEEE, 69(1):65-79 (January 1981);

Vander Lugt, A., "Signal Detection By Complex Spatial Filtering", IEEE Transactions On Information Theory, IT-10, 2:139-145 (April 1964);

Psaltis, D., "Two-Dimensional Optical Processing Using One-Dimensional Input Devices", Proceedings of the IEEE, 72(7):962-974 (July 1984);

Molley, P., et al., "A High Dynamic Range Acousto-Optic Image Correlator for Real-Time Pattern Recognition", SPIE, 938:55-65 (1988).

U.S. Pat. No. 5,063,602, incorporated herein by reference, also relates to an optical image correlators. Also of interest is Li, H. Y., Y. Qiao and D. Psaltis, Applied Optics (April, 1993), incorporated herein by reference. See, See also, Bains, S., "Trained Neural Network Recognizes Paces", Laser Focus World, June, 1993, pp. 26-28; Bagley, H. & Sloan, J., "Optical Processing: Ready For Machine Vision?", Photonics Spectra, August 1993, pp. 101-106.

Optical pattern recognition is useful, especially for two dimensional patterns. In an optical pattern recognition system, an image is correlated with a set of known image patterns represented on a hologram, and the product is a pattern according to a correlation between the input pattern and the provided known patterns. Because this is an optical technique, it is performed nearly instantaneously, and the output information can be reentered into an electronic digital computer through optical transducers known in the art. Such a system is described in Casasent, D., Photonics Spectra, November 1991, pp. 134-140, which is incorporated herein by reference. The references cited therein provide further details of the theory and practice of such a system, and they are also incorporated herein by reference. Lendaris, G. G., and Stanely, G. L., "Diffraction Pattern Sampling for Automatic Target Recognition", Proc. IEEE 58:198-205 (1979); Ballard, D. H., and Brown, C. M., Computer Vision, Prentice Hall, Englewood Cliffs, N.J. (1982); Optical Engineering 28:5 (May 1988)(Special Issue on product inspection); Richards J., and Casasent, D., "Real Time Hough Transform for Industrial Inspection" Proc. SPIE Technical Symposium, Boston 1989 1192:2-21 (1989); Maragos, P., "Tutorial Advances in Morphological Image Processing" Optical Engineering 26:7:623-632 (1987); Casasent, D., and Tescher, A., Eds., "Hybrid Image and Signal Processing II", Proc. SPIE Technical Symposium, April 1990, Orlando Fla. 1297 (1990); Ravichandran, G. and Casasent, D., "Noise and Discrimination Performance of the MINACE Optical Correlation Filter", Proc. SPIE Technical Symposium, April 1990, Orlando Fla., 1471 (1990); Weshsler, H. Ed., "Neural Nets For Human and Machine Perception", Academic Press, New York (1991).

In addition, the following patents are considered relevant to the data compression and pattern recognition functions of the apparatus and interface of the present invention and are incorporated herein by reference: U.S. Pat. Nos. 3,950,733; 4,044,243; 4,254,474; 4,326,259; 4,442,544; 4,449,240; 4,468,704; 4,491,962; 4,501,016; 4,543,660; 4,547,811; 4,630,308; 4,656,665; 4,658,429; 4,658,370; 4,660,166; 4,677,680; 4,682,365; 4,685,145; 4,695,975; 4,710,822; 4,710,964; 4,719,591; 4,731,863; 4,736,439; 4,742,557; 4,752,890; 4,760,604; 4,764,971; 4,771,467; 4,773,024; 4,773,099; 4,774,677; 4,783,752; 4,790,025; 4,799,270; 4,802,103; 4,803,103; 4,803,736; 4,805,224; 4,805,255; 4,809,341; 4,817,171; 4,821,333; 4,823,194; 4,831,659; 4,833,637; 4,837,842; 4,845,610; 4,864,629; 4,872,024; 4,876,731; 4,884,217; 4,887,304; 4,888,814; 4,891,762; 4,897,811; 4,905,296; 4,906,099; 4,914,708; 4,920,499; 4,926,491; 4,931,926; 4,932,065; 4,933,872; .4,941,193; 4,944,023; 4,958,375; 4,958,375; 4,965,725; 4,972,499; 4,979,222; 4,987,604; 4,989,258; 5,014,219; 5,014,327; 5,018,218; 5,018,219; 5,020,112; 5,022,062; 5,034,991; 5,038,379; 5,038,390; 5,040,134; 5,046,121; 5,046,122; 5,046,179; 5,048,112; 5,050,223; 5,051,840; 5,052,043; 5,052,045; 5,052,046; 5,053,974; 5,054,093; 5,054,095; 5,054,101; 5,054,103; 5,055,658; 5,055,926; 5,056,147; 5,058,179; 5,058,180; 5,058,186; 5,059,126; 5,060,276; 5,060,277; 5,060,279; 5,060,282; 5,060,285; 5,061,063; 5,063,524; 5,063,525; 5,063,603; 5,063,605; 5,063,608; 5,065,439; 5,065,440; 5,065,447; 5,067,160; 5,067,161; 5,067,162; 5,067,163; 5,067,164; 5,068,664; 5,068,723; 5,068,724; 5,068,744; 5,068,909; 5,068,911; 5,247,651; 5,388,198; 5,390,125; 5,390,281; H 331; and Re. 33,316. The aforementioned patents, some of which are mentioned elsewhere in this disclosure, and which form a part of this disclosure, may be applied in known manner by those skilled in the art in order to practice various embodiments of the present invention.

The following scientific articles, some of which are discussed elsewhere herein, are incorporated by reference, and their relevance is understood by those skilled in the art and relate to the pattern recognition and image compression functions of the apparatus and interface of the present invention:

Liepins, G. E., M. R. Hilliard, "Genetic Algorithms: Foundations & Applications", Annals of Operations Research, 21:31-58 (1989).

Fitzpatrick, J. M., J. J. Grefenstette, D. Van Gucht, "Image Registration by Genetic Search", Conf. Proc., IEEE Southeastcon 1984, pp.460-464.

McAulay, A. D., J. C. Oh, "Image Learning Classifier System Using Genetic Algorithms", IEEE Proc. of the National Aerospace & Electronics Conference, 2:705-710 (1989).

Wasserman, Philip D., "Neural Computing-Theory & Practice", 1989, pp. 128-129.

Nilsson, N. J., The Mathematical Foundations of Learning Machines ((c) 1990: Morgan Kaufman Publishers, San Mateo, Calif.) and particularly section 2.6 "The Threshold Logic Unit (TLU)", pp. 21-23 and Chapter 6, "Layered Machines" pp. 95-114.

Martin, G. L. et al., "Recognizing Hand-Printed Letters and Digits Using Backpropagation Learning", Technical Report of the MCC, Human Interface Laboratory, Austin, Tex., January 1990, pp. 1-9.

Jean, J. S. N., et al., "Input Representation and Output Voting Considerations for Handwritten Numeral Recognition with Backpropagation", International Joint Conference on Neural Networks, Washington, D.C., January 1990, pp. I-408 to I-411.

Zhu, X., et al., "Feature Detector and. Application to Handwritten Character Recognition", International Joint Conference on Neural Networks, Washington, D.C., January 1990, pp. II-457 to II-460.

Haruki, K. et al., "Pattern Recognition of Handwritten Phonetic Japanese Alphabet Characters", International Joint Conference on Neural Networks, Washington, D.C., January 1990, pp. II-515 to II-518.

Miller, R. K., Neural Networks ((c) 1989: Fairmont Press, Lilburn, Ga.), pp. 2-12 and Chapter 4, "Implementation of Neural Networks", pp. 4-1 to 4-26.

Hayashi, Y., et al., "Alphanumeric Character Recognition Using a Connectionist Model with the Pocket Algorithm", Proceedings of the International Joint Conference on Neural Networks, Washington, D.C. Jun. 18-22, 1989, vol. 2, pp. 606-613.

Caudill, M., "Neural Networks Primer-Part III", Al Expert, June 1988, pp. 53-59.

Burr, D. J., "A Neural Network Digit Recognizer", Proceedings of the 1986 IEEE International Conference of Systems, Man and Cybernetics, Atlanta, Ga., pp. 1621-1625.

Rumelhart, D. E., et al., Parallel Distributed Processing, ((c) 1986: MIT Press, Cambridge, Mass.), and specifically Chapter 8 thereof, "Learning Internal Representations by Error Propagation", pp. 318-362.

Danielsson, Erik, et al., "Computer Architectures for Pictorial Inf. Systems", IEEE Computer, November, 1981, pp. 53-67.

Hopfield et al., "Computing with Neural Circuits: A Model", Science, 233:625-633 (8 August 1986).

Hinton et al., "Boltzmann Machines: Constraint Satisfaction Networks that Learn", Tech. Report CMU-CS-85-119, Carnegie-Mellon Univ, 5/84.

Hopfield, "Neurons with graded response have collective computational properties like those of two-state neurons", Proc. Natl. Acad. Sci. USA, 81:3088-3092 (May 1984).

Willshaw et al., "Non-Holographic Associative Memory", Nature, 222:960-962 (Jun. 7, 1969).

Cooper, L. N., "A Possible Organization of Animal Memory and Learning", Nobel 24, (1973), Collective Properties of Physical Systems, pp. 252-264

Hopfield, "Neural Networks and Physical Systems with Emergent Collective Computational Abilities", Proc. Natl. Acad. Sci. USA, 79:2554-2558 (April 1982).

Batchelor, B. G., "Practical Approach to Pattern Classification", Plenum Press, London and New York, (1974).

Batchelor, B. G., "Pattern Recognition, Ideas in Practice", Plenum Press, London and New York, (1978).

Udagawa, K., et al, "A Parallel Two-Stage Decision Method for Statistical Character Recognition . . . , Electronics and Communications in Japan (1965).

Schurmann, J., "Zur Zeichen und Worterkennung beim Automatischen Anschriftenlesen", Wissenschaftlichl, Berichte, 52(1/2) (1979).

Computers and Biomedical Research 5, 388-410 (1972).

Proceedings, 6th International Conference on Pattern Recognition 1982, pp. 152-136.

Information Processing 71, North-Holland Publishing Company (1972) pp. 1530-1533.

Scientific American, "Not Just a Pretty Face", March 1990, pp. 77-78.

Farrelle, Paul M. and Jain, Anil K., "Recursive Block Coding-A New Approach to Transform Coding", IEEE Transactions on Communications, Com. 34(2) (February 1986).

Yamane et al., "An Image Data Compression Method Using Two-Dimensional Extrapolative Prediction-Discrete Sine Transform", Oct. 29-31, 1986, pp. 311-316.

Chen et al., "Adaptive Coding of Monochrome and Color Images", November 1977, pp. 1285-1292.

O'Neal et al., "Coding Isotropic Images", November 1977, pp. 697-707.

Anderson, F., W. Christiansen, B. Kortegaard, "Real Time, Video Image Centroid Tracker", Apr. 16-20, 1990.

Kortegaard, B. L., "PAC-MAN, a Precision Alignment Control System for Multiple Laser Beams Self-Adaptive Through the Use of Noise", Los Alamos National Laboratory, date unknown.

Kortegaard, B. L., "Superfine Laser Position Control Using Statistically Enhanced Resolution in Real Time", Los Alamos National laboratory, SPIE-Los Angeles Technical Symposium, Jan. 23-25, 1985.

Aleksander, I., "Guide to Pattern Recognition Using Random-Access Memories", Computers and Digital Techniques, 2(1):2940 (February 1979).

Rumelhart, D. E., et al., "Learning Internal Representations by Error Propagation", Parallel Distr. Proc.: Explorations in Microstructure of Cognition, 1:318-362 (1986).

Lippmann, R. P., "An Introduction to Computing with Neural Nets", IEEE ASSP Magazine, vol. 4(2):4-22 (April 1987).

LeCun, Y., "Connectionism in Perspective", in R. Pfeifer, Z. Schreter, F. Fogelman, L. Steels (Eds.), 1989, "Generalization and Network Design Strategies", pp. 143-155.

LeCun, Y. et al., "Handwritten Digit Recognition: Applications of Neural . . . ", IEEE Comm. Magazine, November 1989, pp. 41-46.

Denker, 1984 International Test Conf., October 1984, Philadelphia, Pa., pp. 558-563.

Gogoussis et al., Proc. SPIE Intl. Soc. Opt. Eng., November 1984, Cambridge, Mass., pp. 121-127.

Svetkoff et al., Hybrid Circuits (GB), No. 13, May 1987, pp. 5-8.

Kohonen, "Self-Organization & Memory", Second Ed., 1988, Springer-Verlag, pp. 199-209.

Specht, IEEE Internatl. Conf. Neural Networks, 1:I525-I532 (July 1988), San Diego, Calif.

Wald, Sequential Analysis, Dover Publications Inc., 1947, pp. 34-43.

Rosenfeld, Azriel and Avinash C. Kak, Digital Picture Processing, Second Edition, Volume 2, Academic Press, 1982.

Mori, "Towards the construction of a large-scale neural network", Electronics Information Communications Association Bulletin PRU 88-59, pp. 87-94.

Yamada et. al., "Character recognition system using a neural network", Electronics Information Communications Association Bulletin PRU 88-58, pp. 79-86.

Crawford et al., "Adaptive Pattern Recognition Applied To An Expert System For Fault Diagnosis In Telecommunications Equipment", pp. 10/1-8 (Inspec. Abstract No. 86C010699, Inspec IEE (London) & IEE Coll. on "Adaptive Filters", Digest No. 76, Oct. 10, 1985)

Rutter et al., "The Timed Lattice-A New Approach To Fast Converging Equalizer Design", pp. VIII/1-5 (Inspec. Abstract No. 84C044315, Inpec IEE (London) & IEE Saraga Colloquium on Electronic Filters, May 21, 1984)

Simpson, W. R., C. S. Dowling, "WRAPLE: The Weighted Repair Assistance Program Learning Extension", IEEE Design & Test, 2:66-73 (April 1986).

Dunning, B. B., "Self-Learning Data-Base For Automated Fault Localization", IEEE, 1979, pp. 155-157.

Stewart, R. M., "Expert Systems For Mechanical Fault Diagnosis", IEEE, 1985, pp. 295-300.

Lin, H. K., et al., "Real-Time Screen-Aided Multiple-Image Optical Holographic Matched-Filter Correlator", Applied Optics, 21(18):3278-3286 (Sep. 15, 1982)

Vander Lugt, A., et al., "The Use of Film Nonlinearites in Optical Spatial Filtering", Applied Optics, 9(1):215-222 (January 1970).

Vander Lugt, A., "Practical Considerations for the Use of Spatial Carrier-Frequency Filters", Applied Optics, 5(11):1760-1765 (November 1966).

Silverston et al., "Spectral Feature Classification and Spatial Pattern Rec.", SPIE 201:17-26, Optical Pattern Recognition (1979).

Perry et al., "Auto-Indexing Storage Device", IBM Tech. Disc. Bulletin, 12(8):1219 (January 1970).

Vitols, "Hologram Memory for Storing Digital Data", IBM Tech. Disc. Bulletin 8(11):1581-1583 (April 1966).

Stanley R. Sternberg, "Biomedical Image Processing", IEEE Computer, 1983, pp. 22-34.

Rutherford, H. G., F. Taub and B. Williams, "Object Identification and Measurement from Images with Access to the Database to Select Specific Subpopulations of Special Interest", May 1986.

Ney, H., et al., "A Data Driven Organization of the Dynamic Programming Beam Search for Continuous Speech Recognition", Proc. ICASSP 87, pp. 833-836, 1987.

Sakoe, H., "A Generalization of Dynamic Programming Based Pattern Matching Algorithm Stack DP-Matching", Transactions of the Committee on Speech Research, The Acoustic Society of Japan, p. S83-23, 1983.

Sakoe, H., "A Generalized Two-Level DP-Matching Algorithm for Continuous Speech Recognition", Transactions of the IECE of Japan, E65(11):649-656 (November 1982).

Mahalanobis, A., et al., "Minimum Average Correlation Energy Filters", Applied Optics, 26(17):3633-40 (Sep. 1, 1987).

Spragueu, R. A., "A Review of Acousto-Optic Signal Correlators", Optical Engineering, 16(5):467-74 (September/October 1977)

Casasent, D., et al., "General I and Q Data Processing on a Multichannel AO System", Applied Optics, 25(18): 3217-24 (Sep. 15, 1986).

Vannicola et al., "Applications of Knowledge Based Systems to Surveillance", Proceedings of the 1988 IEEE National Radar Conference, 20-21 April 1988, pp. 157-164.

Ksienski et al., "Low Frequency Approach to Target Identification", Proc. of the IEEE, 63(12):1651-1660 (December 1975).

Appriou, A., "Interet des theories de l'incertain en fusion de donnees", Colloque International sur le Radar Paris, 24-28 avril 1989.

Appriou, A., "Procedure d'aide a la decision multi-informateurs. Applications a la classification multicapteurs de cibles", Symposium de l'Avionics Panel (AGARD) Turquie, 25-29 avril 1988.

Arrow, K. J., "Social choice and individual valves", John Wiley and Sons Inc. (1963).

Blair, D., R. Pollack, "La logique du choix collectif", Pour la Science (1983).

Scharlic, A., "Decider sur plusieurs criteres. Panorama de l'aide a la decision multicritere", Presses Polytechniques Romandes (1985).

Keeney, R. L., B. Raiffa, "Decisions with multiple objectives: Preferences and value tradeoffs", John Wiley and Sons, New York (1976).

Jeffrey, R. J., "The logic of decision", The University of Chicago Press, Ltd., London (1983)(2nd Ed.).

Roy, B., "Classements et choix en presence de points de vue multiples", R.I.R.O.-2eme annee-no. 8, pp. 57-75 (1968).

Roy, B., "Electre HI: un algorithme de classements fonde sur une representation floue des preferences en presence de criteres multiples", Cahiers du CERO, 20(1): 3-24 (1978).

Duda, R. O., P. E. Hart, M. J. Nilsson, "Subjective Bayesian methods for rule-based inference systems", Technical Note 124, Artificial Intelligence Center, SRI International.

Bhatnagar, R. K., L. N. Kamal, "Handling uncertain information: a review of numeric and non-numeric methods", Uncertainty in Artificial Intelligence, L. N. Kamal and J. F. Lemmer, Eds. (1986).

Dempster, A. P., "Upper and lower probabilities induced by a multivalued mapping", Annals of mathematical Statistics, no. 38 (1967).

Dempster, A. P., "A generalization of Bayesian inference", Journal of the Royal Statistical Society, Vol. 30, Series B (1968).

Shafer, G., "A mathematical theory of evidence", Princeton University Press, Princeton, N.J. (1976).

Dubois, D., N. Prade, "Combination of uncertainty with belief functions: a reexamination", Proceedings 9th International Joint Conference on Artificial Intelligence, Los Angeles (1985).

Kyburg, H. E., "Bayesian and non Bayesian evidential updating", Artificial Intelligence 31:271-293 (1987).

Fua, P. V., "Using probability density functions in the framework of evidential reasoning Uncertainty in knowledge based systems", B. Bouchon, R. R. Yager, Eds. Springer Verlag (1987).

Chao, J. J., E. Drakopoulos, C. C. Lee, "An evidential reasoning approach to distributed multiple hypothesis detection", Proceedings of the 20th Conference on decision and control, Los Angeles, Calif., December 1987.

Yager, R. R., "Entropy and specificity in a mathematical theory of Evidence", Int. J. General Systems, 9:249-260 (1983).

Ishizuka, M., "Inference methods based on extended Dempster and Shafer's theory for problems with uncertainty/fuzziness", New Generation Computing, Ohmsha, Ltd, and Springer Verlag, 1:159-168 (1983).

Zadeh, L. A., "Fuzzy sets", Information and Control, 8:338-353 (1965).

Zadeh, L. A., "Probability measures of fuzzy events", Journal of Mathematical Analysis and Applications, 23:421-427 (1968).

Kaufmann, A., "Introduction a la theorie des sousensembles flous", Vol. 1, 2 et 3, Masson, Paris (1975).

Sugeno, M., "Theory of fuzzy integrals and its applications", Tokyo Institute of Technology (1974).

Bellman, R. E., L. A. Zadeh, "Decision making in a fuzzy environment", Management Science, 17(4) (December 1970).

Dubois, D., N. Prade, "Fuzzy sets and systems-Theory and applications", Academic Press, New York (1980).

Zadeh, L. A., "Fuzzy sets as a basis for a theory of possibility", Fuzzy sets and Systems, 1:3-28 (1978).

Dubois, D., "Modeles mathematiques de l'imprecis et de l'incertain en vue d'applications aux techniques d'aide a la decision", Doctoral Thesis, University of Grenoble (1983).

Dubois, D., N. Prade, "Theorie des possibilites: application a la representation des connaissances en informatique", Masson, Paris (1985).

Barnsley et al., "Hidden Variable Fractal Interpolation Functions", School of Mathematics, Georgia Institute of Technology, Atlanta, Ga. 30332, July, 1986.

Anson, L., M. Barnsley, "Graphics Compression Technology", SunWorld, pp. 43-52 (October 1991).

Caffery, B., "Fractal Compression Breakthrough for Multimedia Applications", Inside, Oct. 9, 1991.

"Fractal Modelling of Real World Images", Lecture Notes for Fractals: Introduction, Basics and Perspectives, Siggraph (1987).

"Fractal Geometry-Understanding Chaos", Georgia Tech Alumni Magazine, p. 16 (Spring 1986).

"Fractals Yield High Compression", Electronic Engineering Times, Sep. 30, 1991, p. 39.

"Fractals-A Geometry of Nature", Georgia Institute of Technology Research Horizons, p. 9 (Spring 1986).

"Fractal Modelling of Biological Structures", School of Mathematics, Georgia Institute of Technology (date unknown).

Peterson, Ivars, "Packing It In", Science News, 131(18): 283-285 (May 2, 1987).

Barnsley et al., "A Better Way to Compress Images", Byte Magazine, January 1988.

Barnsley et al., "Harnessing Chaos For Images Systhesis", Computer Graphics, 22(4) (8/1988).

Naik et al., "High Performance Speaker Verification . . . ", ICASSP 86, Tokyo, CH22434/86/0000-0881, IEEE 1986, pp. 881-884.

"Voice Recognition and Speech Processing", Elektor Electronics, September 1985, pp. 56-57.

Shinan et al., "The Effects of Voice Disguise . . . ", ICASSP 86, Tokyo, CH2243-4/86/0000-0885, IEEE 1986, pp. 885-888.

Computer Visions, Graphics, and Image Processing, 1987, 37:54-115.

Jackel, L. D., H. P. Graf, J. S. Denker, D. Henderson and I. Guyon, "An Application of Neural Net Chips: Handwritten Digit Recognition", ICNN Proceeding, 1988, pp. II-107-15.

Carpenter, G. A., S. Grossberg, "The Art of Adaptive Pattern Recognition by a Self-Organizing Neural Network", IEEE Computer, March 1988, pp. 77-88.

Pawlicki, T. F., D. S. Lee, J. J. Hull and S. N. Srihari, "Neural Network Models and their Application to Handwritten Digit Recognition", ICNN Proceeding, 1988, pp. II-63-70.

Gullichsen, E., E. Chang, "Pattern Classification by Neural Network: An Experiment System for Icon Recognition", ICNN Proceeding on Neural Networks, March 1987, pp. IV-725-32.

Grossberg, S., G. Carpenter, "A Massively Parallel Architecture for a Self-Organizing Neural Pattern Recognition Machine", Computer Vision, Graphics, and Image Processing, 1987, 37, 54-115, 252-315.

Lippman, R. P., "An Introduction to Computing with Neural Nets", IEEE ASSP Magazine, April 1987, pp. 4-22.

Psaltis, D., "Incoherent Electro-Optic Image Correlator", Optical Engineering, 23(1):12-15 (January/February 1984).

Kellman, P., "Time Integrating Optical Signal Processing", Ph. D. Dissertation, Stanford University, 1979, pp. 51-55.

Molley, P., "Implementing the Difference-Squared Error Algorithm Using An Acousto-Optic Processor", SPIE, 1098:232-239 (1989).

Rhodes, W., "Acousto-Optic Signal Processing: Convolution and Correlation", Proc. of the IEEE, 69(1):65-79 (January 1981).

Vander Lugt, A., "Signal Detection By Complex Spatial Filtering", IEEE Transactions On Information Theory, IT-10, 2:139-145 (April 1964).

Psaltis, D., "Two-Dimensional Optical Processing Using One-Dimensional Input Devices", Proceedings of the IEEE, 72(7):962-974 (July 1984).

Molley, P., et al., "A High Dynamic Range Acousto-Optic Image Correlator for Real-Time Pattern Recognition", SPIE, 938:55-65 (1988).

Shimizu et al., "Principle of Holonic Computer and Holovision", Journal of the Institute of Electronics, Information and Communication, 70(9):921-930 (1987).

Omata et al., "Holonic Model of Motion Perception", IEICE Technical Reports, Mar. 26, 1988, pp. 339-346.

Ohsuga et al., "Entrainment of Two Coupled van der Pol Oscillators by an External Oscillation", Biological Cybernetics, 51:225-239 (1985).

Kim, D. H.; Caulfield, H. J.; Jannson, T.; Kostrzewski, A.; Savant, G, "Optical fractal image processor for noise-embedded targets detection", Proceedings of the SPIE—The International Society for Optical Engineering, Vol: 2026 p. 144-9 (1993) (SPIE Conf: Photonics for Processors, Neural Networks, and Memories 12-15 July 1993, San Diego, Calif., USA).

Cheong, C. K.; Aizawa, K.; Saito, T.; Hatori, M., "Adaptive edge detection with fractal dimension", Transactions of the Institute of Electronics, Information and Communication Engineers D-II, J76D-II(11):2459-63 (1993).

Hayes, H. I.; Solka, J. L.; Priebe, C. E.; "Parallel computation of fractal dimension", Proceedings of the SPIE—The International Society for Optical Engineering, 1962:219-30 (1993).

Priebe, C. E.; Solka, J. L.; Rogers, G. W., "Discriminant analysis in aerial images using fractal based features", Proceedings of the SPIE—The International Society for Optical Engineering, 1962: 196-208(1993).

Liu, Y., "Pattern recognition using Hilbert space", Proceedings of the SPIE—The International Society for Optical Engineering, 1825:63-77 (1992).

Liu, Y., "Extensions of fractal theory", Proceedings of the SPIE—The International Society for Optical Engineering, 1966:255-68(1993).

Sadjadi, F., "Experiments in the use of fractal in computer pattern recognition", Proceedings of the SPIE—The International Society for Optical Engineering, 1960: 214-22(1993).

Reusens, E., "Sequence coding based on the fractal theory of iterated transformations systems", Proceedings of the SPIE—The International Society for Optical Engineering, 2094(pt. 1): 132-40(1993).

Hurtgen, B.; Buttgen, P., "Fractal approach to low rate video coding", Proceedings of the SPIE—The International Society for Optical Engineering, 2094(pt. 1): 120-31(1993).

Zhi-Yan Xie; Brady, M., "Fractal dimension image for texture segmentation", ICARCV '92. Second International Conference on Automation, Robotics and Computer Vision, p. CV4.3/1-5 vol.1, (1992).

Rahmati, M.; Hassebrook, L. G., "Intensity- and distortion-invariant pattern recognition with complex linear morphology", Pattern Recognition, 27 (4):549-68 (1994).

Sprinzak, J.; Werman, M., "Affine point matching", Pattern Recognition Letters, 15(4):337-9(1994).

Chao, T.-H.; Hegblom, E.; Lau, B.; Stoner, W. W.; Miceli, W. J., "Optoelectronically implemented neural network with a wavelet preprocessor", Proceedings of the SPIE—The International Society for Optical Engineering, 2026:472-82(1993).

Hoare, F.; de Jager, G., "Neural networks for extracting features of objects in images as a pre-processing stage to pattern classification", Proceedings of the 1992 South African Symposium on Communications and Signal Processing. COMSIG '92 (Cat. No.92TH04820). Inggs, M. (Ed.), p. 239-42 (1992).

The above-mentioned references are exemplary, and are not meant to be limiting in respect to the resources and/or technologies available to those skilled in the art. Of course it should be realized that the hardware for implementing a system may be integrally related to the choice of specific method or software algorithm for implementing the system, and therefore these together form a system. It is noted that in view of the present disclosure, it is within the skill of the artisan to combine in various fashions the available methods and apparatus to achieve the advanced interface and control system of the present invention.

SUMMARY AND OBJECTS OF THE INVENTION

The present invention relates to programmable man-machine interfaces, especially to computer graphic user interfaces. These interfaces are ergonomically adapted to provide an optimized environment for human interaction with the device. One factor limiting productivity of computer operators is the time necessary to communicate a desired action through an interface to a computerized device. The present technologies seek to reduce this limitation and make use of surplus processing capacity of the computer to predict a most likely input from the operator and present this as an easily available option. The technologies also extend beyond core theme in many differing ways, depending on the particular context and environment.

A major theme of the present invention is the use of intelligent, adaptive pattern recognition in order to provide the operator with a small number of high probability choices, which may be complex, without the need for explicit definition of each atomic instruction comprising the desired action. The interface system predicts a desired action based on the user input, a past history of use, a context of use, and a set of predetermined or adaptive rules.

Because the present invention emphasizes adaptive pattern recognition of both the input of the user and data which may be available, the interface system proposes the extensive use of advanced signal processing and neural networks. These processing systems may be shared between the interface system and the functional system, and therefore a controller for a complex system may make use of the intrinsic processing power available rather than requiring additional computing power, although this unification is not required. In fact, while hardware efficiency dictates that near term commercial embodiments employ common hardware for the interface system and the operational routine, future designs may successfully separate the interface system from the operational system, allowing portability and efficient application of a single interface system for a number of operational systems.

The adaptive nature of the present invention derives from an understanding that people learn most efficiently through the interactive experiences of doing, thinking, and knowing. For ease-of-use, efficiency, and lack of frustration of the user, the interface of the device should be intuitive and self explanatory, providing perceptual feedback to assist the operator in communicating with the interface, which in turn allows the operational system to receive a description of a desired operation. Another important aspect of man-machine interaction is that there is a learning curve, which dictates that devices which are especially easy to master become frustratingly elemental after continued use, while devices which have complex functionality with many options are difficult to master and may be initially rejected, or the user stops exploring. The present invention addresses these issues by determining the most likely instructions of the operator, and presenting these as easily available choices, by analyzing the past history data and by detecting the "sophistication" of the user in performing a function, based on all information available to it. The context of use may also be a significant factor. The interface seeks to optimize the relevant portion of the interface adaptively and immediately in order to balance and optimize the interface for both quantitative and qualitative factors. This functionality may greatly enhance the quality of interaction between man and machine, allowing a higher degree of overall system sophistication to be tolerated and a greater value added than other interface designs. See, Commaford, C., "User-Resonsive Software Must Anticipate Our Needs", PC Week, May 24, 1993.

The present interface system analyzes data from the user, which may be both the selections made by the user in context, as well as the efficiency by which the user achieves the selection. Thus, information concerning both the end-points and time-dependent path of the process are considered and analyzed by the interface system.

The interface of the present invention may be advantageously applied to an operational system which has a plurality of functions, certain of which are unnecessary or are rarely used in various contexts, while others are used with greater frequency. In such systems, the functionality use is usually predictable. Therefore, the present invention provides an optimized interface system which, upon recognizing a context, dynamically reconfigures the availability or ease of availability of functions and allow various subsets to be used through "shortcuts". The interface presentation will therefore vary over time, use and the particular user.

The advantages to be gained by using an intelligent data analysis interface for facilitating user control and operation of the system are more than merely reducing the average number of selections or time to access a given function. Rather, advantages also arise from providing a means for access and availability of functions not necessarily previously existing or known to the user, therefore improving the perceived quality and usefulness of the product. Further advantages over prior interfaces accrue due to the availability of pattern recognition functionality as a part of the interface system.

In those cases where the pattern recognition functions are applied to large amounts of data or complex data sets, in order to provide a sufficient advantage and acceptable response time, powerful computational resources, such as advanced digital signal processor (DSP) or neural network processors are made available to the interface system. On the other hand, where the data is simple or of limited scope, aspects of the technology may be easily implemented as added software functionality as improvements of existing products having limited computational resources.

The application of these technologies to multimedia systems provides a new model for performing image pattern recognition on multimedia data and for the programming of applications including such data. The ability of the interface of the present invention to perform abstractions and make decisions regarding a closeness of presented data to selection criteria makes the interface suitable for use in a programmable control, i.e., determining the existence of certain conditions and taking certain actions on the occurrence of detected events. Such advanced technologies might be especially valuable for disabled users.

In a multimedia environment, a user often wishes to perform an operation on a multimedia data event. Past systems have required explicit indexing of images and events. The present technologies, however, allow an image, diagrammatic, abstract or linguistic description of the desired event to be acquired by the interface system from the user and applied to identify or predict the multimedia event(s) desired without requiring a separate manual indexing or classification effort. These technologies may also be applied to single media data.

The interface system according to the present invention is not limited to a single data source, and may analyze data from many different sources for its operation. This data may be stored data or present in a data stream. Thus, in a multimedia system, there may be a real-time data stream, a stored event database, as well as an exemplar or model database. Further, since the device is adaptive, information relating to past experience of the interface, both with respect to exposure to data streams and user interaction, is also stored. This data analysis aspect of the operation of the present interface system may be substantially processor intensive, especially where the data includes abstract or linguistic concepts or images to be analyzed. Interfaces which do not relate to the processing of such data may be implemented on simpler hardware. On the other hand, systems which handle complex data types may necessarily include sophisticated processors, adaptable for use with the interface system, thus minimizing the additional computing power necessary in order to implement the interface according to the present invention. A portion of the data analysis may also overlap the functional analysis of the data for operation.

A fractal-based image processing system exemplifies one application of the technologies. A fractal-based system includes a database of image objects, which may be preprocessed in a manner which makes them suitable for comparison to a fractal-transformed image representation of an image to be analyzed. Thus, corresponding "fractal" transforms are performed on the unidentified image or a portion thereof and on an exemplar of a database. A degree of relatedness is determined in this "fractal transform domain", and the results used to identify objects within the image. The system then makes decisions based on the information content of the image, i.e. the objects contained therein.

The fractal-based image processing system presents many advantages. First, fractal-processed images may have dramatically reduced storage size requirements as compared to traditional methods while substantially retaining information important for image recognition. The process may be parallelized, and the exemplars may be multidimensional, further facilitating the process of identifying a two-dimensional projection of an object. The efficient storage of information allows the use of inexpensive storage media, i.e., compact disk-read only memory (CD-ROM), or the use of an on-line database through a serial data link, while allowing acceptable throughput. See, Zenith Starsignt Telecast brochure, (1994)

As applied to a multimedia database storage and retrieval system, the user programs, through an adaptive user interface according to the present invention, the processing of data, by defining a criteria and the actions to be taken based on the determination of the criteria. The criteria, it is noted, need not be of a predefined type, and in fact this is a particular feature of the present invention. A pattern recognition subsystem is employed to determine the existence of selected criteria. To facilitate this process, a database of image objects may be stored as two counterparts: first, the data is stored in a compressed format optimized for normal use, such as human viewing on a video monitor, using, e.g., MPEG-2 or JPEG compression; second, it is stored in a preprocessed and highly compressed format adapted to be used with the pattern recognition system. Because the preprocessed data is highly compressed and used directly by the pattern recognition system, great efficiencies in storage and data transmission are achieved. The image preprocessing may include fractal, Fourier, discrete cosine transforms (DCT), wavelet, Gabor, or model-based approaches.

The potential significant hardware requirement is counterbalanced by the enhanced functionality available by virtue of the technologies. When applied to multimedia devices, the interface system allows the operator to define complex criteria with respect to image, abstract or linguistic concepts, which would be difficult or impossible to implement with prior systems. Thus, the interface system becomes part of a computational system which would otherwise be too cumbersome for use.

A pattern recognition subsystem allows a "description" of an "event" without explicit definition of the data representing the "event". Thus, instead of requiring explicit programming, an operator may merely define parameters of the desired "event". This type of system is useful, for example, where a user seeks a generic type of data representing a variety of events. This eliminates the need for preindexing or standardized characterization of the data. The interface system therefore facilitates the formulation of a request, and then searches the database for data which corresponds to the request. Such preindexing or standardized characterization is extremely limiting with image and multimedia data, because a picture is worth a thousand words", and without a priori knowing the ultimate search criteria, all possible criteria must be accounted for. Pattern recognition systems do not require initial translation of visual aspects into linguistic concepts, thus allowing broader searching capability. Of course, a pattern recognition system may be used in conjunction with other searching schemes, to mutual advantage.

The pattern recognition functionality of the interface system is not limited to multimedia data, and may be applied to data of almost any type, e.g., real-time sensor data, distributed control, linguistic data, etc.

Another notable aspect of the technologies is the contextual analysis. Often, multimedia data often includes a data component which closely corresponds to a format of a search criteria. Thus, while a search may seek a particular image, other portions of the datastream correlate well with the aspect of the image being searched, and may be analyzed by proxy, avoiding the need for full image analysis. The resulting preselected reduced number of images may then be fully analyzed, if necessary. Thus, especially as with respect to consumer electronics applications, where absolute accuracy may not be required, the processing power available for pattern recognition need not be sufficient for complete real-time signal analysis of all data. The technologies therefore propose use of a variety of available data in order to achieve the desired level functionality at minimum cost.

One aspect of the present invention therefore relates to a mechanism for facilitating a user interaction with a programmable device. The interface and method of use of the present invention serves to minimize the leaning and searching times, better reflect users' expectations, provide better matching to human memory limits, be usable by both novices and experienced users, reduce intimidation of novice users by the device, reduce errors and simplify the entering of programming data. The present invention optimizes the input format scheme for programming an event-driven device, and can also be applied to many types of programmable devices. Thus, certain human factors design concepts, heretofore unexploited in the design of consumer electronics devices and industrial controls, have been incorporated, and new precepts developed. Background and theory of various aspects of the present invention is disclosed in "AN IMPROVED HUMAN FACTORED INTERFACE FOR PROGRAMMABLE DEVICES: A CASE STUDY OF THE VCR", Master's Thesis, Tufts University (Master of Sciences in Engineering Design, November, 1990, publicly available January, 1991), by Linda I. Hoffberg. This thesis, and cited references, are incorporated herein by reference, and attached hereto as an appendix. Also incorporated by reference are: Hoffberg, Linda I., "Designing User Interface Guidelines For Time-Shift Programming of a Video Cassette Recorder (VCR)", Proc. of the Human Factors Soc. 35th Ann. Mtg. pp. 501-504 (1991); and Hoffberg, Linda I., "Designing a Programmable Interface for a Video Cassette Recorder (VCR) to Meet a User's Needs", Interface 91 pp. 346-351 (1991). See also, U.S. patent application Ser. No. 07/812,805, incorporated herein by reference in its entirety, including appendices and incorporated references.

The present invention extends beyond simple predictive schemes which present exclusively a most recently executed command or most recently opened files. Thus, the possible choices are weighted in a multifactorial method, e.g., history of use, context and system status, rather than a single simple criterion alone. Known simple predictive criteria often exclude choices not previously selected, rather than weighing these choices in context with those which have been previously selected. While the system according to the present invention may include initial weightings, logical preferences or default settings, through use, the derived weightings are obtained adaptively based on an analysis of the status, history of use and context. It is noted that not all of the possible choices need be weighted, but rather merely a subset thereof.

For a given system, status, history of use and context may be interrelated factors. For example, the status of the machine is determined by the prior use, while the status also intersects context. The intended meaning of status is information relating to a path independent state of the machine at a given point in time. History of use is intended to implicate more than the mere minimum instructions or actions necessary to achieve a given state, and therefore includes information unnecessary to achieve a given state, i.e., path dependent information. Context is also related to status, but rather is differentiated in that context refers to information relating to the environment of use, e.g., the variable inputs or data upon which the apparatus acts or responds. Status, on the other hand, is a narrower concept relating more to the internal and constant functionality of the apparatus, rather than the particularities of its use during specific circumstances.

U.S. Pat. No. 5,187,797 relates to a machine interface system having hierarchical menus, with a simple (three button) input scheme. The choice(s) presented relate only to the system status, and not the particular history of use employed to obtain the system status nor the context of the choice. This system has a predetermined hierarchical menu structure, which is invariant with usage. The goal of this interface system is not to provide a learning interface, but rather to teach the user about or conform the user to the dictates of the predetermined and invariant interface of the device. While many types of programmable devices are known to exist, normally, as provided in U.S. Pat. No. 5,187,797, instructions are entered and executed in a predetermined sequence, with set branch points based on input conditions or the environment. See also U.S. Pat. Nos. 4,878,179, 5,124,908, and 5,247,433.

The present invention provides a device having a predetermined or a generic style interface upon initial presentation to the user, with an adaptive progression in which specialized features become more easily available to a user who will likely be able to make use of them, while unused features are "buried" within the interface. The interface also extracts behavioral information from the user and to alter the interface elements to optimize the efficiency of the user.

A video-cassette recorder is a ubiquitous example of a programmable device, and therefore forms the basis of much of the discussion herein. It should, of course, be realized that many of the aspects of the present invention could be applied by one of ordinary skill in the art to a variety of controls having human interfaces, and that these other applications are included within the scope of the present invention.

The VCR apparatus typically involves a remote control entry device, and the interface of the present invention contains a graphical interface displayed for programming programmable devices. This aspect of the present invention seeks more accurate programming through the use of program verification to ensure that the input program is both valid and executable. Thus, it has a mechanism to store and check to verify that there are no conflicting programs. An apparatus according to the present invention can be connected, for example, to any infrared programmable device in order to simplify the programming process. By way of example only, an improved VCR interface forms the basis of a disclosed example. It is, of course, realized that the present method and apparatus may be applied to any programmable controller, i.e., any device which monitors an event or sensor and causes an event when certain conditions or parameters are met, and may also be used in other programming environments, which are not event driven. While the present interface is preferably learning and adaptive, it may also detect events and make decisions based on known or predetermined characteristics. Where a number of criteria are evaluated for making a decision, conflicts among the various criteria are resolved based on a strength of an evaluated criteria, a weighting of the criteria, an interactivity function relating the various criteria, a user preference, either explicitly or implicitly determined, and a contextual analysis. Thus, a user override or preference input may be provided to assist in resolving conflicts.

The present invention may incorporate an intelligent program recognition and characterization system, making use of any of the available cues, which allows an intelligent determination of the true nature of the broadcast and therefore is able to make a determination of whether parameters should be deemed met even with an inexact match to the specified parameters. Therefore, in contradistinction with VPV, which the present invention is intelligent. The VPV is much more like the "VCR Plus" device, known to those skilled in the art, which requires that a broadcast be associated with a predetermined code, with the predetermined code used as a criteria for initiating recording. Some problems with VCR Plus include identification of the codes which identify channel and time, post scheduling changes, incorrect VCR clock setting, and irregular schedules. VCR Plus also is limiting with respect to new technologies and cable boxes.

The videotext signal of the prior art includes a digitally encoded text message which may be displayed in conjunction with the displayed image, similar to the closed caption system. The aforementioned West German system demonstrates one way in which the transmitted signal may be received by a device and interpreted to provide useful information other than the transmitted program itself. However, the prior art does not disclose how this signal may be used to index and catalog the contents of a tape, nor does it disclose how this signal may be used to classify or interpret the character of the broadcast. In other words, in one embodiment of the present invention, the videotext or closed caption signal is not only interpreted as a literal label, as in the prior art, but is also further processed and analyzed to yield data about the content of the broadcast, other than merely an explicit identification of the simultaneously broadcast information.

Beyond the visible region of an NTSC broadcast video frame are a number of scan lines which are dedicated to presenting digital information, rather than analog picture information. Various known coding schemes are available for transmitting and receiving information in this non-viewing portion of the video transmission. Of course, various other transmission schemes provide a format for transmitting data. For example, standard frequency modulation (FM) transmissions may be associated with digital data transmissions in a subcarrier. Likewise, satellite transmissions may include digital data along with an audio data stream or within a video frame, which may be in analog format or digitally encoded.

Cable systems may transmit information either in the broadcast band or in a separate band. HDTV schemes also generally provide for the transmission of digital data of various sorts. Thus, known audio and video transmission systems may be used, with little or no modifications to provide enhanced functionality, according to the present invention. It is therefore possible to use known and available facilities for transmitting additional information relating to the broadcast information, in particular, the characteristics of the video broadcast, and doing so could provide significant advantages, used in conjunction with the interface and intelligent pattern recognition controller of the present invention. If this information were directly available, there would be a significantly reduced need for advanced image recognition functions, such advanced image recognition functions requiring costly hardware devices, while still maintaining the advantages of the present invention.

It is noted, however, that the implementation of a system in which characterization data of the broadcast is transmitted along therewith might require a new set of standards and the cooperation of broadcasters, as well as possibly the government regulatory and approval agencies. The present invention does not require, in all of its aspects, such standardization, and therefore may advantageously implement substantial data processing locally to the receiver. It is nevertheless within the scope of the invention to implement such a broadcast system with broadcast of characterization data in accordance with the present invention. Such broadcast characterization data may include characterizations as well as preprocessed data useful for characterizing according to flexible criteria in the local receiving device.

According to the present invention, if such characterizations are broadcast, they may, as stated above, be in band or out of band, e.g., making use of unused available spectrum bandwidth within the NTSC channel space, or other broadcast system channel space, or may be "simulcast" on a separate channel, such as an FM sideband or separate transmission channel. Use of a separate channel would allow a separate organization, other than the network broadcasters, to provide the characterization data for distribution to users of devices that make use of the present intelligent system for controlling a VCR or other broadcast information processing device. Thus, the characterization generating means need not be directly linked to the local user machine in order to fall within the scope of the present invention. The present invention also provides a mechanism for copyright holders or other proprietary interests to be protected, by limiting access to information be encryption or selective encryption, and providing an accounting system for determining and tracking license or broadcast fees.

Research has been performed relating to VCR usability, technology, implementation, programming steps, current technology, input devices, and human mental capacity. This research has resulted in a new paradigm for the entry of programming data into a sequential program execution device, such as a VCR, by casual users.

Four major problems in the interfaces of VCRs were found to exist. The first is that users spend far too much time searching for necessary information, which is necessary in order to complete the programming process. Second, many people do not program the VCR to record at a later time (time-shift) frequently, and thus forget the programming steps in the interim, i.e., the inter-session decay of the learning curve is significant. Third, the number of buttons on many remote control devices has become overwhelming. Fourth, people have become reluctant to operate or program VCRs because of their difficult operation. It was found that, by minimizing the learning and searching times, the user's programming time and frustration level can be greatly reduced. If VCRs are easier to program, users might program them more frequently. This would allow more efficiency and flexibility in broadcast scheduling, especially late night for time shift viewing. The present invention therefore provides an enhanced VCR programming interface having a simplified information structure, an intuitive operational structure, simplified control layout and enhanced automated functionality.

These concepts are easily applied to other special purpose programmable devices, and also to general purpose programmable devices wherein the programming paradigm is event-driven, as well as other programming systems. It should also be noted that it is within the scope of the present invention to provide an improved interface and programming environment for all types of programmable devices, and in this regard, the present invention incorporates adaptive features which optimize the programming environment for both the level of the user and the task to be programmed.

In optimizing the interface, four elements are particularly important: the input device, the display format, the sequence of the programming operation, and the ability of the device to properly interpret the input as the desired program sequence.

The present invention proceeds from an understanding that an absence of user frustration with respect to a programmable consumer or industrial device or interface, may be particularly important with respect to achieving the maximum potential functionality thereof. The interface must be designed to minimize the user's frustration level. This can be accomplished by clearly furnishing the possible choices, presenting the data in a logical sequence, and leading the user through the steps necessary to program the device.

When applied to other than audiovisual and/or multimedia application, the pattern recognition function may be used to control the execution of a program or selectively control execution of portions of the software. For example, in a programmable temperature controller application, a sensor or sensor array could be arranged to detect a "door opening". On the occurrence of the door opening, the system would recognize this pattern, i.e. a mass of air at a different temperature entering the environment from a single location, or a loss of climate controlled air through a single location. In either event, the system would take appropriate action, including: halt of normal climate control and impose a delay until the door is closed; after closure, set a time constant for maintenance of a steady state of the replaced air with the climate controlled air; based on the actual climatic condition after assimilation, or a predicted climatic condition after assimilation, begin a climate compensation control; optionally, during the door opening, control a pressure or flow of air to counterbalance the normal flow through the door, by using a fan or other device. The climate may differ in temperature, humidity, pollutants, or the like, and appropriate sensors may be employed.

The present invention also allows a dynamic user preference profile determination based on explicit or implicit desires, e.g., moods, which assist in processing data to make decisions which conform to the user preference at a given point in time. For example, voice patterns, skin temperature, heat pulse rate, external context, skin resistance (galvanic skin response), blood pressure, stress, as determined by electromyograph (EMG), electorencephalogram (EEG) or other known methods, spontaneous motor activity or twitching, may be detected in order to determine or infer a user mood, which may be used as a dynamic influence on the user preference. These dynamic influences are preferably stored separately from static influences of the preferences, so that a resultant determined preference includes a dynamic influence based on a determined mood or other temporally varying factor and a static influence associated with the user.

When a group of people are using the system simultaneously, the system must make a determination of a composite preference of the group. In this case, the preferences of the individuals of the group, if known, may be correlated to produce an acceptable compromise. Where individual preferences are not a priori known, individual or group "interviews" may be initially conducted to assist in determining the best composite group preference.

It is therefore an object according to the present invention to provide a radio receiver or video receiver device, having a plurality of different available program sources, determining a program preference for one or more individuals subject to a presented program, comparing the determined program preference and a plurality of different program sources, and selects at least one program based on said comparison.

In formulating a group preference, individual dislikes may be weighted more heavily than likes, so that the resulting selection is tolerable by all and preferable to most group members. Thus, instead of a best match to a single preference profile for a single user, a group system provides a most acceptable match for the group. It is noted that this method is preferably used in groups of limited size, where individual preference profiles may be obtained, in circumstances where the group will interact with the device a number of times, and where the subject source program material is the subject of preferences. Where large groups are present, demographic profiles may be employed, rather than individual preferences. Where the device is used a small number of times by the group or members thereof, the training time may be very significant and weigh against automation of selection. Where the source material has little variety, or is not the subject of strong preferences, the predictive power of the device as to a desired selection is limited.

In yet another embodiment, a present mood of a user is determined, either explicitly or implicitly, and the device selects program material which assists in a desired mood transition. The operation of the device may additionally acquire data relating to an individual and the respective moods, desires and characteristics, altering the path provided to alter the mood based on the data relating to the individual. As stated above, in a group setting, a most acceptable path is presented rather than a most desirable path as presented for an individual.

In determining mood, a number of physiologic parameters may be detected. In a training circumstance, these set of parameters are correlated with a temporally associated preference. Thus, when a user inputs a preference into the system as feedback, mood data is also obtained. Invariant preferences may be separated, and analyzed globally, without regard for temporal variations, while varying preferences are linked with information regarding the surrounding circumstances and stored. For example, the preference data may be used to train a neural network, e.g., using back-propagation of errors or other known methods. The inputs to the neural network include available data about surrounding context, such as time, environmental brightness, and persons present; source program choices, which may be raw data, preprocessed data, and abstracted data; explicit user input; and, in this embodiment, mood parameters, which may be physiological or biometric data, voice pattern, or implicit inputs. An example of an implicit input is an observation of a man-machine interaction, such as a video game. The manner in which a person plays a video game or otherwise interacts with a machine may provide valuable data for determining a mood or preference.

According to one embodiment of the invention, the image is preprocessed to decompose the image into object-elements, with various object-elements undergoing separate further processing. For example, certain backgrounds may be aesthetically modeled using simple fractal equations. While, in such circumstances the results may be inaccurate in an absolute sense, they may be adequate in a performance sense. Faces, on the other hand, have common and variable elements. Therefore, a facial model may be based on parameters having distinguishing power, such as width between eyes, mouth, shape of ears, and other proportions and dimensions. Thus, along with color and other data, a facial image may be stored as a reference to a facial model with the distinguishing parameters for reconstruction. Such a data processing scheme may produce a superior reconstructed image and allow for later recognition of the face, based on the stored parameters in reference to the model. Likewise, many different elements of an image may be extracted and processed in accordance with specific models to produce differentiating parameters, wherein the data is stored as a reference to the particular model along with the particular data set derived from the image. Such a processing scheme allows efficient image storage along with ease of object recognition, i.e., distinction between objects of the same class. This preprocessing provides a highly asymmetric scheme, with a far greater processing complexity to initially process the image than to subsequently reconstruct or otherwise later employ the data.

By employing a model-based object extraction system, the available bandwidth may be efficiently used, so that objects which fall within the scope of an available model may be identified with a model identification and a series of parameters, and objects not within the scope of a model may be allocated a comparatively greater bandwidth for general image description, e.g., JPEG, MPEG-1/MPEG-2, standard fractal image compression, or other image processing schemes. In a worst case, therefore, the bandwidth required will be only slightly greater than that required for a corresponding standard method, due only to the additional overhead to define data types, as necessary. However, by employing a model based-object decomposition processing system, recognized elements may be described using only a small amount of data and a greater proportion of data used to describe unrecognized elements. Further, the models available may be dynamically updated, so that, as between a communicating transmitted and receiver, retransmission of unrecognized elements will be eliminated as a model is constructed.

Where image processing systems may produce artifacts and errors, an error minimization function may also be provided which compares an original image with a decomposed-recomposed image and produces an error function which allows correction for these errors. This error function may be transmitted with the processed data to allow more faithful reproduction. In a pattern recognition context, the error function may provide useful data relating to the reliability of a pattern correlation, or may provide useful data outside of the model and associated parameters for pattern recognition.

Thus, in the case of an object-extraction model-based processing system, the resulting data stream may be appropriate for both viewing and recognition. Of course, acoustic data may be likewise processed using acoustic models with variable parameters. However, in such a system, information for pattern recognition may be filtered, such as eliminating the error function or noise data. Further, certain types of objects may be ignored, for example, under normal circumstances, clouds in the sky provide little information for pattern recognition and may be removed. In such a system, data intended for viewing or listening will likely contain all objects in the original data stream, with as much original detail as possible given data storage and bandwidth constraints.

An object extraction model based processing system also allows for increased noise rejection, such as over terrestrial broadcast channels. By transmitting a model, the receiving system may interpolate or extrapolate data to fill in for missing data. By extrapolate, it is meant that past data is processed to predict a subsequent condition. By interpolate, it is meant that data presentation is delayed, and missing data may therefore be predicted from both past and subsequent data transmission. Missing portions of images may also be reconstructed from existing portions. This reconstruction process is similar to that described in U.S. Pat. No. 5,247,363, to reconstruct MPEG images; except that where model data is corrupted, the corruption must be identified and the corrupt data eliminated and replaced with predicted data.

It is therefore an object according to the present invention to provide a programmable control, having a status, responsive to an user input and a signal received from a signal source, comprising a controller for receiving the user input and the signal and producing a control output; a memory for storing data relating to an activity of the user; a data processing system for adaptively predicting a most probable intended action of the user based on said stored data relating to said activity of the user and derived weighing of at least a subset of possible choices, said derivation being based on a history of use, a context of a respective choice and said status of the control; and a user feedback data presenting system comprising an output device for presentation of a variable sequence of programming options to the user, including said most probable intended action of the user, in a plurality of output messages, said output messages differing in available programming options.

The programmable control may be employed for performing an action based on user input and an information content of a signal received from a signal source, wherein said output device includes a display device, further comprising a user controlled direct manipulation-type input device, associated with said display device, having a device output, said device output being the user input; a plant capable of performing the action, being responsive to an actuator signal; and said controller, being for receiving data from said device output of said input device and the signal, and displaying user feedback data on said display device, said logical sequence of said user feedback data including at least one sequence of options sufficient to define an operable control program, and a presentation of additional programming options if said control program is not operable.

The programmable control may further comprise a user input processing system for adaptively determining a viewer preference based on the user input received by said controller; a program material processing system for characterizing the program material based on its content; a correlator for correlating said characterized content of the program material with said determined viewer preference to produce a correlation index; and a processor, selectively processing the program material based on said correlation index, said data processing system receiving an input from said processor.

The programmable control may also comprise a plurality of stored profiles, a processor for characterizing said user input to produce a characterized user input; and means for comparing said characterized user input with at least one of said plurality of stored profiles to produce a comparison index, wherein said variable sequence of programming options is determined on the basis of said comparison index. The processor for characterizing may perform an algorithm on said signal comprising a transform selected from the group consisting of an Affine transformation, a Fourier transformation, a discrete cosine transformation and a wavelet transformation.

It is a further object according to the present invention to provide a programmable controller for controlling a recording device for recording an analog signal sequentially on a recording medium having a plurality of uniquely identifiable storage locations, further comprising a sequential recording device for recording the analog signal, and a memory for storing, in a directory location on the recording medium which is separate from the storage location of the analog signal, information relating to said signal, processed to selectively retain characterizing information, and an identifier of a storage location on the recording medium in which said analog signal is recorded.

It is another object according to the present invention to provide a control, wherein program material is encrypted, further comprising a decryption system for decrypting the program material if it is selected to produce unencrypted program material and optionally an associated decryption event; a memory for storing data relating to the occurrence of said decryption event; and a central database for storing data relating to the occurrence of said decryption event in association with data relating to the viewer.

It is still another object according to the present invention to provide a control wherein said user input processing system monitors a pattern of user activity and predicts a viewer preference; said program material processing system comprising a processor for preprocessing the program material to produce a reduced data flow information signal substantially retaining information relating to said abstract information content of the program material and selectively eliminating data not relating to said abstract information content of the program material and for characterizing said information signal based on said abstract information content; and a comparing system for determining if said correlation index is indicative of a probable high correlation between said characterization of said information signal and said viewer preference and causing said stored program material to be processed by said processing means based on said determination. The system according to this aspect of the present invention preferably comprises an image program material storage and retrieval system.

The present invention further provides a control further comprising a memory for storing a characterization of the program material; an input for receiving a feedback signal from the viewer indicating a degree of agreement with said correlation index determination, wherein said feedback signal and said stored characterization are used by said viewer preference predicting means to predict a new viewer preference.

According to another aspect of the invention, it is an object to provide an image information retrieval apparatus, comprising a memory for storing compressed data representing a plurality of images; a data storage system for retrieving compressed data representing at least one of said plurality of images and having an output; a memory for storing characterization data representing a plurality of image types, having an output; and an image processor, receiving as inputs said outputs from said data storage system and said characterization data memory, and producing a signal corresponding to a relation between at least one of said plurality of images of said compressed data and at least one of said image types of said characterization data.

It is a still further aspect of the present invention to provide a video interface device for a user comprising a data transmission system for simultaneously transmitting data representing a plurality of programs; a selector for selecting at least one of said plurality of programs, being responsive to an input; a program database containing information relating to said plurality of programs, having an output; a graphical user interface for defining commands, comprising (a) an image display device having at least two dimensions of display, being for providing visual image feedback; and (b) a multidimensional input device having at least two dimensions of operability, adapted to correspond to said two dimensions of said display device, and having an output, so that the user may cause said input device to produce a corresponding change in an image of said display device by translating an indicator segment of said display in said at least two dimensions of display, based on said visual feedback received from said display device, said indicator segment being moved to a translated location of said display device corresponding to a user command; and a controller for controlling said graphical user interface and for producing said input of said selector, receiving as a control said output of said multidimensional input device, said controller receiving said output of said program database and presenting information relating to at least one of said plurality of programs on said display device associated with a command, said command being interpreted by said control means as said user command to produce said input of said selector to select said at least one of said plurality of programs associated with said command.

Another object of the present invention is to provide an apparatus, receiving as an input from a human user having a user characteristic, comprising an input device, producing an input signal from the human user input; a display for displaying information relating to the input from the user and feedback on a current state of the apparatus, having an alterable image type; an input processor for extracting an input instruction relating to a desired change in a state of the apparatus from the input signal; a detector for detecting one or more temporal-spatial user characteristics of the input signal, independent of said input instruction, selected from the group consisting of a velocity component, an efficiency of input, an accuracy of input, an interruption of input and a high frequency component of input; a memory for storing data related to said user characteristics; and a controller for altering said image type based on the user characteristics. The controller may alter said image type based on an output of said detector and said stored data so that said display displays an image type which corresponds to said detected user characteristics. The controller may further be for controlling the causation of an action on the occurrence of an event, further comprising a control for receiving said input instruction and storing a program instruction associated with said input instruction, said control having a memory sufficient for storing program instructions to perform an action on the occurrence of an event; and a monitor for monitoring an environment of said apparatus to determine the occurrence of the event, and causing the performance of the action on the occurrence of the event. The controller may also alters said image type based on an output of said detector and said stored data so that said display means displays an image type which corresponds to said detected user characteristics.

It is another object of the present invention to provide an adaptive programmable apparatus having a plurality of states, being programmable by a programmer and operating in an environment in which a plurality of possible events occur, each of the events being associated with different data, comprising an data input for receiving data; an programmer input, producing an input signal from the programmer; a memory for storing data relating to said data input or said input signal; a feedback device for adaptively providing information relating to said input signal and a current status of the apparatus to the programmer, based on said data input or said programmer input, said stored data, and derived weighing of at least a subset of possible choices, said derived weighing being based on a history of use, a context of a respective choice and said current status of the apparatus; a memory for storing programming data associated with said input signal; and a processor, having a control output, for controlling the response of said apparatus relating to the detection of said input signal or said data in accordance with said stored programming data, said processor: (a) processing said at least one of said input signal or said data to reduce an amount of information while substantially retaining an abstract portion of said information; (b) storing a quantity of said abstracted information; (c) processing said abstract portion of said information in conjunction with said stored quantity of abstracted information; and (d) providing said control output based on said processed abstract portion of said information and said stored programming data. The apparatus may further comprise an input for receiving a programming preference from the programmer indicating a plurality of possible desired events; said processor further including a correlator for correlating said programming preference with said data based on an adaptive algorithm and for determining a likelihood of occurrence of at least one of said desired events, producing said control output. The apparatus may further comprise an input for receiving feedback from the programmer indicating a concurrence with said control output of said processor, and modifying said response control based on said received feedback to increase a likelihood of concurrence. The apparatus may still further verify said programming data to ensure that said programming data comprise a complete and consistent set of instructions; and include a feedback system for interactively modifying said programming data. The apparatus may also comprise a chronological database and an accessing system for accessing said chronological database on the basis of said programming data stored in said memory.

It is also an object according to the present invention to provide an apparatus comprising an input for receiving a programming preference from the programmer indicating a plurality of possible desired events; and a correlator for correlating said programming preference with said data based on an adaptive algorithm and for determining a likelihood of occurrence of at least one of said desired events, producing said output, said output being associated with the initiation of the said response.

The present invention also provides as an object an apparatus comprising an input for receiving feedback from the programmer indicating a concurrence with said output of said correlator, and modifying said algorithm based on said received feedback, said feedback device comprising a display and said input device is remote from said display, and providing a direct manipulation of display information of said display.

According to an aspect of the present invention, a processor of the programmable apparatus verifies said program instructions to ensure that said program instructions are valid and executable by said processor; an output for providing an option, selectable by said programmer input for changing an instruction stored by said processor, such that said apparatus enters a state wherein a new instruction may be input to substitute for said instruction, wherein said processor verifies said instructions such that said instructions are valid; and wherein said feedback device further presents information requesting confirmation from the programmer of the instructions associated with the input signal. The apparatus may further comprise a chronological database and an accessing system for accessing said chronological database on the basis of said program instructions stored in said memory.

The processor of the programmable apparatus may receive information from said input signal and/or from said data input; and may further comprise an input signal memory for storing at least a portion of said input signal or said data, a profile generator for selectively generating a profile of said input signal or said data, and an input signal profile memory for storing said profile of said input signal or said data separately from said input signal or said data in said input signal memory. The programmable apparatus may further comprise a processor for comparing said input signal or said data with said stored profile of said input signal or said data to determine the occurrence of an event, and said data optionally comprises image data and said processor for comparing performs image analysis. The image data may comprise data having three associated dimensions obtained by a method selected from the group consisting of synthesizing a three dimensional representation based on a machine based model derived from two dimensional image data, synthesizing a three dimensional representation derived from a time series of pixel images, and synthesizing a three dimensional representation based on a image data representing a plurality of parallax views each having at least two dimensions.

A user feedback data presenting device according to the present invention may comprise a display having a plurality of display images, said display images differing in available programming options.

According to another aspect of the present invention, a program material processing system is provided comprising means for storing template data; means for storing the image data; means for generating a plurality of domains from the stored image data, each of the domains representing different portions of the image information; means for creating, from the stored image data, a plurality of addressable mapped ranges corresponding to different subsets of the stored image data, the creating means including means for executing, for each of the mapped ranges, a procedure upon the one of the subsets of the stored image data which corresponds to the mapped range; means for assigning identifiers to corresponding ones of the mapped ranges, each of the identifiers specifying for the corresponding mapped range an address of the corresponding subset of stored image data; means for selecting, for each of the domains, the one of the mapped ranges which most closely corresponds according to predetermined criteria; means for representing at least a portion of the image information as a set of the identifiers of the selected mapped ranges; and means for selecting, from the stored templates, a template which most closely corresponds to the set of identifiers representing the image information. Said means for selecting may comprise means for selecting, for each domain, the mapped range which is the most similar, by a method selected from at least one of the group consisting of selecting a minimum Hausdorff distance from the domain, selecting the highest cross-correlation with the domain and selecting the lowest mean square error of the difference between the mapped range and the domain. Said means for selecting may also comprise, for each domain, the mapped range with the minimum modified Hausdorff distance calculated as D[db,mrb]+D[1−db,1−mrb], where D is a distance calculated between a pair of sets of data each representative of an image, db is a domain, mrb is a mapped range, 1−db is the inverse of a domain, and 1−mrb is an inverse of a mapped range. Said means for representing may further comprise means for determining a feature of interest of the image data, selecting a mapped range corresponding to the feature of interest, storing the identifiers of the selected mapped range, selecting a further mapped range corresponding to a portion of image data having a predetermined relationship to the feature of interest and storing the identifiers of the further mapped range.

According to an embodiment of the present invention, said image data comprises data having three associated dimensions obtained by a method selected from the group consisting of synthesizing a three dimensional representation based on a machine based prediction derived from two dimensional image data, synthesizing a three dimensional representation derived from a time series of pixel images, and synthesizing a three dimensional representation based on a image data representing a plurality of parallax views having at least two dimensions.

It is therefore an object of the present invention to provide a programmable apparatus for receiving instructions from a programmer and causing an action to occur on the happening of an event, comprising an input device, producing an input instruction signal; a control means for receiving said input instruction signal, and storing a program instruction associated with said input instruction signal, said control means storing sufficient program instructions to perform an action on the occurrence of an event, said control means monitoring a status of said apparatus to determine the occurrence of various events, comparing the determined events with the program instructions, and performing said action on the occurrence of said event; a display means for interactively displaying information related to the instructions to be received, and responsive thereto, controlled by said control means, so that the programmer is presented with feedback on a current state of the apparatus and said program instruction; wherein said control means further comprises means for detecting one or more characteristics of said input instruction signal independent of said program instruction selected from the group consisting of a velocity component, an efficiency of input, an accuracy of input, an interruption of input, a high frequency component of input and a past history of input by the programmer, whereby when said control means detects a characteristic indicating that said display means is displaying information in a suboptimal fashion, said control means controls said display means to display information in a more optimal fashion.

It is also an object of the present invention to provide a programmable apparatus for receiving instructions from a programmer and causing an action to occur on the happening of an event, comprising an input device, producing an input instruction signal; a control means for receiving said input instruction signal, and storing a program instruction associated with said input instruction signal, said control means storing sufficient program instructions to perform an action on the occurrence of an event, said control means monitoring a status of said apparatus to determine the occurrence of various events, comparing the determined events with the program instructions, and performing said action on the occurrence of said event; a display means for interactively displaying information related to the instructions to be received, and responsive thereto, controlled by said control means, so that the programmer is presented with feedback on a current state of the apparatus and said program instruction; wherein said control means further comprises means for detecting a need by the programmer for more detailed information displayed on said display means, by detecting one or more characteristics of said input instruction signal independent of said program instruction selected from the group consisting of a velocity component, an efficiency of input, an accuracy of input, an interruption of input, a high frequency component of input and a past history of input by the programmer, whereby when said control means detects a characteristic indicating that said display means is insufficiently detailed information, said control means controls said display means to display more detailed information.

It is a further object of the present invention to provide a programmable apparatus having a data input, said apparatus receiving instructions from a programmer and causing an action to occur on the receipt of data indicating an event, comprising an input device, producing an input instruction signal; a control means for receiving said input instruction signal, and storing a program instruction associated with said input instruction signal, said control means storing sufficient program instructions to perform an action on the receipt of data indicating an event, said control means monitoring the data input; a display means for interactively displaying information related to the instructions to be received, and responsive thereto, controlled by said control means, so that the programmer is presented with feedback on a current state of the apparatus and said program instruction; wherein said control means receives a programming preference indicating a desired event from said input device which does not unambiguously define said event, and said control means monitors said data and causes the occurrence of the action when a correlation between said programming preference and said monitored data is above a predetermined threshold, indicating a likely occurrence of said desired event. It is also object of the present invention to provide the programmable aforementioned apparatus, wherein said input device is remote from said display means, and provides a direct manipulation of display information of said display means, further comprising means for verifying said program instructions so that said program instructions are executable by said control means. The control means may further comprise a calendar or other chronological database.

Another object of the present invention provides a programmable information storage apparatus having a data input, for receiving data to be stored, said apparatus receiving instructions from a programmer and causing an action to occur on the receipt of data indicating an event, comprising means for storing data from said data input; an input device, producing an input instruction signal; a control means for receiving said input instruction signal, and storing a program instruction associated with said input instruction signal, said control means storing sufficient program instructions to perform an action on the receipt of data from said data input indicating an event, said control means monitoring the data input to determine the occurrence of various events, comparing the determined events with the program instructions, and performing for storing the data said action on the occurrence of said event; wherein said control means receives identifying data from at least one of said input device and the data input, said identifying data being stored separately from said input data on a storage medium. The programmable information storage apparatus may also include means for reading said identifying data stored separately on said storage medium, and may also receive as an input said identifying data.

It is also an object of the present invention to provide a programmable apparatus, wherein said control means provides an option, selectable by said input means in conjunction with said display means, for changing an input program instruction prior to execution by said control means, so that said apparatus enters a state wherein a new program instruction may be input to substitute for said changed input step, wherein said control means verifies said program instructions so that said program instructions are executable by said control means.

It is still another object of the present invention to provide a programmable apparatus, wherein said control means further causes said display means to display a confirmation screen after said program instructions are input, so that the programmer may confirm said program instructions.

Another object of the present invention is to provide a programmable information storage apparatus, wherein said control means further comprises means for recognizing character data present in a data stream of said input data, said identifying data comprising said recognized character data.

It is a still further object of the present invention to provide a video tape recording apparatus, comprising a video signal receiving device, a recording device for recording said video signal, wherein said control analyzes said video signal for the presence of a symbol, and recognizes said symbol as one of a group of recognized symbols, and said control stores said recognized symbol separately from said video signal.

Another object of the present invention is to provide a recording device for recording an analog signal sequentially on a recording medium, comprising means for characterizing the analog signal, wherein data representing said characterization and a location of the analog signal on the recording medium are stored in a directory location on the recording medium separately from the analog signal.

It is a further object of the present invention to provide an interface for a programmable control for input of a program for a controller to execute, which performs an action based on an external signal, comprising an input device, a controller for receiving data from said input device and from an external stimulus, a plant being controlled by said controller based on an input from said input device and said external stimulus, and a display device being controlled by said controller, for providing visual feedback to a user operating said input device, wherein a predetermined logical sequence of programming options is presented to the user on said display device, in a plurality of display screens, each of said display screens differing in available programming choices; said logical sequence including a correct sequence of choices to set an operable control program, so that no necessary steps are omitted; said external stimulus comprises a timing device, and said display comprises a display option for programming said plant to perform an action at a time which is input through said input device as a relative position on said display device, said relative position including a means for displaying an absolute time entry and means for displaying a relative time entry, said display also comprising a display option means for performing an action at a time; said control comprises means for presenting the user, on said display device, with a most probable action, which may be selected by the user through activation of said input device without entering data into said controller through said input device relating to both said action and said event; said display also comprising means for indicating completion of entry of a programming step, which means indicates to the user an indication that said programming step is not completed if information necessary for execution of said step is not available to said controller; and said controller being capable of controlling said display device to present information to the user relating to the use of the apparatus if necessary for use of the device by the user.

Another object of the present invention provides a system for presenting a program to a viewer, comprising a source of program material; means for determining a viewer preference, said viewer preference optionally being context sensitive; means for receiving the program material from said source; means for characterizing the program material based on its content; means for correlating said characterized content of the program material with said determined viewer preference to produce a correlation index; and means for presenting the program material to the viewer, if said correlation index indicates a probable high correlation between said characterization of the program material and said viewer preference.

Another object of the present invention is to provide a system for presenting a program to a viewer, comprising a source of program material; means for determining a viewer preference; means for receiving the program material from said source; means for storing the program material; means for preprocessing the program material to produce a reduced data flow information signal retaining information relating to a character of the program material and eliminating data not necessary to characterize the program material; means for characterizing said information signal based on its content; means for correlating said characterized content of said information signal with said determined viewer preference to produce a correlation index; and means for presenting said stored program material to the viewer, if said correlation index indicates a probable high correlation between said characterization of said information signal and said viewer preference. The system may also include a means for storing said information signal, wherein said characterizing means characterizes said stored information signal, and also a memory for storing the program material while said characterizing means produces characterized content and said correlating means produces said correlation index.

Still another object of the present invention is to provide a system, wherein said program material is encrypted, further comprising means for decrypting the program material to produce a decryption event; and means for charging an account of the viewer based on the occurrence of a decryption event. Thus, a decryption processor and an accounting database are provided for these purposes.

Another object of the present invention is to allow said means for characterizing the program material to operate without causing a decryption event. Thus, the data stream may include characterization data specifically suitable for processing by a characterizing system, or the decryption processor may be provided with multiple levels of functionality, or both. Further, the system may comprise a memory for storing the program material while said characterizing means produces characterized content and said correlating means produces said correlation index. The characterizing means may also characterize the program material stored in memory, and the program material stored in memory may be compressed.

Another object of the present invention is to provide a controller for controlling a plant, having a sensor for sensing an external event and producing a sensor signal, an actuator, responsive to an actuator signal, for influencing said external event, and a control means for receiving said sensor signal and producing an actuator signal, comprising means for inputting a program; means for storing said program; means for characterizing said sensor signal to produce a characterized signal; and means for comparing said characterized signal with a pattern stored in a memory to produce a comparison index, wherein said actuator signal is produced on the basis of said comparison index and said program, wherein said characterization comprises an Affine transformation of said sensor signal. The characterization may comprise one or more transformation selected from the group consisting of an Affine transformation, a Fourier transformation, a Gabor transformation, and a wavelet transformation.

It is another object of the present invention to provide a method for automatically recognizing digital image data consisting of image information, the method comprising the steps performed by a data processor of storing a plurality of templates; storing the image data in the data processor; generating a plurality of addressable domains from the stored image data, each of the domains representing a portion of the image information; creating, from the stored image data, a plurality of addressable mapped ranges corresponding to different subsets of the stored image data, the creating step including the substep of (a) executing, for each of the mapped ranges, a corresponding procedure upon the one of the subsets of the stored image data which corresponds to the mapped ranges; (b) assigning identifiers to corresponding ones of the mapped ranges, each of the identifiers specifying for the corresponding mapped range a procedure and a address of the corresponding subset of the stored image data; (c) optionally subjecting a domain to a transform selected from the group consisting of a predetermined rotation, an inversion, a predetermined scaling, and a predetermined preprocessing in the time, frequency, and/or wavelet domain; (d) selecting, for each of the domains or transformed domains, the one of the mapped ranges which most closely corresponds according to predetermined criteria; (e) representing the image information as a set of the identifiers of the selected mapped ranges; and (f) selecting, from the stored templates, a template which most closely corresponds to the set of identifiers representing the image information. The step of selecting the mapped ranges may also include the substep of selecting, for each domain, a most closely corresponding one of the mapped ranges.

It is another object of the present invention to provide a method-wherein the step of selecting the most closely corresponding one of the mapped ranges includes the step of selecting, for each domain, the mapped range which is the most similar, by a method selected from one or more of the group consisting of selecting minimum Hausdorff distance from the domain, selecting the highest cross-correlation with the domain, selecting the highest fuzzy correlation with the domain and selecting the minimum mean square error with the domain.

Another object of the present invention provides a method wherein the step of selecting the most closely corresponding one of mapped ranges includes the step of selecting, for each domain, the mapped range with the minimum modified Hausdorff distance calculated as D[db,mrb]+D[1−db,1−mrb], where D is a distance calculated between a pair of sets of data each representative of an image, db is a domain, mrb is a mapped range, 1−db is the inverse of a domain, and 1−mrb is an inverse of a mapped range.

Another object of the present invention provides a method wherein the digital image data consists of a plurality of pixels each having one of a plurality of associated color map values, further comprising the steps of optionally transforming the color map values of the pixels of each domain by a function including at least one scaling function for each axis of the color map, each of which may be the same or different, and selected to maximize the correspondence between the domains and ranges to which they are to be matched; selecting, for each of the domains, the one of the mapped ranges having color map pixel values which most closely correspond to the color map pixel values of the domain according to a predetermined criteria, wherein the step of representing the image color map information includes the substep of representing the image color map information as a set of values each including an identifier of the selected mapped range and the scaling functions; and selecting a most closely corresponding stored template, based on the identifier of the color map mapped range, the scaling functions and the set of identifiers representing the image information. The first criteria may comprise minimizing the Hausdorff distance between each domain and the selected range.

Another object of the present invention is to provide a method further comprising the steps of storing delayed image data, which represents an image of a moving object differing in time from the image data in the data processor; generating a plurality of addressable further domains from the stored delayed image data, each of the further domains representing a portion of the delayed image information, and corresponding to a domain; creating, from the stored delayed image data, a plurality of addressable mapped ranges corresponding to different subsets of the stored delayed image data; matching the further domain and the domain by subjecting a further domain to one or both of a corresponding transform selected from the group consisting of a null transform, a rotation, an inversion, a scaling, a translation and a frequency domain preprocessing, which corresponds to a transform applied to a corresponding domain, and a noncorresponding transform selected from the group consisting of a rotation, an inversion, a scaling, a translation and a frequency domain preprocessing, which does not correspond to a transform applied to a corresponding domain; computing a motion vector between one of the domain and the further domain, or the set of identifiers representing the image information and the set of identifiers representing the delayed image information, and storing the motion vector; compensating the further domain with the motion vector and computing a difference between the compensated further domain and the domain; selecting, for each of the delayed domains, the one of the mapped ranges which most closely corresponds according to predetermined criteria; representing the difference between the compensated further domain and the domain as a set of difference identifiers of a set of selected mapping ranges and an associated motion vector and representing the further domain as a set of identifiers of the selected mapping ranges; determining a complexity of the difference based on a density of representation; and when the difference has a complexity below a predetermined threshold, selecting, from the stored templates, a template which most closely corresponds to the set of identifiers of the image data and the set of identifiers of the delayed image data.

Another object of the present invention provides an apparatus for automatically recognizing digital image data consisting of image information, comprising means for storing template data; means for storing the image data; means for generating a plurality of addressable domains from the stored image data, each of the domains representing a different portion of the image information; means for creating, from the stored image data, a plurality of addressable mapped ranges corresponding to different subsets of the stored image data, the creating means including means for executing, for each of the mapped ranges, a procedure upon the one of the subsets of the stored image data which corresponds to the mapped range; means for assigning identifiers to corresponding ones of the mapped ranges, each of the identifiers specifying for the corresponding mapped range an address of the corresponding subset of stored image data; means for selecting, for each of the domains, the one of the mapped ranges which most closely corresponds according to predetermined criteria; means for representing the image information as a set of the identifiers of the selected mapped ranges; and means for selecting, from the stored templates, a template which most closely corresponds to the set of identifiers representing the image information.

Other objects and features of the present invention will become apparent from the following detailed description considered in conjunction with the accompanying drawings. It is to be understood, however, that the drawings are designed solely for the purposes of illustration and not as a definition of the limits of the invention, for which reference should be made to the appended claims.

BRIEF DESCRIPTION OF THE DRAWINGS

Embodiments of the present invention are shown in the figures in the drawings, in which.

DETAILED DESCRIPTION OF THE PREFERRED EMBODIMENTS

Figure 1:
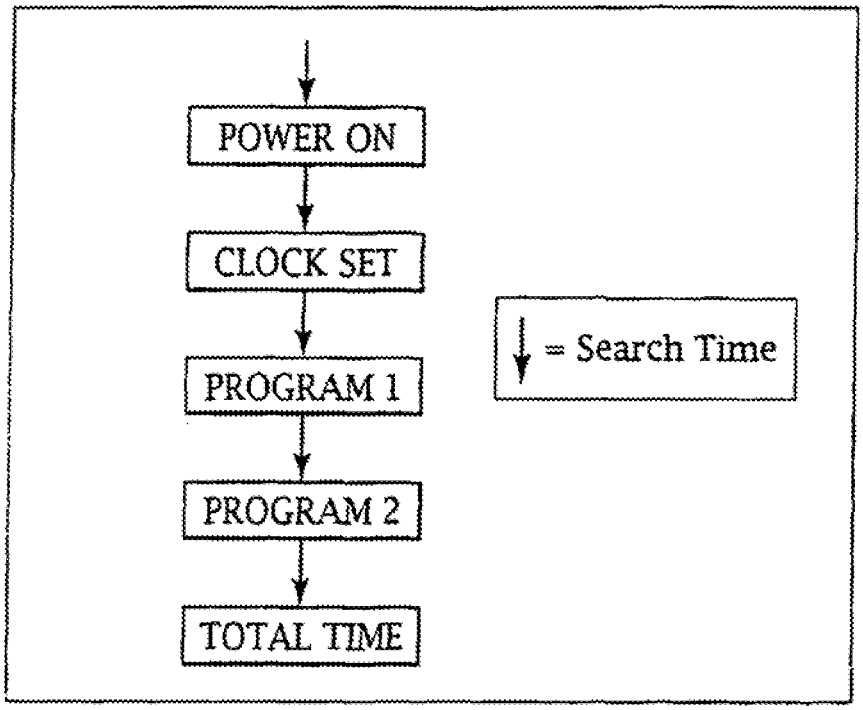
FIG. 1 is a flow chart of the steps required to set a VCR.
Figure 2:
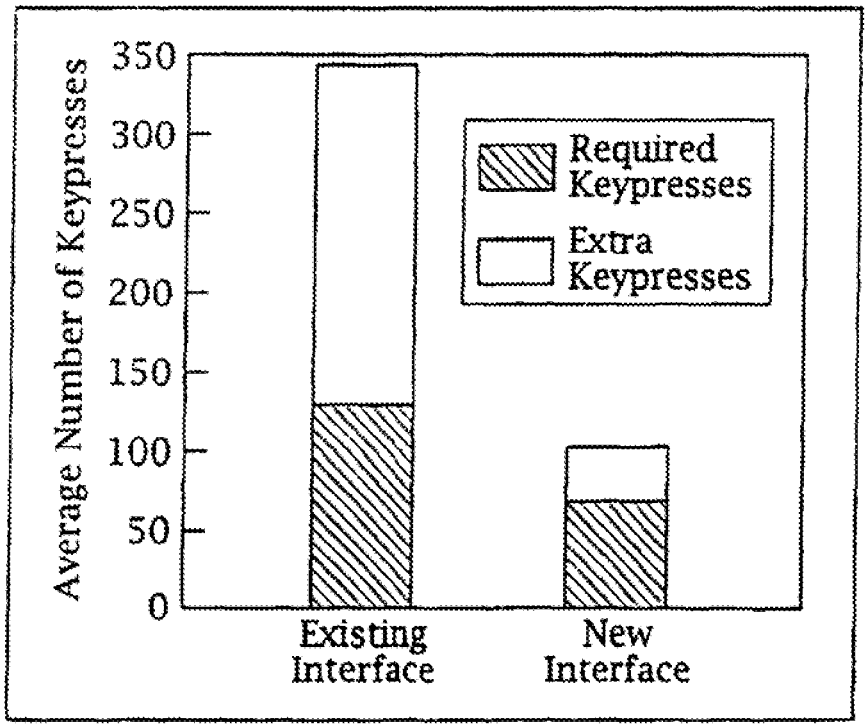
FIG. 2 shows a graphical comparison of required and extra keypresses for the prior art and the interface of the present invention.
Figure 3:
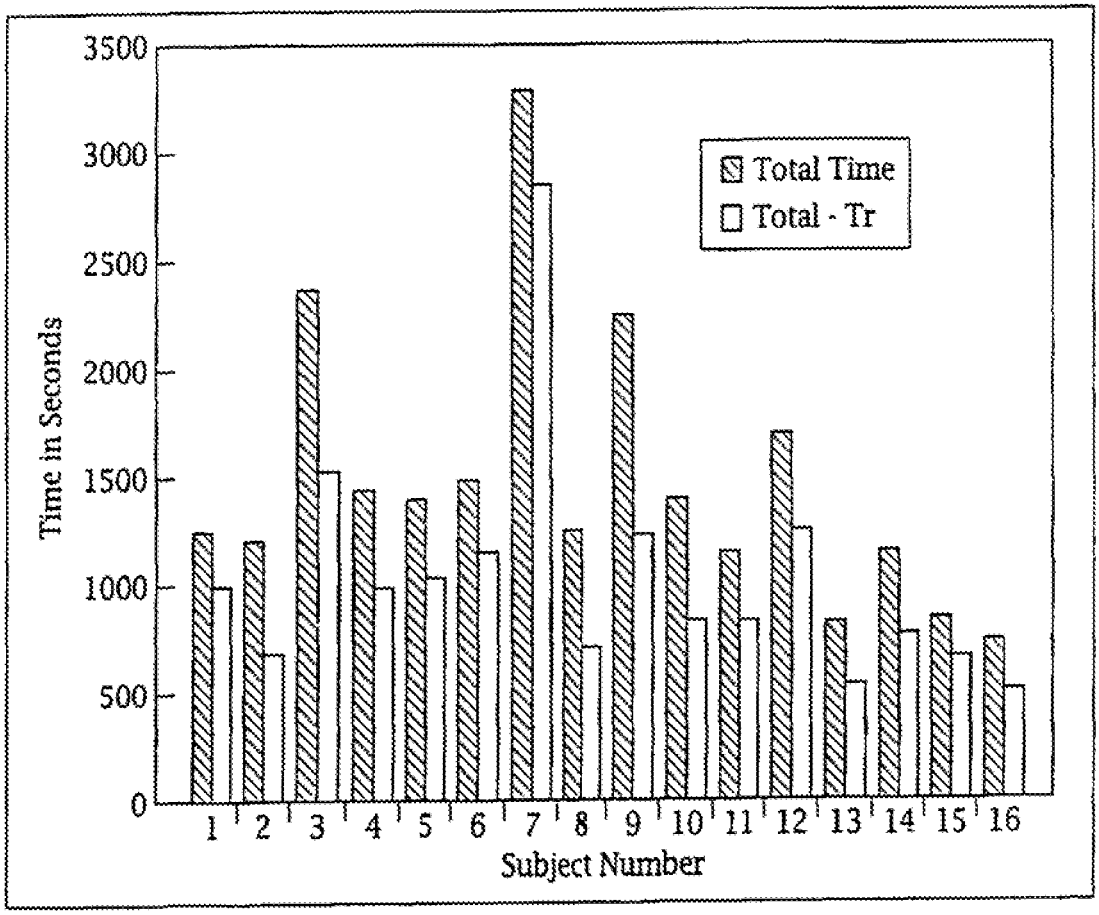
FIG. 3 graphically shows the differences in seconds between total time for the prior art for each user.
Figure 4:
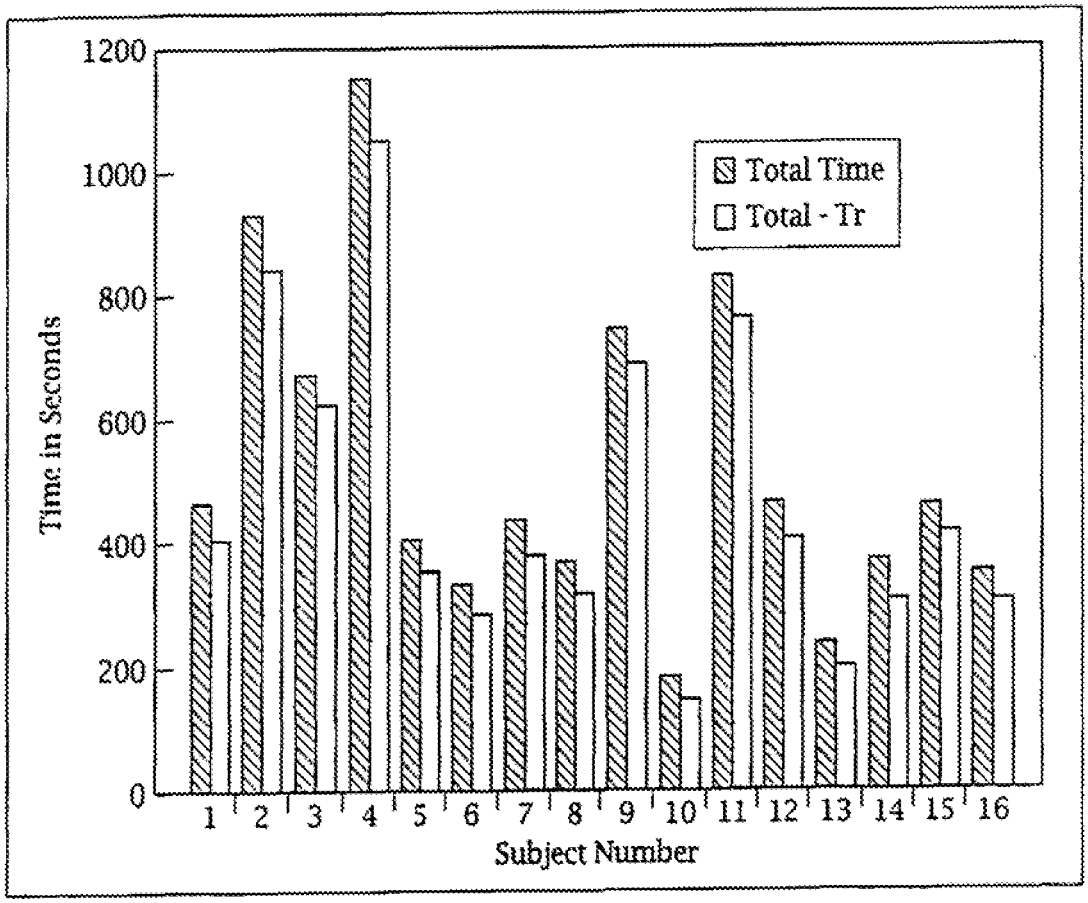
FIG. 4 graphically shows the differences in seconds between total time for the interface of the present invention for each user.
Figure 5:
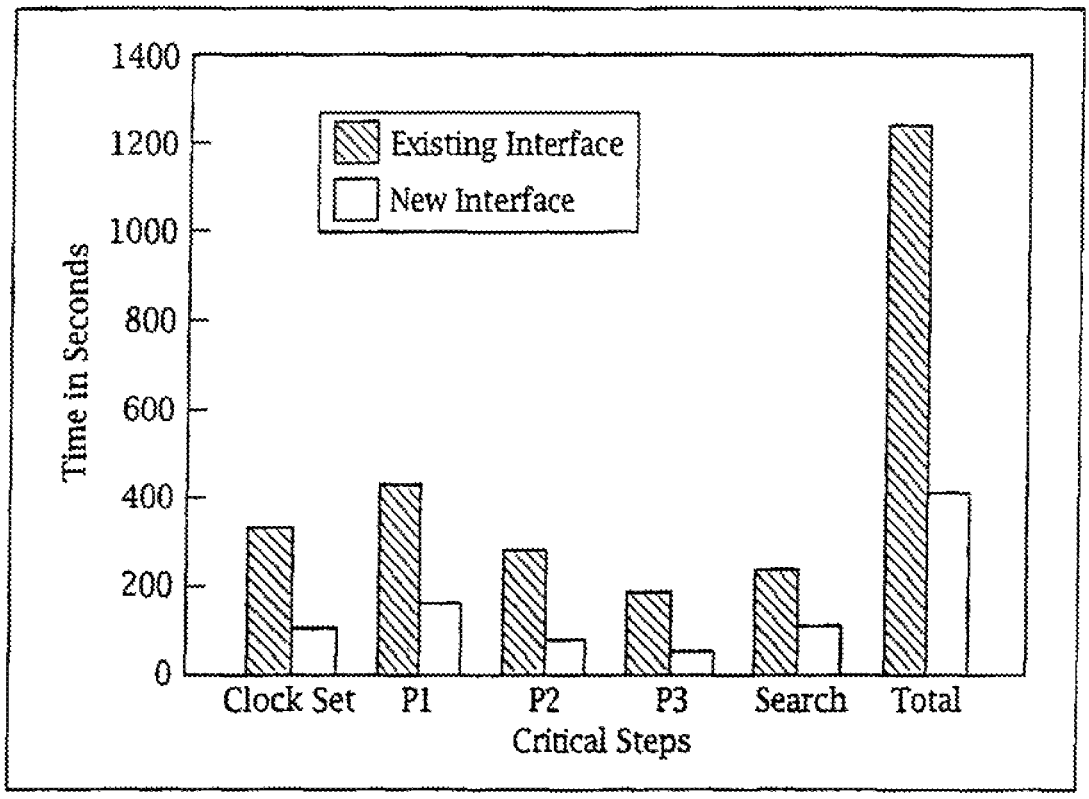
FIG. 5 graphically shows the programming steps for the comparison of the prior art and the interface of the present invention.
Figure 6:
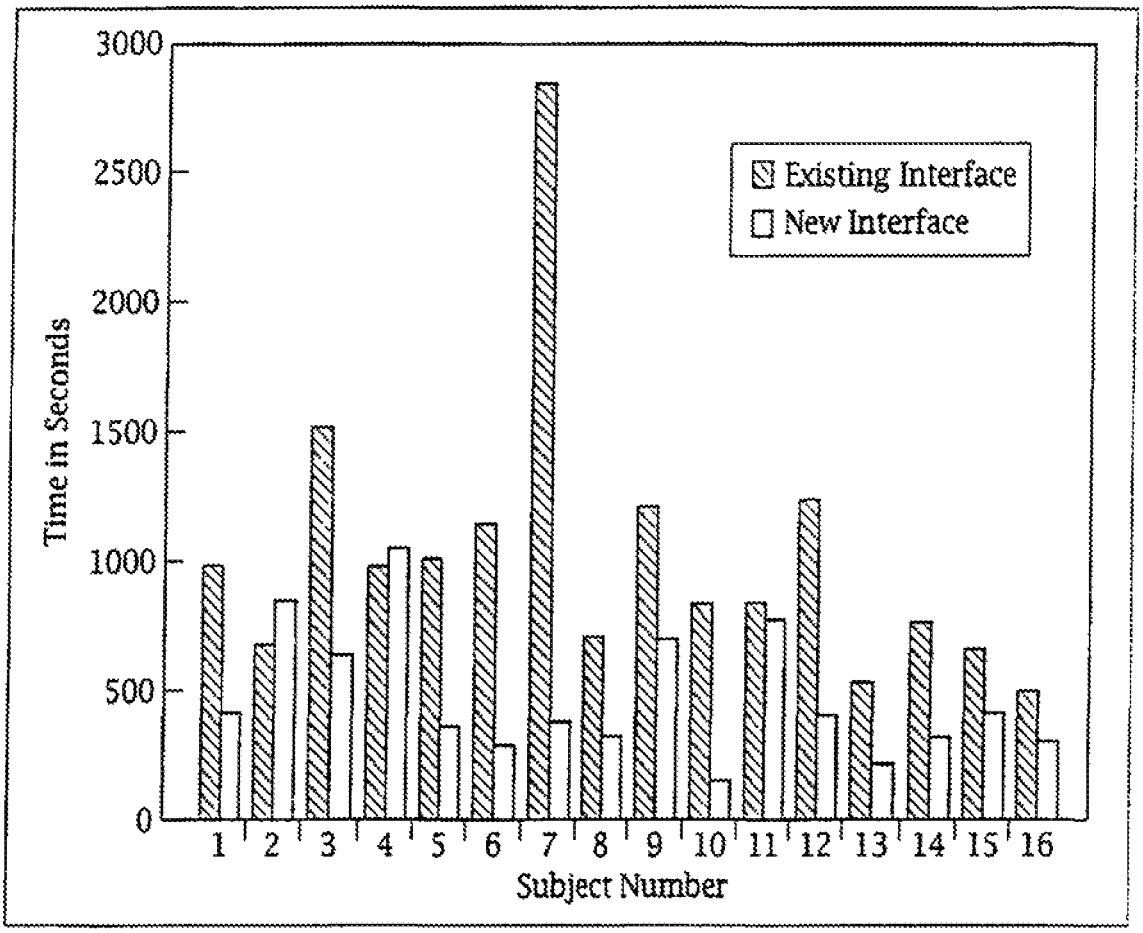
FIG. 6 graphically shows comparative statistics by user comparing the prior art and the interface of the present invention.
Figure 7:
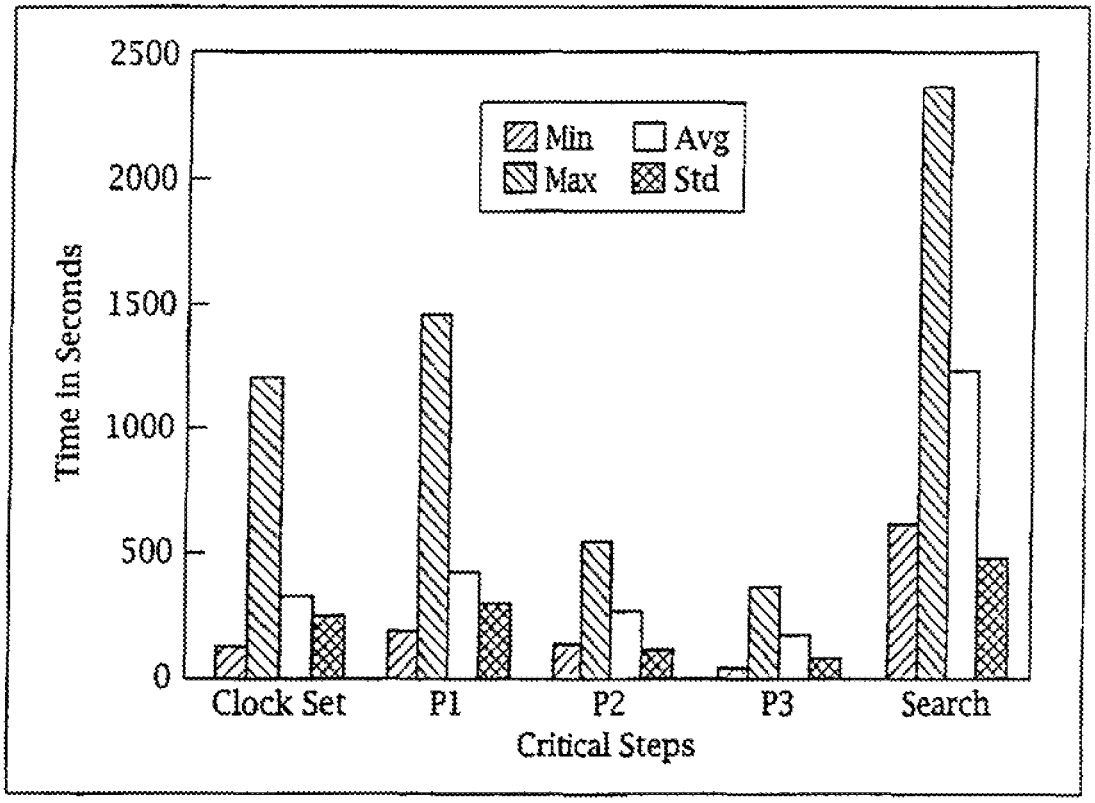
FIGS. 7 and 8 graphically show the critical steps in programming the prior art and the interface of the present invention.
Figure 8:
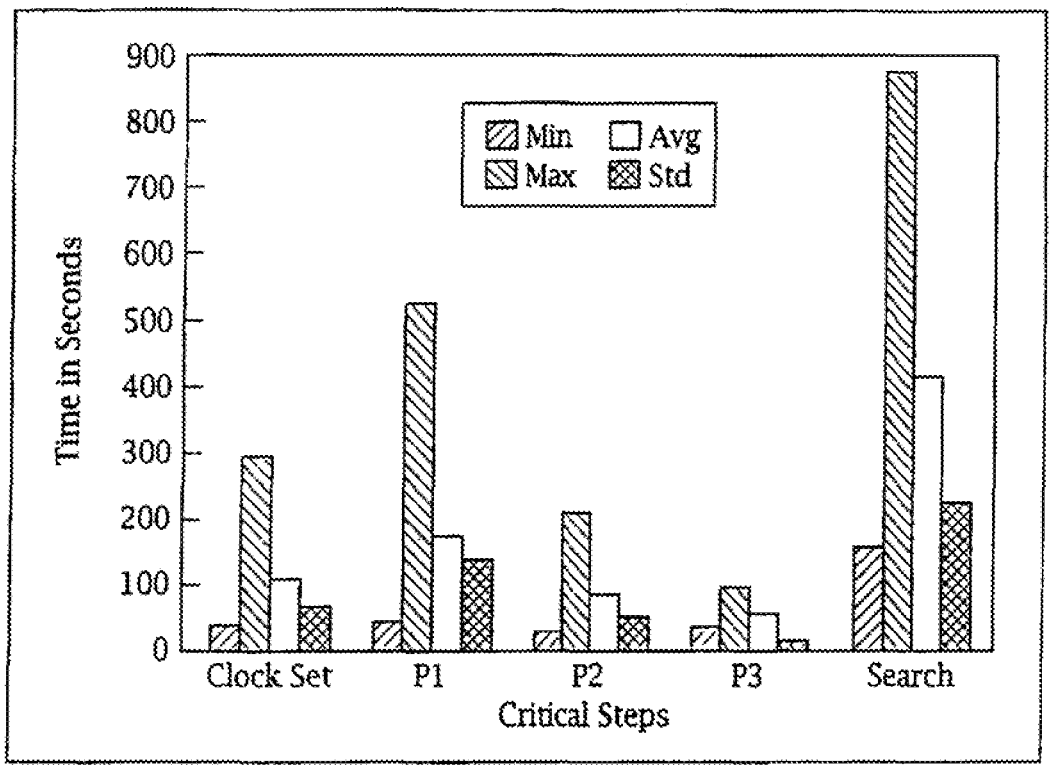
Figure 9:
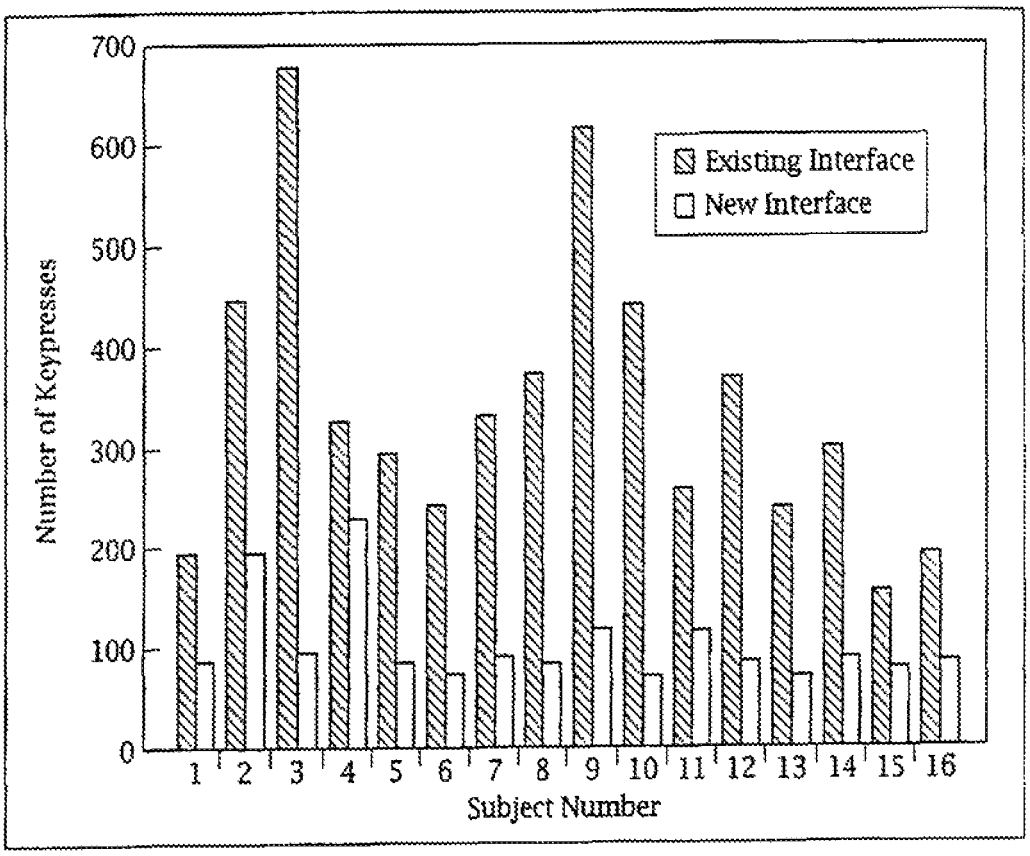
FIG. 9 graphically shows the number of keypresses made by test participants comparing the prior art and the interface of the present invention.
Figure 10:
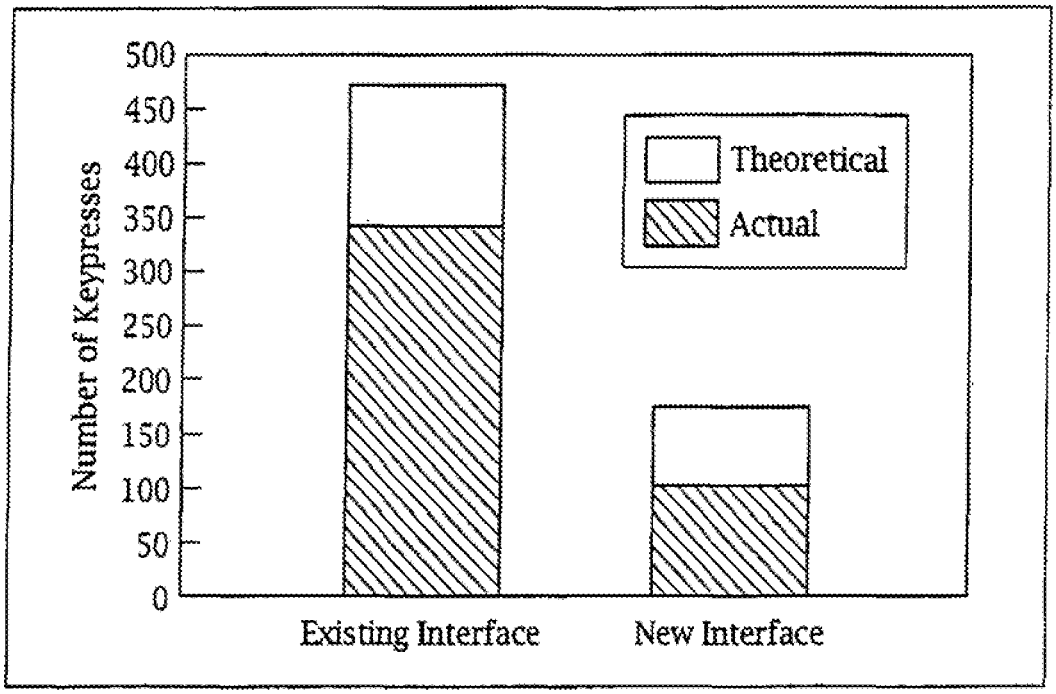
FIG. 10 graphically shows the comparison of the actual and theoretical number of keypresses necessary for programming the prior art and the interface of the present invention.
Figure 11:
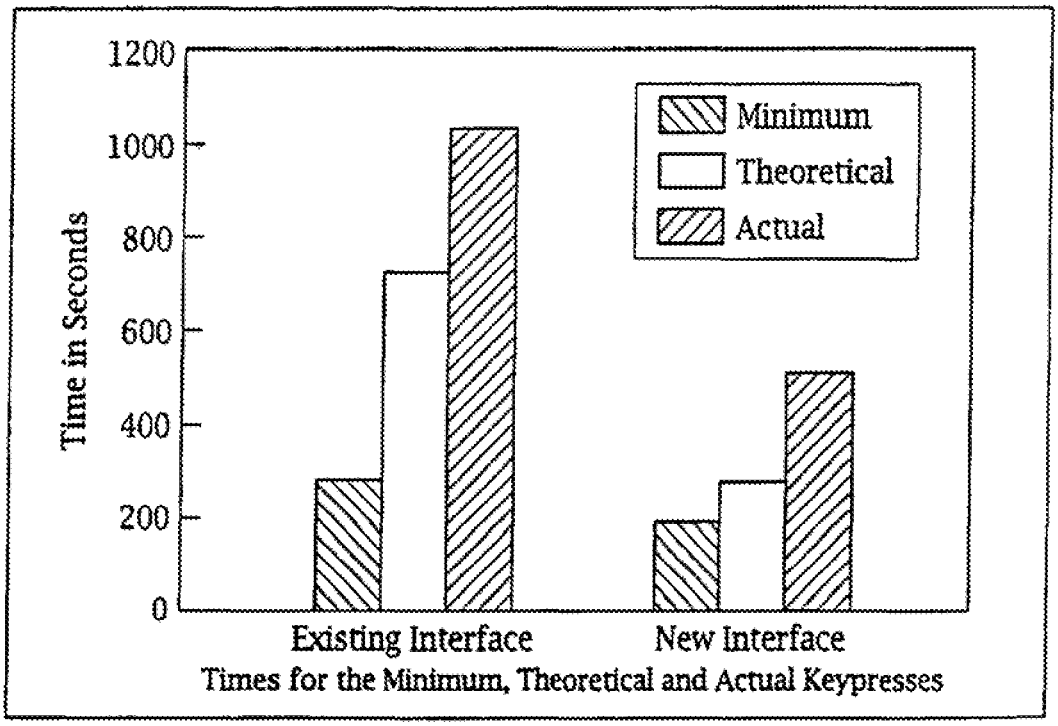
FIG. 11 graphically compares the actual and theoretical time necessary for programming the prior art and the interface of the present invention.
Figure 12A:
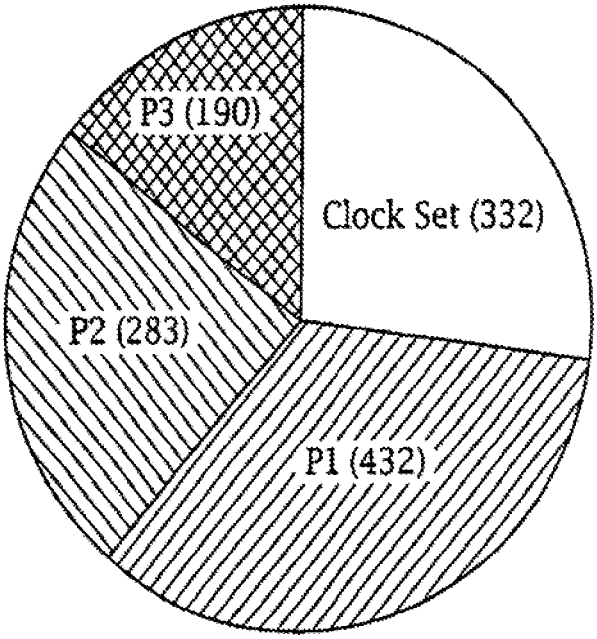
FIGS. 12a and 12b graphically compares the actual and theoretical time necessary for setting the programs in the prior art and the interface of the present invention.
Figure 12B:
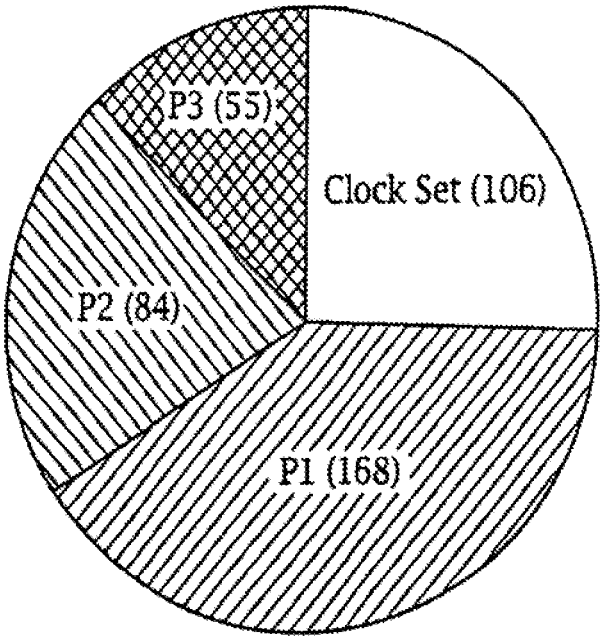
Figure 13:
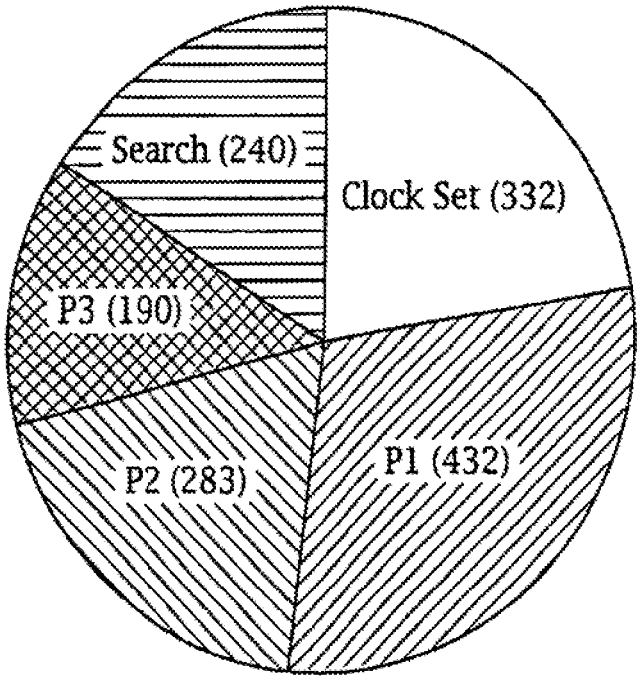
FIGS. 13 and 14 graphically show the percentage time for the critical steps in programming the prior art and the interface of the present invention.
Figure 14:
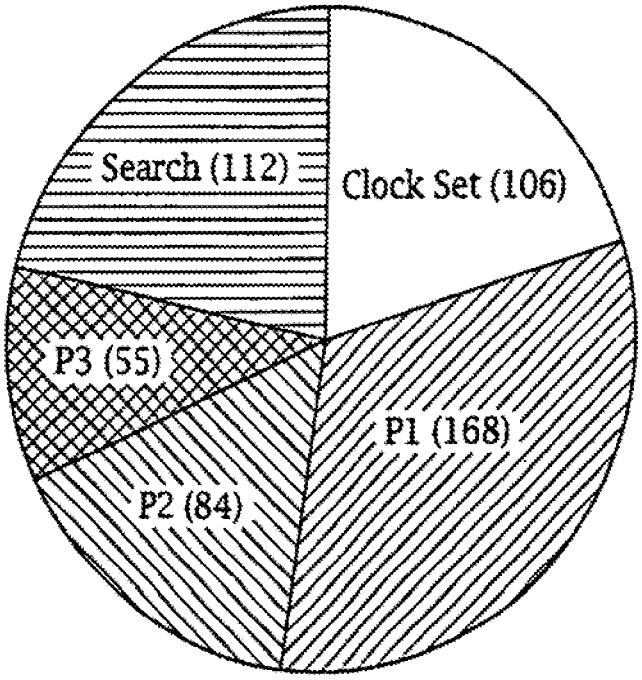

The preferred embodiments of the present invention will now be described with reference to the Figures. Identical elements in the various figures are designated with the same reference numerals.

EXAMPLE 1

VCR Interface

A preferred embodiment of the interface of the present invention, described in the present example, provides automatic sequencing of steps, leading the user through the correct sequence of actions to set a program on the screen, so that no necessary steps are omitted, and no optional steps are accidentally or unintentionally omitted. These steps are shown diagrammatically in FIG. 15 of the present invention. In addition, such a system does not burden the user with the necessity of inputting superfluous information, nor overwhelm the user with the display of unnecessary data. See, Hoffberg, Linda I., "AN IMPROVED HUMAN FACTORED INTERFACE FOR PROGRAMMABLE DEVICES: A CASE STUDY OF THE VCR", Master's Thesis, Tufts University; Hoffberg, Linda I., "Designing User Interface Guidelines For Time-Shift Programming of a Video Cassette Recorder (VCR)", Proc. of the Human Factors Soc. 35th Ann. Mtg. pp. 501-504 (1991); and Hoffberg, Linda I., "Designing a Programmable Interface for a Video Cassette Recorder (VCR) to Meet a User's Needs", Interface 91 pp. 346-351 (1991). See also, U.S. patent application Ser. No. 07/812,805, incorporated herein by reference in its entirety, including appendices and incorporated references.

Many design considerations were found to be important in the improved interface of the present invention:

The interface should preferably employ only minimal amounts of abbreviations and the use of complete words is especially preferred, except where a standard abbreviation is available or where an "iconic" or symbolic figure or textual cue is appropriate. Thus, standard abbreviations and symbols are acceptable, and displayed character strings may be shortened or truncated in order to reduce the amount of information that is to be displayed, where necessary or desirable. An option may be provided to the user to allow full words, which may decrease the information which may be conveyed on each screen and increase the number of screens that must be displayed, or abbreviations and symbols, which may minimize the number of displayed screens of information, thus allowing the user to make the compromise. This aspect of the system may also be linked to the adaptive user level function of the present invention, wherein abstract symbols and abbreviations are presented to advanced users, while novices are presented with full words, based on an implicit indication of user level. These abstract symbols and abbreviations may be standard elements of the system, or user designated icons. Of course, the user could explicitly indicate his preference for the display type, thus deactivating the automatic adaptive user level function.

If multiple users use the device, then the device identifies the relevant users. This may be by explicit identification by keyboard, bar code, magnetic code, smart card (which may advantageously include a user profile for use with a number of devices), an radio frequency identification (RF-ID) or infrared identification (IR-ID) transponder, voice recognition, image recognition, or fingerprint identification. It is noted that smart cards or other intelligent or data-containing identifications systems may be used with different types of devices, for example video, audio, home appliances, heating, ventilation, air conditioning (HVAC) and automobile systems.

Where a new user is identified to the system, an initial query may be made to determine an optimum initial user level. This allows further identification of the user and preference determination to occur more efficiently.

In applications in which a user must program an event on a certain date, at a certain time, a built-in calendar menu screen is preferably employed so that the user cannot set the device with a program step that relies on a non-existent date. Technology that will help eliminate the human problem of setting the wrong (yet existing) date may also be employed. Such technology might include accessing an on-line or other type of database containing media programming information, and prompting the user regarding the selected choice. In situations where it is applicable, the interface should indicate to the user the number of characters the interface is expecting, such as when entering the year.

Figure 16:
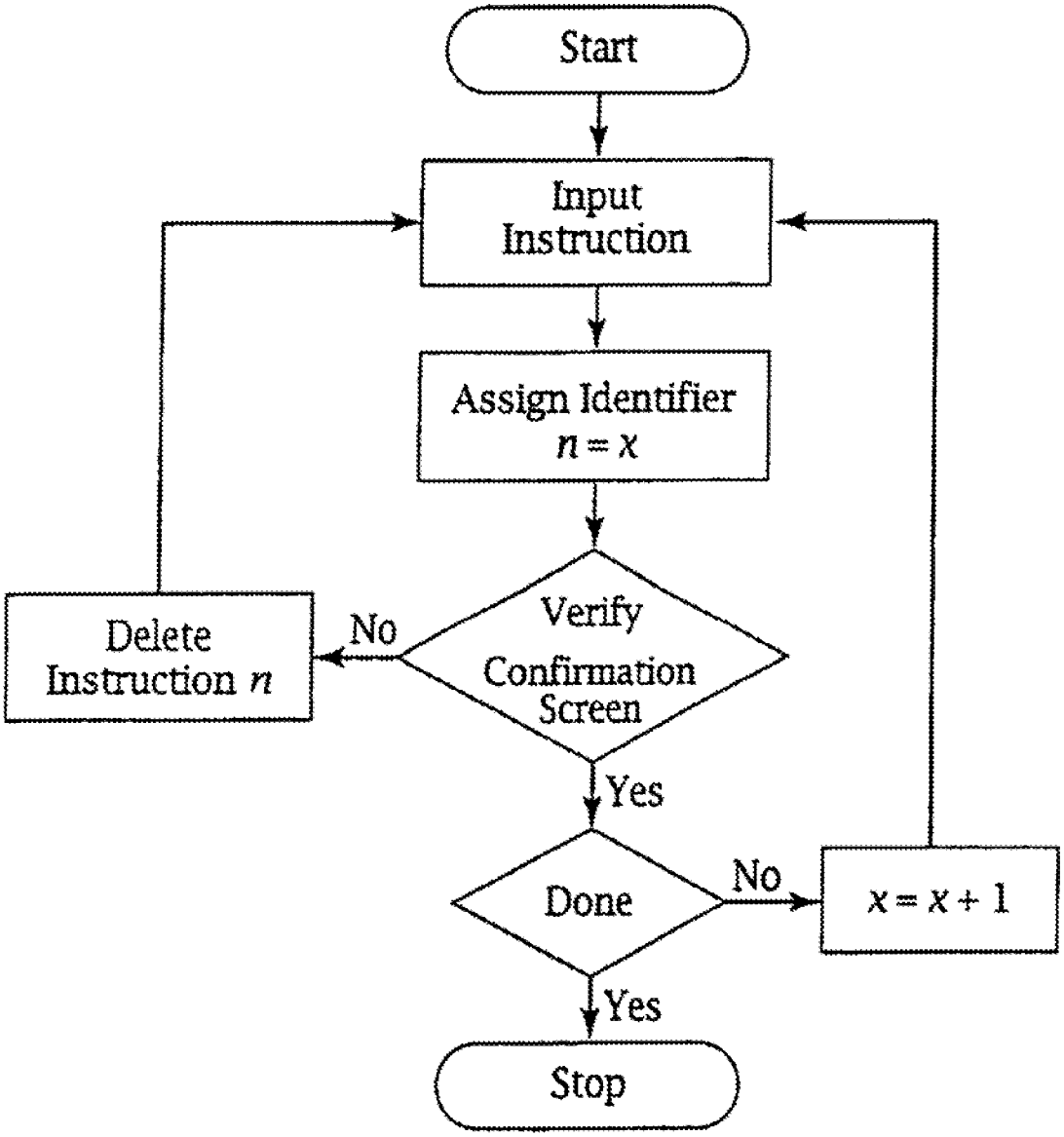
FIG. 16 is a flow diagram of the program input verification system of the present invention.

The interface system provides an easily accessible CHANGE, CANCEL or UNDO (single or multiple level) feature, which facilitates backtracking or reprogramming the immediately previously entered information rather than forcing the user to repeat all or a substantial portion of the programming steps. A method of the type described is shown in FIG. 16 of the present invention. User input is also facilitated by the provision of frequently used settings as explicit choices, such as, referring to the VCR example, "Record today," "Record tomorrow," "Noon," and "Midnight," so that the user does not have to specify a date in these cases. This will eliminate extra keypresses, and reduce the programming time. In addition, this could eliminate user errors. Frequently used choices for program selections are also provided to the user to reduce the number of programming steps necessary and provide the user with all the frequently used selections. The especially preferred choices are "Once On . . . ", "Once a Week on . . . ", "Monday-Friday at . . . ", "Everyday at . . . ". These redundant, complex instructions reduce the number of keystrokes required for data entry, and reduce the amount of programming time required.

The presently described interface system also provides, in the event that a color screen is available, conservatively used color coding, which allows the user to effectively and quickly acknowledge the function of each aspect of the screen. When programming, the preferred colors are royal blue for "help," red for mistakes, light blue for information previously entered, and yellow for current information being entered. Of course, other colors could be used, according to the user's or designer's preference, cultural differences, and display parameters.

When viewing, it is preferable that screen colors change to indicate status changes, such as viewed/unviewed, or to categorize the shows.

Figure 15:
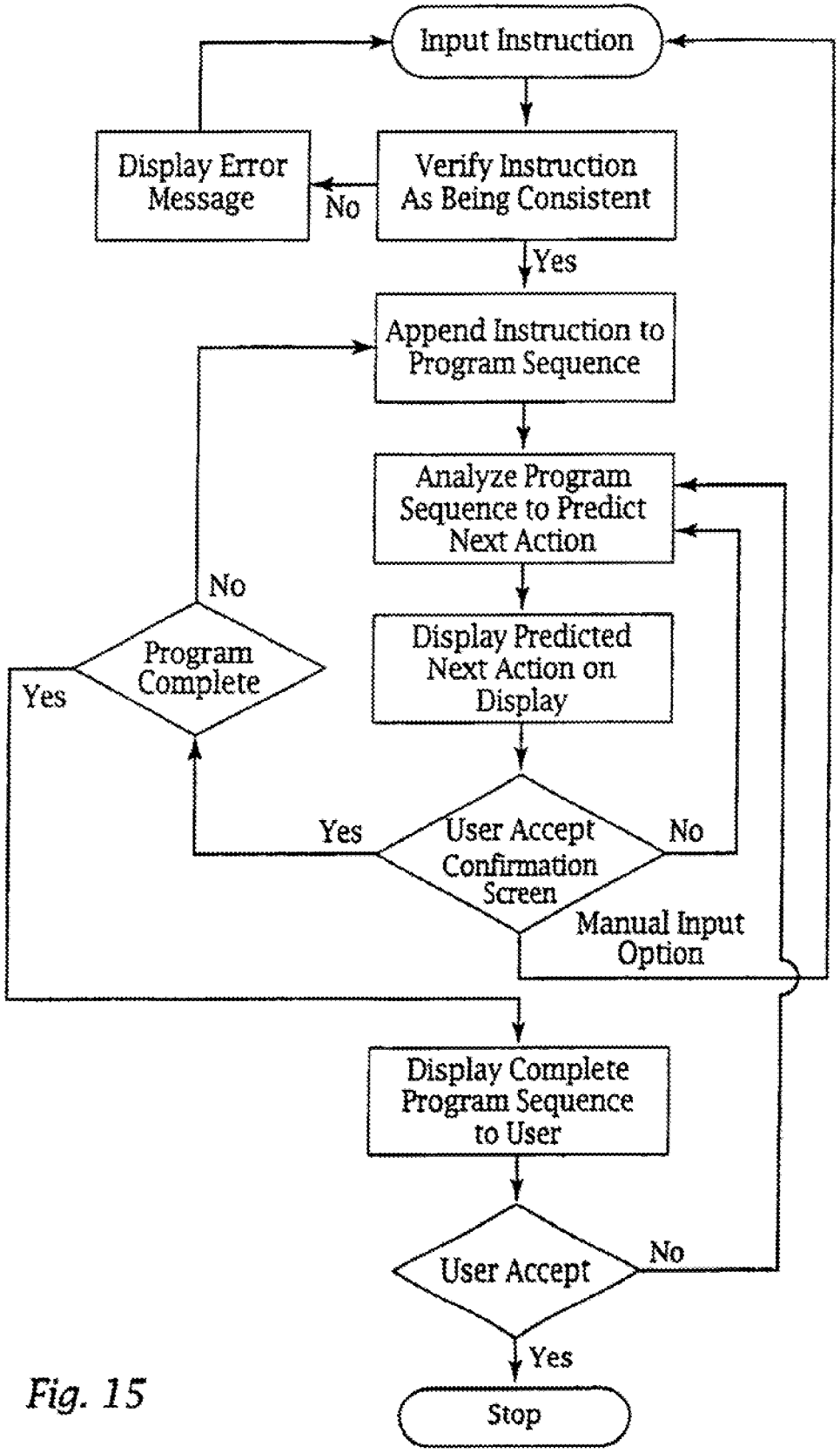
FIG. 15 is a flow diagram of a predictive user interface of the present invention.

The interface includes a confirmation screen which displays to the user all of the categories and selections previously explicitly entered or otherwise inferred, and should be easily understandable. This is shown in FIG. 15 of the present invention. All of the necessary information is displayed on this screen, in addition to the change and cancel options, if possible.

The entering of information on each screen is preferably consistent throughout the various interface options and levels. All of the screens preferably have similar layouts. "Buttons" or screen locations which are keyed to a particular function, which appear on multiple screens, should appear in approximately the same location on all screens. However, in certain cases, relatively more important information on a given screen may be displayed more prominently, and possibly in a different screen location, in order to reduce the search time. Further, when other factors dictate, each screen may be independently optimized for the prescribed function. For example, a representation of an analog clock dial may be used to set time information. However, even if the format does change, a standard scheme should be maintained, such as the use of a particular color to indicate that a particular program aspect has been changed.

The interface should display data consistent with standards and conventions familiar to users. For, e.g., when entering dates, users are most familiar with calendars. However, this type of presentation of choices does not eliminate the human problem of entering incorrect information, e.g., setting a wrong, but existing, date. The problem of ensuring the accuracy of user input may be addressed by an intelligent interface which stores data concerning programming, user preferences, and by means of some logical method, such as Boolean logic, fuzzy logic, neural network theory, or any other system which may be used to generate a prediction, to determine if an entry is likely in error, by comparing the prediction with the entry. Of course, these predictive systems would also provide an initial default entry, so that an a priori most probably action or actions may be initially presented to the user.

In addition to following conventions of information presentation to the user, the interface of the present invention may also provide emulations of other user interfaces of which a particular user may be familiar, even if these are not optimized according to the presently preferred embodiments of the present invention, or not otherwise well known. These emulations need not even be of the same type of device, so that a broad based standard for entry of information into a programmable controls, regardless of their type, may be implemented. By allowing emulation, the interface could provide compatibility with a standard or proprietary interface, with enhanced functionality provided by the features of the present interface.

These enhanced functional intelligent aspects of the controller may be implemented by means of software programming of a simple microcomputer, or by use of more specialized processors, such as a Fuzzy Set Processor (FSP) or Neural Network Processor to provide real-time responsiveness, eliminating delays associated with the implementation of complex calculations on general purpose computing devices.

In the various embodiments according to the present invention, various control strategies are employed. Depending on the application, fuzzy set processors (FSP's) may be preferred because they have the advantage of being easier to program through the use of presumptions or rules for making the fuzzy inferences, which may be derived by trial and error or the knowledge of experts, while Neural Networks are less easily explicitly programmed and their network weighing values are not easily understood in the abstract, but these systems may be applied to learn appropriate responses from test data. Thus, neural networks tend to require extensive "training", while Fuzzy Set Processors may be explicitly programmed without the need of duplicating or simulating actual operating conditions, but may require "fine tuning".

The most frequently used choices preferably should be displayed as the default setting. The screen cursor preferably appears at the "accept" screen button, when the screen is displayed. This default can either be set in advance, or acquired by the system. In the case of acquired defaults, these may be explicitly set by the user or adaptively acquired by the system through use. The interface of the present invention may be taught, in a "teach" mode, the preferences of the user, or may also acquire this information by analyzing the actual choices made by the user during operation of the interface and associated controller. This type of operation is shown schematically in FIG. 15 of the present invention. The options of "Midnight" (12:00 AM) and "Noon" (12:00 PM) should preferably be present, as some people often become confused when distinguishing between them. Icons, such as those indicative of the "sun" and the "moon", may also be used to facilitate data entry for AM and PM. The interface should preferably utilize an internal clock and calendar so that the user cannot set the time or program to record on a nonexistent date. Such a system could also compensate for daylight-savings time seasonal adjustments.

The cursor is preferably distinctive and readily distinguished from other parts of the screen. This may be by color, attribute (i.e. blinking), size, font change of underlying text, or by other means.

The user can preferably exit the programming sequence at any time by selecting a "Main Menu" button which may exist on the lower left-hand corner of every screen. The user is preferably provided with an adequate amount of feedback, and error messages should be directive in nature. Some form of an acknowledgement is preferably displayed after each entry. The user should preferably not be able to go to the next programming step until the current step has been completed. A message to convey why the user can not continue should appear when an attempt to prematurely continue is recognized.

The "help" function is available for when the user does not know what to do. The "help" screen(s) preferably explains the functions of each of the available buttons or functions, but may also be limited to those that are ambiguous. The "help" screen may also be used to indicate a current status of the interface and the controller. Further, the "help" function may also provide access to various other functions, such as advanced options and configurations, and thus need not be limited to merely providing information on the display. The help system may incorporate a hypertext-type system, wherein text or information relating to concepts that are conceptually linked may be easily accessed by indicating to the interface system that the related information is desired. To eliminate the possibility of the user trying to make selections on merely informative help screens, the cursor, in these cases, should be locked to a choice which returns the user to where they left off in the programming sequence, and this choice should be highlighted.

The "help" function may also comprise "balloon help" similar to the system adopted by Apple Computer, Inc. in Macintosh Operating System, e.g., 7.0, 7.1, 7.5, etc.

The interface preferably initiates the programming sequence where the user wants to be, so that the interface has so-called "smart screens". For example, when a VCR is first powered up or after an extended power failure, and the time and date are not stored in the machine, the "set date" and "set time" screens should appear. The sequence of screens may also vary depending on the system predicted requirements of the user and various aspects of the improved interface of the present invention. This is shown schematically in FIG. 17 of the present invention.

The preferable input device for the interface of the present invention provides as few buttons as possible to achieve the required functionality, thus reducing potential user intimidation, focusing the user's attention on the interactive display screen, where the available choices are minimized to that number necessary to efficiently allow the user to program the discrete task presented. Such a minimization of discrete inputs facilitates a voice recognition input, which may be used as an alternative to mechanical input devices. The preferred embodiment includes a direct-manipulation type interface, in which a physical act of the user causes a proportionate change in the associated interface characteristic, such as cursor position. A computer mouse, e.g. a two dimensional input device, with 1 to 3 buttons is the preferred input device, for use with a general purpose computer as a controller, while a trackball on a remote control device is especially preferred for limited purpose controllers because they do not require a flat surface for operation. Other stationary or movement sensitive input devices may, of course be used, such as joysticks, gyroscopes, sonic echo-location, magnetic or electrostatic location devices, RF phase location devices, Hallpots (joystick-like device with magnets that move with respect to Hall effect transducers), etc. The present interface minimizes the number of necessary keys present on an input device, while maintaining the functionality of the interface. It is noted that a strict minimization without consideration of functionality, might lead to inefficiency. For example, in a VCR device, if the user wants to record a program which airs Monday through Friday, he would have to set five separate programs, rather than one program if a "weeknights" choice is made available.

The interface preferably should be easy to learn and should not require that a user have prior knowledge of the interface in order to use it. An attempt has been made to minimize the learning curve, i.e., to minimize the time it takes to learn how to use the device.

Menu options are preferably displayed in logical order or in their expected frequencies. Research has shown that a menu-driven interface is best for applications involving new users and does not substantially hinder experienced users. Menu selection is preferably used for tasks which involve limited choices. They are most helpful for users with little or no training. Each menu should preferably allow only one selection at a time. Most of the information is preferably entered using a numeric keypad (entry method), rather than using up and down arrow keys (selection method). In addition, no leading zeros are required for entry. If there is more than one keystroke required, the user must then select an "OK" button to continue in the programming sequence. However, if the selection method is used, all of the choices are displayed on the screen at once. The number of steps required to complete the task through a sequence of menus should be minimized. The choice of words used to convey information should not be device specific, i.e., computer terms, but rather normal, everyday terms which are easy to understand. In addition, very few abbreviations should be used. All necessary information which the user needs should preferably be displayed at once. A user preferably should not have to rely on his memory or his previous experience, in order to find the correct choice, at least at the lower user levels. If all selections cannot be displayed at once, a hierarchical sequence is preferably used. A main menu should preferably provide a top level to which the user can always return and start over.

Searching and learning times should be kept to a minimum in order to obtain a subjectively better interface. The system's logic should reflect the users' expectations, offer visual clues and feedback, and stay within human memory limits. For example, the VCR should turn on not only with the "Power" button, but also when inserting a tape into the device. In addition, the sequence of steps for setting the machine to record, if the user does not indicate implicitly or explicitly that he knows how to use the device, should assume that the user is a novice, and fully prompt the user for elemental items of information. Nothing should be taken for granted. By developing an improved interface, an attempt is made to: reduce the searching time; reduce the learning time; simplify the entering of data; and, reduce the intimidation experienced by certain persons when using electronic devices.

Tests by an inventor hereof show that people do not program their VCRs often, and they often forget the sequence of steps between recording sessions. Thus, the present invention preferably incorporates an adaptive user level interface, wherein a novice user is presented with a simpler interface with fewer advanced features initially available, so that there is reduced searching for the basic functions. A more advanced user is presented with more advanced choices and functions available initially, as compared to a novice user.

Figure 17:
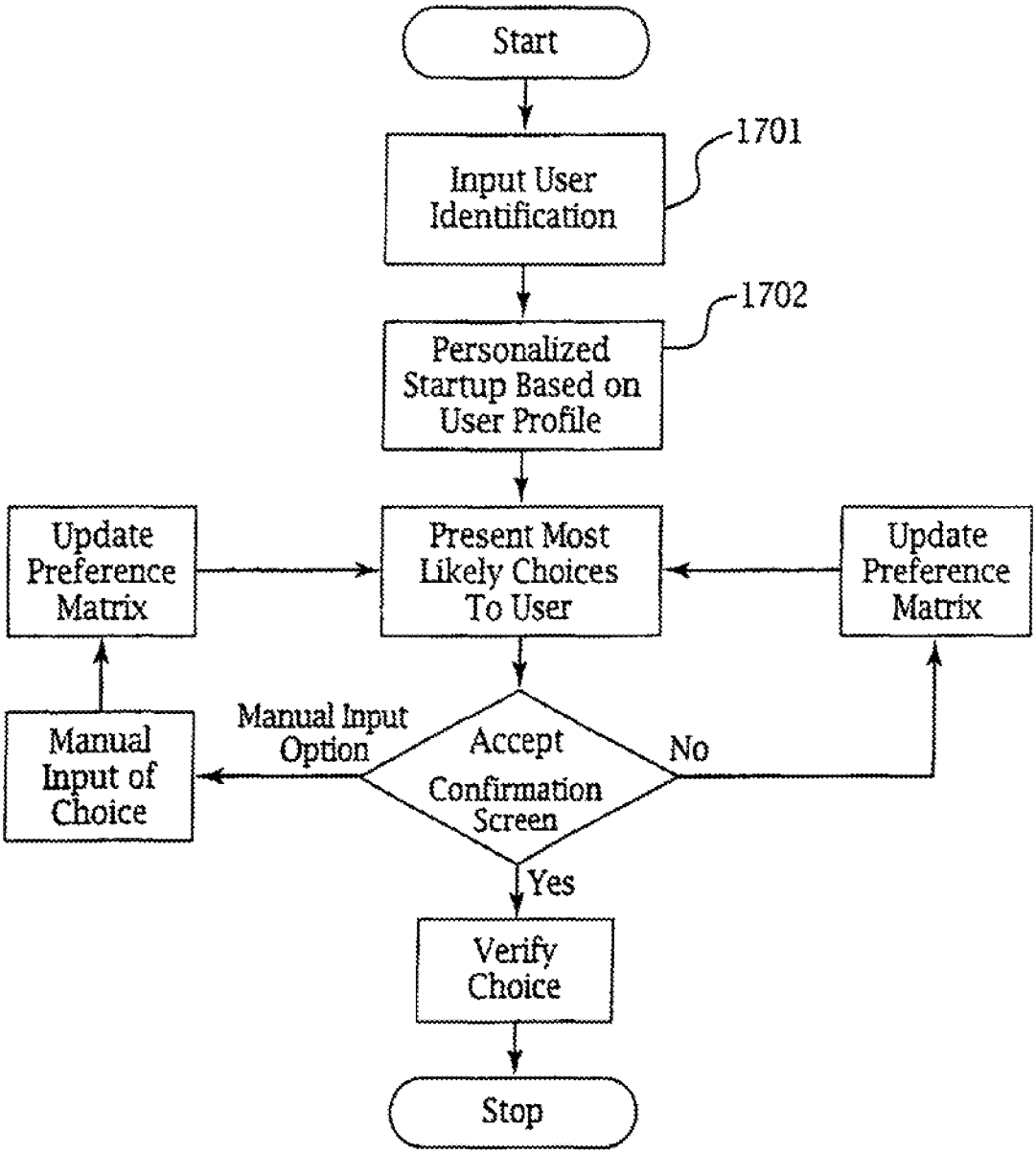
FIG. 17 is a flow diagram of a predictive user preference aware interface of the present invention.

Thus, as shown in FIG. 17, the user identifies himself to the controller in block 1701. The controller 1806 of FIG. 18 thereafter uses a stored profile of the identified user in controlling the interaction with the user, as shown in block 1702 of FIG. 17, from information stored in the database 1807 of FIG. 18 of the present invention. It has been found that in the case of novice users, a greater number of simple instructions may be more quickly and easily input rather than a potentially fewer number of a larger set of more complex instructions. It has further been found that, even if presented with a set of instructions which will allow a program to be entered with a fewer number of inputs, a novice user may choose to input the program using the simple instructions exclusively, thus employing an increased number of instructions and being delayed by an increased search time for those instructions that are used, from the larger set.

Other characteristics of this interface include color coding to help prompt the user as to which data must be entered. Red text signifies instructions or errors, yellow text represents data which must be entered or has not been changed, and blue text shows newly entered program data or status information. Blue buttons represent buttons which should normally be pressed during the programming sequence. Red buttons signify an erratic pattern in the data entry, such as the "cancel" and "return to main menu" buttons. Of course, these colors can be replaced by other display attributes, such as intensity, underline, reverse video, blinking and pixel dithering pattern, in addition to the use of various fonts. Such a situation would include a monochrome monitor or display.

The date may be entered in the form of a calendar rather than as numbers (i.e., "9/6/91"). This calendar method is advantageous because users may wish to input date data in one of three ways: day of the week, day relative to the present, and day of the month. The present method allows the current date to be highlighted, so that the calendar may be used to easily enter the absolute day, absolute date, and relative day. Further, the choices "today" and "tomorrow", the most frequently used relative recording times, are included in addition to a month-by-month calendar. This information is provided to avoid an unnecessary waste of time and user frustration. Thus, another aspect of the present invention is to provide a partially redundant interactive display input system which allows, according to the highest probability, the choices to be prominently displayed and easily available, in addition to allowing random access to all choices.

The present device allows common user mistakes to be recognized and possibly addressed, such as the confusion between 12:00 PM and 12:00 AM with midnight and noon, respectively. Therefore, the options of "noon" and "midnight" are provided in addition to a direct numeric clock input. When entering time information, leading zeros need not be entered, and such information may be entered in either fashion.

The criteria for system acceptance of input depends on how many keystrokes are required on the screen. If only one keystroke is required to complete input of the information, upon depressing the key, the programming sequence will continue. If more than one keypress is required, the user must depress the "OK" button to continue programming. This context sensitive information entry serves to avoid unnecessary input.

An on-line "help" system and on-line feedback is preferably provided to the user throughout various aspects of the interface. Other features include minimizing the number of keypresses required to program the device. These features, together with other aspects of the present invention allow the user to achieve a greater efficiency with the input device than with prior art devices.

The interface of the present invention applied to a VCR control preferably comprises a virtual keypad entry device (i.e. a representation of an array of choices), a directional input control for a cursor on a display screen, and selection buttons. The input device has an input corresponding to a direction of movement relative to the cursor position. Thus, since the present input device seeks to minimize the physical control elements of the human interface device, the display elements for a preferred embodiment of the present interface include:

1. number keys 0-9
2. enter key
3. cancel key
4. status indicator
5. return to menu option button
6. program type indicator: program once, program once a week, program Monday-Friday, program everyday
7. Day indicators: 7 week days, today, tomorrow
8. Noon and midnight choices
9. Help button 10. Main menu options: Review, Enter new recording time, Set time, Set date
11. Timer button
12. Power button
13. AM/PM choices
14. 31 day calendar
15. 12 month Choices
16. 3 tape speed choices User dissatisfaction is generally proportionate to the length of "search time," the time necessary in order to locate and execute the next desired function or instruction. Search time may be minimized by the inclusion of up to a maximum of 4-8 choices per screen and by use of consistent wording and placement of items on the display.

The present invention proceeds from the understanding that there are a number of aspects of a programmable interface that are desirable:

First, users should be able to operate the system successfully, without wide disparities in time. It should take, e.g., a normal person interacting with a VCR interface, less than seven minutes to set the time and two programs. Searching time spent in setting the clock, programming, getting into the correct mode, and checking whether or not the VCR is set correctly should be kept to a minimum through the appropriate choices of menu layout and the presentation of available choices.

Second, programming should be a stand-alone process, and not require an instruction manual. A help system should be incorporated in the interface. Word choices should be understandable, with a reduction in the use of confusing word terminology. Error messages should be understandable. The system should provide the ability to cancel, change or exit from any step.

Third, the system should provide on-screen understandable information, with adequate visual feedback. The displays should be consistent. Color coding should be employed, where applicable, using, e.g. blue—new input; red—error condition; yellow—static, unchanged value. Layouts should be logical, and follow a predictable pattern. There should be a maximum of 4-8 choices per screen to minimize searching time. Keys should be labelled with text rather than with ambiguous graphics. However, a combination of both may be preferable in some cases.

Fourth, steps required to complete tasks should be simple, require a short amount of time and not create user frustration. The system should guide the user along a decision path, providing automatic sequencing of steps. The most frequently used choices should be provided as defaults, and smart screens may be employed. The learning curve should be minimized through the use of easily understandable choices. As a user becomes more sophisticated, the interface may present more advanced choices.

Fifth, there should be a reminder to set the timer and to insert the tape once the programming information is entered. This reminder may also be automated, to eliminate the commonly forgotten step of setting the timer, so that the VCR automatically sets the timer as soon as the necessary information is entered and a tape is inserted. Once the program is set in memory, a message should appear if a tape is not inserted. If the VCR is part of a "jukebox" (automatic changer), the tape may be automatically loaded. The VCR should preferably turn on when a tape is inserted. In addition, users should also be able to control the VCR with a Power button.

Sixth, the VCR should be programmable from both the remote device and the control panel.

Seventh, each operation should require only one keypress, if possible, or otherwise reduce the number of keypresses required. There should be a 12 hour clock, not a 24 hour clock. There should be an on-screen keypad with entry keys, not "up" and "down" selector keys, allowing for the choice of specific day or time entry. There should be a "start" and a "stop" recording time, rather than "start" time and "length of program" or duration exclusively. The number of buttons on the remote control should be minimized so that as few buttons as are required are provided. The input device should provide for the direct manipulation of screen elements. A menu driven interface should be provided.

The interface of the present invention provides an automatic sequencing of steps which does not normally let the user think the previous step is complete. This is shown schematically in FIG. 16. In this manner, important steps will not be inadvertently omitted. Upon entering the programming sequence, if the current date or time is not set, the interface will prompt the user to enter this information. Thereafter, the interface will normally default to the main menu, the most frequently used first screen. Thus, the interface of the present invention is adaptive, in that its actions depend on the current state of the device, including prior programming or use of the device by the user. It can be appreciated that this adaptive behavior can be extended to include extended "intelligence". For example, if the device is similarly programmed on a number of occasions, then the default setup may be adapted to a new "normal" program mode. Further, the apparatus could provide multiple levels of user interface, e.g. beginner, intermediate, and advanced, which may differ for various functions, based on the behavior of the user. This user interface level determining feature extraction system is shown diagrammatically in FIG. 18. In contrast, prior art interfaces that have different user interface levels, allow the user to explicitly choose the interface level, which will then be used throughout the system until reset.

The present system allows discrete tasks to be conducted more quickly, more efficiently, with reduced search time and with fewer errors than prior art systems.

EXAMPLE 2

Serial Recording Medium Index

Figure 19:
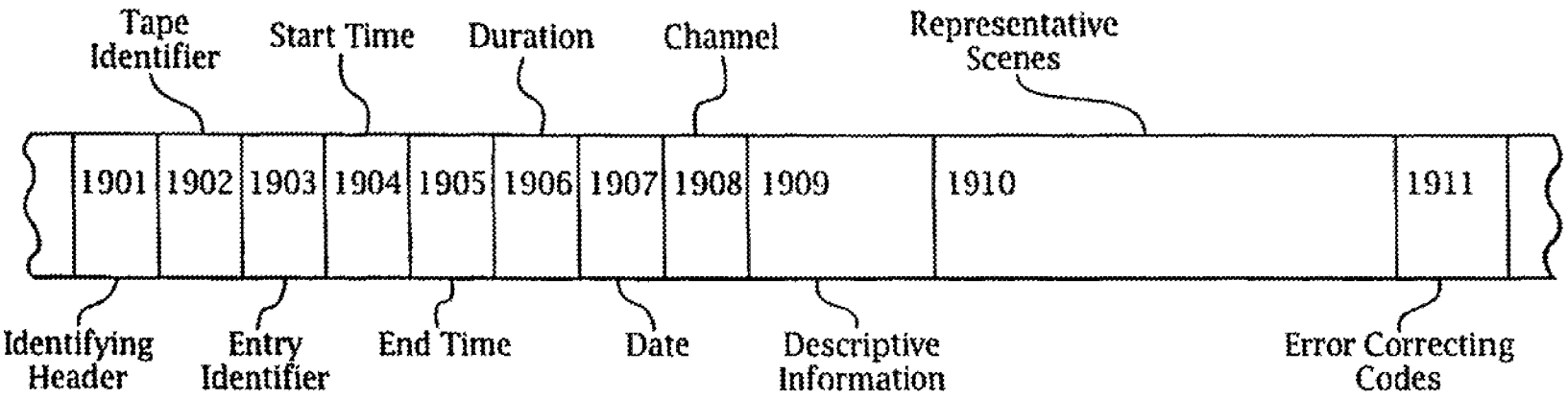
FIG. 19 is a diagram of a block of information for a catalog entry of the present invention.

In a preferred embodiment of the present invention, in a VCR, in order to track the content of the tape, a directory or a catalog is recorded, preferably digitally, containing the programming information, as well as additional information about the recorded programs, in a header, i.e., at the beginning of the tape, or at other locations on the tape. The device may also catalog the tape contents separately, and based on an identification of the tape, use a separately stored catalog. A preferred format for storing information is shown in FIG. 19.

Thus, if there are a number of selections on the tape, the entire contents of the tape could be accessible quickly, without the need for searching the entire tape. In a sequential access medium, the tape transport apparatus must still shuttle to the location of the desired material, but it may do so at increased speeds, because there is no need to read the tape once the location is determined; after the tape transport nears the desired spot, the tape may be slowed or precisely controlled to reach the exact location.

Figure 20:
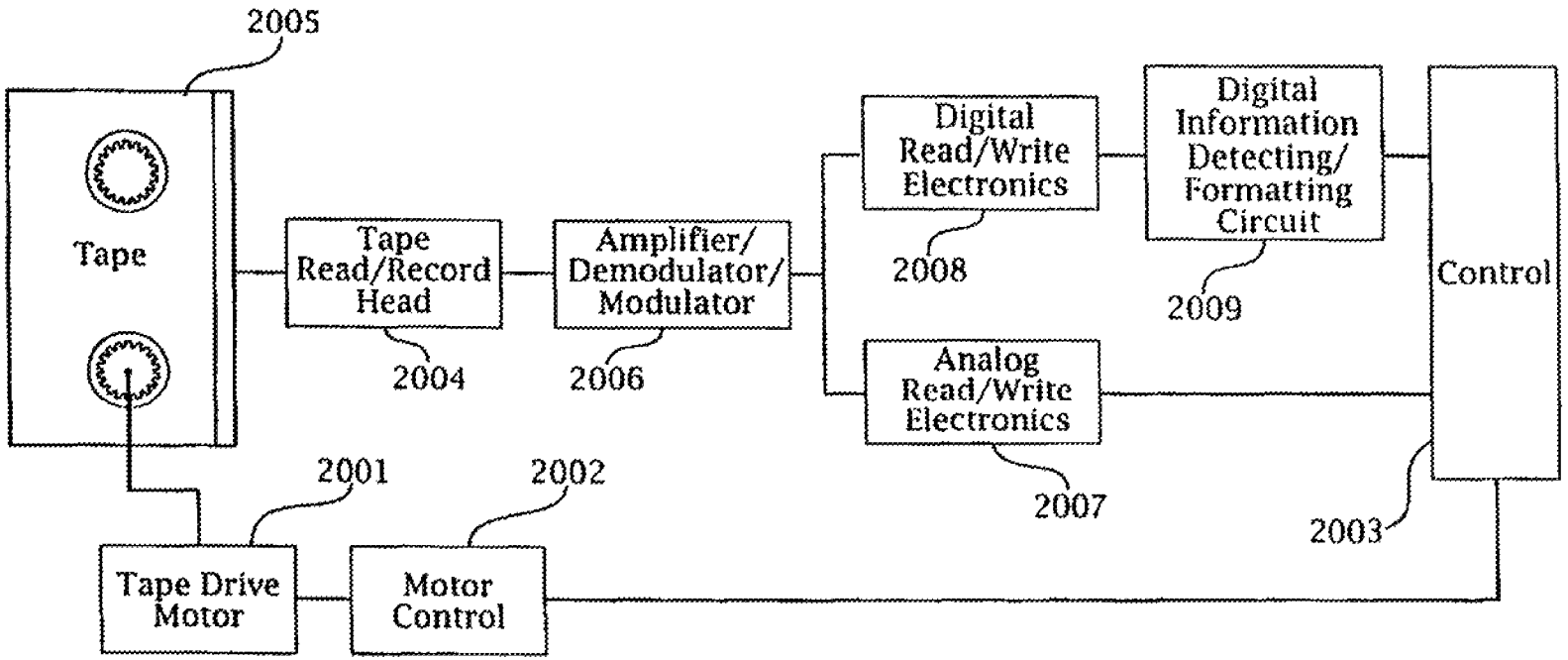
FIG. 20 is a block diagram of a digital information and analog signal reading/recording apparatus

The tape read and drive system is shown schematically in FIG. 20. The algorithm used in the final stage of approach to the desired portion of the tape or other recording medium may incorporate a control employing Fuzzy logic, Neural Networks, mathematical formulae modeling the system (differential equations) in a Model-based system, a Proportional-Differential-Integral (PID) system, or a controller employing an algorithm of higher order, or other known control methods.

If a selection is to be recorded over, the start and stop locations would be automatically determined from the locations already indicated on the tape. Further, this information could be stored in memory device (which reads a catalog or index of the tape when a new tape is loaded) or non-volatile memory device (which stores information relating to known tapes within the device) or both types of memory in the VCR, so that an index function may be implemented in the VCR itself, without the need to read an entire tape. Optionally, a printer, such as a thermal label printer (available from, e.g. Seiko Instruments, Inc.), attached to the device, could be available to produce labels for the tapes, showing the index, so that the contents of a tape may be easily indicated. A label on the tape may also include a bar code or two-dimensional coding system to store content or characterization information. The stored identification and index information is thus stored in a human or machine readable form.

These contents, or a list of contents, need not necessarily be manually entered by the user or created by the apparatus, rather, these may be derived from published data or a database, data transmitted to the control, and/or data determined or synthesized by the control itself. For example, broadcast schedules are available in electronic or machine readable form, and this information may be used by the apparatus.

EXAMPLE 3

Serial Data Medium Index

Another aspect of the present invention relates to the cataloging and indexing of the contents of a storage medium. While random access media normally incorporate a directory of entries on a disk, and devices such as optical juke boxes normally are used in conjunction with software that indexes the contents of the available disks, serial access mass storage devices, such as magnetic tape, do not usually employ an index; therefore, the entire tape must be searched in order to locate a specific selection.

In the present invention, an area of the tape, preferable at the beginning of the tape or at multiple locations therein, is encoded to hold information relating to the contents of the tape. This encoding is shown in FIG. 19, which shows a data format for the information. This format has an identifying header 1901, a unique tape identifier 1902, an entry identifier 1903, a start time 1904, an end time 1905 and/or a duration 1906, a date code 1907, a channel code 1908, descriptive information 1909 of the described entry, which may include recording parameters and actual recorded locations on the tape, as well as a title or episode identifying information, which may be a fixed or variable length entry, optionally representative scenes 1910, which may be analog, digital, compressed form, or in a form related to the abstract characterizations of the scenes formed in the operation of the device. Finally, there are error correcting codes 1911 for the catalog entry, which may also include advanced block encoding schemes to reduce the affect of non-Gaussian correlated errors which may occur on video tape, transmission media and the like. This information is preferably a modulated digital signal, recorded on, in the case of Hi-Fi VHS, one or more of the preexisting tracks on the tape, including the video, overscan area, Audio, Hi-Fi stereo audio, second audio program (AUP) or control tracks. It should be noted that an additional track could be added, in similar fashion to the overlay of Hi-Fi audio on the video tracks of Hi-Fi VHS. It is also noted that similar techniques could be used with Beta format, 8 mm, or other recording systems, to provide the necessary indexing functions.

Digital data may also be superimposed as pseudonoise in the image information, or as other information intermixed or merged with the video information.

The recording method is preferable a block encoding method with error correction within each block, block redundancy, and interleaving. Methods are known for reducing the error rate for digital signals recorded on unverified media, such as videotape, which are subject to burst errors and long term non-random errors. Such techniques reduce the effective error rate to acceptable levels. These are known to those skilled in the art and need not be discussed herein in detail. A standard reference related to this topic is Digital Communications by John G. Proakis, McGraw-Hill (1983), which is incorporated herein by reference. The digital data recording scheme is best determined according to the characteristics of the recording apparatus. Therefore, if an, e.g. Sony Corporation helical scan recording/reproducing apparatus was employed, one of ordinary skill in the art would initially reference methods of the Sony Corporation initially for an optimal error correcting recording scheme, which are available in the patent literature, in the U.S., Japan, and internationally, and the skilled artisan would also review the known methods used by other manufacturers of digital data recording equipment. Therefore, these methods need not be explained herein in detail.

The catalog of entries is also preferably stored in non-volatile memory, such as hard disk, associated with the VCR controller. This allows the random selection of a tape from a library, without need for manually scanning the contents of each tape. This also facilitates the random storage of recordings on tape, without the requirement of storing related entries in physical proximity with one another so that they may be easily located. This, in turn, allows more efficient use of tape, because of reduced empty space at the end of a tape. The apparatus is shown schematically in FIG. 20, in which a tape drive motor 2001, controlled by a transport control 2002, which in turn is controlled by the control 2003, moves a tape 2005 past a reading head 2004. The output of the reading head 2004 is processed by the amplifier/demodulator 2006, which produces a split output signal. One part of the output signal comprises the analog signal path 2007, which is described elsewhere. A digital reading circuit 2008 transmits the digital information to a digital information detecting circuit 2009, which in turn decodes the information and provides it to the control 2003.

In order to retrieve an entry, the user interacts with the same interface that is used for programming the recorder functions; however, the user selects different menu selections, which guide him to the available selections. This function, instead of focusing mainly on the particular user's history in order to predict a selection, would analyze the entire library, regardless of which user instituted the recording. Further, there would likely be a bias against performing identically the most recently executed function, and rather the predicted function would be an analogous function, based on a programmed or inferred user preference. This is because it is unlikely that a user will perform an identical action repeatedly, but a pattern may still be derived.

It is noted that the present library functions differ from the prior art VHS tape index function, because the present index is intelligent, and does not require the user to mark an index location and explicitly program the VCR to shuttle to that location. Rather, the index is content based. Another advantage of the present library function is that it can automatically switch media and recording format, providing an adaptive and/or multimode recording system. Such a system might be used, for example, if a user wishes to record, e.g., "The Tonight Show With Johnny Carson" in highly compressed form, e.g. MPEG-2 at 200:1 compression, except during the performance of a musical guest, at which time the recording should have a much lower loss, e.g., MPEG-2 at 20:1, or in analog format uncompressed. A normal VCR could hardly be used to implement such a function even manually, because the tape speed (the analogy of quality level) cannot generally be changed in mid recording. The present system could recognize the desired special segment, record it as desired, and indicate the specific parameters on the information directory. The recorded information may then be retrieved sequentially, as in a normal VCR, or the desired selection may be preferentially retrieved. If the interface of the present invention is set to automatically record such special requests, the catalog section would then be available for the user to indicate which selections were recorded based upon the implicit request of the user. Because the interface has the ability to characterize the input and record these characterizations in the index, the user may make an explicit request different from the recording criteria, after a selection has been recorded. The controller would then search the index for matching entries, which could then be retrieved based on the index, and without a manual search of the entire tape. Other advantages of the present system are obvious to those of ordinary skill in the art.

A library system is available from Open Eyes Video, called "Scene Locator", which implements a non-intelligent system for indexing the contents of a videotape. See New-Media, November/December 1991, p. 69.

It is noted that, if the standard audio tracks are used to record the indexing information, then standard audio frequency modems and recording/receiving methods are available, adapted to record or receive data in half-duplex mode. These standard modems range in speed from 300 baud to 19,200 baud, e.g. v.29, v.17, v.32, v.32bis, v.Turbo (proposed V.32ter), v.FAST, v.34, etc. While these systems are designed for dial-up telecommunications, and are therefore are designed for the limited data rates available from plain old telephone service (POTS). These are limited to a slower speed than necessary and incorporate features unnecessary for closed systems, they require a minimum of design effort and the same circuitry may be multiplexed and also be used for telecommunication with an on-line database, such as a database of broadcast listings, discussed above. It should be noted that a full-duplex modem should be operated in half duplex mode when reading or recording on a media, thus avoiding the generation of unnecessary handshaking signals. Alternatively, a full duplex receiver may be provided with the resulting audio recorded. A specially programmed receiver may extract the data from the recording. Dual tone, multiple frequency (DTMF) codes may also be employed to stored information.

The Videotext standard may also be used to record the catalog or indexing information on the tape. This method, however, if used while desired material is on the screen, makes it difficult (but not impossible) to change the information after it has been recorded, without rerecording entire frames, because the videotext uses the video channel, during non-visible scan periods thereof. The video recording system according to the present invention preferably faithfully records all transmitted information, including SAP, VAR, closed caption and videotext information, which may be used to implement the various functions.

The use of on-line database listings may be used by the present interface to provide information to be downloaded and incorporated in the index entry of the library function, and may also be used as part of the intelligent determination of the content of a broadcast. This information may further be used for explicitly programming the interface by the user, in that the user may be explicitly presented with the available choices available from the database.

EXAMPLE 4

Controlled Encryption and Accounting System

The present invention also allows for scrambling, encryption and locking of source material, and the receiving device selectively implements an inverse process or a partial inverse process for descrambling, decryption or unlocking of the material, much as the Videocipher series systems from General Instruments, and the fractal enciphering methods of Entertainment Made Convenient$^2$ Inc. (EMC$^2$) and Iterated Systems, Inc. The present invention, however, is not limited to broadcasts, and instead could implement a system for both broadcasts and prerecorded materials. In the case of copying from one tape to another, such a system could not only provide the herein mentioned library functions of the present invention according to Example 2, it could also be used to aid in copy protection, serial copy management, and a pay-per-view royalty collection system.

Figure 18:
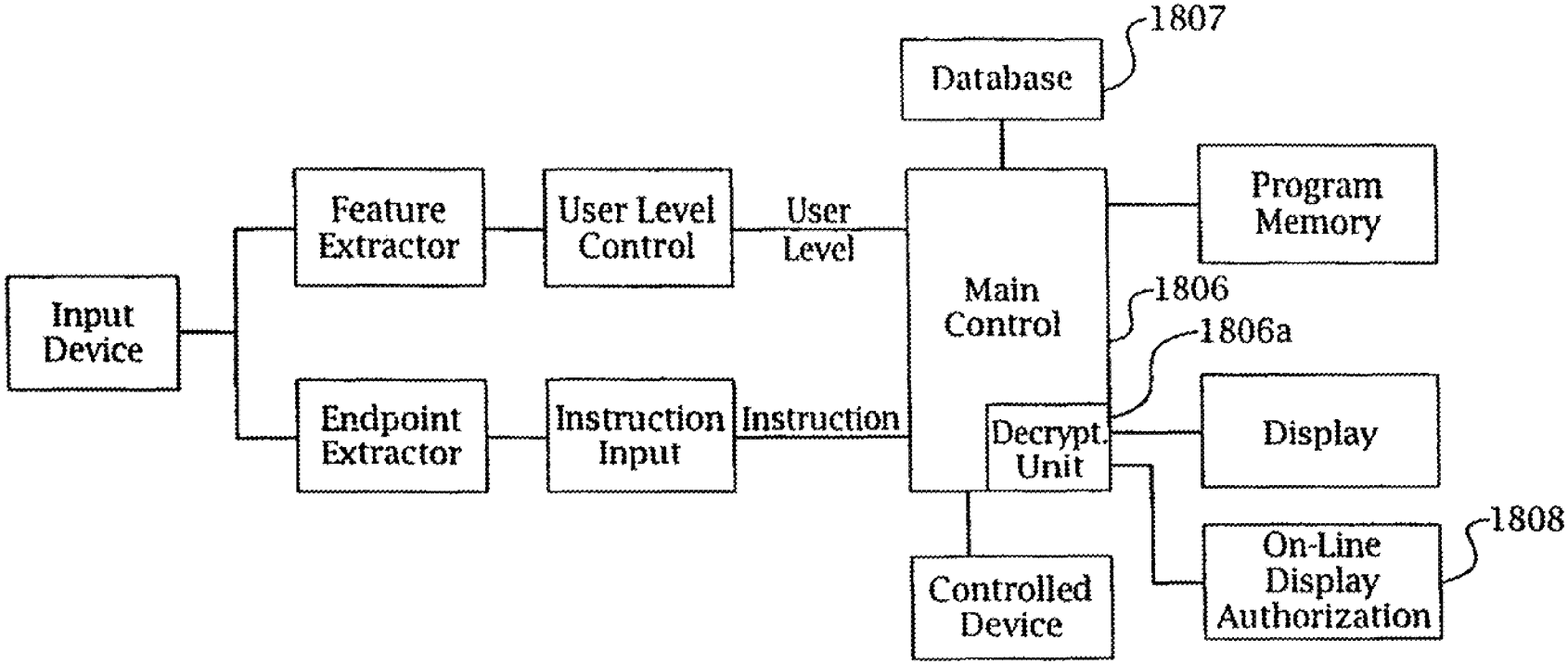
FIG. 18 is a block diagram of a non-program information feature extraction circuit of the present invention.

Such a system could be implemented by way of a telecommunication function incorporated in the device, shown as block 1808 of FIG. 18, or an electronic tag which records user activity relating to a tape or the like. Such tags might take the form of a smart card, PCMCIA device, or other type of storage device. A royalty fee, etc., could automatically be registered to the machine either by telecommunication or registry with the electronic tag, allowing new viewer options to be provided as compared with present VCR's.

Numerous digital data encryption and decryption systems are known. These include data encryption standard (DES), "Clipper", public key/private key (RSA, etc.), pretty good privacy (PGP), and others. Digital encryption allows a sender to scramble a message so that, with an arbitrary degree of difficulty, the message cannot be determined without use of a decryption key.

An encrypted tape or other source material may be decrypted with a decryption key available by telecommunication with a communication center, remote from the user, in a decryption unit, shown schematically as the decrypt unit 1806a of FIG. 18. Such an encryption/decryption scheme requires special playback equipment, or at least equipment with decryption functionality, and thus any usage or decrypted data my be registered as a result of the requirement to receive a decryption key. The decryption unit may be part of an addressable remote unit for control of the unit remotely.

During acquisition of the electronic decryption key, a VCR device of an embodiment of the present invention would indicate its identity or electronic address, and an account is charged a fee for such use. The negotiation for the electronic key is also preferably encrypted. In addition, the decryption key may be specific for a particular decoder. Such a system could also be used for controlled access software, for example for a computer, wherein a remote account is charged for use of the software. Information communication may be through the internet or through an on-line service such as America Online or Compuserve.

Such a system differs from the normal hardware "key" or "dongle" (device which attaches to standard hardware port for authentication and usage limitation) because it requires on-line or electronic access for an encryption key, which may offer different levels of use. It also differs from a call-in registration, because of the automatic nature of the telecommunication. This presently described system differs from normal pay-per-view techniques because it allows, in certain instances, the user to schedule the viewing. Finally, with an encryption function implemented in the VCR, the device allows a user to create and distribute custom "software" or program material. In addition, the present controller could then act as the "telecommunication center" and authorize decryption of the material.

If the source signal is in digital form, a serial copy management scheme system is preferably implemented.

The present invention is advantageous in this application because it provides an advanced user interface for creating a program (i.e. a sequence of instructions), and it assists the user in selecting from the available programs, without having presented the user with a detailed description of the programs, i.e., the user may select the choice based on characteristics rather than literal description.

In the case of encrypted program source material, it is particularly advantageous if the characterization of the program occurs without charging the account of the user for such characterization, and only charging the account if the program is viewed by the user. The user may make a viewing decision based on the recommendation of the interface system, or may review the decision based on the title or description of the program, or after a limited duration of viewing. Security of the system could then be ensured by a two level encryption system, wherein the initial decryption allows for significant processing, but not comfortable viewing, while the second level of decryption allows viewing, and is linked to the accounting system. Alternatively, the decryption may be performed so that certain information, less than the entirety, is available in a first decryption mode, while other information comprising the broadcast information is available in a second decryption mode.

The transmission encryption system may be of any type, but for sensitive material, i.e. where mere distortion of the material (e.g., loss of synchronization information and phase distortion) would be insufficient, an analog multiple subband transform, with spread spectrum band hopping and digital encryption of various control signals, would provide a system which would be particularly difficult for the user to view without authorization, and could be effectively implemented with conventionally available technology. The fractal compression and encryption of the $EMC^2$ and Iterated Systems, Inc. system is also particularly preferred, in instances where the broadcast may be precompressed prior to broadcast. Of course, if a digital storage format is employed, a strict digital encryption system of known type may be used, such as those available from RSA. The implementation of these encryption systems is known to those skilled in the art. These may include the National Bureau of Standards (NBS), Verifiable Secret Sharing (VSS) and National Security Agency (NSA) encryption standards, as well as various proprietary standards.

EXAMPLE 5

User Interface

In one embodiment of the present invention, the apparatus comprises a program entry device for a VCR. The human interface element has an infrared device to allow wireless communication between the human interface device and the VCR apparatus proper. The human interface device also includes a direct-manipulation type input device, such as a trackball or joystick. Of course it is understood that various known or to-be developed alternatives can be employed, as described above.

It is noted that many present devices, intended for use in computers having graphic interfaces, would advantageously make use of an input device which is accessible, without the necessity of moving the user's hands from the keyboard. Thus, for example, Electronic Engineering Times (EET), Oct. 28, 1991, p. 62, incorporated herein by reference, discloses a miniature joystick incorporated into the functional area of the keyboard. This technique is directed at a different aspect of user interaction with a programmable device than certain preferred embodiments of the present invention, in that the input device does not have a minimal number of keys. While the device disclosed in EET is intended for use in a full function keyboard, the preferred embodiment of the present invention is directed towards the minimization of the number of keys and avoidance of superfluous keys by provision of a pointing device. Of course, the present invention could be used with a full function input device, where appropriate, and the joystick of EET (Oct. 28, 1991, p. 62) would be suitable in this case.

The interface of the present invention studies the behavior and moods of the user, in context, during interactions to determine the expected user level of that user as well as the preferences of the user. These user characteristics may change over time and circumstances. This means that the system studies the interaction of the user to determine the skill of the user or his or her familiarity with the operation and functionality of the system. By determining the skill of the user, the system may provide a best compromise. The purpose of this feature is to provide a tailored interface adapted to the characteristics of the user, thus adaptively providing access to various features in a hierarchical manner such that a most likely feature to be used is more easily accessible than an unlikely feature, but that features can generally be accessed from all or most user levels. The user level analysis also allows the system to teach the user of the various functions available, particularly when it becomes apparent that the user is being inefficient in the use of the system to perform a given task. Therefore, the menu structure may also be adaptive to the particular task being performed by the user. When combined with the user level analysis feature, the user efficiency feature will provide a preferable interface, with reduced learning time and increased usability for a variety of users.

Thus, an important concept is that the system has at least one object having a plurality of functions, certain of which are unnecessary or are rarely used for various applications or in various contexts, while these are used with greater frequency in other contexts. Further, based upon predetermined protocols and learned patterns, it is possible to predict which functions will be used and which will not be used.

Therefore, the system, upon recognizing a context, will reconfigure the availability or ease of availability of functions and allow various subsets to be used through "shortcuts". Thus, to some extent, the interface structure may vary from time to time based upon the use of the system. The prior art apparently teaches away from this concept, because it is believed to prevent standardization, limits the "recordability" of macros and/or instruction sheets for casual users and limits the availability of technical support. Each of these can be addressed, to some extent by the availability of a default mode (so that users can access all information), and because the interface is self-simplifying in case of difficulty. However, forcing all users to always work in a default mode limits the improvements in productivity that may be gained by a data-sensitive processing system, and hence this standardization for its own sake is rejected by the present invention.

The improvements to be gained by using an intellegent data analysis interface for facilitating user control and operation of the system are more than merely reducing the average number of keystrokes or time to access a given function. Initial presentation of all available information to a new user might be too large an information load, leading to inefficiency, increased search time and errors. Rather, the improvements arise from providing a means for access of and availability to functions not necessarily known to the user, and to therefore improve the perceived quality of the product.

The system to determine the sophistication of the user includes a number of storage registers, for storing an analysis of each act for each user. A given act is represented in a plurality of the registers, and a weighting system to ensure that even though an act is represented in a number of registers, it is not given undue emphasis in the analysis. Thus, each act of the user may be characterized in a number of ways, and each characteristic stored in an appropriate register, along with a weighting representing an importance of the particular characteristic, in relation to other identified characteristics and in relation to the importance of the act as a whole. The act is considered in context, and therefore, the stored information relates to the act, the sequence of acts prior to the act, acts of the user occur after the act, the results of the sequence of acts which include the act, and characteristics of the user which are not "acts", but rather include timing, mouse path efficiency, and an interaction with other users.

Figure 21:
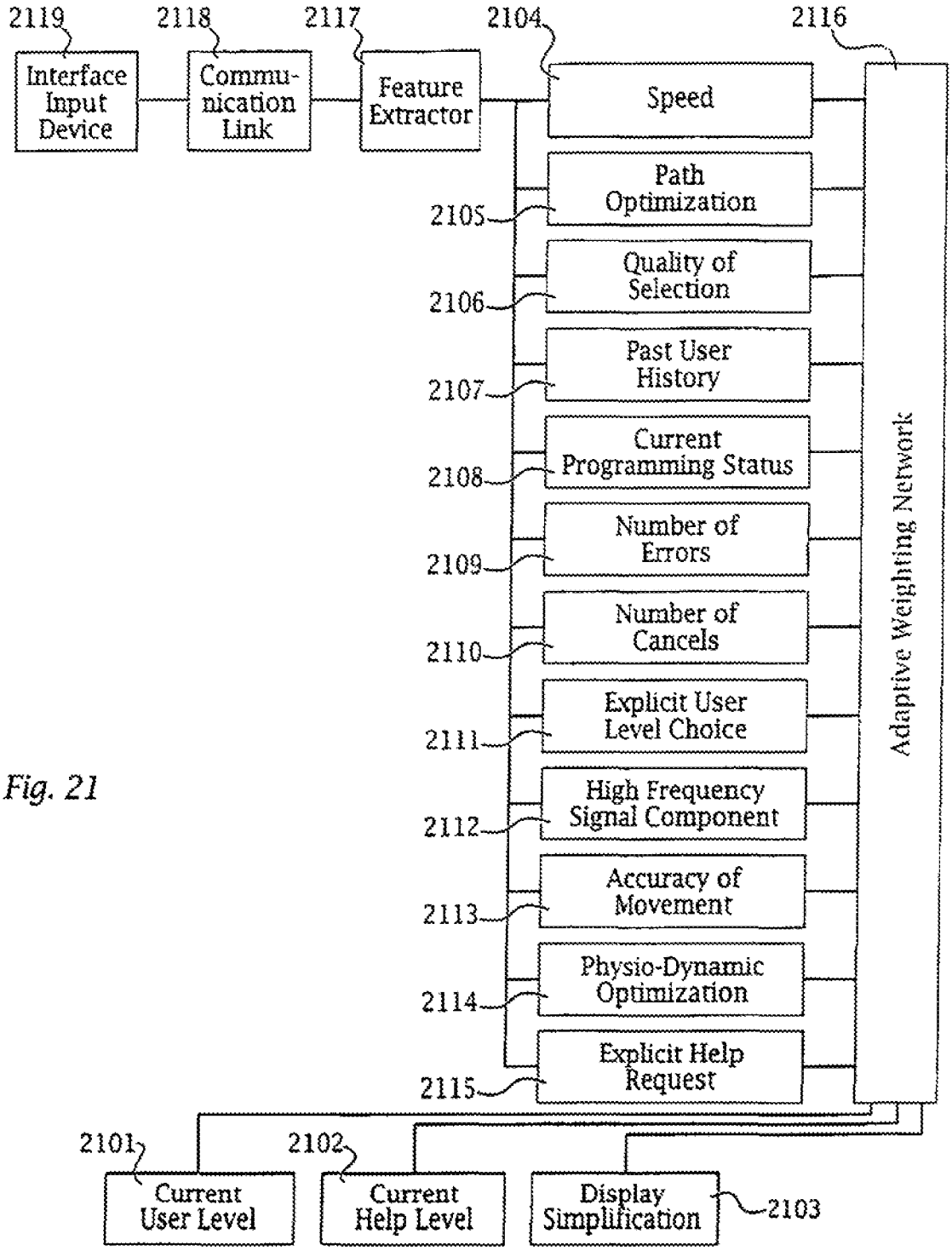
FIG. 21 is a block diagram of a user level determining system of the present invention.

An apparatus for performing a path information or efficiency determining function is shown schematically in FIG. 18, and in more detain in FIG. 21. Thus, for example, if a characteristic of the user is an unsteady hand while using the cursor control device, e.g. mouse, producing a high frequency or oscillating component, the existence of this characteristic is detected and quantified by the high frequency signal component detector 2112, and, depending on the amplitude, frequency and duration (e.g. path length), may also be detected by the path optimization detector 2105. Once this characteristic is detected and quantified, an adaptive filter may be applied by the main control 1806 to selectively remove the detected component from the signal, in order to improve the reliability of the detection of other characteristics and to determine the intended act of the user.

It should be noted that the various charateristic filters preferably act in "parallel" at each stage of the characteristic recognition, meaning that one characteristic is defined simultaneously with the detection of other characteristics, which assists in resolving ambiguities, allows for parallel processing by a plurality of processing elements which improves real-time recognition speed, and allows a probability-based analysis to proceed efficiently. Such a "parallel" computation system is included in a neural net computer, and a hardware-implementation of a neural net/fuzzy logic hybrid computer is a preferred embodiment, which allows fuzzy rules to be programmed to provide explicit control over the functioning of the system. It is preferred that a human programmer determine the basic rules of operation of the system, prior to allowing a back-propagation of errors learning algorithm to improve and adapt the operation of the system.

The adaptive system implemented according to the present invention, by detecting a user level, allows a novice user to productively interact with the system while not unnecessarily limiting the use of the adaptive interface by an advanced user, who, for example, wishes to move the cursor quickly without the limiting effects of a filter which slows cursor response.

Another example of the use of an adaptive user interface level is a user who repeatedly requests "help" or user instructions, through the explicit help request detector 2115, which causes an output from the current help level output 2102; such a user may benefit from an automatic context-sensitive help system, however such a system may interfere with an advanced user, and is unnecessary in that case and should be avoided. This adaptive user interface level concept is not limited to a particular embodiment of the present invention, such as a VCR, and in fact, may be broadly used wherever a system includes an interface which is intended for use by both experienced and inexperienced users. This differs from normal help systems which must be specifically requested, or "balloon help" (Apple Computer, Macintosh System 7.0, 7.1, 7.5) which is either engaged or disengaged, but not adaptive to the particular situation based on an implicit request or predicted need. In the case of a single user or group of users, the interface could maintain a history of feature usage for each user, as in the past user history block 2107, and provide a lower user interface level for those features which are rarely used, and therefore less familiar to the user, through the current user level output 2101.

It should be noted that the present system preferably detects an identity of a user, and therefore differentiates between different users by an explicit or implicit identification system. Therefore, the system may accumulate information regarding users without confusion or intermingling.

EXAMPLE 6

VCR Programming Preference Prediction

The device according to the present invention is preferably intelligent. In the case of a VCR, the user could also input characteristics of the program material that are desired, and characteristics of that program material which is not desired. The device would then, over time, monitor various broadcast choices, and determine which most closely match the criteria, and thus be identified. For example, if the user prefers "talk-shows", and indicates a dislike for "situation comedies" ("sitcoms"), then the device could scan the various available choices for characteristics indicative of one or the other type of programming, and perform a correlation to determine the most appropriate choice(s). A sitcom, for example, usually has a "laugh track" during a pause in normal dialogue. The background of a sitcom is often a confined space (a "set"), from different perspectives, which has a large number of "props" which may be common or unique. This set and the props, however, may be enduring over the life of a show.

A talk-show, on the other hand, more often relies on actual audience reaction (possibly in response to an "applause" sign), and not prerecorded or synthesized sounds. The set is simple, and the broadcast often shows a head and neck, or full body shot with a bland background, likely with fewer enduring props. A signal processing computer, programmed for audio and/or video recognition, is provided to differentiate between at least the two types with some degree of efficiency, and with a possibly extended sampling time, have a recognition accuracy, such that, when this information is integrated with other available information, a reliable decision may be made. The required level of reliability, of course, will depend on the particular application and a cost-benefit analysis for the required system to implement the decision-making system.

Since the system according to the present invention need not display perfect accuracy, the preferred embodiment according to the present example applies general principles to new situations and receives user or other feedback as to the appropriateness of a given decision. Based on this feedback, subsequent encounters with the same or similar data sets will produce a result which is "closer" to an optimal decision. Therefore, with the aid of feedback, the search criterion would be improved. Thus, a user could teach the interface through trial and error to record the desired broadcast programs. Thus, the presently described recognition algorithms may be adaptive and learning, and need not apply a finite set of predetermined rules in operation. For such a learning task, a neural network processor may be implemented, as known in the art.

Figure 22:
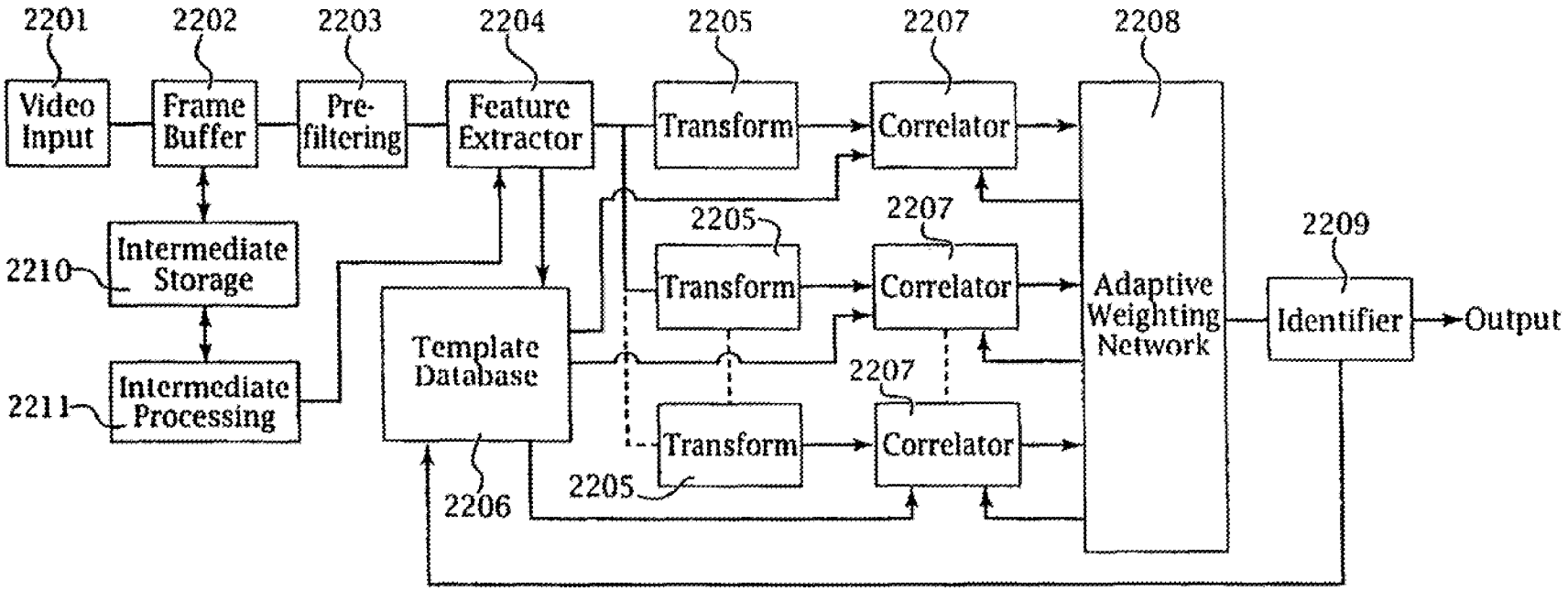
FIG. 22 is a block diagram of a template-based pattern recognition system of the present invention.

The feature extraction and correlation system according to the present invention is shown in FIG. 22. In this figure, the multimedia input, including the audio signal and all other available data, are input in the video input 2201. The video portion is transferred to a frame buffer 2202, which temporarily stores all of the information. All other information in the signal, including audio, VIR, videotext, close caption, SAP (second audio program), and overscan, is preferably stored in a memory, and analyzed as appropriate. The frame buffer 2202 may have an integral or separate prefiltering component 2203. The filtered signal(s) are then passed to a feature extractor 2204, which divides the video frame into a number of features, including movement, objects, foreground, background, etc. Further, sequences of video frames are analyzed in conjunction with the audio and other information, and features relating to the correlation of the video and other information, e.g., correlation of video and audio, are extracted. Other information is also analyzed and features extracted, e.g., audio and close caption. All extracted features relating to the multimedia input are then passed to a transform engine or multiple engines in parallel, 2205. These transform engines 2205 serve to match the extracted features with exemplars or standard form templates in the template database 2206.

It should be noted that even errors or lack of correlation between certain data may provide useful information. Therefore, a mismatch between audio and close caption or audio and SAP may be indicative of useful information. For non-video information, exemplars or templates are patterns which allow identification of an aspect of the signal by comparing the pattern of an unidentified signal with the stored pattern. Thus, the voice patterns of particular persons and audio patterns of particular songs or artists may be stored in a database and employed to identify a source signal.

The transformed extracted features and the templates are then correlated by a correlator or correlators 2207. The parallelization of implementation of the transforms and correlators serves to increase the recognition speed of the device. It should be understood that appropriate systems for parallelization are known in the art. For example, the TMS 320C80, also known as the TI MVP (Texas Instruments multimedia video processor) contains four DSP engines and a reduced instruction set computer (RISC) processor with a floating point unit on a single die. A board including a TMS 320C80 is available from General Imaging Corp., Billerica Mass., the S/IP80, which may be programmed with ProtoPIPE. In addition, a board including a TMS 320C80 is also available from Wintriss Engineering Corp., San Diego, Calif. Multiple MVP processors may also be parallelized for additional computing power. The MVP may be used to analyze, in parallel, the multimedia input signal and correlate it with stored patterns in a database. In this context, correlation does not necessarily denote a strict mathematical correlation, but rather indicates a comparison to determine the "closeness" of an identified portion of information with an unidentified portion, preferably including a reliability indicator as well. Therefore, since there may be multiple recognizable aspects of the unidentified data, and various degrees or genericness of the characteristic recognized, it is preferred that at this initial stage of the recognition process that the output of the correlators 2207 be a data set, e.g. a matrix, series of pointers, or other arrangement, so that sufficient information is available for higher level processing to allow application of an appropriate decision process. Of course, if the characteristic to be detected is simple and well defined, and the decision-making process may be implemented with a simple correlation result, then a complex data set output is not required. In fact, the output of the correlator may have a number of different forms, based on the context of the recognition process.

If, for example, an exact match to an entire frame is sought, partial match information is not particularly useful, and is ignored in this process. (Of course, since the system is "self-learning", the processing results may be maintained and analyzed for other purposes). If the system, on the other hand, is analyzing novel data, a full analysis would likely be necessary including partial results and low correlation results.

The outputs of the correlators are input into an adaptive weighing network 2208, to produce a probability of a match between a given feature and a given template. The recognition is completed in an identifier 2209, which produces a signal identifying one or more objects in the video frame input. The identifier 2209 also has an output to the template database 2206, which reinforces the recognition by providing feedback; therefore, if the same object appears again, it will be more easily recognized. The template database 2206 therefore also has an input from the feature extractor 2204, which provides it with information regarding the features recognized. It is also noted that, in addition to allowing recognition, the parallel transform engines 2205, correlators 2207, and adaptive weighing network 2208 also allows the system to ignore features that, though complex, do not aid in recognition.

For example, during dialogue, the soundtrack voice may correlate with the mouth movements. Thus, the mouth movements aid little in recognition, and may be virtally ignored, except in the case where a particular person's mouth movements are distinctive, e.g., Jim Nabors ("Gomer Pyle"), and Tim Curry ("Rocky Horror Picture Show"). Thus, the complexity and parallelism in the intermediate recognition stages may actually simplify the later stages by allowing more abstract features to be emphasized in the analysis. Animation poses a special example where audio and image data may be separated, due to the generally non-physiologic relation between the image and soundtrack.

The pattern recognition function of the present invention could be used, in a VCR embodiment according to the present invention to, e.g., to edit commercials out of a broadcast, either by recognition of characteristics present in commercials, in general, or by pattern recognition of specific commercials in particular, which are often repeated numerous times at various times of the day, and on various broadcast channels. Therefore, the system may acquire an unidentified source signal, which may be, for example, a 30 second segment, and compare this with a database of characteristics of known signals. If the signal does not match any previously known or identified signals, it is then subject to a characterization which may be the same or different than the characterization of the identified signals. The characterizations of the unidentified signal are then compared to characteristics to be recognized. If the unidentified signal meets appropriate criteria, a presumptive generic characterization is made. This characterization is preferably confirmed by a user later, so that a positively identified signal is added to the database of identified signals; however, under certain circumstances no confirmation is required.

Certain media present a recognizable audio or video cue when a commercial break has ended. (E.g. often sports events, such as the Olympic Games, will have theme music or distinctive images). The present device need not respond immediately to such cues, and may incorporate a delay, which would store the information while a decision is being made. In the case of a video tape, the delay may be up to the time between the time of recording and the time of playback. Further, the temporary storage medium may be independent of the pattern recognition system. Thus, a system provided according to the present invention may actually include two independent or semi-independent data streams: the first serving as the desired signal to be stored, retaining visually important information, and the second providing information for storage relating to the pattern recognition system, which retains information important for the recognition process, and may discard this information after the pattern recognition procedure is complete.

A system which provides a plurality of parallel data streams representing the same source signal may be advantageous because is allows a broadcast quality temporary storage, which may be analog in nature, to be separate from the signal processing and pattern recognition stage, which may be of any type, including digital, optical, analog or other known types, which need only retain significant information for the pattern recognition, and therefore may be highly compressed (e.g. lossy compression), and devoid of various types of information which are irrelevant or of little importance to the pattern recognition functions. Further, the temporary storage may employ a different image compression algorithm, e.g. MPEG-2 or MPEG-1, which is optimized for retention of visually important information, while the recognition system may use a compression system optimized for pattern. recognition, which may retain information relevant to the recognition function which is lost in other compression systems, while discarding other information which would be visually important.

In a particularly advantageous arrangement, the compression algorithm is integral to the recognition function, preparing the data for the pattern matching and characterization, and therefore is optimized for high throughput. According to this embodiment, the initial compression may include redundant or uncompressed information, if necessary in order to achieve real-time or near real-time recognition, and, thus may actually result in a larger intermediate data storage requirement than the instantaneous data presented to the recognition system; however, the term "compression", in this case, applies to the long term or steady state status of the device, and in a real-time recognition function, the amount of data stored for use in recognition is preferably less than the cumulative amount of data presented, except during the very initial stages of data acquisition and possibly rare peaks.

In the case where a high quality (low loss, e.g. broadcast quality) intermediate storage is employed, after a decision is made as to whether the data should be stored permanently or otherwise further processed or distributed, the data may be transferred to the appropriate system or subsystem of the apparatus. Alternatively, the high quality intermediate storage is retained, and no further processing is performed. In either case, the purpose of this storage is to buffer the source data until the computational latency resolves any decisions which must be made.

According to one aspect of the present invention, the source image may be compressed using the so called "fractal transform", using the method of Barnsley and Sloan, which is implemented and available as a hardware accelerator in product form from Iterated Systems, Inc., Norcross, Ga., as the FTC-II, which incorporates eight fractal transform integrated circuit chips, 1 MByte of Random Access Memory (RAM), and an Intel i80960CA-25 μP, and operates in conjunction with P.OEM™ (Iterated Systems, Inc., Norcross, Ga.) software, which operates under MicroSoft-Disk Operating System (MS-DOS). Fractal Transform Card (FTC) II hardware compression requires approximately 1 second per frame, while software decompression on an Intel 80486-25 based MS-DOS computer, using "Fractal Formatter" software, can be performed at about 30 frames per second, which allows approximately real time viewing. The Fractal Video Pro 1.5 is a video codec for Microsoft Windows Operating System, allowing software only playback at 15-30 fps, 70-150 Kbytes/sec. This is a non-symmetrical algorithm, requiring more processing to compress than to decompress the image. The FTC-IV Compression Accelerator Board is presently available.

This fractal compression method allows data compression of upwards of 2000:1, while still maintaining an aesthetically acceptable decompressed image result. Further, since the method emphasizes structural aspects of the image, as opposed to the frequency decomposition used in DCT methods (JPEG, MPEG), elements of the fractal method could be used as a part of the image recognition system. Of course, it should be appreciated that other fractal processing methods are available and may be likewise employed.

Audio data is also compressible by means of fractal transforms. It is noted that the audio compression and image recognition functions cannot be performed on the FTC-II board, and therefore an alternate system must be employed in order to apply the pattern recognition aspects of the present invention. It should also be noted that an even more efficient compression-pattern recognition system could be constructed by using the fractal compression method in conjunction with other compression methods, which may be more efficient under certain circumstances, such as discrete cosine transform (DCT), e.g. JPEG or modified JPEG or wavelet techniques. Fractal compression systems are also available from other sources, e.g. the method of Greenwood et al., Netrologic Inc., San Diego, Calif. See also, Shepard, J. D., "Tapping the Potential of Data Compression", Military and Aerospace Electronics, May 17, 1993, pp. 25-27.

A preferred method for compressing audio information includes a model-based compression system. This system may retain stored samples, or derive these from the data stream. The system preferably also includes high-level models of the human vocal tract and vocalizations, as well as common musical instruments. This system therefore stores information in a manner which allows faithful reproduction of the audio content and also provides emphasis on the information-conveying structure of the audio signal. Thus, a preferred compression for audio signals retains, in readily available form, information important in a pattern recognition system to determine an abstract information content, as well as to allow pattern matching. Of course, a dual data stream approach may also be applied, and other known compression methods may be employed.

Because of the high complexity of describing a particular signal pattern or group of audio or image patterns, in general, the system will learn by example, with a simple identification of a desired or undesired pattern allowing analysis of the entire pattern, and extraction of characteristics thereof for use in preference determination.

Barnsley and Sloan's method for automatically processing digital image data consisting of image information, disclosed in U.S. Pat. Nos. 5,065,447 and 4,941,193, both expressly incorporated herein by reference, consists of the steps of storing the image data in the data processor, then generating a plurality of uniquely addressable domain blocks from the stored image data, each of the domain blocks representing a different portion of the image information such that all of the image information is contained in at least one of the domain blocks. A plurality of uniquely addressable mapped range blocks corresponding to different subsets of the stored image data are created, from the stored image data, with each of the subsets having a unique address. This step includes the substep of executing, for each of the mapped range blocks, a corresponding procedure upon the one of the subsets of the stored image data which corresponds to the mapped range block. Unique identifiers are then assigned to corresponding ones of the mapped range blocks, each of the identifiers specifying for the corresponding mapped range block a procedure and a address of the corresponding subset of the stored image data. For each of the domain blocks, the one of the mapped range blocks which most closely corresponds according to predetermined criteria is selected. Finally, the image information is represented as a set of the identifiers of the selected mapped range blocks. This method allows a fractal compression of image data. In particular, Drs. Barnsley and Sloan have optimized the match of the domain blocks with the mapping region by minimizing the Hausdorff distance. A decompression of the data precedes analogously in reverse order starting with the identifiers and the mapping regions to produce a facsimile of the original image. This system is highly asymmetric, and requires significantly more processing to compress than to decompress. Barnsley and Sloan do not suggest a method for using the fractal compression to facilitate image recognition, which is a part of the present invention.

Basically, the fractal method proceeds from an understanding that real images are made up of a plurality of like subcomponents, varying in size, orientation, etc. Thus, a complex block of data may be described by reference to the subcomponent, the size, orientation, etc. of the block. The entire image may thus be described as the composite of the sub-images. This is what is meant by iterative function systems, where first a largest block is identified, and the pattern mapping is repetitively performed to describe the entire image.

The Iterated Systems, Inc. FTC-H or FTC-IV board, if applied as a part of a system according to the present invention, is preferably used in conjunction with a frame-grabber board, such as Matrox, Quebec, Canada, Image-LC board, or a Data Translation DT1451, DT2651, DT2862, DT2867, DT2861 or DT2871, which may perform additional functions, such as preprocessing of the image signal, .and may be further used in conjunction with an image processing system, such as the Data Translation DT2878. Of course, it should be understood that any suitable hardware, for capturing, processing and storing the input signals, up to and including the state of the art, may be incorporated in a system according to the present invention without exceeding the scope hereof, as the present invention is not dependent on any particular subsystem, and may make use of the latest advances. The Texas Instruments TMS320C80 provides a substantial amount of computing power and is a preferred processor for certain computationally intensive operations. A system employing a parallel TMS 320C40 processors may also be used.

A pattern recognition database system is available from Excalibur Technologies, San Diego, Calif. Further, IBM has had pattern recognition functionality available for its DB/2 database system, and has licensed Excalibur's XRS image retriever recognition software for DB/2. See, Lu, C., "Publish It Electronically", Byte, September 1993, pp. 94-109, incorporated herein by reference. Apple Computer has included search by sketch and search by example functions in PhotoFlash 2.0. See also, Cohen, R., "FullPixelSearch Helps Users Locate Graphics", MacWeek, Aug. 23, 1993, p. 77.

Image processing hardware and systems are also available from Alacron, Nashua N.H.; Coreco, St. Laurent, Quebec; Analogic, and others.

A fractal-based system for real-time video compression, satellite broadcasting and decompression is also known from Iterated Systems, Inc. and Entertainment Made Convenient, Inc. ($EMC^2$). In such a system, since the compressed signal is transmitted, the remote receiving system need not necessarily complete decompression prior to the intelligent pattern recognition function of the present invention. This system also incorporates anticopy encryption and royalty and accounting documentation systems. It is noted that the $EMC^2$ system does not incorporate the intelligent features of the present invention.

A preferred fractal-based system according to the present information provides the source data preprocessed to allow easy and efficient extraction of information. While much precharacterization information may be provided explicitly, the preferred system allows other, unindexed information to also be extracted from the signal. Further, the preferred system provides for an accounting system which facilitates pay-per-view functions. Thus, the interface of the present invention could interact with the standard accounting system to allow royalty-based recording or viewing, and possibly implement a serial-copy recording prevention system. Prior art systems require a user to explicitly select a program, rather than allow an intelligent system to assist in selection and programming of the device. The $EMC^2$ system is described in "$EMC^2$ Pushes Video Rental By Satellite", Electronic Engineering Times, Dec. 2, 1991, p.1, p. 98, which is incorporated herein by reference. See also, Yoshida, J., "The Video-on-demand Demand", Electronic Engineering Times, Mar. 15, 1993, pp. 1, 72.

Fractal techniques may be used to store images on a writable mass storage medium, e.g. CD-ROM compatible. The present system may thus be used to selectively access data on the CD-ROM by analyzing the images, without requiring full decompression of the image data.

Thus, one embodiment of the device according to the present invention may incorporate a memory for storing a program, before being transferred to a permanent storage facility, such as tape. Such a memory may include a hard disk drive, magnetic tape loop, a rewritable optical disk drive, or semiconductor memories, including such devices as wafer scale memory devices. This is shown diagrammatically as the intermediate storage 2210 of FIG. 22. The capacity of such a device may be effectively increased through the use of image data compression, which may be proprietary or a standard format, i.e. MPEG, MPEG-2 (Motion Picture Experts Group standard employing DCT encoding of frames and interframe coding), JPEG (Joint Photographic Experts Group standard employing DCT encoding of frames), Px64 (Comitè Consultatif International des Telegraph et telephone (International telegraph and telephone consultative committee) (CCITT) standard H.261, videoconferencing transmission standard), DVI (Digital Video Interactive), CDI (Compact Disk Interactive), etc. Standard devices are available for processing such signals such as the Integrated Information Technology, Inc. (IIT, now 8×8, Inc.) Vision Processor (VP) chip, Integrated Information Technology Inc., Santa Clara, Calif., the C-Cube CL55OB (JPEG) and CL950 (MPEG decoding), SGS-Thompson ST13220, STV3200, STV3208 (JPEG, MPEG, Px64), LSI Logic L64735, L64745 and L64765 (JPEG) and Px64 chip sets, and the Intel Corp. i750B DVI processor sets (82750PB, 82750DB). Programmable devices, including the Texas Instruments TMS32OC80 MVP (multimedia video processor) and members of the Intel DVI family may be used to process information according to standard methods, and further provide the advantage of customizability of the methods employed.

Various alternative image processing chips are available as single chips and chip sets; in board level products, such as the Super Motion Compression and Super Still-Frame Compression by New Media Graphics of Billerica, Mass., for the Personal Computer-Advanced technology (PC-AT, an IBM created computer standard) bus; Optibase, Canoga Park, Calif. (Motorola DSP with dedicated processor for MPEG); NuVista+ from Truevision (Macintosh video capture and output); New Video Corp. (Venice, CA) EyeQ Delivery board for Macintosh NuBus systems (DVI); Intel Corp. ActionMedia II boards for Microsoft Windows and IBM OS/2 in Industry Standard Adapter (ISA, the IBM-PC bus standard) (AT bus); Micro Channel Architecture (MCA) (e.g., DVI, Presentation Level Video (PLV) 2.0, Real Time Video (RTV) 2.0) based machines; and as complete products, such as MediaStation by VideoLogic. The TMS320C80 is available in a development system from Texas Instruments, Inc. The use and interfacing of chip sets and multimedia boards such as those described are known to those skilled in the art. It is noted that the present interface does not depend on a particular compression format or storage medium, so that any suitable format may be used. The following references describe various video compression hardware, and are incorporated herein by reference: Kim, Y., "Chips Deliver Multimedia", Byte, December 1991, pp. 163-173; and Donovan, J., "Intel/IBM's Audio-Video Kernel", Byte, December, 1991, pp. 177-202.

Various available DSP chips, exemplary board level signal processing products and available software are described in more detail in "32-bit Floating-Point DSP Processors", EDN, Nov. 7, 1991, pp. 127-146, incorporated herein by reference. The TMS320C80 includes four DSP elements and a RISC processor with a floating point unit.

It should also be noted that the data compression algorithm applied for storage of the received data may be lossless or lossy, depending on the application. Various different methods and paradigms may be used. For example, DCT (discrete cosine transform) based methods, wavelets, fractals, and other known methods may be used. These may be implemented by various known means. A compressed image may also be advantageously used in conjunction with the image recognition system of the present invention, as described above. In such a case, the compression system would retain the information most important in the recognition function, and truncate the unimportant information.

A further method of performing pattern recognition, especially of two dimensional patterns, is optical pattern recognition, where an image is correlated with a set of known image patterns represented on a hologram, and the product is a pattern according to a correlation between the input pattern and the provided known patterns. Because this is an optical technique, it is performed nearly instantaneously, and the output information can be reentered into an electronic digital computer through optical transducers known in the art. Such a system is described in Casasent, D., Photonics Spectra, November 1991, pp. 134-140, which is incorporated herein by reference. See also references cited therein.

These optical recognition systems are best suited to applications where an uncharacterized input signal frame is to be compared to a finite number of visually different comparison frames (i.e., at least one, with an upper limit generally defined by the physical limitations of the optical storage media and the system for interfacing to the storage media), and where an optical correlation will provide useful information. Thus, if a user wished to detect one of, e.g., "David Letterman", "Jay Lenno", or "David Koppel", a number of different planar views, or holograms in differing poses, of these persons would be formed as a holographic correlation matrix, which could be superimposed as a multiple exposure, stacked in the width dimension, or placed in a planar matrix, side by side. The detection system produces, from the uncharacterized input image and the holographic matrix, a wavefront pattern that is detectable by photonic sensors.

It is preferred that if multiple holographic images of a particular characterization are employed, that they each produce a more similar resulting wavefront pattern than the holographic images of other characterizations, in order to enhance detection efficiency. The optical pattern recognition method is limited in that a holographic image must be prepared of the desired pattern to be detected, and that optically similar images might actually be of a different image, if the differences are subtle. However, this method may be used in conjunction with electronic digital pattern recognition methods, to obtain the advantages of both. Methods are also known to electronically write an image to a holographic storage medium, thereby facilitating its use in a general-purpose image recognition system. Of course, the system may also be used to identify talk show guests, such as "Richard Gere" or "Cindy Crawford", or these same individuals in other contexts.

If image compression is used, once an image is compressed, it need not be decompressed and returned to pixel, NTSC or other standard transmission or format for storage on tape, and thus the compressed image information may be stored in the same format as is present in the temporary storage medium. Thus, the block labelled intermediate processing 2211 of FIG. 22 shows that the intermediate storage need not retain the information as received from the frame buffer 2202, and in fact, may prepare it for the feature extractor 2204. In addition, the storage medium itself need not be normal videotape (VHS, Beta, 8 mm) and may be an adapted analog storage technique or a digital storage technique. Various magneto-optical recording techniques for disc storage are available which can store between 128 MB (3½") and around 5 GB (11"), uncompressed, which might be suitable for storing compressed digital or analog information. Multilayer CD-ROM and short wavelength (e.g., blue) laser systems allow storage densities of about 3.5 to 10 Gbytes per disk, allowing storage of over two hours of MPEG-2 encoded video.

It is also noted that the present technology could also be applied to any sort of mass storage, such as for a personal computer. In such a case, a characteristic of the computer file, which is analogous to the broadcast program in temporary storage of a VCR, is classified according to some criteria, which may be explicit, such as an explicit header or identifying information, or implicit, such as a document in letter format, or a memorandum, as well as by words and word proximity. In particular, such a recognition system could differentiate various clients or authors based on the content of the document, and these could be stored in different manners. The text analysis system of a text-based computer storage system is analogous to the program classification system of the VCR embodiment of the present invention. However, there is a further analogy, in that the VCR could incorporate optical character recognition of text displayed in the program material, employ voice recognition, or directly receive text information as a part of a closed caption or videotext system. Thus, the VCR device according to the present invention could recognize and classify programs based on textual cues, and make decisions based on these cues. This might also provide a simple method of discriminating program material, for example, if a commercial does not include close caption or Second Audio Program (SAP), while the desired program does, or vice versa, then a commercial could be discriminated from a program with very little computational expenditure.

EXAMPLE 7

VCR Interface

A particular VCR interface system according to one aspect of the present invention includes an internal clock, four program memory, and the capability to display a graphical color interface. By providing the user with the aforementioned features, this design is a unique implementation for an instrument to be used for programming an event driven controller via an interactive display. All information that the user needs is displayed on the screen to avoid or minimize the unnecessary searching for information. This information includes the current date and current time.

A simulation of the AKAI VCR VS303U (on-screen programming) and the interface of the present invention, were tested to evaluate users' performances. The AKAI interface of the prior art, hereinafter referred to as the prior art interface, was chosen because users made the fewest errors while using this machine, and no user quit while programming, as compared to three other VCRs tested, a Panasonic PV4962 (Bar Coder), an RCA VKP950 (on-screen programming), Panasonic PV4700 (Display Panel).

The present embodiment was constructed and tested using HyperPAD™, a rapid prototyping package for an IBM-PC Compatible Computer. It is, of course obvious that the present embodiment could be incorporated in a commercial VCR machine by those skilled in the art, or be implemented on many types of general purpose computers with output screens which allow on-screen feedback for the programming operation. Further, the system of the present embodiment can include a remote-control device which communicates with a VCR through an infrared beam or beams, and can thus exert control over an infrared remote controlled VCR, or translate the programming information and communicate through an infrared remote control, using the standard type infrared transmitter.

An IBM PC-AT compatible (MS-DOS, Intel 80286-10 MHz) computer was used to test the two simulations. In order to simulate the use of a remote control device in programming the VCR, an infrared device made by NViewm was attached to the computer. This device came with a keyboard that was used to "teach" a Memorex™ Universal Remote so that the desired actions could be obtained. By using a universal remote, the computer could be controlled by using a remote control.

The present embodiment incorporates a mouse input device. It is understood that a small trackball with a button for selection, mounted on a remote control may also be employed, and may be preferable in certain circumstances. However, a computer mouse is easily available, and the mouse and trackball data are essentially similar for the type of task implemented by the user, with trackball performance being slightly faster. For daily use on a VCR however, a trackball would be a more preferable input device because it does not require a hard, flat surface, which is not always available to a user when programming a VCR, such as in the situation where a person is watching television while sitting in a chair or sofa.

A Genius™ Mouse was used as the input device in the prototype of the interface of the present invention. With the mouse, the user could view all of the choices at once on the display screen, and then make a selection from the items on the screen by moving the cursor and then pressing the left mouse button.

The interface of the present example focuses on attending to the user's needs, and the interface must be modified for each application. By reducing the searching, learning times, and entry times, the mental load is also minimized. Some tradeoffs are necessary as a result of subjective and objective data. Because of the difficulty in optimizing a single interface design for all levels of users, a menu system was used in an attempt to satisfy all these user types.

The interface of the present example reduced the number of incorrect recordings by 50%. The severity of the errors is unimportant here because one wrong entry will cause an irretrievable mistake and the user will not record the intended program. One study reported that faulty inputs, which lead to missing the program, can be reported by almost every present day owner of a VCR.

EXAMPLE 8

Programmable Device Interface

It is also noted that the interface of the present invention need not be limited to audio-visual and multimedia applications, as similar issues arise in various programmable controller environments. Such issues are disclosed in Carlson, Mark A., "Design Goals for an Effective User Interface", Electro/82 Proceedings, 3/1/1-3/1/4; Kreifeldt, John, "Human Factors Approach to Medical Instrument Design", Electro/82 Proceedings, 3/3/1-3/3/6; Wilke, William, "Easy Operation of Instruments by Both Man and Machine", Electro/82 Proceedings, 3/2/1-3/2/4; Green, Lee, "Thermo Tech: Here's a common sense guide to the new thinking thermostats", Popular Mechanics, October 1985, 155-159; Moore, T. G. and Dartnall, "Human Factors of a Microelectronic Product: The Central Heating Timer/Programmer", Applied Ergonomics, 1983, Vol. 13, No.1, 15-23; and "The Smart House: Human Factors in Home Automation", Human Factors in Practice, December 1990, 1-36, all of which are incorporated herein by reference.

Figure 23:
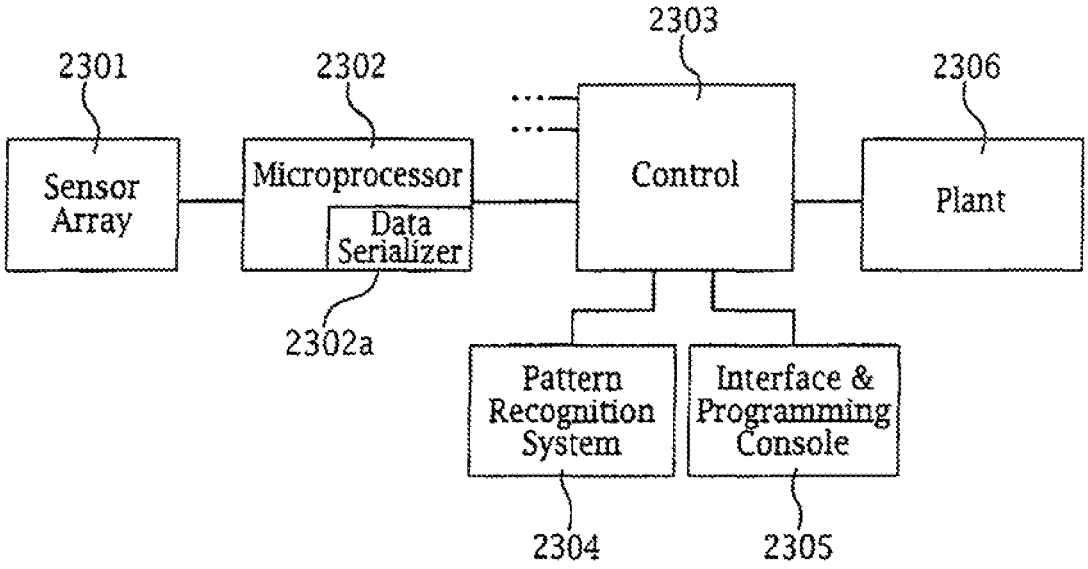
FIG. 23 is a block diagram of a control system of the present invention incorporating a pattern recognition element and an interface.

This generalized system is shown in FIG. 23, in which the sensor array 2301 interfaces with a microprocessor 2302 with a serial data port 2302a, which transmits sensor data to a control 2303. The control 2303 further interfaces or includes a data pattern recognition system 2304 and an interface and programming console 2305 according to the present invention, using the aforementioned intelligent features and adaptive pattern recognition techniques. The control 2203 controls the plant 2306, which includes all the controlled actuators, etc.

EXAMPLE 9

Adaptive Graphic Interface

A "smart screen" aspect according to the present invention is further explored in the present example. This aspect of the present invention allows the interface to anticipate or predict the intent of the user, to provide, as a default user choice, the most likely action to be taken by the user of the programmable device as a default, which may be either accepted or rejected by the user, without inordinate delay to the user. The intelligent selection feature may also automatically choose an option and execute the selected option, without further intervention, in cases where little or no harm will result. Examples of such harm include a loss of data, a substantial waste of the user's time and an inappropriate unauthorized allocation of computational resources.

When a user regularly applies the VCR device, for example, to record a particular television show which appears weekly on a given television channel, at a given time, on a given channel, such an action could be immediately presented to the user as a first option, without forcing him to explicitly program the entire sequence. Likewise, if the user has already entered such a command, the presented choices could include a second most likely selection, as well as the possibility of cancelling the previously entered command.

Further, if an entire television programming guide for a week or month is available as a database, the interface could actively determine whether the desired show is preempted, a repeat (e.g., one which has been previously recorded by the system), changed in time or programming slot, etc. Thus, the interface could present information to the user, of which he might not be aware, and/or predict an action based on that information. Such a device could, if set in a mode of operation that allows such, automatically execute a sequence of instructions based on a predicted course of action. Thus, if a user is to be absent for a period, he could set the machine to automatically record a show, even if the recording parameters are not known with precision at the time of setting by the user. Of course, this particular embodiment depends on the availability of a database of current broadcast schedules, however, such a database may generally be available, e.g., in an on-line database.

Such an on-line database system of known type may be used and need not be described in detail herein. Alternately, a printed schedule of broadcasts may be scanned into a computer and the printed information deciphered (e.g., optical character recognition (OCR)) to gain access to a database. Other methods may also be used to access scheduling information, e.g. access channels on cable systems, as well as other broadcast information identifying future and imminent programming. Together, these methods allow semiautonomous operation, guided by programming preferences rather than explicit programs, where such explicit instruction is absent.

The smart screens according to the present invention may be implemented as follows. The controller may be, for example, an Apple Power Macintosh 8100/110 AV computer, operating under Macintosh 7.5 operating system. The Hypercard™ 2.3 software may be used to implement the screen interface, which incorporates the above-described features, which is generally compatible with the Hyperpad software described above. HyperCard™ is mentioned due to its capabilities to reference external programs, thus allowing interfacing to various software and hardware devices. A more global scripting language, such as Frontier by UserLand Software Inc., may also be used, especially where low level hardware control of interfaced devices, such as a-VCR, multimedia adapter, or the like is desired. Apple Applescript may also be used. The Quicktime format may be used to store and recall data, however, many acceptable formats exist. The input device is an Apple Desktop Bus (ADB) mouse, and the output display is an 8 bit or 24 bit graphics color adapter connected to, e.g., a 14" color monitor. In addition, various parameters concerning the use of the interface are stored in the computer's memory, and a non-volatile mass storage device, such as a hard disk drive, or Electrically Erasable Programmable read Only Memory (EEPROM) or Erasable Programmable Read Only Memory (EPROM) as well as battery backed RAM could also be used.

Intel Pentium-based platforms may also be used, preferably in IBM-PC compatible implementations. Intel 80860 and/or Intel 80960 processor platforms may also be used.

Alternatively, other Apple Power PC, Macintosh (MC680X0 series) or IBM Power PC implementation may be used, providing the advantage of increased processing power over Motorola 680X0 derivatives. The specific Power PC employed may be any version, including desktop system versions available from Apple and IBM and embedded versions from IBM and Motorola. These Power PC processors may also be provided in a parallel processing implementation. Further, custom implementations of Power PC hardware optimized for the relevant computational tasks may be employed.

Of course, other systems, including DEC Alpha and HP 9000 systems may also be employed, as well as SPARC, MIPS, and other available RISC systems. While RISC systems, possibly supplemented with DSP hardware, are presently preferred because of their efficiency in executing the pattern recognition tasks, Complex Instruction Set Computer (CISC), hybrid and other known processing systems may be employed. The Texas Instruments TMS320C80 combines a RISC processor, arithmatic logic unit (ALU) and four DSP processors on a single chip, and is therefore a preferred processor for implementing various aspects of the system, especially mathematical processing including DCT and correlations.

According to the present invention, the interface may perform comparatively simple tasks, such as standard graphic user interface implementation with optimized presentation of screen options, or include more complex functionality, such as pattern recognition, pattern matching and complex user preference correlations. Therefore, hardware requirements will range from basic 68040, 80486, Pentium, Power PC, MIPS, SPARC, DEC Alpha, or other microprocessors which are used to perform visual or audio interface functions, to much special purpose processors for implementation of complex algorithms, including mathematical, neural network, fuzzy logic, and iterated function systems (fractals).

It should be noted that, while many aspects of the intelligent interface according to the present invention do not require extremely high levels of processing power, and therefore may be provided with inexpensive and commonly available computing hardware, other aspects involve complex pattern recognition and advantageously employ powerful processors to achieve a short processing latency. Both simple and complex interface systems, however, are included within the scope of the present invention. Processing may be distributed in different fashions, so that complex functionality may be implemented with relatively simple local hardware, with a substantial amount of required processing for a high level of functionality performed centrally, and for a large number of users.

From the stored information regarding the prior use of the interface by the user, including prior sessions and the immediate session, and a current state of the machine (including a received data stream and information relating to the data stream previously stored), a predicted course of action or operation may be realized. This predicted operation is, in the context of the current user interface state, the most probable next action to be taken by the user.

The predicted operation is based on: the identity of the user, if more than one user operates the interface and machine, the information already entered into the interface during the present programming session, the presently available choices for data entry, settings for the use of the machine, which may be present as a result of a "setup" operation, settings saved during a prior session, and a database of programming choices. In the case of a HyperCard script, the interface software calls another program which has access to the necessary data in the memory, as well as access to any remote database which may be necessary for implementation of the function. Using a predictive technology, such as Boolean logic, fuzzy logic, neural network logic, or other type of artificial intelligence, a most probable choice may be presented to the user for his approval, or another alternative choice may be selected. Further, a number of most probable choices may be presented simultaneously or in sequence, in order to improve the probability that the user will be immediately or quickly presented with an acceptable choice. If multiple choices are presented, and there is limited room on the display, two (or more) similar choices may be merged into a single menu selection, which may be resolved in a secondary menu screen. e.g. a submenu or dialog box.

Figure 24:
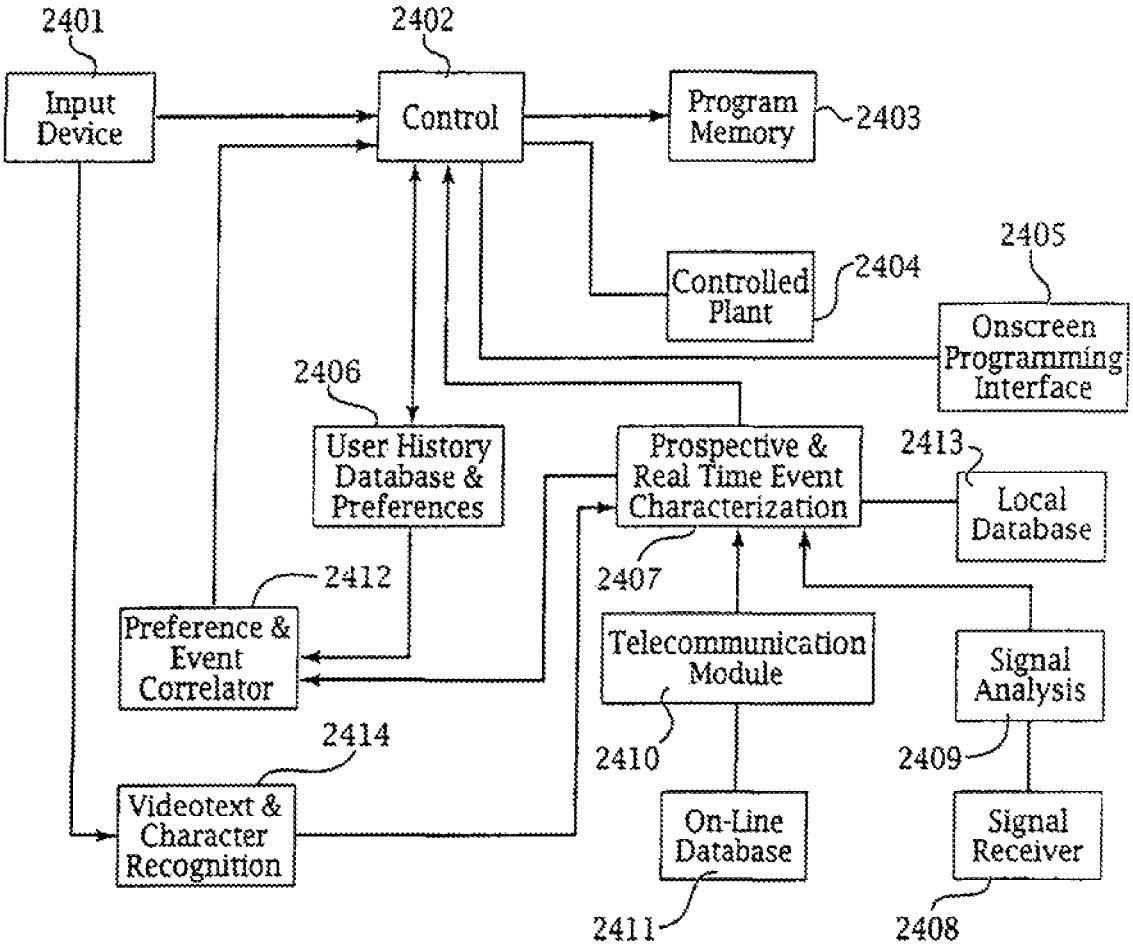
FIG. 24 is a block diagram of a control system for characterizing and correlating a signal pattern with a stored user preference of the present invention.
Figure 25:
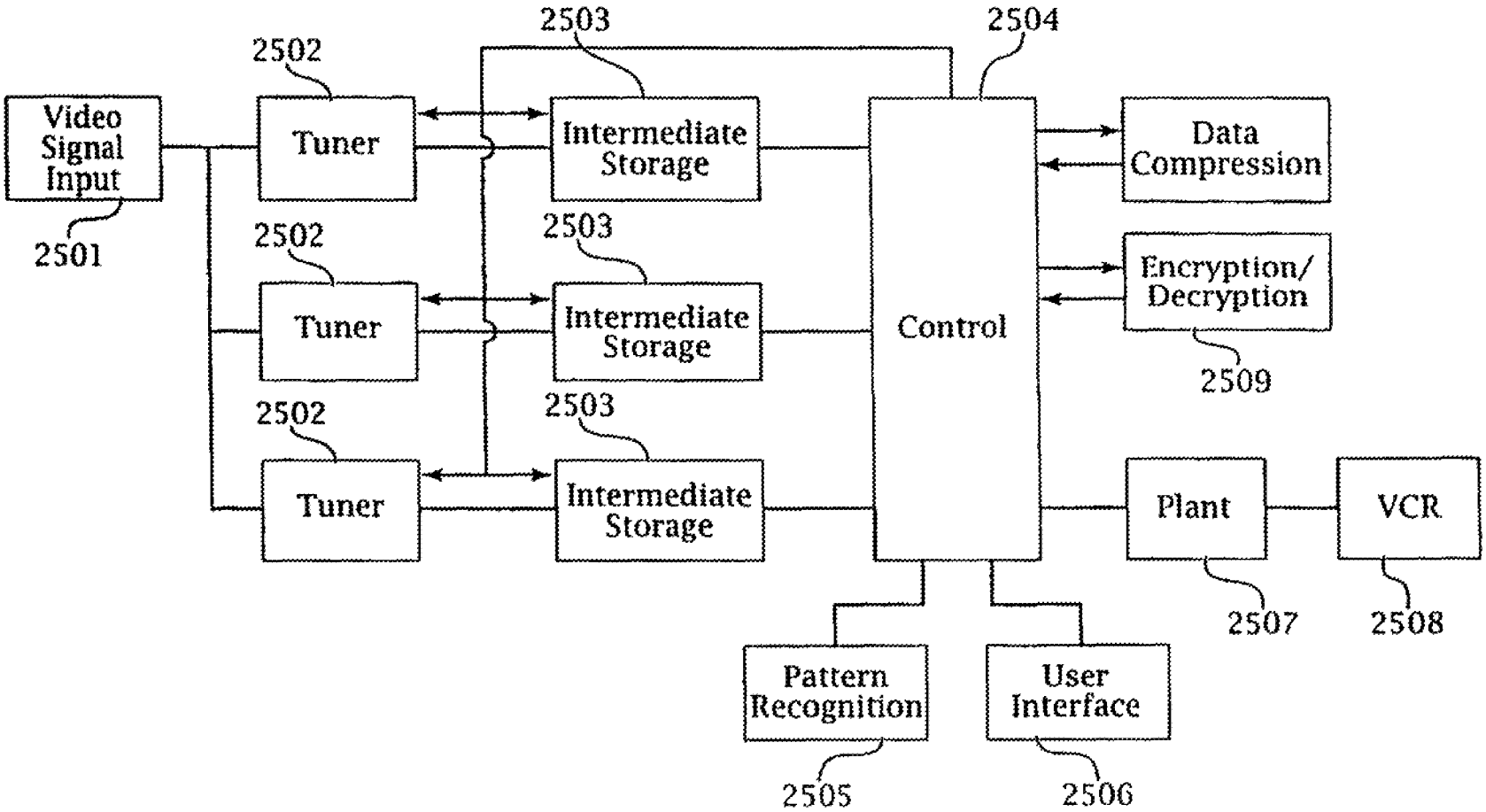
FIG. 25 is a block diagram of a multiple video signal input apparatus, with pattern recognition, data compression, data encryption, and a user interface of the present invention.

FIG. 24 shows a system for correlating a user's preferences with a prospective or real-time occurrence of an event. The input device 2401, which is a remote control with a pointing device, such as a trackball, provides the user's input to the control 2402. The program is stored in a program memory 2403, after it is entered. The control 2402 controls a plant 2404, which is a VCR. The control also controls an on-screen programming interface 2405, through which the user interactively enters the program information. Each program entry of the user is submitted to the user history database and preferences module 2406, which may also receive explicit preference information, input by the user through the input device 2401. The prospective and real time event characterization unit 2407 uses any and/or all relevant information available in order to determine the character of a signal input, which is a video signal, from the signal receiver 2408. A signal analyzer 2409 provides a preliminary analysis and characterization of the signal, which is input to the prospective and real time event characterization unit 2407. The prospective and real time event characterization unit 2407 also interacts and receives an input from a telecommunication module 2410, which in turn interacts and receives information from an on-line database 2411. A user preference and event correlator 2412 produces an output relating to a relatedness of an event or prospective event and a user preference. In the event of a high correlation or relatedness, the control 2402 determines that the event or prospective event is a likely or most likely predicted action. The prospective event discussed above refers to a scheduled event, which is likely to occur in the future. The characterization unit also has a local database 2413 for storing schedule information and the like.

In the particular context of a videotape, one consideration of the user is the amount of time remaining on the tape. Generally, users wish to optimally fill a tape without splitting a program, although the optimization and non-splitting parameters may vary between users. Therefore, the length of the tape and the amount and character of other items on the tape are also factors to be employed in determining a most desired result. With respect to this issue, the interface may maintain a library function which allows the identification of a partially filled tape for recording under given circumstances. The interface may also optimize a playback by selecting a tape containing a desired sequence of materials.

The intelligent interface may also be used as a part of an educational system, due to its ability to adapt to the level of the user and dynamically alter an information presentation based on the "user level", i.e. the training status of the user, and its ability to determine areas of high and low performance. Likewise, the intelligent interface according to the present invention may also be used in a business environment for use by trained individuals who require relatively static software interface design for consistence and "touch typing" with memorized keystroke or mouse click sequences. In this case, the intelligent functionality is segregated into a separate user interface structure, such as an additional "pull down menu" or other available screen location. While the interface always monitors user performance, the impact of the analysis of the user is selectively applied. User analysis may also be used for performance evaluation according to an objective criteria, based on continuous monitoring. In a network environment, user profile and evaluation may be made portable, stored so as to be accessible from any networked device the user may interact with, from office computers to thermostats to photocopying machines to coffee machines.

EXAMPLE 10

Intelligent Adaptive VCR Interface

A user interacting with the device intends to record a particular program, "Married With Children" (Fox, Sunday, 9:00 p.m., etc.) on its ever occurrence. This intent, however, is to provide a full library of episodes, and not to duplicate episodes. The particular program is subject to the occurrence of reruns, syndicated distribution, time shifting of performance, preview scenes and advertisements. Further, various actors appearing in the particular program also appear in other capacities and roles on television. Therefore, after this intent is elucidated, the interface scans available directories of programming to determine when "Marries With Children" will be broadcast. In addition, to the extent possible, all channels may be monitored, in the event that the directories or erroneous or incomplete.

It is noted that the interface may be quite effective if it is used for a number of applications, such as television, radio, desktop computer, and even kitchen and HVAC system. For example, preferences for processing MTV or other music video information may be directly relevant to processing of radio or other music reproduction devices, and vice versa.

At some point in the process, preferably prior to substantive programming input, the interface performs a self-diagnostic check to determine whether the machine is set up and operating correctly. This would include a determination of whether the clock has been set and thereafter operating continuously. Of course, the clock could have, in practice, a battery to minimize the occurrence of problems relating to clock function. The interface would then, if the clock is not properly set, and if there is no telecommunication or other external means for automatically determining the exact time, present the user with a menu selection to set the proper time. Of course, if the correct time is available to the apparatus in some form, this could be automatically obtained, and the internal clock updated, without intervention. These same sources may be used to verify the accuracy of an internal clock. Further, if a reliable external clock system is available, an internal clock may be dispensed with or ignored. Time may also be inferred based on the regular schedules of broadcasts, e.g., the 11:00 p.m. news begins at 11:00 p.m. If the user does not have access to a source of the exact time, the step of correcting the time may be deferred, although at some point the user should be reminded to verify the clock information. The user may thus be able to override a machine-generated request or attempt to correct the time data.

If the machine has access to an external source of the exact time, it would then preferably access this source first. Such sources of exact time include a telephone connection to a voice line which repeats the time. The computer would then perform a speech recognition algorithm which would be used to determine the time. Such a speech recognition algorithm could also be used as a part of the user interface for other purposes, i.e. a speech recognition system is not supplied solely for obtaining time information. Alternatively, a modem or communication device could be used to obtain the time in digitally coded form over a network, which would alleviate the need for speech recognition capabilities for this function. An on-line connection could also be used in order to obtain information concerning television scheduling.

A further method for obtaining accurate time information is to access a video signal which contains the desired time information. For example, many cable broadcasting systems have a channel which continuously broadcasts the time in image form. The interface tunes this channel, and acquires a representation of the screen image, thereafter performing a character recognition algorithm to capture the time information. This character recognition algorithm could also be used to obtain or capture information regarding programming schedules, stock prices, and other text information which may appear on certain cable broadcast channels.

Thus, the interface, in obtaining necessary information, employs such available data source access methods as speech recognition, character recognition, digital telecommunication means, radio wave reception and interpretation, and links to other devices.

In interacting with the apparatus, the user first identifies himself/herself to the machine, which can occur in a number of ways. This step may be dispensed with, or at least trivialized, if only one user regularly interacts with the apparatus. Otherwise, such identification may be important in order to maintain the integrity of the user profiles and predictive aspects of the interface. An radio frequency transponder (RF-ID), infrared transponder (IR-ED) system may automatically determine the user based on a devices, which may be concealed in a piece of jewelry or wristwatch. The user may also be identified by voice pattern recognition, speaker independent voice recognition, video pattern recognition, fingerprint, retinal scan, or other biometric evaluation. An explicit entry of the user identity may also be employed, wherein the user types his/her name on a keyboard or selects the name or unique identifier from a "pick-list". The-interface, upon identifying the user, retrieves information regarding the user, which may include past history of use, user preferences, user sophistication, patterns of variation of user, which may be based on, e.g., time, mood, weather, lighting, biometric factor or other factors.

Thus, after completing system diagnostics, including the time-check function referred to above, the system next determines or predicts the desired function of the user. In this regard, if more than one user has access to the system, the user identifies himself to the interface, in a user identification step 1701 or an analogous action, which may be a coded entry, or a selection from the menu. If the interface has voice recognition capability, then the user may be recognized by his voice pattern, or merely by stating his name. The interface then accesses the memory for a profile of the past use of the machine by the user, which may include the entire prior history, relevant abstracts of the history, or derived user preferences, as shown in the personalized startup based on user profile step 1702, which information is also stored and used in the past user history determining element 2107. These choices differ in the amount of storage necessary in order to retain the desired information.

Thus, if the user has only used the VCR to record, e.g., the NBC 11 o'clock news, i.e., record all days from 11:00 p.m. to 11:30 p.m. on NBC, in the past, the most likely current predicted choice would be the NBC 11 o'clock news. If the interface were to present a number of choices, having lower probability, then it interprets the recording history to be "news" based on a database of broadcast information. Therefore, a prediction of lower probability would be ABC or CBS news at, e.g., 11:00 p.m., and the NBC news at, e.g., 5:00 p.m. In a cable television system, there may be a number of NBC affiliated news alternatives, so that these alternatives may be investigated first before other networks or the like are presented as likely choices. In addition, where a video feed is unavailable, a text feed from the internet or an on-line service may be acquired as a probable alternative.

Thus, a number of likely choices, based on intelligently determined alternatives, as well as adaptation based on determined user preferences, are initially presented to the user, along with a menu selection to allow rejection of these predicted choices. In this case, the user selects the "reject" selection, and the system presents the user with a next predicted desired menu choice. Since the user history, in this case, does not provide for another choice of particularly high probability, the user is prompted to explicitly choose the program sequence by day, time, channel, and duration. The user then enters the starting time for recording according to the methods described above. The interface then searches its databases regarding the user and broadcast listings to present a most likely choice given that parameter, as well as all available alternatives. In this case, the user history is of little help, and is not useful for making a prediction. In other cases, the system uses its intelligence to "fill in the blanks", which could, of course, be rejected by the user if these are inaccurate or inappropriate. The most likely choices are then those programs that begin at the selected time. If the user had input the channel or network, instead of starting time, then the presented choices would be the broadcast schedule of the channel, e.g. channel 5 or Fox, for the selected day.

The user then selects one of the available choices, which completes the programming sequence. If no database of broadcasts is available, then the user explicitly defines all parameters of the broadcast. When the programming is completed, the interface then updates its user database, prompts the user to set the VCR to record, by, e.g., inserting a blank or recordable tape.

If the predicted desire of the user is of no help, or the user seeks to explicitly program the system, a manual program entry system is available. Where there is no useful prediction of the user, the interface may request a training session, which may be a general inquiry, or specifically directed to immediately forthcoming broadcasts, or both.

In this case, after a failure to predict a desired program, the user then proceeds to explicitly program the VCR interface to record "Married with Children" on Fox at 9:00 p.m. on Sunday evening. If a database is available, it might also show that "Married with Children" is also syndicated in re-runs, and therefore various episodes may be available on other channels at other times. Thus, during the subsequent session, both the premier showing and re-run of "Married With Children" would be available predicted choices, along with the 11 o'clock News on NBC.

The user having demonstrated a preference for "Married with Children", the interface then characterizes the program. This includes, for example, a characterization of the soundtrack, the background, foreground, actors and actresses present, credits, etc. The interface then attempts to correlate the features present in the reference selection with other available selections. This comparison may be with a preformed database, providing immediate results, or prospectively, after entry of the reference selection. Of course, a number of correlation functions may proceed simultaneously, and various choices may be merged to form a compound reference selection, any ambiguity in which to be later resolved. Further, as various "episodes" of the reference selection occur, the system appends and integrates the most recent occurrence with the stored reference information, thus updating the reference database.

When an occurrence is identified, it is immediately buffered, until such time as the particular episode may be compared against previously stored episodes. If two identical broadcasts occur simultaneously, one may be selected, i.e., the one with the best reception. When the episode is identified, if it is new, the buffered broadcast information is permanently stored; if it is previously stored, the buffer is flushed and the occurrence is further ignored as a "hit". Since the apparatus is now not responding to a direct request, it may then perform various housekeeping functions, including updating databases of broadcasts and the like. This is because, although the apparatus is preferably highly trained upon manufacture, a large number of new broadcasts are always being created and presented, so that the apparatus must constantly maintain its "awareness" of data types and trends, as well as update its predicted preferences of the user(s).

Based on input from the user, other programming including the same actors and/or actresses may be processed, e.g., recorded. For example. Katey Segal periodically appears on "Jay Leno" as a musical guest, and therefore may be recorded in these appearances.

EXAMPLE 11

Intelligent Adaptive VCR Interface

Another example of the use of the present programming system allows a hybrid request which does not correspond to any single broadcast schedule entry. In this case, if the user instead wishes to record weather reports on all channels, the interface may be of further help. The interface controls a plurality of tuner elements 2502 of a video signal reception device 2501, so that a plurality of broadcasts may be simultaneously received. Using the mass storage and possibly image data compression described above, a plurality of broadcasts may also be recorded simultaneously in the intermediate storage 2503. The mass storage may be multiple VCRs, optical storage, magnetooptical storage, magnetic storage including disk (e.g. single disks, multimedia compatible disks, redundant array of inexpensive disks (RAID), etc.) tape (quarter inch cartridge (QIC), 8 mm, 4 mm, etc.). The optical recording tape produced by ICI, Ltd. might also be a useful storage medium for large volumes of data, as might be generated by recording multiple video signals, although the present implementations make this ICI system best suited for commercial or industrial use and not for individual consumer use. In this case, the interface 2506 accesses its associated database 2413 to determine, at a given time, which channels are broadcasting "news". The interface system might also randomly or systematically monitor or scan all or a portion of the available broadcasts for "special reports". The interface system then monitors these channels for indicia of a "weather" information content broadcast.

For example, the newscaster who appears to report the weather on a given show is usually the same, so that a pattern recognition system 2505 of the video frame could indicate the presence of that newscaster. In addition, the satellite photographs, weather radar, computer generated weather forecast screens, etc. are often similar for each broadcast. Finally, news segments, such as "weather" often appear at the same relative time in the broadcast. Using this information, the interface system selects certain broadcast segments for retention.

This retention begins at a beginning of a news segment, such as "weather", stop recording during commercials, and continues after return from break, on all selected channels. In order to assist in making accurate decisions, the monitored broadcasts may be stored in a temporary storage medium until a decision is made, and thereafter transfer the recording to a more permanent storage medium if that be appropriate. It is noted that the system of the present invention is intelligent, and may therefore "learn" either explicitly, or through training by example. Therefore, if the system made an error during the process, the user may define the error of the system, e.g., a substitute newscaster or rearrangement of news segments, so that the interface system is less likely to make the same error again. Thus, while such a system is inherently complex, it poses significant user advantages. Further, while the interface system itself is sophisticated, it provides simplicity, with inductive reasoning and deductive reasoning for the user.

Thus, a minimum of user interaction is required even for complex tasks, and nearly full automation is possible, as long as the user and apparatus are able to communicate to convey a preference. As a further embodiment according to the present invention, the interface system will stored transmitted data, and subsequently review that data, extracting pertinent information. The stored data may then be deleted from the storage medium. In this regard, the system may be self learning, It is noted that various algorithms and formulae for pattern recognition, correlation, data compression, transforms, etc., are known to those skilled in the art, and are available in compendiums, such as Netravali, Arun N., and Haskell, Barry G., "Digital Pictures Representation and Compression", Plenum Press, New York (1988); Baxes, Gregory A., "Digital Signal Processing, A Practical Primer", Prentice-Hall, Englewood Cliffs, N.J. (1984); Gonzalez, Rafael C., "Digital Image Processing", Addison-Wesley, Reading, Mass. (1987), and, of a more general nature, Press, William H. et al, "Numerical Recipes in C The Art of Scientific Computing", Cambridge University Press, 1988, which are incorporated herein by reference.

EXAMPLE 12

Intelligent Adaptive VCR Interface

A further example of the use of the advanced intelligent features of the present invention is the use of the system to record, e.g., "live" musical performances. These occur on many "talk" shows, such as "Tonight Show" (NBC, 11:30 p.m. to 12:30 p.m., weeknights), "Saturday Night Live" (NBC 11:30 p.m. to 1:00 a.m. Saturday-Sunday), and other shows or "specials" such as the "Grammy Awards". The interface, if requested by the user to record such performances, then seeks to determine their occurrence by, e.g.: analyzing a broadcast schedule; interacting with the on-line database 2411; and by reference to the local database 2413. When the interface determines with high probability that a broadcast will occur, it then monitors the channel(s) at the indicated time(s), through the plurality of tuners 2502. The system may also autonomously scan broadcasts for unexpected occurrences.

In the case of pay-per-view systems and the like, which incorporate encrypted signals, an encryption/decryption unit 2509 is provided for decrypting the transmitted signal for analysis and viewing. This unit also preferably allows encryption of material in other modes of operation, although known decryption systems without this feature may also be employed with the present system. During the monitoring, the interface system acquires the audio and video information being broadcast, through the signal receiver 2408, and correlates this information with a known profile of a "live musical performance", in the preference and event correlator 2412. This must be distinguished from music as a part of, e.g., a soundtrack, as well as "musicals" which are part of movies and recorded operas, if these are not desired by the user. Further, music videos may also be undesirable. When the correlation is high between the broadcast and a reference profile of a "live musical performance", the system selects the broadcast for retention. In this case, the information in the intermediate storage 2503 is transferred to the plant 2507, which includes a permanent storage device 2508. The intermediate storage 2503 medium is used to record a "buffer" segment, so that none of the broadcast is lost while the system determines the nature of the broadcast. This, of course, allows an extended period for the determination of the type of broadcast, so that, while real-time recognition is preferred, it is not absolutely necessary in order to gain the advantages of the present invention. The buffer storage data, if not deleted, also allows a user to select a portion for retention that the interface system has rejected.

Thus, while it is preferable to make a determination in real time, or at least maintain real time throughput with a processing latency, it is possible to make an ex post facto determination of the nature of the broadcast program. By using an available delay, e.g., about 5 to about 300 seconds, or longer, the reliability of the determination can be greatly increased as compared to an analysis of a few frames of video data, e.g., about 15 to about 300 mS. An intermediate reliability will be obtained with a delay of between about 300 to about 5000 mS. As stated above, the storage system for this determination need not be uncompressed nor lossless, so long as features necessary to determine the character of the broadcast are present. However, it is preferred that for broadcast recording intended for later viewing, the storage be as accurate as possible, so that if a compression algorithm is implemented, it be as lossless as reasonable given the various constraints. The MPEG-2 standard would be applicable for this purpose, though other video compression systems are available.

In a preferred situation, approximately 5 minutes of broadcast material is analyzed in order to make a determination of the content. This broadcast material is stored in two media. First, it is stored in a format acceptable for viewing, such as video tape in a videotape recorder, or in digital video format, e.g., uncompressed, MPEG-2. Second, it is received in parallel by the computer control, where the data is subject to a number of recognition and characterization processes. These are performed in parallel and in series, to produce a stored extracted feature matrix. This matrix may contain any type of information related to the broadcast material, including an uncompressed signal, a compressed signal, a highly processed signal relating to information contained in particular frames and abstract features, spatially and temporally dissociated from the broadcast signal, yet including features included in the broadcast which relate to the content of the broadcast.

A preferred method incorporates one or more digital signal processor based coprocessor elements, which may be present on, e.g., Nubus cards in the Macintosh Quadra 950, Apple Power PC, PCI card in Pentium-based MS-DOS/Windows 3.1, 3.11, '95, NT computers, other Power PC based computers. These elements may be based on C-Cube CL550 (JPEG compression), Analog Devices ADSP-21020, Analog Devices ADSP-21060, AT&T DSP32C, AT&T DSP3210, AMD 29000 series, Motorola DSP 96000ADS, Texas Instruments TMS 320C40, TMS 320C80, IBM Mwave, or a combination of types. Other devices are also available from Analog Devices, AT&T, DSP Group, Motorola, NEC, SGS-Thomson, Sharp, Texas Instruments, Zilog, Zoran, and other vendors. See, EDN, May 11, 1995, pp. 40-106; Bursky, D., "Improved DSP ICs Eye New Horizons", Electronic Design, Nov. 11, 1993, pp. 69-82. DSP systems, which generally have an architecture optimized for the efficient and rapid execution of repetitive numeric calculations, are desirable for certain pattern recognition tasks, and may be provided as a tightly coupled parallel processing array to increase throughput.

A known board containing a DSP is the MacDSP3210 by Spectral Innovations Inc., containing an AT&T digital signal processor and an MC68020 CISC processor, and which uses the Apple Real-time Operating System Executive (A/ROSE) and Visible Cache Operating System (VCOS). It is preferred that the processors employed be optimized for image processing, because of their higher throughput in the present image processing applications, to process the video signals, and more other signal processors to analyze the audio signals. Of course, general purpose processors may be used to perform all calculations. An array processor which may be interfaced with a Macintosh is the Superserver-C available from Pacific Parallel Research Inc., incorporating parallel Inmos Transputers. Such an array processor may be suitable for parallel analysis of the image segment and classification of its attributes.

Pattern recognition processing, especially after preprocessing of the data signal by digital signal processors and image compression engines, may also be assisted by logical inference engines, such as FUTURE (Fuzzy Information Processing Turbo Engine) by The Laboratory for International Fuzzy Engineering (LIFE), which incorporates multiple Fuzzy Set Processors (FSP), which are single-instruction, multiple data path (SIMD) processors.. Using a fuzzy logic paradigm, the processing system may provide a best fit output to a set of inputs more efficiently than standard computational techniques, and since the presently desired result requires a "best guess", rather than a very accurate determination, the present interface is an appropriate application of this technology.

As noted above, these processors may also serve other functions such as voice recognition for the interface, or extracting text from video transmissions and interpreting it. It is also noted that, while some of these coprocessing engines are now costly, these costs are decreasing and the present invention therefore includes the use of sophisticated present designs as well as future devices which may be used to perform the stated functions. The continued development of optical computers may also dramatically reduce the cost of implementing this aspect of the present invention; however, the present state of the art allows the basic functions to be performed. See attached appendix of references, incorporated herein by reference, detailing various optical computing designs.

Systems which run under SPDX DSP operating system, IBM's Mwave operating system and AT&T's VCOS operating system may be employed. These operating systems, and possibly others, are to be supported by Microsoft Inc.'s Windows 95 operating system Resource Manager function.

It is noted that various methods are available for determining a relatedness of two sets of data, such as an image or a representation of an image. These include the determination of Hausdorff distance, fuzzy correlation, arithmetic correlation, mean square error, neural network "energy" minimization, covariance, cross correlation, and other known methods, which may be applied to the raw data or after a transformation process, such as an Affine transformation, a Fourier transformation, a Gabor transformation, a warping transformation, a color map transformation, and the like. Further, it is emphasized that, in image or pattern recognition systems, there is no need that the entire image be correlated or even analyzed, nor that any correlation be based on the entirety of that image analyzed. Further, it is advantageous to allow redundancy, so that it is not necessary to have unique designations for the various aspects of the data to be recognized, nor the patterns to be identified as matching the uncharacterized input data.

The MSHELL from Applied Coherent Technology is a software system that runs on a Mercury MC3200 array processor, in conjunction with a Data Translation DT2861 or DT2862. The NDS1000 Development System from Nestor, Inc., provides image recognition software which runs on a PC compatible computer and a Data Translation DT2878. The above mentioned processing hardware and software, as known, is incorporated herein.

The C-Cube CL550 is fully disclosed in "C-Cube CL550 JPEG Image Compression Processor", Preliminary Data Book, August 1991, and addendum dated Nov. 20, 1991, incorporated herein by reference, and products incorporating the CL550 include the JPEG Video Development Kit (ISA bus card with Chips and Technologies PC video 82C9001A Video Window Controller), and the C-Cube CL550 Development Board/PC for ISA Bus (CL550, for use with Truevision TARGA-16 or ATVista cards) or for NuBus (Macintosh). The so called C-Cube "CL950" is a MPEG decoder device. Such a device as the CL950 may be particularly useful for use in the present VCR for reproducing compressed program material, which may be compressed by the present apparatus, or may be used for decompressing precompressed program material. Other MPEG-1 and MPEG-2 encoding and decoding devices are known.

It is noted that all functions of a VCR would also be facilitated by the use of such powerful processors, and thus it is not only these advanced functions which are enabled by these advanced processors and coprocessors. It is also noted that these image recognition functions need not necessarily all be executed local to the user, and may in fact be centralized with resultant processed data transmitted to the remote user. This would be advantageous for two reasons: first, the user need not have an entire system of hardware localized in the VCR, and second, many of the operations which must be performed are common to a number of users, so that there is a net efficiency to be gained.

EXAMPLE 13

Intelligent Adaptive VCR Interface

The interface of the present invention incorporates an intelligent user interface level determination. This function analyzes the quality of the user input, rather than its content. Thus, this differs from the normal interface user level determination which requires an explicit entry of the desired user level, which is maintained throughout the interface until explicitly changed. The present interface may incorporate the "smart screen" feature discussed above, which may, through its analysis of the past user interaction with the interface predict the most likely predicted user input function. Thus, the predictive aspects of the present invention may be considered a related concept to the intelligent user level interface of the present invention. However, the following better serves to define this aspect of the invention.

The input device, in addition to defining a desired command, also provides certain information about the user which has heretofore been generally ignored or intentionally removed. With respect to a two-dimensional input device, such as a mouse, trackball, joystick, etc., this information includes a velocity component, an efficiency of input, an accuracy of input, an interruption of input, and a high frequency component of input. This system is shown schematically in FIG. 21, which has a speed detector 2104, a path optimization detector 2105, a selection quality detector 2106, a current programming status 2108, an error counter 2109, a cancel counter 2110, a high frequency signal component detector 2112, an accuracy detector 2113 and a physio-dynamic optimization detector 2114. In addition, FIG. 21 also shows that the interface also uses a past user history 2107, an explicit user level choice 2111 and an explicit help request 2115.

This list is not exclusive, and is somewhat dependent on the characteristics of the specific input device. For a mouse, trackball, or other like device, the velocity or speed component refers to the speed of movement of the sensing element, i.e. the rotating ball. This may also be direction sensitive, i.e., velocity vector. It is inferred that, all other things being equal, the higher the velocity, the more likely that the user "knows" what he is doing.

The efficiency of input refers to two aspects of the user interface. First, it refers to the selection of that choice which most simply leads to the selection of the desired selection. For example, if "noon" is an available choice along with direct entry of numbers, then the selection of "noon" instead of "12:00 p.m." would be more efficient. The second aspect of efficiency has to do with the path taken by the user in moving a graphic user interface cursor or input device from a current position to a desired position. For example, a random curve or swiggle between locations is less efficient than a straight line. This effect is limited, and must be analyzed in conjunction with the amount of time it takes to move from one location of a cursor on the screen to another; if the speed of movement is very rapid, i.e. less than about 400 mS for a full screen length movement, or less than about 300 nS for small movements, then an inefficiency in path is likely due to the momentum of the mouse and hand, momentum of the rolling ball, or a physiological arc of a joint. This aspect is detected by the physio-dynamic optimization detector 2114. Thus, only if the movement is slow, deliberate, and inefficient, should this factor weigh heavily. It is noted that arcs of movement, as well as uncritical damping of movement around the terminal position may be more efficient, and a straight path actually inefficient, so that the interface may therefore calculate efficiency based on a complex determination, and act accordingly where indicated.

Thus, an "efficient" movement would indicate an user who may work at a high level, and conversely, an inefficient movement would indicate a user who should be presented with simpler choices. The efficiency of movement is distinguished from gestures and path dependent inputs, such as drawing and painting. These may be distinguished based on machine status or context. Further, the interface may recognize gestures in may contexts. Therefore, gesticulations must be distinguished from command inputs before further processing. Gesticulations, like path efficiency, may also be analyzed separately from the basic command input, and therefore may be provided as a separate input stream on an interface level rather than an application level, thus allowing cross application operation.

Likewise, if a movement is abrupt or interrupted, yet follows an efficient path, this would indicate a probable need for a lower user interface level. This would be detected in a number of elements shown in FIG. 21, the speed detector 2104, a high frequency signal component detector 2112, an accuracy detector 2113 and a physio-dynamic optimization detector 2114. In addition, FIG. 21 also shows the use of a past user history 2107, an explicit user level choice 2111 and an explicit help request 2115.

While the interface may incorporate screen buttons which are smart, i.e. those which intelligently resolve ambiguous end locations, the accuracy of the endpoint is another factor in determining the probable level of the user. Thus, for example, if a 14" color monitor screen is used, having a resolution of 640 by 480 pixels, an accurate endpoint location would be within a central area of a screen button of size about 0.3" by about 1.0", would be an area of about 0.25" by about 0.75". A cursor location outside this location, but inside the screen button confines would indicate an average user, while a cursor location outside the screen button may be inferred to indicate the button, with an indication that the user is less experienced in using the pointing device.

Finally, in addition to the efficiency of the path of the cursor pointing device, a high frequency component may be extracted from the pointer signal by the high frequency signal component detector 2112, which would indicate a physical infirmity of the user (tremor), a distraction in using the interface, indecision in use, or environmental disturbance such as vibration. In this case, the presence of a large amount of high frequency signal indicates that, at least, the cursor movement is likely to be inaccurate, and possibly that the user desires a lower user level. While this is ambiguous based on the high frequency signal content alone, in conjunction with the other indicia, it may be interpreted. If, for example, the jitter is due to environmental vibrations, and the user is actually a high level user, then the response of the user level adjust system would be to provide a screen display with a lowered required accuracy of cursor placement, without necessarily qualitatively reducing the implied user level of the presented choices, thus, it would have an impact on the display simplification 2103, with only the necessary changes in the current user level 2101.

Alternatively, the user may input a gesture, i.e., a stylized input having no other command input meaning, which may be detected by analyzing the input. The input may be a manual input, voice, image or the like. A number of different gestures may be recognized. These gestures are generally explicit inputs, which allow a voluntary action to be interpreted as input information to the interface.

EXAMPLE 14

Intelligent Telephone Device Interface

Likewise, the present interface could be used to control complex telecommunications functions of advanced telephone and telecommunications equipment. In such a case, the user display interface would be a video display, or a flat panel display, such as an LCD display. The interface would hierarchically present the available choices to the user, based on a probability of selection by the user. The input device would be, for example, a small track ball near the keypad. Thus, simple telephone dialing would not be substantially impeded, while complex functions, such as call diversion, automated teledictation control, complex conferencing, caller identification-database interaction, and videotel systems, could easily be performed.

EXAMPLE 16

Character Recognition of Video

The present invention may incorporate character recognition from the video broadcast for automatic entry of this information. This is shown schematically in FIG. 24, with the inclusion of the videotext and character recognition module 2414. This information is shown to be transmitted to the event characterization unit 2407, where the detected information is correlated with the other available information. This information may also be returned to the control 2402. Examples of the types of information which would be recognized are titles of shows, cast and crew from programming material, broadcast special alerts, time (from digital display on special access channels), stock prices from "ticker tape" on special access channels, etc. Thus, this technology adds functionality to the interface. In addition, subtitled presentations could be recognized and presented through a voice synthesizer, to avoid the necessity of reading the subtitle. Further, foreign language subtitles could be translated into, e.g., English, and presented. In a particular embodiment, certain game shows, such as "Wheel of Fortune" have alphanumeric data presented as a part of the programming. This alphanumeric text may be extracted from the image.

In a preferred embodiment, the character recognition is performed in known manner on a buffer memory containing a frame of video, from a device such as a Data Translation DT2851, DT2853, DT2855, DT2867, DT2861, DT2862 and DT2871. A contrast algorithm, run on, for example, a Data Translation DT2858, DT2868, or DT2878, first removes the background, leaving the characters. This works especially well where the characters are of a single color, e.g. white, so that all other colors are masked. After the "layer" containing the information to be recognized is masked, an algorithm similar to that used for optical character recognition (OCR) is employed. These methods are well known in the art. This may be specially tuned to the resolution of the video device, e.g. NTSC, S-VHS, IDTV, Enhanced Definition Television (ETDT), MUSE, PAL, SECAM, MPEG-2 digital video, etc. In addition, since the text normally lasts for a period in excess of one frame, a spatial-temporal image enhancement algorithm may be employed to improve the quality of the information to be recognized, if it is indistinct in a single frame.

EXAMPLE 17

Smart House Interface

The present invention may also be incorporated into other types of programmable controls, for example those necessary or otherwise used in the control of a smart house. See, "The Smart House: Human Factors in Home Automation", Human Factors in Practice, December 1990, 1-36. The user interface in such a system is very important, because it must present the relevant data to the user for programming the control to perform the desired function. A smart house would likely have many rarely used functions, so that both the data and the available program options must be presented in the simplest manner consistent with the goal of allowing the user to make the desired program choice. For example, a smart house system with appropriate sensors might be used to execute the program: "start dishwasher, if more than half full, at 9:00 p.m." This program might also include a program to load soap into the dishwasher or to check if soap is already loaded. A user who wishes to delay starting until 11:00 p.m. would be initially presented with the defaults, including start time as an option, which would be simply modified by correcting the starting time. The next time the same user wishes to program the device, an algorithm might change the predicted starting time to, e.g. 10:00 p.m., which is a compromise between the historical choices. Alternatively, the new predicted start time might be 11:00 p.m., the last actually programmed sequence. Finally, the next predicted start time might remain at 9:00 p.m. The resolution of these choices would depend on a number of factors: a preprogrammed expert system; any other prior history of the user, even with respect to other appliances or in other situations; the context, meaning any other contemporaneously programmed sequences; and an explicit input from the user as to how the inputs should be evaluated for predictive purposes.

The expert system would balance factors, including disturbing noise from the dishwasher, which might be objectionable while persons are near the dishwasher, people are sleeping, or during formal entertainment. On the other hand, if the dishwasher is full, or its cleaned contents are needed, the dishwasher should run. Some persons prefer to reshelve dishes in the evening, before sleep, so in those cases, the dishwasher should complete its cycle before bedtime. The dishwasher, on a hot water cycle, should not run during showers or baths, and preferably should not compete with a clothes washer for hot water. The dishwasher preferably does not run during peak electrical demand times, especially if electrical rates are higher. Water conserving cycles should be selected, especially during droughts or water emergencies. If dishes remain in the dishwasher for an extended period, e.g., overnight, a moistening cycle may be employed to help loosen dirt and to help prevent drying. Thus, the expert system is preprogrammed for a number of high level considerations that might be common to a large number of users of the system, thus shortening the required training time of the system to learn the preferences of the user. Such a sophisticated system may eliminate the need entirely for adaptive responses, based on weighing of considerations provided by the user. Of course, other considerations may also be included for the operation or delay of operation of the dishwasher. Further, these considerations are exemplary of the types of considerations which might be employed in an expert system in a smart house.

The prior history of the user provides an excellent source of information regarding the preferences of the user, although this is sometimes not the most efficient means, and may often include contradictory data. This historical use data is therefore analyzed in a broad context in order to extract trends, which over a number of uses may be further extracted as "rules". Often, the user history data will be applied at a high level, and will interact with preexisting rules of the expert system, rather than to create new rules. In this case, the expert system preferably includes a large number of "extra rules", i.e., those with an a priori low probability or low weighing, providing a template for future pattern matching. The past history may be evaluated in a number of ways. First, an expert system may be used to analyze the past usage pattern. Second, a neural network may be trained using the historical data along with any corrective feedback. Third, the historical data may be used to alter fuzzy logic rules or classifications, either by expert system, neural network, or by other known means.

The context of use may also be used to determine a desired or predicted action. Therefore, if on a single occasion, a number of changes are made, for example during a large house party, the standard predictions would not be altered, and thus a normal program would remain in effect. Of course, a new "house party" sequence would then be recognized and included as a new type of sequence for future evaluation.. For example, a house party sequence might encompass a number of house systems. Thus, the delay of dishwasher until 11:00 p.m. allows all dishes from the party to be placed in the dishwasher before starting. An alarm system would be generally deactivated, although various zones may be provided with different protection; e.g., a master suite may be off-limits, with an alarm transmitting a signal to a user's beeper, rather than a call to police or alarm service company. During the summer, the air conditioner might run even if doors and windows are open, even if the normal program prompts for door closings before the air conditioner is turned on. Likewise, exterior lighting would be turned on at dusk, with bug lights turned on during the entire party. The user might individually make such decisions, which would be recognized as a group due to their proximity in time, or delineate the actions as a group. Thereafter, where some of these choices are made, and the profile of choices matches a "party" style, the remainder of the choices may be presented as a most likely or predicted choice. The group of choices together might also be selected from a menu of choices.

Context also relates to sensor data, which might include sensors in particular appliances or unrelated sensors. For example, infrared motion detectors may be used to estimate the number of persons present in a house. Likewise, heavy use of a bathroom, as detected by flushes, frequent light transitions or door openings, might also be useful as data to estimate a crowd size. Temperature sensors, video imaging sensors, perimeter sensors, electrical sensors relating to the status of appliances and machinery, and other types of sensors may provide data for context determination.

Of course, explicit inputs must also be accommodated, which may be atomic instructions or complex combinations of instructions which may control a single house system or a number of house systems simultaneously. The explicit input preferably comes by way of the adaptive interface described throughout the present application, or an interface incorporating particular aspects thereof.

The smart house system also controls the climate control system. Thus, it could coordinate temperatures, air flow and other factors, based on learned complex behaviors, such as individual movement within the dwelling. Since the goal of the programming of the smart house is not based on the storage of discrete information, but rather the execution of control sequences at various times and under certain circumstances, the control would differ in various ways from that of a VCR. However, the user interface system, adaptive user level, help system, and the like would be common to both types of system. This differs from the Fuzzy Logic controlled air conditioner available (in Japan) from Mitsubishi in that these prior art devices do not have an intelligent interface of the present invention. It should also be noted that the control for the VCR could be the same control as that for the smart house, so that the common elements are not redundant. Therefore, by applying a single control to many tasks, a common user interface is used, and the cost is reduced.

EXAMPLE 18

Programmable Environmental Controller

The present Example relates to a programmable environmental controller application. In this case, a sensor or sensor array is arranged to detect a change in the environment which is related to a climatic condition, such as an open door. On the occurrence of the door opening, the system would apply a pattern recognition analysis to recognize this particular sensor pattern, i.e. a mass of air at a different temperature entering the environment from a single location, or a loss of climate controlled air to a single location. These sensor patterns must be distinguished from other events, such as the action of appliances, movement of individuals in the vicinity of the sensor, a shower and other such events. It is noted that in this instance, a neural network based adaptive controller may be more efficient than a standard fuzzy logic system, because the installation and design of such a system is custom, and therefore it would be difficult to program fuzzy set associations a priori. In this case, a learning system, such as a neural network, may be more efficient in operation and produce a better result than other adaptive methods. The training procedure may be fully automated, (with manual feedback provided where necessary to adjust the control parameters) so long as sufficient sensors are provided for controlling the system, and also that an initial presumption of the control strategy is workable during the training period. In the case of an HVAC system, the initial strategy incorporated is the prior art "bang-bang" controller, which operates as a simple thermostat, or multi-zone thermostat. As a better starting point, a fuzzy logic temperature controller may be modeled and employed. Other known strategies which are not often used in environmental control include the proportional-integral-differential controller (PID).

It is noted that the HVAC system may also be of a type which is inoperable with standard type controllers; for example, the system may be such as to produce temperature oscillations, or significant temperature or pressure gradients. In this case, the default control system must be provided to compensate the system, allowing more subtle corrections and adjustments to be made based on preferences. Thus, an expert system is provided, which is updated based on user input, and which receives context information, including sensor data and other inputs. Explicit user preferences and programming are also input, preferably with an interface in accordance with the present invention or incorporating aspects thereof.

In this example, which may be described with reference to FIG. 23, sufficient sensors in a sensor array 2301 are provided, being light, temperature, humidity, pressure, air flow and possibly a sensor for determining an event proximate to the sensor, such as door opening. While a single sensor array 2301 provides input to the present control, a plurality of sensor arrays are preferably employed in complex installations, such as that described here. The sensors, with the possible exceptions of the flow sensor and event sensor, are housed in a single sensor head. Further, the temperature and pressure sensors may be combined in a single integrated circuit by known means. The light and temperature sensors are known to those skilled in the art, and need not be described herein. The pressure sensor may be a Sensym strain gage pressure transducer, a Motorola pressure transducer device, or the like, which are known in the art. Alternatively, other types of sensors may be used, for example a micromachined silicon force balance pressure transducer, similar in electrical design to the Analog Devices monolithic accelerometers, ADXL-50 or ADXL-05.

The humidity sensor is preferably an electronic type, producing an electrical signal output. It need not be internally compensated for the other measured environmental factors, as the constellation of sensors may compensate each other. The air flow sensor may be based on pressure differentials, using the electronic pressure sensor described above, or may be a mechanical vane type, which is based on flows. In most applications, a single flow axis will be sufficient, however, in some circumstances, a two or greater axis sensor will be required. Further, in the case of large volume areas, complex turbulent flow patterns may be relevant, for which known sensors exist. Laser based air flow sensors may be employed, if desired. LIDAR sensors may be used to determine flow rate, direction, and turbulence.

The event sensor may be of any type, and depends particularly on the event being measured. In the present case, where a door opening is to be detected, it is preferred that the environmental control be interfaced with a perimeter intrusion alarm system, which, for example, provides a magnet embedded in the door and a magnetic reed switch in the door frame. Individual sensors are normally wired to the alarm control panel, thus providing central access to many or all of the desired event detection sensors while minimizing the added cost. The event detector may also be an ultrasonic, infrared, microwave-Doppler, mechanical, or other type of sensor. Wireless sensors may also be used, communicating via infrared beams, acoustic, radio frequency, e.g., 46-49 MHz, 900 MHz, or other bands, using analog, digital or multilevel quantized digital amplitude modulation (AM), frequency modulation (FM), phase shift keying (PSK), quadrature amplitude modulation (QAM) or other modulation scheme, or a combination thereof. Spread spectrum devices may be employed, as well as time, code or frequency multiplexing or a combination thereof. Various failsafe mechanisms are preferably included, including those identifying transmitter or receiver failure, communication interference or message collision, and other conditions. A reverse communication channel may also be included, either symmetric in band, or asymmetric in band or out of band, for communication with the sensor or apparatus associated with the sensor, and as part of the failsafe system. A forward error correction protocol is preferably effected, which may detect errors and include error correcting codes for digital transmissions. Digital data may be encrypted, and the transmission modulation scheme may also include an encrypted sequence of frequency, phase, convolution, noise, or other modulation parameter.

While wireless data transmission as described above may be used, the preferred method of receiving sensor information is through a serial digital or analog (i.e., 4-20 mA transmitter) data transmission which may be multiplexed and/or part of a local area network scheme, with minimal local processing of the sensor data by the microprocessor 2302 with the serial link 2302a in the sensor head. Such serial digital protocols include Echelon LON-works, BSR X-10, CEBUS, RS-232, RS-423, Apple ADB, Appletalk, Ethernet (10 base T, 10 Base 2, 10 base 5, 100 base VG), asynchronous transfer mode (ATM), etc. This system allows the central control 2303 to incorporate the desired processing, e.g., by the pattern recognition system 2304, etc., while minimizing the installation expense. A simple microprocessor device 2302 in the sensor head interfaces the sensing elements, and may provide analog-to-digital conversion, or other conversion which may be necessary, of the sensor signal. In the case of a serial digital data transmission, the local microprocessor formats the sensor data, including a code indicating the sensor serial number and type, the sensor status (i.e., operative, defective, in need of maintenance or calibration, etc.), the sensor data, and an error correcting code. In the case that the data is transmitted on a local area network, the microprocessor also arbitrates for bus usage and the messaging protocol.

The control, it must be understood, has a number of available operative systems at its disposal, comprising the plant 2306. In this case, the system is a forced air heating and cooling system. This system has a heating unit, a humidifier, blowers, a cooling unit (which also dehumidifies), ducts, dampers, and possible control over various elements, such as automated door openers.

As described above, the system is installed with a complete array of sensors, some of which may be shared with, or a part of, other control systems in the environment, and begins operation with a basic acceptable initial control protocol. The system then receives data from the sensors, and correlates data from the various sensors, including the event sensors, with the operation of the systems being controlled. In such a case, a "door open" event may be correlated with a change in other measured variables. The system then correlates the control status with the effect on the interrelation of the measured variables. Thus, the system would detect that if the blower is operating while the door is open, then there is a high correlation that air will flow out of the door, unless a blower operates to recirculate air from a return near the door. Thus, the system will learn to operate the proximate return device while the door is open and the blower is on. Once this correlation is defined, the system may further interrelate the variables, such as a wind speed and direction outside the door, effects of other events such as other open doors, the absolute and relative speeds of the blowers and the return device, the effect of various damper devices, etc. It is further noted that, under some circumstances, an exchange of air through an open door is desired, and in such instance, the system may operate to facilitate the flow through such an open door. Finally, the system must be able to "learn" that conditions may exist which produce similar sensor patterns which should be handled differently. An example is a broken, defective or inoperative sensor. In such a case, the system must be able to distinguish the type of condition, and not execute an aggressive control algorithm in an attempt to compensate for an erroneous reading or otherwise normal event. This requires the intelligent control of the present invention. In order to distinguish various events, sensors which provide overlapping or redundant information, as well as providing a full contextual overview, should be provided as a part of the system.

It is further noted that energy efficiency is a critical issue in climate control systems, and an absolute and continuous control over the internal environment may be very inefficient. Thus, the starting of large electrical motors may cause a large power draw, and simultaneous starting of such equipment may increase the peak power draw of a facility, causing a possible increase in the utility rates. Further, some facilities may operate on emergency or private power generation (co-generation) which may have different characteristics and efficiency criteria. These factors may all be considered in the intelligent control. It is also noted that a higher efficiency may also be achieved, in certain circumstances, by employing auxiliary elements of the climate control system which have a lower capacity and lower operating costs than the main elements. Thus, for example, if one side of a building is heated by the sun, it may be more efficient to employ an auxiliary device which suitably affects, i.e. compensates, only a part of the building. If such equipment is installed, the aggregate efficiency of the system may be improved, even if the individual efficiency of an element is lower. Likewise, it may be preferable to run a 2½ ton air conditioning unit continuously, rather than a 5 ton air conditioning unit intermittently. The present intelligent control allows a fine degree of control, making use of all available control elements, in an adaptive and intelligent manner.

Returning to the situation of a door opening event, the system would take appropriate action, including: interruption of normal climate control until after the disturbance has subsided and normal conditions are achieved; based on the actual climatic conditions or predicted climatic conditions begin a climate compensation control, designed to maximize efficiency and also maintain climatic conditions during the disturbance, as well as return to normal after the disturbance; optionally, during the door opening disturbance, the system would control a pressure or flow of air to counterbalance a flow through the door, by using a fan, blower or other device, or halting such a device, if necessary. It is also noted that the climatic control system could also be outfitted with actuators for opening and closing doors and windows, or an interface with such other system, so that it could take direct action to correct the disturbance, e.g., by closing the door. The climate between the internal and external ambients may differ in temperature, humidity, pollutants, or the like, and appropriate sensors may be employed.

It is thus realized that the concepts of using all available resources to control an event, as well as using a predictive algorithm in order to determine a best course of action and a desired correction are a part of the present invention.

EXAMPLE 19

Remote Control Hardware

A remote control of the present invention may be constructed from, for example, a Micromint (Vernon, Conn.) RTC-LCD, RTC-V25 or RTC-HC11 or RTC180 or RTC31/52, and RTC-SIR, in conjunction with an infrared transmitter and receiver, input keys and a compatible trackball, which may provide raw encoder signals, or may employ a serial encoder and have a serial interface to the processor module. A power supply, such as a battery, is used. The use, interfacing and programming of such devices is known to those skilled in the art, and such information is generally available from the manufacturer of the boards and the individual circuit elements of the boards. The function of such a remote control is to receive inputs from the trackball and keys and to transmit an infrared signal to the controller.

The processor and display, if present, may provide added functionality by providing a local screen, which would be useful for programming feedback and remote control status, as well as compressing the data stream from the trackball into a more efficient form. In this case, certain of the extracted information may be relevant to the determination of the user level, so that information related to the user level would be analyzed and transmitted separately to the controller by the infrared transmitter. If the local LCD screen is used in the programming process, then the main controller would transmit relevant information to the remote display, by a reverse-channel infrared link. These components are known in the art, and many other types may also be used in known manner.

In known manner, available personal digital assistants ("PDAs"), available from Apple ("Newton" model 100, 110, 120), Tandy, Poquet, Sharp, Casio, AT&T (Eo 440), Hewlett-Packard, etc. may also be employed as a human interface device.

EXAMPLE 20

Medical Device Interface

The interface and intelligent control of the present invention are applicable to control applications in medicine or surgery. This system may also be described with reference to the generic system drawings of FIGS. 23 and 24. In this case, an operator identifies himself and enters information regarding the patient, through the interface 2305. The interface 2305 automatically loads the profile 2406 of both the operator and the patient, if the device is used for more than one at a time, and is connected to a database containing such information, such as a hospital central records bureau. The interface may be connected to various sensors, of the input device 2401, such as ambient conditions (temperature, humidity, etc.), as well as data from the patient, such as electrocardiogram (EKG or ECG), electromyograph (EMG), electroencephalogram (EEG), Evoked Potentials, respirator, anesthesia, temperature, catheter status, arterial blood gas monitor, transcutaneous blood gas monitor, urinary output, IV solutions, pharmaceutical and chemotherapy administration data, mental status, movement, pacemaker, etc. as well as sensors and data sources separate from the patient such as lab results, radiology and medical scanner data, radiotherapy data and renal status, etc. Based on the available information, the interface 2405, using the simple input device and the display screen described above, presents the most important information to the operator, along with a most probable course of action. The user then may either review more parameters, investigate further treatment options, input new data, or accept the presented option(s). The system described has a large memory in the signal analysis module 2409 for recording available patient data from the signal receiver 2408, and thus assists in medical record keeping and data analysis, as well as diagnosis. While various systems are available for assisting in both controlling medical devices and for applying artificial intelligence to assist in diagnosis, the present system allows for individualization based on both the service provider and the patient. Further, the present invention provides the improved interface for interaction with the system.

It is further noted that, analogously to the library function discussed above, medical events may be characterized in the characterization unit 2407 and recorded by the plant 2404, so that a recording of the data need not be reviewed in its entirety in order to locate a particular significant event, and the nature of this event need not be determined in advance. It is also noted that the compression feature of the recorder of the present invention could be advantageously employed with the large volume of medical data that is often generated. Medical data image data may be compressed as known in the art, by standard image compression techniques, and/or image compression techniques optimized for radiology, nuclear medicine and ultrasonography data. Other types of data may be compressed using lossless algorithms, or by various vector quantization, linear excited models, or fractal compression methods. It is finally noted that, because of its ability to store and correlate various types of medical data in the characterization unit 2407, the system could be used by the operator to create notes and discharge summaries for patients, using the database stored in the local database 2413, as well as the user history and preferences 2406. Thus, in addition to saving time and effort during the use of the device, it would also perform an additional function, that of synthesizing the data, based on medical significance.

In addition to providing the aforementioned intelligence and ease of use, the present example also comprises a control 2402, and may interface with any of the sensors and devices, performing standard control and alarm functions. However, because the present control 2402 is intelligent and has pattern recognition capability, in addition to full data integration from all available data sources, it may execute advanced control functions. For example, if the present control 2402 is interfaced to a controlled infusion pump for, e.g., morphine solution, in e.g., a terminally ill patient, then certain parameters must be maintained, while others may be flexible. For example, a maximum flow rate is established as a matter of practice as a safety measure; too high a flow rate could result in patient death. However, a patient may not need a continuous infusion of a constant dose of narcotic. Further, as the patient's status changes, the level of infusion may be advantageously altered. In particular, if the renal status of the patient were to change, the excretion of the drug may be impaired. Therefore, by providing the controller with a urinary output monitor, it could immediately suppress the morphine infusion as soon as the renal output is recognized as being decreased, and further indicate an alarm condition. Further, it may be advantageous to provide a diurnal variation in the infusion rate, to provide a "sleep" period and a period of heightened consciousness with correspondingly lower levels of narcosis. Where various tests, procedures or interviews are scheduled, an appropriate level of narcosis and/or analgesia may also be anticipatorily provided at an appropriate time.

As another example of the use of the present device as a medical controller, the control 2402 could be interfaced with a cardiac catheter monitor, as a part of the signal receiver 2408. In such a case, normally, alarms are set based on outer ranges of each sensor measurement, and possibly a simple formula relating two sensor measurements, to provide a useful clinical index. However, by incorporating the advanced interface and pattern recognition function of the present invention, as well as its ability to interface with a variety of unrelated sensors, the present device, including the present control, may be more easily programmed to execute control and alarm functions, may provide a centralized source of patient information, including storage and retrieval, if diverse sources of such information are linked, and may execute advanced, adaptive control functions. The present control 2402 is equipped to recognize trends in the sensor data from the signal receiver 2408, which would allow earlier recognition and correction of various abnormal conditions, as well as recognizing improvements m conditions, which could allow a reduction in the treatment necessary. Further, by allowing a fine degree of control, parameters may be maintained within optimal limits for a greater percentage of the time. In addition, by monitoring various sensors, various false alarms may be avoided or reduced. In particular, false alarms may occur in prior art devices even when sensors do not indicate a dangerous condition, merely as a safety precaution when a particular parameter is out of a specified range. In such a case, if a cause of such abnormal condition may be identified, such as patient movement or the normal activities of the patient's caretakers, then such condition may be safely ignored, without indicating an alarm. Further, even if a sensor parameter does in and of itself indicate a dangerous condition, if a cause, other than a health risk, may be identified, then the alarm may be ignored, or at least signalled with a different level of priority. By providing an intelligent and active filter for false alarm events, the system may be designed to have a higher level of sensitivity and specificity to real health risks, and further to provide a finer level of control based on the sensor readings, with fewer false positive readings.

EXAMPLE 21

Securities Trading Terminal Interface

The present invention is also of use in automated securities, debt, variable yield and currency trading systems, where many complex functions are available, yet often a particular user under particular circumstances will use a small subset of the functionality available at a given time. Such a situation would benefit from the present interface, which provides adaptive user levels, prioritized screen information presentation, and pattern recognition and intelligent control. A securities trading system is disclosed in U.S. Pat. No. 5,034,916, for a mouse driven Fast Contact Conversational Video System, incorporated herein by reference. The present system relates primarily to the user terminal, wherein the user must rapidly respond to external events, in order to be successful. In such a case, the advantages of the application of an interface according to the present invention are obvious, and need not be detailed herein. However, the pattern recognition functions of the present invention may be applied to correspond to the desired actions of the trader, unlike in prior intelligent trading systems, where the terminal is not individually and adaptively responsive to the particular user. Thus, the system exploits the particular strengths of the user, facilitating his actions, including: providing the desired background information and trading histories, in the sequence most preferred by the user; following the various securities to determine when a user would execute a particular transaction, and notifying the user that such a condition exists; monitoring the success of the user's strategy, and providing suggestions for optimization to achieve greater gains, lower risk, or other parameters which may be defined by the user. Such a system, rather than attempting to provide a "level playing field" to all users of like terminals, allows a user to use his own strategy, providing intelligent assistance. By enhancing the interface, a user becomes more productive with fewer errors and faster training.

EXAMPLE 22

Fractal Theory Pattern Recognition

Affine transforms are mathematical manipulations of data in two dimensions, wherein the manipulation comprises a rotation, scaling and a displacement for each of the two coordinates. Schroeder, M., Fractals, Chaos, Power Laws, W.H. Freeman & Co., New York (1991), incorporated herein by reference. Of course, Affine transforms of higher dimensionality may also be employed. In describing an image using Affine transforms, the degree of matching between an image and the mathematical description of that image may be related by a number of iterations, and the fewer the iterations, the less data used to describe the image. Of particular importance in the field of graphics is the speed of "convergence", i.e., that a relatively few iterations are necessary in order to describe an image with sufficient precision to be visually useful. Therefore, the Affine transform mathematical specifications may be far more compact than the raw image data, and these specifications compare favorably to other types of image compression, such discrete cosine transformation (DCT) compression schemes, including JPEG, depending on a number of factors.

Because the Affine transform may be used to produce a compact visual description of an image, amoung other reasons, the present invention applies this transform to a pattern matching system for analyzing image contents.

Pattern recognition, in this case, may proceed on an image basis, to match similar images, or on an object basis, in which portions of images are matched. It is preferred that the pattern matching system be robust, i.e., tolerant of various alterations of an image, artifacts, interference and configurational changes, while specific enough to allow object differentiation.

In the case of video images, therefore, it is preferred that various two-dimensional projections of three-dimensional objects, in various "poses", be classified the same. This therefore requires that, in analyzing a two-dimensional image, the object be extracted from a background image and separated from other objects. Further, degrees of freedom may be determined, such as through analysis of a sequence of frames to reveal relative motion or change of portions of the object with respect to other portions. Finally, the object in the image must be compared to three dimensional models, through various projections.

In the case of two dimensional image analysis, the image should be analyzed according to a robust starting criteria, so that the similarity of images may be determined by comparison of normalized Affine transformation coefficients.

Fractal analysis, the study of self-similarity, and a superset of Affine transformation, allows a compact representation of an image or an object in an image, and due to its encompassing of various spatial relationships of object parts, allows normalized transforms to be compared. In other words, assuming that the object is extracted from a background scene, and various degrees of freedom are identified, an Affine transformation may be applied, which will yield a similar result for an image of the same object in a different "pose", i.e., with different exercise of its degrees of freedom. While in general, Affine transformations are described with respect to two-dimensional images, these may also be applied to three dimensional images. Thus, if a triangular polygon is rotated, scaled and displaced in a two dimensional image, a tetrahedron is rotated, scaled and displaced in a three dimensional system. Further, analogies may also be drawn to the time dimension (although geometric forms which are rotated, scaled and displaced over time are not given trivial names). Because, in a contractive Affine transformation (one in which the scaling factor of successive iterations is less than 1), continued iterations are less significant, objects described with varying level of detail may be compared. Even images which are not normalized may still be compared, because at every level of the transform, slight changes in rotation, scale and displacement are accounted for.

According to the present invention, nonlinear self-similarity may also be used. Further, in objects having more than two dimensions, linear scaling other than rotation, scaling and displacement may be described.

It is noted that many types of optical computers, especially those including holographic elements, employ transformations similar to Affine transformations. Therefore, techniques of the present invention may be implemented using optical computers or hybrid optical-electronic computers.

Thus, according to the present invention, the fractal method employing Affine transforms may be used to recognize images. This method proceeds as follows. A plurality of templates are stored in a memory device, which represent the images to be recognized. These templates may be preprocessed, or processed in parallel with the remainder of the procedure, in a corresponding manner. Image data, which may be high contrast line image, greyscale, or having a full color map, the greyscale being a unidimensional color map, is stored in the data processor, provided for performing the recognition function.

The image is preprocessed to extract various objects from the background, and to separate objects. This preprocessing may be performed in standard manner. The method of U.S. Pat. No. 5,136,659, incorporated herein by reference, may also be used. As a part of this preprocessing, a temporal analysis of the object through a series of image frames, is performed to provide four dimensional data about the object, i.e., the two dimensions from the image, a third image imputed from differing perspective views of the object, and time. Certain objects may be immediately recognized or classified, without further processing. Further, certain objects, without full classification or identification, may be "ignored" or subjected to a lesser level of final processing. During the classification processing, various objects may be selected for different types of processing, for example, people, automobiles, buildings, plants, etc.

After classification, and temporal analysis, an object for further processing is analyzed for degrees of freedom, i.e., joints of a person, moving parts of an object, etc. These degrees of freedom may then be corrected, e.g., the object itself altered, to change the image into a standard format, or the degree of freedom information processed with the object to allow mathematical normalization without actual change of the image.

The information describing the object image is stored. A plurality of addressable domains are generated from the stored image data, each of the domains representing a portion of the image information. As noted above, the entire image need not be represented, and therefore various objects separately analyzed. Further, only those parts of the image or object necessary for the recognition, need be analyzed. While it may be unknown which image components are unnecessary, sometimes this may be determined.

From the stored image data, a plurality of addressable mapped ranges are created, corresponding to different subsets of the stored image data. Creating these addressable mapped ranges, which should be uniquely addressable, also entails the step of executing, for each of the mapped ranges, a corresponding procedure upon the one of the subsets of the stored image data which corresponds to the mapped ranges. Identifiers are then assigned to corresponding ones of the mapped ranges, each of the identifiers specifying, for the corresponding mapped range, a procedure and a address of the corresponding subset of the stored image data.

To ensure comparability, the processing treatment of the template and the image data are analogous. Of course, template data may be stored in preprocessed form, so that the image data need only be processed according to the same rules. The domains are optionally each subjected to a transform, which may be a predetermined rotation, an inversion, a predetermined scaling, and a displacement. Because of the nature of these linear superposable transforms, the earliest iterations will include data about gross morphology, later iterations will include data about configuration, and latest iterations will include data about texture.

In addition, nonlinear alterations, and frequency, Gabor or wavelet transform preprocessing may be applied. A warping or other kind of transform may also be applied. These types of transforms are generally not included in Affine transform analysis, yet judiciously applied, may produce more rapid convergence, greater data storage efficiency, computational advantages or pattern matching advantages.

This transform is used to optimize the procedure, and also to conform the presentation of the image data with the template, or vice versa. Each of the domains need not be transformed the same way, and in fact it is the transform coefficients which are stored to describe the transformed object, so that differences in coefficients relate to differences in objects;

For each of the domains or transformed domains, as may be the case, the one of the mapped ranges which most closely corresponds according to predetermined criteria, is selected. The image is then represented as a set of the identifiers of the selected mapped ranges.

Finally, from the stored templates, a template is selected which most closely corresponds to the set of identifiers representing the image information. This matching process is optimized for the data type, which is a string of iterative transform coefficients, of a contractive transform.

It is preferred that, for each domain, a most closely corresponding one of the mapped ranges be selected. By performing analogous operations on a template and an unrecognized object in an image, a correspondence between the two may be determined. Thus, libraries of template image portions may be provided, with associated transform information, which may increase the computational efficiency of the system.

In selecting the most closely corresponding one of the mapped ranges, for each domain, the mapped range is selected which is the most similar, by a method which is appropriate, and may be, for example, selecting minimum Hausdorff distance from the domain, selecting the highest cross-correlation with the domain, the minimum mean square error with the domain and selecting the highest fuzzy correlation with the domain, based on rules which may be predetermined. Neural network energy minimization may also yield the best fit, and other techniques may also be appropriate.

In particular, the step of selecting the most closely corresponding one of mapped ranges according to the minimum modified Hausdorff distance includes the step of selecting, for each domain, the mapped range with the minimum modified Hausdorff distance calculated as D[db,mrb]+D[1−db,1−mrb], where D is a distance calculated between a pair of sets of data each representative of an image, db is a domain, mrb is a mapped range, 1−db is the inverse of a domain, and 1−mrb is an inverse of a mapped range.

It is important that the selection criteria be tolerant to variations of the type seen in image data, e.g., video, so that like objects have similar transforms. Thus, the selection criteria is not particularly directed to-optimal data compression, although the two criteria may coincide for some types of data.

In the case where the digital image data consists of a plurality of pixels, each having one of a plurality of associated color map values, the method includes a matching of the color map, which as stated above, encompasses a simple grey scale, natural color representation, and other color types. In such a case, the method is modified to optionally transform the color map values of the pixels of each domain by a function including at least one scaling function, for each axis of said color map, each of which may be the same or different, and selected to maximize the correspondence between the domains and ranges to which they are to be matched. For each of the domains, the one of the mapped ranges having color map pixel values is selected which most closely corresponds to the color map pixel values of the domain according to a predetermined criteria, wherein the step of representing the image color map information includes the substep of representing the image color map information as a set of values each including an identifier of the selected mapped range and the scaling functions. The correspondence method may be of any sort and, because of the added degree of complexity, may be a different method than that chosen for non-color images. The method of optimizing the correspondence may be minimizing the Hausdorff distance or other "relatedness" measurement between each domain and the selected range. The recognition method concludes by selecting a most closely corresponding stored template, based on the identifier of the color map mapped range and the scaling functions, which is the recognized image.

Color information may have less relevance to pattern recognition than, for example, edge information, and therefore may be subjected to a lesser degree of analysis. The color information may also be analyzed separately, using a different technique.

EXAMPLE 24

Image Analysis

Alternatively to the object extraction, the image as a whole may be analyzed. In the case of moving images, the aforementioned method is further modified to accommodate time varying images. These images usually vary by small amounts between frames, and this allows a statistical improvement of the recognition function by compensating for a movement vector, as well as any other transformation of the image. This also allows a minimization of the processing necessary because redundant information between successive frames is not subject to the full degree of processing. Of course, if the image is substantially changed, then the statistical processing ceases, and a new recognition function may be begun, "flushing" the system of the old values. The basic method is thus modified by storing delayed image data information, i.e., a subsequent frame of a moving image. This represents an image of a moving object differing in time from the image data in the data processor.

A plurality of addressable further domains are generated from the stored delayed image data, each of the further domains representing a portion of the delayed image information, and corresponding to a domain. Thus, an analogous transform is conducted so that the further domains each are corresponding to a domain. A plurality of addressable mapped ranges corresponding to different subsets of the stored delayed image data are created from the stored delayed image data. The further domain and the domain are optionally matched by subjecting a further domain to a corresponding transform selected from the group consisting of a rotation, an inversion, a scaling, and a displacement, which corresponds to a transform applied to a corresponding domain, and a noncorresponding transform selected from the group consisting of a rotation, an inversion, a scaling, a translation which does not correspond to a transform applied to a corresponding domain. For each of the further domains or transformed further domains, the one of the mapped ranges is selected which most closely corresponds according to predetermined criteria. As stated above, these domains may also be subjected to corresponding and noncorresponding frequency domain processing transforms, Gabor transforms, and wavelet transforms.

A motion vector is then computed between one of the domain and the further domain, or the set of identifiers representing the image information and the set of identifiers representing the delayed image information, and the motion vector is stored. The further domain is compensated with the motion vector and a difference between the compensated further domain and the domain is computed. For each of the delayed domains, the one of the mapped ranges is selected which most closely corresponds according to predetermined criteria. The difference between the compensated further domain and the domain is represented as a set of difference identifiers of the selected mapping ranges and an associated motion vector.

Figure 27:
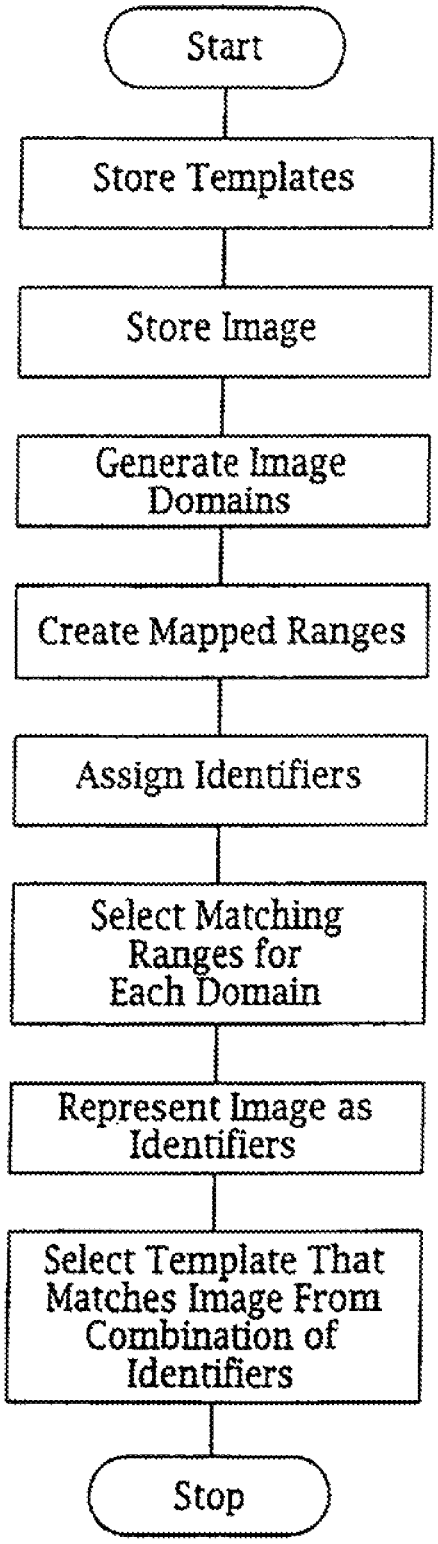
FIGS. 27, 28 and 29 are flow diagrams of an iterated function system method for recognizing a pattern according to the present invention.
Figure 28:
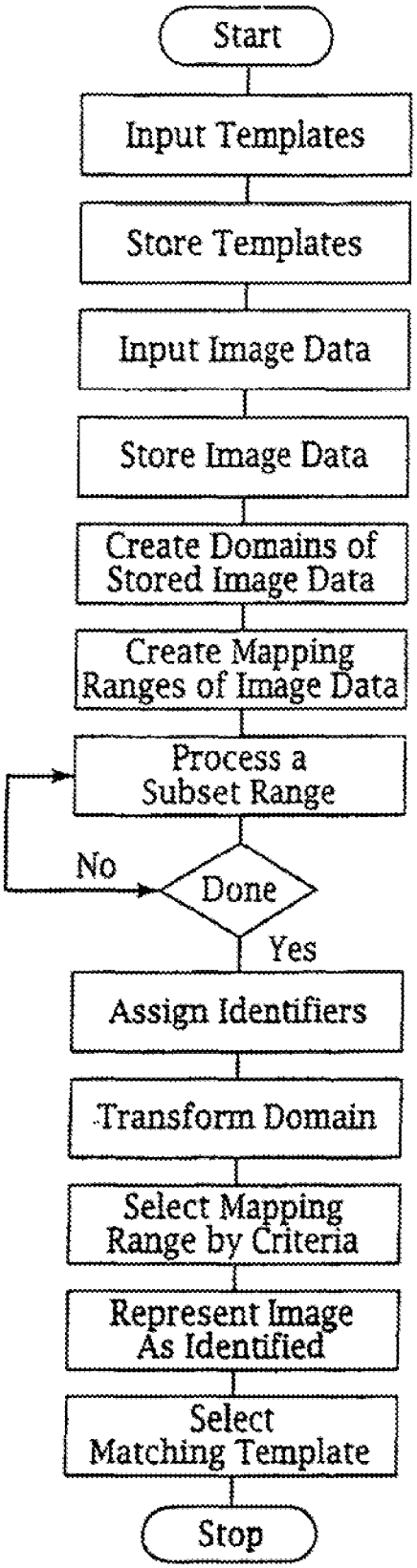
Figure 29:
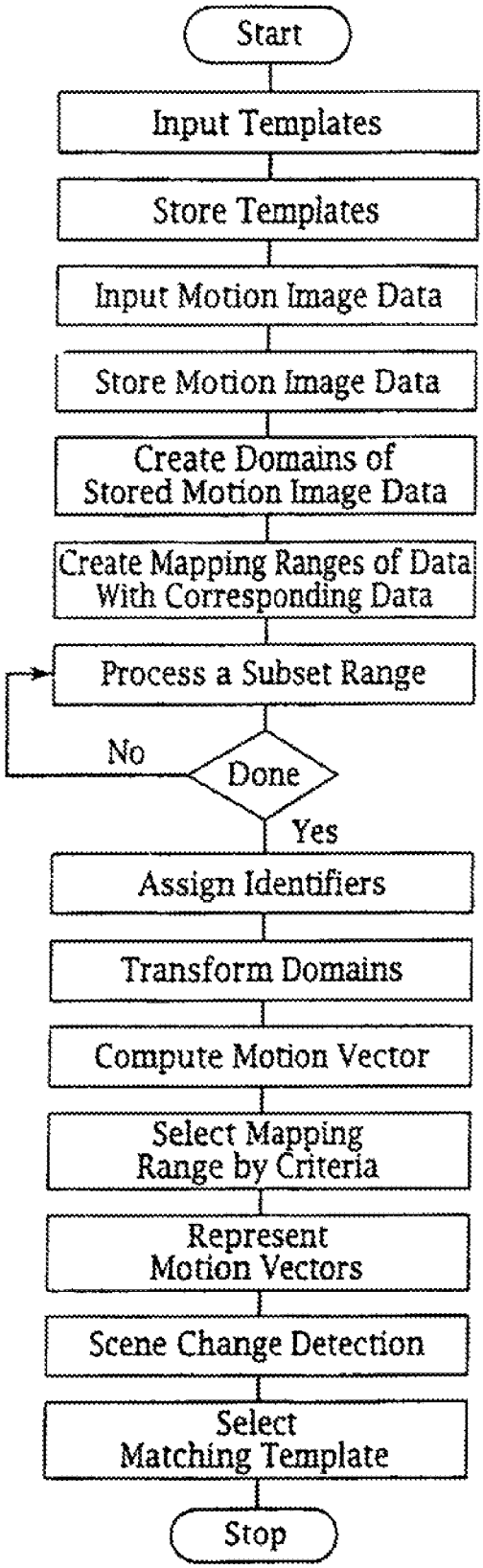

This method is described with respect to FIGS. 27, 28 and 29. FIG. 27 is a basic flow diagram of the recognition system of the present invention. FIG. 28 provides a more detailed description, including substeps, which are included in the major steps shown in FIG. 27. Basically, the image, or a part thereof, is decomposed into a compressed coded version of the scene, by a modified fractal-based compression method. In particular, this differs from the prior compression algorithms in that only a part, preferably that part containing objects of interest, need be fully processed. Thus, if a background is known (identified) or uninteresting, it may be ignored. Further, the emphasis is on matching the available templates to produce an image recognition, not achieving a high degree of compression. Therefore, the image, or domains thereof, may be transformed as required in order to facilitate the matching of the templates. As with respect to single images, the templates are represented in analogous form, having been processed similarly, so that a comparison of the relatedness of an object in an image and the templates may be performed. In particular, if an oblique view of an object is presented, then either the object may be transformed to achieve a predicted front view, or the template transformed or specially selected to correspond to the oblique view. Further, once a recognition has taken place with a high degree of certainty, the system need only ensure that the scene has not changed, and need not continually fully process the data. This has implications where multiple recognition processes are occurring simultaneously, either in a single scene or in different images, wherein the throughput of the recognition apparatus need not meet that required for de novo real time recognition of all aspects of all the objects or images.

In order to limit processing of portions of images, exclusionary criteria may be applied which allow truncation of processing when it is determined that an option is precluded or there exists a significantly higher probability alternative. The processing system may use primarily exclusionary criteria to select the best predictions, or after preselection, employ a highest probability selection system on the remaining choices.

Figure 30:
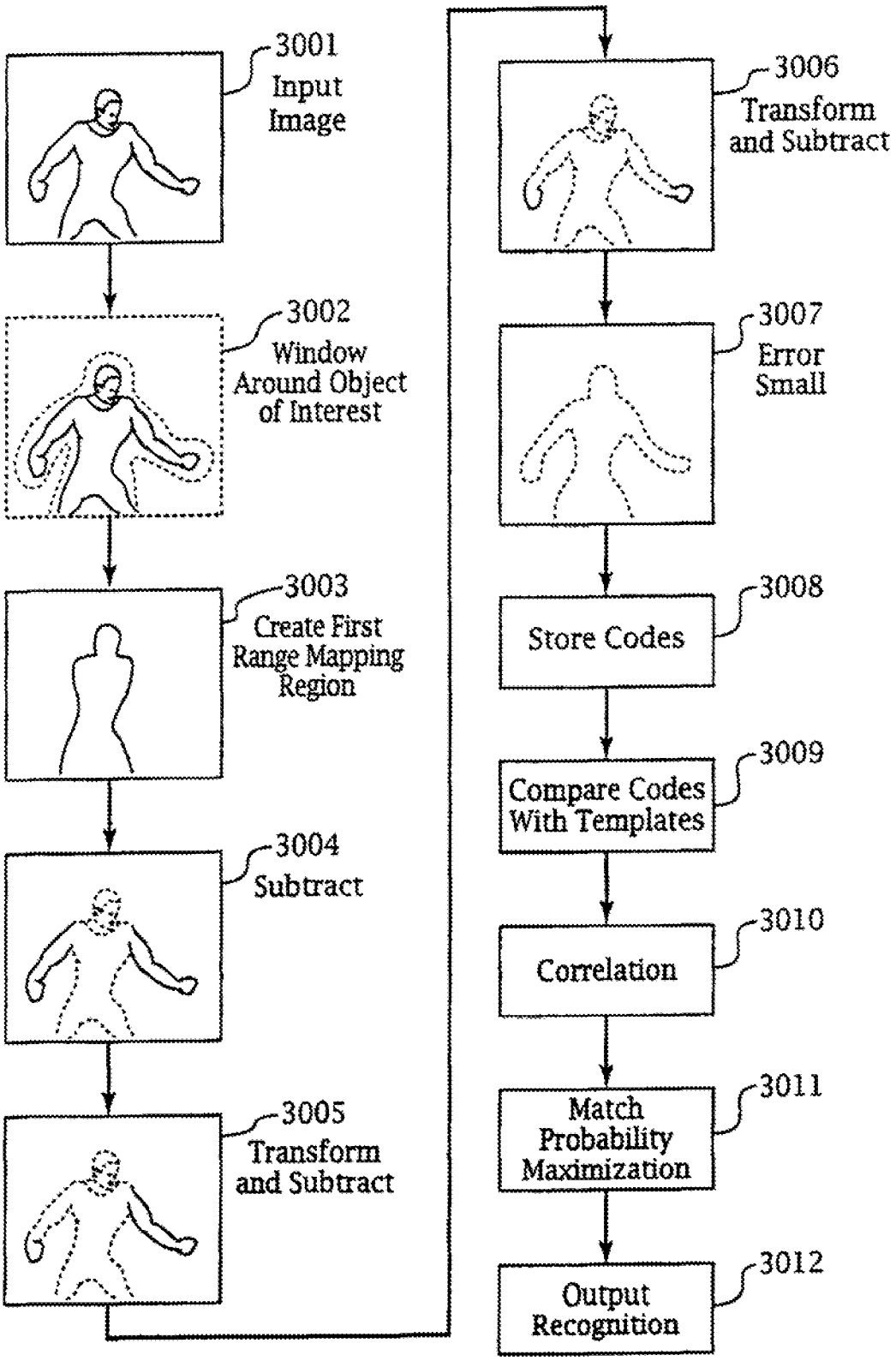
FIG. 30 is a semi-cartoon flow diagram of the object decomposition and recognition method of the present invention.

FIG. 30 shows a flow diagram of a cartoon-like representation of an image recognition method of the present invention. It shows initially, an input image 3001, having a degree of complexity. A windowing function 3002 isolates the object from the background. A first order approximation of the image is generated 3003, here called a mapping region. The first order approximation is then subtracted from the initial image to produce a difference 3004. The first order error is then subjected, iteratively, to successive transform and subtract operations 3005 and 3006, until the error is acceptably small, at which point the input image is characterized by a series of codes, representing the first order approximation and the successive transforms, which are stored 3008. These codes are then compared with stored templates 3009. The comparisons are then analyzed to determine which template produces the highest correlation 3010, and the match probability is maximized 3011. The recognized image is then indicated as an output 3012.

Figure 26:
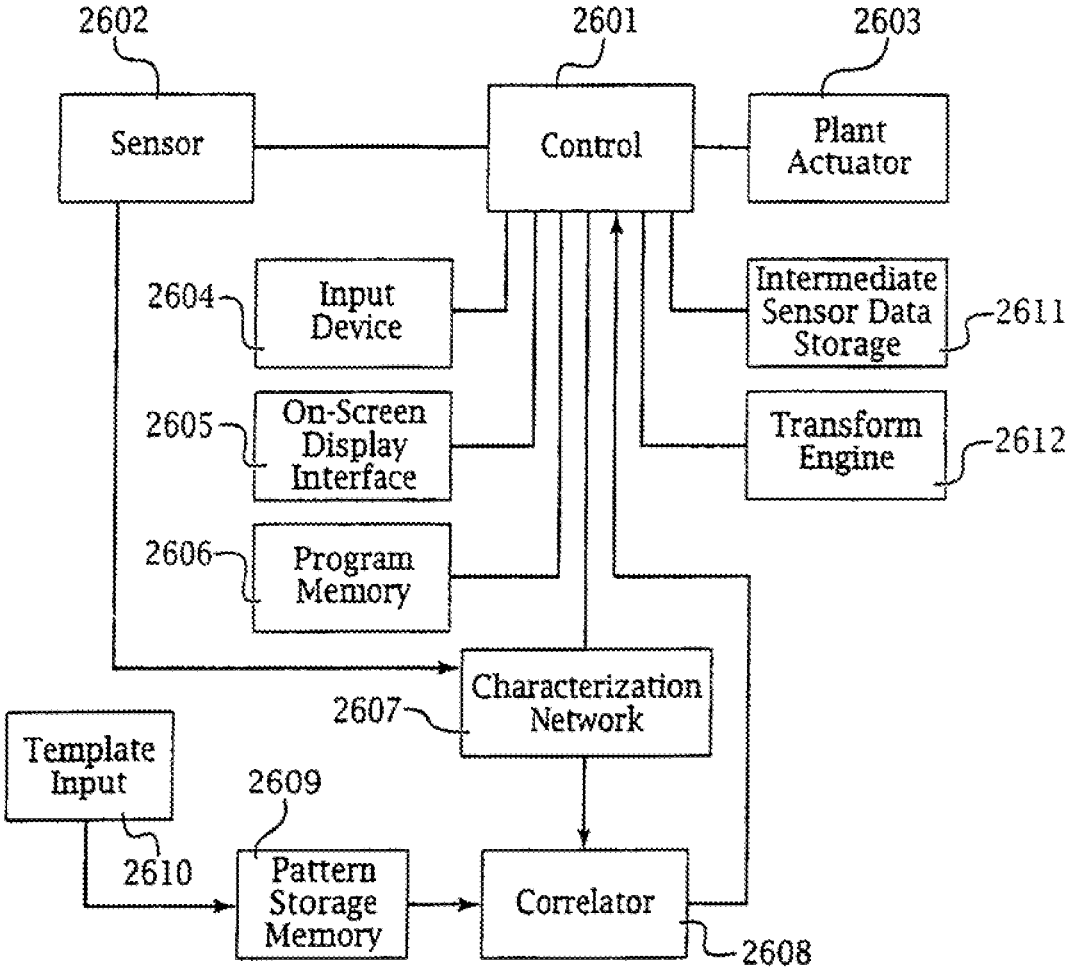
FIG. 26 is a block diagram of a control system for matching a template with a sensor input, of the present invention.

This system is shown in FIG. 26, wherein a sensor 2602 provides data, which may be image data, to a control 2601. The control 2601 serves to control the plant 2603, which has an actuator. The plant 2603 may be a VCR or the like. The control 2601 has associated with it an intermediate sensor data storage unit 2611, which may be, for example a frame buffer or the like. The control 2601 also has associated with it a transform engine 2612, which may perform a reversible or irreversible transform on the data or stored data.

The system also has a template input 2610, which may receive data from the sensor 2602, if accompanied by identifying information. Thus, the pattern storage memory 2609 stores a pattern, such as an image pattern, along with an identifier.

The control 2601 also has an input device 2604, an on-screen display interface 2605, and a program memory 2606, for inputting instructions from a user, providing feedback to the user, and recording the result of the user interaction, respectively. Finally, a characterization network 2607 characterizes the sensor 2602 data, which may be provided directly from the sensor 2602 or preprocessing circuitry, or through the control 2601. A correlator 2608 correlates the output of the characterization network with the stored patterns, representing the templates from the template input 2610. The system therefore operates to recognize sensor patterns, based on the correlator 2608 output to the control 2601.

When analyzing objects in a sequence of images, a determination is made of the complexity of the difference based on a density of representation. In other words, the error between the movement and transform compensated delayed image and the image is quantified, to determine if the compensation is valid, or whether the scene is significantly changed. When the difference has a complexity below a predetermined or adaptive threshold, a template is selected, from the stored templates, which most closely corresponds or correlates with both the set of identifiers of the image data and the set of identifiers of the delayed image data, thus improving recognition accuracy, by allowing a statistical correlation or other technique. The threshold may be set based on an error analysis of the system to determine statistical significance or using other criteria. The threshold may also be adaptively determined based on the history of use of the machine and feedback. For example, if the two images both have a high correlation with one template, while a first of the images has a slightly higher correlation with another template, while the second image has a much lower correlation with that other template, then the system would score the first template as a better match to the first image, based on this differentiation. Thus, templates may be particularly selected to best differentiate similar images of objects.

EXAMPLE 25

Pattern Recognition System

The present system allows for the use of a pattern recognition subsystem for a controller which acts in accordance with a detected pattern. In image, audio and multimedia applications, different types of image processing may take place. First, various processing algorithms may take place in parallel, with an optimum result selected from the results of the various algorithms. Further, various processing schemes may be applied in sequence, with differing sequences applied to different data streams. These processing schemes may be commutative, i.e. yield approximately the same result regardless of the processing order, or may be highly order dependent, in which case a processed data stream must include information relating to the sequence of processing for interpretation.

Various exemplars may reside in a fragment library, for comparison with unidentified data. In the case of processing path dependent systems, an exemplar may be found in multiple forms based on the processing procedure, or in a small subset of corresponding libraries. In general, both lossless compression methods and lossy compression methods employed using high fidelity parameters to minimize loss may be processed to produce a relatively or almost unique result for each unknown data set, while lossy compression or processing methods will be particularly procedure sensitive, especially if differing strategies are employed. These differing strategies may be used to emphasize different features of the unknown data set in order to facilitate comparison. This technique is especially useful when the processing procedures are run in parallel, so that the latency penalty for redundant processing is minimized. Techniques available for this processing include vectorization, fractal processing, iterated function systems, spacial frequency processing (DCT- IPEG, MPEG, etc.), wavelet processing, Gabor transforms, neural nets (static or sequence of images), and other known techniques.

In a preferred embodiment, a spatial frequency or wavelet processing step is performed first, on static image data or a sequence of images, with a fractal domain processing step performed thereafter. This allows high frequency noise to be initially filtered; with subsequent fractal-based correlated noise detection and subtraction, therefore allowing cleanup without loss of high frequency detail. Preferably, before the fractal-based processing, which may be performed by a digital computer or optical processing apparatus, standard edge detection/object separation, e.g., high frequency filtering, contour mapping, artificial intelligence, etc. may be performed. A fractal transform is then performed on the image of a portion thereof, starting in a standardized manner, e.g. at a point of lowest complexity, or the epicenter of the largest feature for beginning a contractive transform. The processed image may then be matched with one or more databases to identify all or a portion of the image. Optionally, after a match has been found and/or confirmed by an operator, using the human interface system, the method is then optimized to minimize the errors and increase the efficiency of later matches. This may be performed by modifying the database record, or related records, as well as modifying the preprocessing algorithm. In a preferred embodiment, the image is processed piecemeal, on an object-by-object basis. Therefore, after an object has been processed, it is extracted from the image so that the remaining information may be processed. Of course, multiple objects may be processed in parallel. The exemplar database is preferably adaptive, so that new objects may be added as they are identified.

The present technology may also be used with a model-based exemplar database, wherein an image object is matched, based on a two dimensional projection, or analysis of a sequence of images, with a multidimensional model of an object. For example, the model may include volume, as well as multiple degrees of freedom of movement. Further, objects may also include "morphing" characteristics, which identify expected changes in an appearance of an object. Other types of characteristics may be included in conjunction with the exemplar in the database.

In a preferred embodiment, a model contained in a database includes a three or more dimensional representation of an object. These models include information processed by a fractal-based method to encode repetitive, transformed patterns in a plane, space, time, etc., as well as to include additional degrees of freedom, to compensate for changes in morphology of the object, to allow continuous object identification and tracking. Thus, once an object is identified, an expected change in that object will not necessitate a reidentification of the object. According to one embodiment, a fractal-like processing is executed by optical elements of an optical or optical hybrid computer. Further, in order to temporarily store an optical image, optically active biological molecules, such as bacteriorhodopsins, etc. may be used. Liquid crystals or other electrophotorefractive active materials may also used. These imagers may be simple two dimensional images, holograms, or other optical storage methods. A preferred holographic storage method is a volume phase hologram, which will transform an impressed image, based on hologram to image correlation. Thus, these models would be somewhat linear transform independent, and would likely show some (planar) transform relationship. Thus, an optical computer may be advantageous because of its high computational speed as compared to digital computers for image analysis, due to inherent parallelism and high inherent speed.

Because of the present limitations in speed of writing an image to optical recording media, especially holographic images, the preferred system includes a plurality of image storage elements, which are operated in parallel. It is noted that absolute accuracy of object identification is not required for "consumer" applications, and therefore partial match results may be considered useful. A plurality of partial results, when taken together, may also increase identification reliability. Critical applications generally differ in quantitative aspects rather than qualitatively, and therefore many aspects of the present invention may be applied to mission critical and other high reliability applications.

A preferred object identification method proceeds by first classifying an object in an image, e.g., "car", "person", "house", etc. Then, based on the classification and object separation, an optimized preprocessing scheme is implemented, based on the classification. This classification preprocessing operates on the raw image data relating only to the object, separated from the background. Then, after the optimized preprocessing, a parallel recognition system would operate to extract unique features and to identify common features to be excluded from the comparison. This step could also identify variable features upon which identification should not be made because the distinctions are useless for the purpose. Thus, the object image at this point loses its relationship to the entire image, and the data reduction might be substantial, providing a compact data representation. The preferred algorithm has a tree structure, wherein the identification need only differentiate a few possibilities, and pass the result to another branch of the tree for further analysis, if necessary. Since the intermediate calculations may help in later computations, these should preferably be retained, in order to avoid duplicative analysis. Further, the order of analysis should be predetermined, even if arbitrary, so that once a useful intermediate calculation is identified, it may be passed in a regular, predictable manner to the next stage processing. Of course, one should not ignore that objects in the entire image may be correlated with one another, i.e. if one object is present, it would increase or decrease the likelihood of another object also being present. Further, temporal correlations should also be noted. Thus, the object identification need not proceed upon each object independently.

Based on time sequences of two-dimensional images, a three dimensional image representation may be constructed. Alternatively, based on various presumptions about extractable "objects" in a single or small group of two dimensional images, a hypothetical three dimensional object may be modelled, which may be later modified to reflect the actual image when an actual view of hidden surfaces is shown. Therefore, by one means or another a three dimensional model is created, having both volume and surface characteristics. Of course, since inner structure may never be seen, the model normally emphasized the surface structure, and is thus a so-called two-and-a-half dimensional surface model. Other non-integral dimension representations may also be useful, and fractal models may efficiently represent the information content of an image model.

When the source signal is an MPEG encoded datastream, it is advantageous to provide an exemplar database which does not require complete expansion of the encoded signal. Thus, the motion vector analysis performed by the MPEG encoder may form a part of the pattern recognition system. Of course, image sequence description formats other than MPEG may be better suited to pattern analysis and recognition tasks. For example, a system may transmit an interframe, by any suitable description method, as well as an object decomposed image in, e.g., fractal transform codes. The transmitted source material, other than interframes, is then transmitted as changes only, e.g. new objects, transforms of existing objects, translations of existing objects, etc.

Color coding may use even more extensive use of fractal compression technology with high compression ratios, because absolute accuracy is not necessary; rather photorealism and texture are paramount, and need not be authentic. Therefore, backgrounds with significant detail, which would require substantial data in a DCT type system, could be simply coded and decoded without loss of significant useful information. Important to the use of this method is to discriminate between background textures and foreground objects, and to encode each separately, optimizing the processing based on the type of object being processed.

EXAMPLE 26

Data Context Sensitive Computer Interface

The present example relates to a context sensitive computer interface in which a characteristic of the interface is modified based on a linguistic or informational content of a data object upon which the interface is operating. For example, a number of alternate feature sets may be made available based on the type of data which is being operated on by the user. For example, differing feature sets would be optimal for each scientific discipline, each type of financial or economic field, marketing, retail, distribution, manufacturing, administration, human resources, etc. Such an interface will make it possible to provide an extended and extensible suite of application modules customized for the user in general, and further adaptive to the particular use to which the user may be making of the apparatus. Thus, complex options particularly suited for the data at hand may be made available without inefficient interface searching, while inappropriate options are not presented. It is noted that this interface is responsive to the data, rather than the programming. Further, the data is analyzed for its meaning, rather than its type.

In a word processing environment, a document or section of a document is analyzed for the presence of particular words or phrases, or for the presence of concepts, interpretable by linguistic concepts. This context-sensitive functionality does not require an explicit definition by the user, but rather will be present even during an incidental occurrence of a recognized context. In accordance with other aspects of the present invention, each context related function may have various user levels, which are selected based on an imputed user level of the user. Thus, the interface program must actually interpret the text or context of the user document in order to select the most likely options for use.

Thus, if a user were to embed a table in a document, the available options would change to table-type options when the "active" portion of the document is at the table, i.e. within the viewable area, etc. Further, and more specifically, if the text and context of the table indicate that this is a financial table, financial options would be initially provided, and standard financial calculation functions immediately made available or performed, in contemplation of their prospective use. Similarly, if the data appears to be scientific, a different set of options would be initially available, and the standard scientific-type calculation functions be made available or performed. If the table relates to chemical or mechanical-type data, chemical or mechanical options might be made available, respectively. Embedded graphics, likewise, would be associated with graphics functions appropriate to the type of graphic. It is noted that, due to the analysis of the content of the document, software having generic functionality may present as special purpose software, based on its actual use.

Thus, in a like manner, the system could determine the "style" of the document and automatically format the data in a predetermined manner to conform with general standards of presentations relating to the desired style. This is similar to style sheets of many programs, but they are self applying, and will, within the same document, be adaptive as the data changes context. Further, since the "styles" would be applied automatically, it would be relatively easy to alter them, requiring only a small amount of manual effort. This is so because the "keys" by which the system determines style could be stored, thus allowing redeterminations to be easily made. This context sensitivity could also assist in spelling and grammar checking, where different rules may apply, depending on the context.

The data object includes information, which might be text, arrays of numbers, arrays of formulas, graphics, or other data types. The system relates parts of the object to each other by "proximity" which could be linear, in the case of a text document, or otherwise, such as in the case of a hypertext document or spreadsheet. Those parts or elements of the object closest to each other, by whatever criteria, are presumed to be topically related, regardless of data type. Thus, if a paragraph of text is proximate to a table for numbers, then the type of numbers presumed to occupy the table would relate to the content of the proximate text. If the text relates to finance, i.e. uses financial-related terms, or series of words that often occur in financial contexts, the table would be presumed to be a financial table.

Once the context of the part of the object is determined, the system then acts based upon this context. The major act is the presentation of tailored menus. This means that if the context is financial, the menus available for use with the numeric table relate to financial tables or spreadsheets. Further, the proximate text would be subject to financial oriented spellcheck and financial oriented grammar or style check. If a graphics-option is selected proximate to the text and table, the menu options would presume a financial graph and present appropriate choices. Of course, the options need not be limited to a few types, and may be hybrid and/or adaptive to the style of the user. However, it is noted that the adaptive menus could be linked to a "corporate style". Thus, communication styles could be dictated by a set of global rules for an organization. Of course, these a priori choices could be overridden.

An advantage of this system is that it allows a software system to include a wide range of functionality which remains "buried", or relatively inaccessible, based on the context of usage. Thus, feature rich software would be considered more usable, and software could be provided in modular fashion. Since the system might allow a user to have potential access to many software modules, the system could also be linked to a license manager and per use billing system for rarely used modules, while allowing these to remain available on, e.g., a CD ROM. Thus, for example, a full integrated package could employ a single, "standard"

interface which would not require task-switching programs, while avoiding presentation of the full range of features to the user at each juncture.

This system provides advantages over traditional systems by providing a non-standardized interface with a variable feature set which attains usability by adapting a subset of the available functionality based on the context of the data.

EXAMPLE 27

Group Aware Adaptive Computer Interface

The adaptive interface according to the present invention may be used in group computing applications. In such a case, the predictive functionality is applied to allow the interface to apply rules from one group member to a project, even when that group member has not contributed personally to a particular aspect. This is thus a type of intelligent agent technology, which, according to the present invention includes the characteristics of abstraction and extrapolation, rather than rule based analysis which would fail based on divergent circumstances. This differs from standard rule-based expert system because the intelligence applied is not necessarily "expert", and may be applied in a relative fashion. Further, extracted user characteristics need not completely define a solution to a problem, and indeed, the use of such a technology in group situations presupposes that a contribution of a number of users is desirable, and therefore that the expertise of any given user is limited.

In order to ensure data integrity after the application or contingent application of user characteristics to a datastream, it is desirable to trace the evolution of data structures. This also allows for assistance in the organization and distribution of workgroup responsibilities. Thus, in a workgroup situation, the goal is not optimization of individual productivity, but rather optimization of the group result, including all levels of review after an initial phase is complete.

Thus, while an individual user may seek various shortcuts to achieve various results, the group would benefit by having available all information relating to the path taken to achieve that result. Further, the desired result may be modified according to the presumed actions of the group, so that the final product is pre-optimized for the group, rather than the individual. Thus, a group member may have his "rules" extracted from his actions, i.e. by neural net backpropagation of errors programming or fuzzy rule definition, to be presented for consideration by another group member. This strategy will allow "better" drafts by considering the predicted input of a member prior to review by that member. A user may further tailor the rules for a given project, and "distilled wisdom" from non-group members may also be employed, as in normal expert (artificial intelligence or AI) systems.

This rule-extraction technology as applied to workgroups is enhanced by the context sensitivity of the software, where the input of each group member may be weighted by considering the context. Again, this technique may be used to increase the efficiency of the primary author of a section of a project, as well as better defining the scope of responsibility of each member, while still respecting the input of other group members.

According to this workgroup rule extraction technology, points of conflict between group members are highlighted for resolution. As an adjunct to this resolution phase of a project, videoconferencing may be employed. Further, where a conflict of a similar type had occurred in the past, data relating to the resolution of that conflict, including recorded videoconference, may be retrieved and presented to one or more members of the workgroup. In this way, such conflicts may be resolved before it becomes adversarial. Thus, each group member may efficiently proceed independently, with only major issues requiring meetings and the like to resolve.

If a workgroup member disagrees with an imputed rule, either explicitly, by review of the rules, or implicitly, by a review of the results, the system will allow a review of all decisions influenced by that faulty rule, as well as a proposed correction. This may be addressed by any member of the group, but usually by the author of the section or the source of the rule will be the relevant reviewing individual. Rules may also be created by the group, rather than from a single individual. Such rules are more often explicitly defined, rather than derived from observation. Such group rules may also be subjected to adaptive forces, especially when overridden frequently.

EXAMPLE 28

Adaptive Interface Vehicular Control System

It is noted that, the adaptive user level interface is of use in uncontrolled environments, such as in a moving vehicle, especially for use by a driver. An intelligent system of the present invention would allow the driver of such a vehicle to execute control sequences, which may compensate for the limited ability to interact with an interface while driving. Thus, the driver need not explicitly control all individual elements, because the driver is assisted by an intelligent interface. Thus, for example, if it begins raining, the interface would predict the windshield wipers should be actuated, the windows and any roof opening closed, and the headlights activated. Thus, the driver could immediately assent to these actions, without individually actuating each control. In such a case, the screen interface, which may be a heads-up display, would provide a small number of choices, which may be simply selected. Further, under such conditions, there would likely be a large amount of mechanical jitter from the input device, which would be filtered to ease menu selection. Further, this jitter would indicate an unstable environment condition, which would cause the interface to present an appropriate display. A voice input may also be used.

EXAMPLE 29

Adaptive Interface Vehicular Control System

An integrated electronics system for an automobile is provided having control over engine, transmission, traction control, braking, suspension, collision avoidance, climate control, and audio systems. Steering and throttle may also be controlled. Based on driver preference and action patterns, the system may optimize the vehicle systems. For example, the vehicle may anticipate voluntary or road conditions based on implicit inputs of the user, thus readying vehicular systems prior to the actual encounter with certain conditions. Further, a user interface may be simplified, based on probable required functionality, thus limiting required attention by the driver in order to activate a particular control. By providing such an interface, controls normally inaccesible may be made accessible, without increasing mechanical complexity, e.g., functions normally controlled by computer may be accessed through a common user interface, rather than through dedicated manual controls.

The automobile control system may also include collision avoidance systems, which may include imaging sensors and radar or LIDAR ranging and velocity measurement. According to the present invention, a heads-up display or simplified graphic user interface in the dashboard or near the steering wheel presents predicted options to the driver. An auxiliary interface may also make certain options available for passengers.

Figure 31:
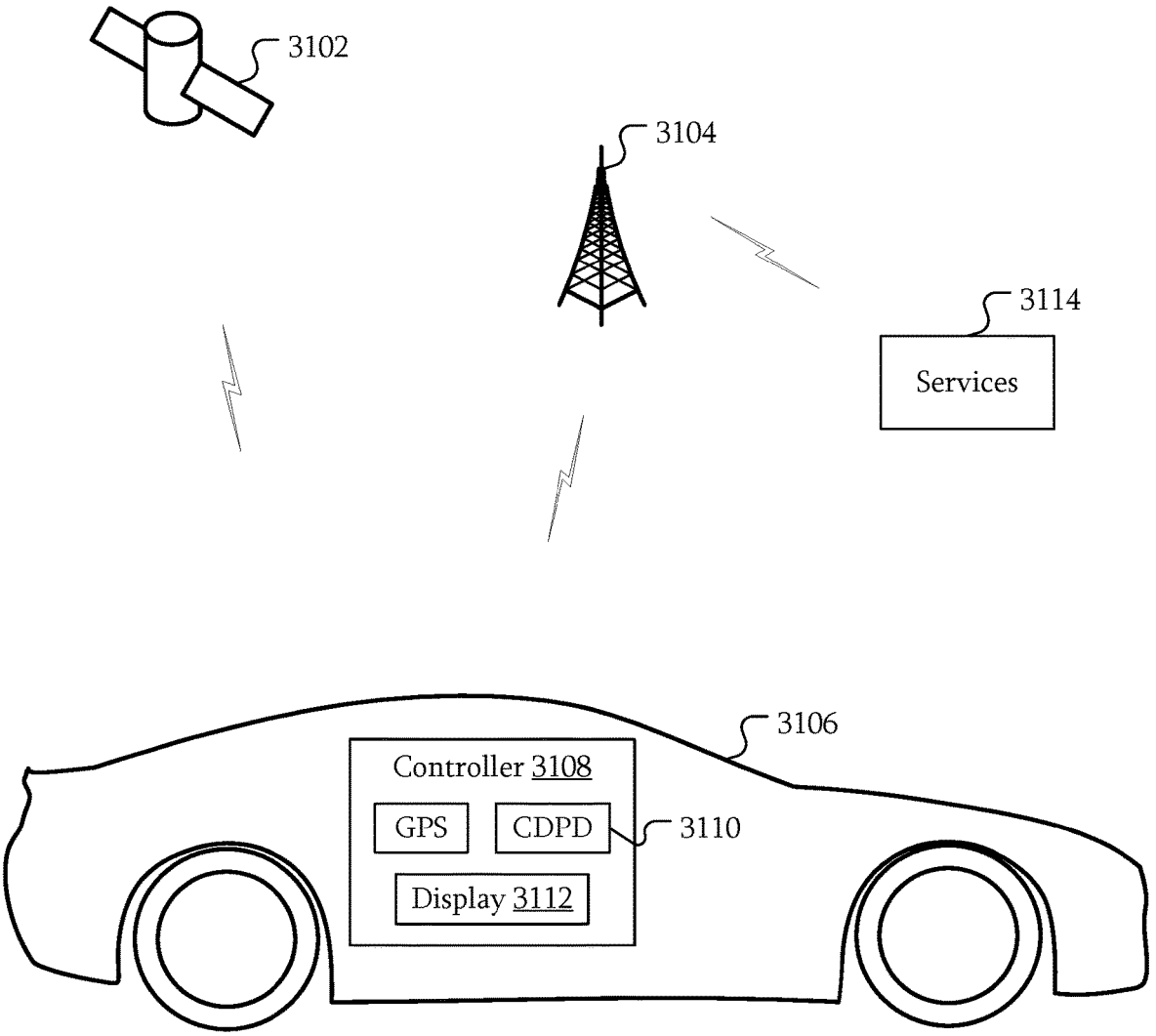
*FIG. 31 is a block diagram of a system according to some embodiments.*

[According] *Referring to FIG. 31, according* to another aspect of the present invention, an automobile positioning system is provided, which may be extraterrestrial, e.g., geographic positioning system (GPS) *3102*, or terrestrial, e.g., cellular base station *3104*, LORAN, etc. Such a system is described in U.S. Pat. No. 5,390,125, incorporated herein by reference; see references cited therein. A controller *3108* in the automobile *3106* is provided with an itinerary for the vehicle travel. Based on position and itinerary, the vehicle *3106* may communicate with various services *3114*, such as food, fuel and lodging providers, to "negotiate" for business. The driver may be provided with customized "billboards", directed to his demographics. Reservations and discounts may all be arranged while en-route. Communication between the automobile *3106* and the services *3114* is preferably provided by cellular data packet device (CDPD) services, which is a cellular based 832 MHz band digital data transmission system. Therefore, an existing cell phone system or CDPD modem system *3110* may be employed for telecommunication. Preferably, a simple display *3112* is provided for presentation of commercial messages to the driver or passenger and for interacting with the service *3114*.

As a matter of practice, the service may be subsidized by the service providers, thus reducing the cost to the consumer. The extent of the subsidy may be determined by the amount of data transmitted or by the eventual consummation of the transaction negotiated.

Because of the positioning system, any variance from the itinerary may be transmitted to the service providers, so that reservations may be cancelled, or substitute services provided in a different location or at a different time.

The telecommunication system may also be used as an emergency system, to contact emergency services and/or police in the event of accident or distress. The transponder system may also be part of an antitheft system. The transponder may also be part of a vehicular maintenance and diagnostic system to ensure proper servicing and to help determine the nature of problems. Raw or processed data may be transmitted to a centralized station for full analysis and diagnosis. Because the vehicle need not be at the repair shop for diagnosis, problems may be analyzed earlier and based on extensive, objective sensor data.

It should be understood that the preferred embodiments and examples described herein are for illustrative purposes only and are not to be construed as limiting the scope of the present invention, which is properly delineated only in the appended claims.

REFERENCES INCORPORATED BY REFERENCE

"32-bit Floating-Point DSP Processors", EDN, Nov. 7, 1991, pp. 127-146.

"A New Class of Markov Processes for Image Encoding", School of Mathematics, Georgia Inst. of Technology (1988), pp. 14-32.

"Bar Code Programs VCR", Design News, Feb. 1, 1988, 26.

"C-Cube CL550 JPEG Image Compression Processor", Preliminary Data Book, August 1991, and addendum dated Nov. 20, 1991.

"Construction of Fractal Objects with Iterated Function Systems", Siggraph '85 Proceedings, 19(3):271-278 (1985).

"Data Compression: Pntng by Numbrs", The Economist, May 21, 1988.

"EMC$^2$ Pushes Video Rental By Satellite", Electronic Engineering Times, Dec. 2, 1991, p.1, p. 98.

"Finger Painting", Information Display 12, p. 18, 1981.

"Fractal Modelling of Real World Images, Lecture Notes for Fractals: Introduction, Basics and Perspectives", Siggraph (1987).

"Fractal Geometry-Understanding Chaos"; Georgia Tech Alumni Magazine; p. 16 (Spring 1986).

"Fractal Modelling of Biological Structures", Perspectives in Biological Dynamics and Theoretical Medicine, Koslow, Mandell, Shlesinger, eds., Annals of New York Academy of Sciences, vol. 504, 179-194 (date unknown).

"Fractals Yield High Compression"; Electronic Engineering Times; Sep. 30, 1991; p. 39.

"Fractals-A Geometry of Nature", Georgia Institute of Technology Research Horizons; p. 9 (Spring 1986).

"How to find the best value in VCRs", Consumer Reports, March 1988, 135-141.

"Low-Cost VCRs: More For Less", Consumer Reports, March 1990, 168-172.

"Machine Now Reads, enters Information 25 Times Faster Than Human Keyboard Operators", Information Display 9, p. 18 (1981).

"New Beetle Cursor Director Escapes All Surface Constraints", Information Display 10, p. 12, 1984.

"Nielsen Views VCRs", Television Digest, Jun. 23, 1988, 15.

"Scanner Converts Materials to Electronic Files for PCs", IEEE CG&A, December 1984, p. 76.

"The Highs and Lows of Nielsen Homevideo Index", Marketing & Media Decisions, November 1985, 84-86+.

"The Smart House: Human Factors in Home Automation", Human Factors in Practice, December 1990, 1-36.

"The Quest for 'User Friendly'", U.S. News & World Report, Jun. 13, 1988. 54-56.

"VCR, Camcorder Trends", Television Digest, Vol.. 29, Mar. 20, 1989, 16.

"VCR's: A Look At The Top Of The Line", Consumer Reports, March 1989, 167-170.

"VHS Videocassette Recorders", Consumer Guide, 1990, 17-20.

"Voice Recognition and Speech Processing", Elektor Electronics, September 1985, pp. 56-57.

Abedini, Kamran, and Hadad, George, "Guidelines For Designing Better VCRs", Report No. IME 462, Feb. 4, 1987.

Abedini, Kamran, "An Ergonomically-improved Remote Control Unit Design", Interface '87 Proceedings, 375-380.

Aleksander, I.; "Guide to Pattern Recognition Using Random-Access Memories"; Computers and Digital Techniques; 2(1):2940 (February 1979).

Anderson, F., W. Christiansen, B. Kortegaard; "Real Time, Video Image Centroid Tracker"; Apr. 16-20, 1990.

Anson, L., M. Barnsley; "Graphics Compression Technology"; SunWorld; pp. 43-52 (October 1991).

Appriou, A., "Interet des theories de l'incertain en fusion de donnees", Colloque International sur le Radar Paris, 24-28 avril 1989.

Appriou, A., "Procedure d'aide a la decision multi-informateurs. Applications a la classification multi-capteurs de cibles", Symposium de l'Avionics Panel (AGARD) Turquie, 25-29 avril 1988.

Arrow, K. J., "Social choice and individual valves", John Wiley and Sons Inc. (1963).

Atkinson, Terry, "VCR Programming: Making Life Easier Using Bar Codes".

Baldwin, William, "Just the Bare Facts, Please", Forbes Magazine, Dec. 12, 1988.

Ballard, D. H., and Brown, C. M., Computer Vision, Prentice Hall, Englewood Cliffs, N.J. (1982).

Barnsley et al., "Harnessing Chaos For Images Systhesis", Computer Graphics, 22(4):131-140 (August, 1988).

Barnsley, M. F., Ervin, V., Hardin, D., Lancaster, J., "Solution of an Inverse Problem for Fractals and Other Sets", Proc. Natl. Acad. Sci. U.S.A., 83:1975-1977 (April 1986).

Barnsley, M. F., "Fractals Everywhere", Academic Press, Boston, Mass., 1988,

Barnsley, M. F., and Demko, S., "Iterated Function Systems and The Global Construction of Fractals", Proc. R. Soc. Lond., A399:243-275 (1985).

Barnsley et al., "Hidden Variable Fractal Interpolation Functions", School of Mathematics, Georgia Institute of Technology, Atlanta, Ga. 30332, July, 1986.

Barnsley et al., "A Better Way to Compress Images", Byte Magazine, January 1988, pp. 213-225.

Barnsley et al., "Chaotic Compression", Computer Graphics World, November 1987.

Batchelor, B. G.; "Practical Approach to Pattern Classification"; Plenum Press, London and New York; (1974).

Batchelor, B. G.; "Pattern Recognition, Ideas in Practice"; Plenum Press, London and New York; (1978).

Baxes, Gregory A., "Digital Signal Processing, A Practical Primer", Prentice-Hall, Englewood Cliffs, N.J. (1984).

Bellman, R. E., L. A. Zadeh, "Decision making in a fuzzy environment", Management Science, 17(4) (December 1970).

Bensch, U., "VPV—VIDEOTEXT PROGRAMS VIDEORECORDER", IEEE Transactions on Consumer Electronics, 34(3):788-792 (1988).

Berger, Ivan, "Secrets of the Universals", Video, February 1989, 45-47+.

Beringer, D. B., "A Comparative Evaluation of Calculator Watch Data Entry Technologies: Keyboards to Chalkboards", Applied Ergonomics, December 1985, 275-278.

Bhatnagar, R. K., L. N. Kamal, "Handling uncertain information: a review of numeric and non-numeric methods", Uncertainty in Artificial Intelligence, L. N. Kamal and J. F. Lemmer, Eds. (1986).

Bishop, Edward W., and Guinness, G. Victor Jr., "Human Factors Interaction with Industrial Design", Human Factors, 8(4):279-289 (August 1966).

Blair, D., R. Pollack, "La logique du choix collectif" Pour la Science (1983).

Brown, Edward, "Human Factors Concepts For Management", Proceedings of the Human Factors Society, 1973, 372-375.

Bulkeley, Debra, "The Smartest House in America", Design News, Oct. 19, 1987, 56-61.

Burr, D. J.; "A Neural Network Digit Recognizer"; Proceedings of the 1986 IEEE International Conference of Systems, Man and Cybernetics, Atlanta, Ga.; pp. 1621-1625.

Bursky, D., "Improved DSP ICs Eye New Horizons", Electronic Design, Nov. 11, 1993, pp. 69-82.

Caffery, B.; Fractal Compression Breakthrough for Multimedia Applications"; Inside; Oct. 9, 1991.

Card, Stuart K., "A Method for Calculating Performance times for Users of Interactive Computing Systems", IEEE, 1979, 653-658.

Carlson, Mark A., "Design Goals for an Effective User Interface", Human Interfacing with Instruments, Electro/82 Proceedings, 3/1/1-3/1/4.

Carpenter, G. A., S. Grossberg, "The Art of Adaptive Pattern Recognition by a Self-Organizing Neural Network," IEEE Computer, March 1988, pp. 77-88.

Carroll, Paul B., "High Tech Gear Draws Cries of "Uncle", Wall Street Journal, Apr. 27, 1988, 29.

Casasent, D., et al.;, "General I and Q Data Processing on a Multichannel AO System"; Applied Optics; 25(18):3217-24 (Sep. 15, 1986).

Casasent, D., Photonics Spectra, November 1991, pp. 134-140.

Casasent, D., and Tescher, A., Eds., "Hybrid Image and Signal Processing II", Proc. SPIE Technical Symposium, April 1990, Orlando Fla. 1297 (1990).

Caudill, M.; "Neural Networks Primer-Part III"; AI Expert; June 1988; pp. 53-59.

Chao, J. J., E. Drakopoulos, C. C. Lee, "An evidential reasoning approach to distributed multiple hypothesis detection", Proceedings of the 20th Conference on decision and control, Los Angeles, Calif., December 1987.

Chao, T.-H.; Hegblom, E.; Lau, B.; Stoner, W. W.; Miceli, W. J., "Optoelectronically implemented neural network with a wavelet preprocessor", Proceedings of the SPIE—The International Society for Optical Engineering, 2026:472-82 (1993).

Chen et al.; "Adaptive Coding of Monochrome and Color Images"; November 1977; pp. 1285-1292.

Cheong, C. K.; Aizawa, K.; Saito, T.; Hatori, M., "Adaptive edge detection with fractal dimension", Transactions of the Institute of Electronics, Information and Communication Engineers D-II, J76D-II(11):2459-63 (1993)

Cobb, Nathan, "I don't get it", Boston Sunday Globe Magazine, Mar. 25, 1990, 23-29.

Computer Visions, Graphics, and Image Processing 1987, 37:54-115.

Computers and Biomedical Research 5, 388-410 (1972).

Cooper, L. N.; "A Possible Organization of Animal Memory and Learning"; Nobel 24; (1973); Collective Properties of Physical Systems; pp. 252-264

Crawford et al.; "Adaptive Pattern Recognition Applied To An Expert System For Fault Diagnosis In Telecommunications Equipment"; pp. 10/1-8 (Inspec. Abstract No. 86CO10699, Insepc IEE (London) & IEE Coll. on "Adaptive Filters", Digest No. 76, Oct. 10, 1985)

Danielsson, Erik, et al.; "Computer Architectures for Pictorial Inf. Systems"; IEEE Computer, Noveber., 1981; pp. 53-67.

Davis, Fred, "The Great Look-and-Feel Debate", A+, 5:9-11 (July 1987).

Dehning, Waltraud, Essig Heidrun, and Maass, Susanne, The Adaptation of Virtual Man-Computer Interfaces to User Requirements in Dialogs, Germany, Springer-Verlag, 1981.

Dempster, A. P., "A generalization of Bayesian inference", Journal of the Royal Statistical Society, Vol. 30, Series B (1968).

Dempster, A. P., "Upper and lower probabilities induced by a multivalued mapping", Annals of mathematical Statistics, no. 38 (1967).

Denker; 1984 International Test Conf., October 1984, Philadelphia, Pa.; pp. 558-563.

Derra, Skip, "Researchers Use Fractal Geometry . . . ", Research and Development Magazine, March 1988.

Donovan, J., "Intel/IBM's Audio-Video Kernel", Byte, December, 1991, pp. 177-202.

Dubois, D., N. Prade, "Fuzzy sets and systems-Theory and applications", Academic Press, New York (1980).

Dubois, D.; "Modeles mathernatiques de l'imprecis et de l'incertain en vue d'applications aux techniques d'aide a la decision"; Doctoral Thesis, University of Grenoble (1983).

Dubois, D., N. Prade, "Combination of uncertainty with belief functions: a reexamination", Proceedings 9th International Joint Conference on Artificial Intelligence, Los Angeles (1985):

Dubois, D., N. Prade, "Theorie des possibilites: application a la representation des connaissances en informatique", Masson, Paris (1985).

Duda, R. O., P. E. Hart, M. J. Nilsson, "Subjective Bayesian methods for rule-based inference systems", Technical Note 124-Artificial Intelligence Center-SRI International.

Dunning, B. B.; "Self-Learning Data-Base For Automated Fault Localization"; IEEE; 1979; pp. 155-157.

Ehrenreich, S. L., "Computer Abbreviations—Evidence and Synthesis", Human Factors, 27(2):143-155 (April 1985).

Electronic Engineering Times (EET), Oct. 28, 1991, p. 62.

Elton, J., "An Ergodic Theorem for Iterated Maps", Journal of Ergodic Theory and Dynamical Systems, 7 (1987).

Farrelle, Paul M. and Jain, Anil K.; "Recursive Block Coding-A New Approach to Transform Coding"; IEEE Transactions on Communications, Corn. 34(2) (February 1986).

Fitzpatrick, J. M., J. J. Grefenstette, D. Van Gucht; "Image Registration by Genetic Search"; Conf. Proc., IEEE Southeastcon 1984; pp. 460-464.

Foley, J. D., Wallace, V. L., Chan, P., "The Human Factor of Computer Graphics Interaction Techniques", IEEE CG&A, November 1984, pp. 1348.

Friedman, M. B., "An Eye Gaze Controlled Keyboard", Proceedings of the 2nd International Conference on Rehabilitation Engineering, 1984, 446-447.

Fua, P. V., "Using probability density functions in the framework of evidential reasoning Uncertainty in knowledge based systems", B. Bouchon, R. R. Yager, Eds. Springer Verlag (1987).

Gilfoil, D., and Mauro, C. L., "Integrating Human Factors and Design: Matching Human Factors Methods up to Product Development", C. L. Mauro Assoc., Inc., 1-7.

Gleick, James, "Making a New Science", pp. 215, 239, date unknown.

Gogoussis et al.; Proc. SPIE Intl. Soc. Opt. Eng., November 1984, Cambridge, Mass.; pp. 121-127.

Gonzalez, Rafael C., "Digital Image Processing", Addison-Wesley, Reading, Mass. (1987).

Gould, John D., Boies, Stephen J., Meluson, Antonia, Rasammy, Marwan, and Vosburgh, Ann Marie, "Entry and Selection Methods For Specifying Dates". Human Factors, 32(2):199-214 (April 1989).

Green, Lee, "Thermo Tech: Here's a common sense guide to the new thinking thermostats", Popular Mechanics, October 1985, 155-159.

Grossberg, S., G. Carpenter, "A Massively Parallel Architecture for a Self-Organizing Neural Pattern Recognition Machine," Computer Vision, Graphics, and Image Processing (1987, 37, 54-115), pp. 252-315.

Grudin, Jonathan, "The Case Against User Interface Consistency", MCC Technical Report Number ACA-HI-002-89, January 1989.

Gullichsen, E., E. Chang, "Pattern Classification by Neural Network: An Experiment System for Icon Recognition," ICNN Proceeding on Neural Networks, March 1987, pp. IV-725-32.

Haruki, K. et al.; "Pattern Recognition of Handwritten Phonetic Japanese Alphabet Characters"; International Joint Conference on Neural Networks, Washington, D.C.; January 1990; pp. II515 to II518.

Harvey, Michael G., and Rothe, James T., "VideoCassette Recorders: Their Impact on Viewers and Advertisers", Journal of Advertising, 25:19-29 (December/January 1985).

Hawkins, William J., "Super Remotes", Popular Science, February 1989, 76-77.

Hayashi, Y., et al.; "Alphanumeric Character Recognition Using a Connectionist Model with the Pocket Algorithm"; Proceedings of the International Joint Conference on Neural Networks, Washington, D.C. Jun. 18-22; 1989; vol. 2, pp. 606-613.

Hayes, H. I.; Solka, J. L.; Priebe, C. E.; "Parallel computation of fractal dimension", Proceedings of the SPIE—The International Society for Optical Engineering, 1962: 219-30 (1993).

Henke, Lucy L., and Donohue, Thomas R., "Functional Displacement of Traditional TV Viewing by VCR Owners", Journal of Advertising Research, 29:18-24 (April-May 1989).

Hinton et al.; "Boltzmann Machines: Constraint Satisfaction Networks that Learn"; Tech. Report CMU-CS-85-119; Carnegie-Mellon Univ; 5/84.

Hirzinger, G., Landzettel, K., "Sensory Feedback Structures for Robots with Supervised Learning", IEEE Conf. on Robotics and Automation, St. Louis, March 1985.

Hoare, F.; de Jager, G., "Neural networks for extracting features of objects in images as a pre-processing stage to pattern classification", Proceedings of the 1992 South African Symposium on Communications and Signal Processing. COMSIG '92 (Cat. No.92TH0482-0). Inggs, M. (Ed.), p. 239-42 (1992).

Hoban, Phoebe, "Stacking the Decks", New York, Feb. 16, 1987, 20:14.

Hoffberg, Linda I., "AN IMPROVED HUMAN FACTORED INTERFACE FOR PROGRAMMABLE DEVICES: A CASE STUDY OF THE VCR", Master's Thesis, Tufts University (Master of Sciences in Engineering Design, November).

Hoffberg, Linda I., "Designing User Interface Guidelines For Time-Shift Programming of a Video Cassette Recorder (VCR)", Proc. of the Human Factors Soc. 35th Ann. Mtg. pp. 501-504 (1991).

Hoffberg, Linda I., "Designing a Programmable Interface for a Video Cassette Recorder (VCR) to Meet a User's Needs", Interface 91 pp. 346-351 (1991).

Hopfield et al; "Computing with Neural Circuits: A Model"; Science; vol. 233:625-633 (8 August 1986).

Hopfield; "Neurons with graded response have collective computational properties like those of two-state neurons"; Proc. Natl. Acad. Sci. USA; 81:3088-3092 (May 1984).

Hopfield; "Neural Networks and Physical Systems with Emergent Collective Computational Abilities"; Proc. Natl. Acad. Sci. USA; 79:2554-2558 (April 1982).

Horgan, H., "Medical Electronics", IEEE Spectrum, January 1984, pp. 90-93.

Howard, Bill, "Point and Shoot Devices", PC Magazine, 6:95-97, August 1987.

Hurtgen, B.; Buttgen, P., "Fractal approach to low rate video coding", Proceedings of the SPIE—The International Society for Optical Engineering, 2094(pt. 1):120-31(1993).

Information Processing 71; North-Holland Publishing Company (1972) pp. 1530-1533.

Ishizuka, M., "Inference methods based on extended Dempster and Shafer's theory for problems with uncertainty/fuzziness", New Generation Computing, 1:159-168 (1983), Ohmsha, Ltd., and Springer Verlag.

Jackel, L. D., H. P. Graf, J. S. Denker, D. Henderson and I. Guyon, "An Application of Neural Net Chips: Handwritten Digit Recognition," ICNN Proceeding, 1988, pp. II-107-15.

Jane Pauley Special, NBC TV News Transcript, Jul. 17, 1990, 10:00 PM.

Jean, J. S. N., et al.; "Input Representation and Output Voting Considerations for Handwritten Numeral Recognition with Backpropagation"; International Joint Conference on Neural Networks, Washington, D.C., January 1990; pp. I-408 to I-411.

Jeffrey, R. J., "The logic of decision", The University of Chicago Press, Ltd., London (1983)(2nd Ed.).

Kaufmann, A., "Introduction a la theorie des sousensembles flous", Vol. 1, 2 et 3-Masson-Paris (1975).

Keeney, R. L., B. Raiffa, "Decisions with multiple objectives: Preferences and value tradeoffs", John Wiley and Sons, New York (1976).

Kellman, P., "Time Integrating Optical Signal Processing", Ph. D. Dissertation, Stanford University, 1979, pp. 51-55.

Kim, D. H.; Caulfield, H. J.; Jannson, T.; Kostrzewski, A.; Savant, G, "Optical fractal image processor for noise-embedded targets detection", Proceedings of the SPIE—The International Society for Optical Engineering, Vol: 2026 p. 1449 (1993) (SPIE Conf: Photonics for Processors, Neural Networks, and Memories 12-15 July 1993, San Diego, Calif., USA).

Kim, Y., "Chips Deliver Multimedia", Byte, December 1991, pp. 163-173.

Knowlton, K., "Virtual Pushbuttons as a Means of Person-Machine Interaction", Proc of Conf. Computer Graphics, Pattern Recognition and Data Structure, Beverly Hills, Calif., May 1975, pp. 350-352.

Koch, H., "Ergonomische Betrachtung von Schreibtastaturen", Humane Production, 1, pp. 12-15 (1985).

Kohonen; "Self-Organization & Memory", Second Ed., 1988; Springer-Verlag; pp. 199-209.

Kolson, Ann, "Computer wimps drown in a raging sea of technology", The Hartford Courant, May 24, 1989, B1.

Kortegaard, B. L.; "PAC-MAN, a Precision Alignment Control System for Multiple Laser Beams Self-Adaptive Through the Use of Noise"; Los Alamos National Laboratory; date unknown.

Kortegaard, B. L.; "Superfine Laser Position Control Using Statistically Enhanced Resolution in Real Time"; Los Alamos National Laboratory; SPIE-Los Angeles Technical Symposium; Jan. 23-25, 1985.

Kraiss, K. F., "Alternative Input Devices For Human Computer Interaction", Forschunginstitut Für Anthropotecahnik, Werthhoven, F.R. Germany.

Kraiss, K. F., "Neuere Methoden der Interaktion an der Schnittstelle Mensch-Maschine", Z. F. Arbeitswissenschaft, 2, pp. 65-70, 1978.

Kreifeldt, John, "Human Factors Approach to Medical Instrument Design",. Electro/82 Proceedings, 3/3/1-3/3/6.

Kreifeldt, J. G., "A Methodology For Consumer Product Safety Analysis", The 3rd National Symposium on Human Factors in Industrial Design in Consumer Products, August 1982, 175-184.

Ksienski et al., "Low Frequency Approach to Target Identification", Proc. of the IEEE, 63(12):1651-1660 (December 1975).

Kuocheng, Andy Poing, and Ellingstad, Vernon S., "Touch Tablet and Touch Input", Interface '87, 327.

Kyburg, H. E., "Bayesian and non Bayesian evidential updating", Artificial Intelligence 31:271-293 (1987).

LeCun, Y., et al., "Handwritten Digit Recognition: Applications of Neural...", IEEE Comm. Magazine, pp. 41-46 (November 1989).

LeCun, Y., "Connectionism in Perspective", in R. Pfeifer, Z. Schreter, F. Fogelman, L. Steels, (Eds.), 1989, "Generalization and Network Design Strategies", pp. 143-55.

Ledgard, Henry, Singer, Andrew, and Whiteside, John, Directions in Human Factors for Interactive Systems, New York, Springer-Verlag, 1981.

Lee, Eric, and MacGregor, James, "Minimizing User Search Time Menu Retrieval Systems", Human Factors, 27(2):157-162 (April 1986).

Lendaris, G. G., and Stanely, G. L., "Diffraction Pattern Sampling for Automatic Target Recognition", Proc. IEEE 58:198-205 (1979).

Leon, Carol Boyd, "Selling Through the VCR", American Demographics, December 1987, 40-43.

Liepins, G. E., M. R. Hilliard; "Genetic Algorithms: Foundations & Applications"; Annals of Operations Research, 21:31-58 (1989).

Li, H. Y. et al, Applied Optics (April, 1993).

Lin, H. K., et al.; "Real-Time Screen-Aided Multiple-Image Optical Holographic Matched-Filter Correlator"; Applied Optics; 21(18):3278-3286 (Sep. 15, 1982)

Lippmann, R. P., "An Introduction to Computing with Neural Nets", IEEE ASSP Magazine, 4(2):4-22 (April 1987).

Liu, Y., "Pattern recognition using Hilbert space", Proceedings of the SPIE—The International Society for Optical Engineering, 1825:63-77 (1992).

Liu, Y., "Extensions of fractal theory", Proceedings of the SPIE—The International Society for Optical Engineering, 1966:255-68(1993).

Long, John, "The Effect of Display Format on the Direct Entry of Numerical Information by Pointing", Human Factors, 26(1):3-17 (February 1984).

Lu, C., "Computer Pointing Devices: Living With Mice", High Technology, January 1984, pp. 61-65.

Mahalanobis, A., et al.; "Minimum Average Correlation Energy Filters"; Applied Optics; 26(17):3633-40 (Sep. 1, 1987).

Mandelbrot, B., "The Fractal Geometry of Nature", W.H. Freeman & Co., San Francisco, Calif., 1982, 1977; and Mantei, Marilyn M., and Teorey, Toby J., "Cost/Benefit Analysis for Incorporating Human Factors in the Software Lifecycle", Association for Computing Machinery, 1988.

Maragos, P., "Tutorial Advances in Morphological Image Processing" Optical Engineering 26:7:623-632 (1987).

Martin, G. L. et al.; "Recognizing Hand-Printed Letters and Digits Using Backpropagation Learning"; Technical Report of the MCC, Human Interface Laboratory, Austin, Tex.; January 1990; pp. 1-9.

McAulay, A. D., J. C. Oh; "Image Learning Classifier System Using Genetic Algorithms"; IEEE Proc. of the National Aerospace & Electronics Conference; 2:705-710 (1989).

Meads, Jon A., "Friendly or Frivolous", Datamation, Apr. 1, 1988, 98-100.

Miller, R. K.; Neural Networks ((c) 1989: Fairmont Press; Lilburn, Ga.); pp. 2-12 and Chapter 4, "Implementation of Neural Networks"; pp. 4-1 to 4-26.

Molley, P., "Implementing the Difference-Squared Error Algorithm Using An Acousto-Optic Processor", SPIE, 1098: 232-239,(1989).

Molley, P., et al., "A High Dynamic Range Acousto-Optic Image Correlator for Real-Time Pattern Recognition", SPIE, 938:55-65 (1988).

Moore, T. G. and Dartnall, "Human Factors of a Microelectronic Product: The Central Heating Timer/Programmer", Applied Ergonomics, 13(1): 15-23 (1983).

Mori; "Towards the construction of a large-scale neural network"; Electronics Information Communications Association Bulletin PRU 88-59; pp. 87-94.

Naik et al., "High Performance Speaker Verification . . . ", ICASSP 86, Tokyo, CH22434/86/0000-0881, IEEE 1986, pp. 881-884.

Netravali, Arun N., and Haskell, Barry G., "Digital Pictures Representation and Compression", Plenum Press, New York (1988).

Ney, H., et al.; "A Data Driven Organization of the Dynamic Programming Beam Search for Continuous Speech Recognition"; Proc. ICASSP 87; pp. 833-836; 1987.

Nilsson, N. J.; The Mathematical Foundations of Learning Machines ((c) 1990: Morgan Kaufmann Publishers, San Mateo, Calif.) and particularly section 2.6 "The Threshold Logic Unit (TLU)", pp. 21-23 and Chapter 6, "Layered Machines" pp. 95-114.

Norman, Donald A., "Infuriating By Design", Psychology Today, 22(3):52-56 (March 1988).

Norman, Donald A., The Psychology of Everyday Things, New York: Basic Book, Inc. 1988.

Norman, D. A., Fisher, D., "Why Alphabetic Keyboards Are Not Easy To Use: Keyboard Layout Doesn't Much Matter", Human Factors 24(5), pp. 509-519 (1982).

O'Neal et al.; "Coding Isotropic Images"; November 1977; pp. 697-707.

Ohsuga et al, "Entrainment of Two Coupled van der Pol Oscillators by an External Oscillation", Biological Cybernetics, 51:225-239 (1985).

Omata et al, "Holonic Model of Motion Perception", IEICE Technical Reports, 3/26/88, pp. 339-346.

Optical Engineering 28:5 (May 1988)(Special Issue on product inspection).

Pawlicki, T. F., D. S. Lee, J. J. Hull and S. N. Srihari, "Neural Network Models and their Application to Handwritten Digit Recognition," ICNN Proceeding, 1988, pp. II-63-70.

Perry et al.; "Auto-Indexing Storage Device"; IBM Tech. Disc. Bulletin, 12(8):1219 (January 1970).

Perspectives: High Technology 2, 1985.

Peterson, Ivars, "Packing It In-Fractals . . . ", Science News, 131(18):283-285 (May 2, 1987).

Platte, Hans-Joachim, Obrkatzas, Gunter, and Voessing, Walter, "A New Intelligent Remote Control Unit for Consumer Electronic Device", IEEE Transactions on Consumer Electronics, Vol. CE-31(1):59-68 (February 1985).

Press, William H. et al, "Numerical Recipes in C The Art of Scientific Computing", Cambridge University Press, 1988.

Priebe, C. E.; Solka, J. L.; Rogers, G. W., "Discriminant analysis in aerial images using fractal based features", Proceedings of the SPIE—The International Society for Optical Engineering, 1962: 196-208(1993).

Proakis, John G., Digital Communications, McGraw-Hill (1983)

Proceedings, 6th International Conference on Pattern Recognition 1982, pp. 152-136.

Psaltis, D., "Two-Dimensional Optical Processing Using One-Dimensional Input Devices", Proceedings of the IEEE, 72(7):962-974 (July 1984).

Psaltis, D., "Incoherent Electro-Optic Image Correlator", Optical Engineering, 23(1):12-15 (January/February 1984).

Rahrnati, M.; Hassebrook, L. G., "Intensity- and distortion-invariant pattern recognition with complex linear morphology", Pattern Recognition, 27 (4):549-68(1994).

Ravichandran, G. and Casasent, D., "Noise and Discrimination Performance of the MINACE Optical Correlation Filter", Proc. SPIE Technical Symposium, April 1990, Orlando Fla., 1471 (1990).

Reusens, E., "Sequence coding based on the fractal theory of iterated transformations systems", Proceedings of the SPIE—The International Society for Optical Engineering, 2094(pt. 1): 132-40(1993).

Rhodes, W., "Acousto-Optic Signal Processing: Convolution and Correlation", Proc. of the IEEE, 69(1):65-79 (January 1981).

Richards J., and Casasent, D., "Real Time Hough Transform for Industrial Inspection" Proc. SPIE Technical Symposium, Boston 1989 1192:2-21 (1989).

Rogus, John G. and Armstrong, Richard, "Use of Human Engineering Standards in Design", Human Factors, 19(1): 15-23 (February 1977).

Rosch, Winn L., "Voice Recognition: Understanding the Master's Voice", PC Magazine, Oct. 27, 1987, 261-308.

Rosenfeld, Azriel and Avinash C. Kak; Digital Picture Processing, Second Edition, Volume 2, Academic Press, 1982.

Roy, B., "Classements et choix en presence de points de vue multiples", R.I.R.O.-2eme annee-no. 8; pp. 57-75 (1968).

Roy, B., "Electre m: un algorithme de classements fonde sur une representation floue des preferences en presence de criteres multiples" Cahiers du CERO, 20(1):3-24 (1978).

Rumelhart, D. E., et al.; Parallel Distributed Processing, ((c) 1986: MIT Press, Cambridge, Mass.), and specifically Chapter 8 thereof, "Learning Internal Representations by Error Propagation"; pp. 318-362.

Rumelhart, D. E., et al.; "Learning Internal Representations by Error Propagation"; Parallel Distr. Proc.: Explorations in Microstructure of Cognition, 1:318-362 (1986).

Rutherford, H. G., F. Taub and B. Williams; "Object Identification and Measurement from Images with Access to the Database to Select Specific Subpopulations of Special Interest"; May 1986.

Rutter et al.; "The Timed Lattice-A New Approach To Fast Converging Equalizer Design"; pp.VIII/11-5 (Inspec. Abstract No. 84C044315, Inspec IEE (London) & IEE Saraga Colloquium on Electronic Filters, May 21, 1984)

Sadjadi, F., "Experiments in the use of fractal in computer pattern recognition", Proceedings of the SPIE—The International Society for Optical Engineering, 1960:214-22 (1993).

Sakoe, H.; "A Generalization of Dynamic Programming Based Pattern Matching Algorithm Stack DP-Matching"; Transactions of the Committee on Speech Research; The Acoustic Society of Japan; p. S83-23; 1983.

Sakoe, H.; "A Generalized Two-Level DP-Matching Algorithm for Continuous Speech Recognition"; Transactions of the IECE of Japan; E65(11):649-656 (November 1982).

Sarver, Carleton, "A Perfect Friendship", High Fidelity, 39:42-49 (May 1989).

Scharlic, A., "Decider sur plusieurs criteres. Panorama de l'aide a la decision multicritere" Presses Polytechniques Romandes (1985).

Schmitt, Lee, "Let's Discuss Programmable Controllers", Modern Machine Shop, May 1987, 90-99.

Schniederman, Ben, Designing the User Interface: Strategies for Effective Human-Computer Interaction, Reading, MA, Addison-Wesley, 1987.

Schurmann, J.; "Zur Zeichen und Worterkennung beim Automatischen Anschriftenlesen"; Wissenschaftlichl, Berichte, 52(1/2) (1979).

Scientific American; "Not Just a Pretty Face"; March 1990, pp. 77-78.

Shafer, G., "A mathematical theory of evidence", Princeton University Press, Princeton, N.J. (1976).

Shimizu et al, "Principle of Holonic Computer and Holovision", Journal of the Institute of Electronics, Information and Communication, 70(9):921-930 (1987).

Shinan et al., "The Effects of Voice Disguise . . . ", ICASSP 86, Tokyo, CH2243-186/0000-0885, IEEE 1986, pp. 885-888.

Silverston et al.; "Spectral Feature Classification and Spatial Pattern Rec."; SPIE 201:17-26, Optical Pattern Recognition (1979).

Simpson, W. R., C. S. Dowling; "WRAPLE: The Weighted Repair Assistance Program Learning Extension"; IEEE Design & Test, 2:66-73 (April 1986).

Smith, Sidney J., and Mosier, Jane N., Guidelines for Designing User Interface Software, Bedford, Mass.; MITRE, 1986.

Specht; IEEE Internatl. Conf. Neural Networks, 1:1525-1532 (July 1988); San Diego, Calif.

Sperling, Barbara Bied, Tullis Thomas S., "Are You a Better 'Mouser' or 'Trackballer'? A Comparison of Cursor—Positioning Performance", An Interactive/Poster Session at the CHI+GI'87 Graphics Interface and Human Factors in Computing Systems Conference.

Spragеu, R. A.; "A Review of Acousto-Optic Signal Correlators"; Optical Engineering; 16(5):467-74 (September/October 1977)

Sprinzak, J.; Werman, M., "Affine point matching", Pattern Recognition Letters, 15(4):337-9(1994).

Stanley R. Sternberg; "Biomedical Image Processing"; IEEE Computer; 1983; pp. 22-34.

Stewart, R. M.; "Expert Systems For Mechanical Fault Diagnosis"; IEEE; 1985; pp. 295-300.

Streeter, L. A., Ackroff, J. M., and Taylor, G. A. "On Abbreviating Command Names", The Bell System Technical Journal, 62(6):1807-1826 (July/August 1983).

Sugeno, M., "Theory of fuzzy integrals and its applications", Tokyo Institute of Technology (1974).

Svetkoff et al.; Hybrid Circuits (GB), No. 13, May 1987; pp. 5-8.

Swanson, David, and Klopfenstein, Bruce, "How to Forecast VCR Penetration", American Demographic, December 1987, 44-45.

Tello, Ernest R., "Between Man And Machine", Byte, September 1988, 288-293.

Thomas, John, C., and Schneider, Michael L., Human Factors in Computer Systems, New Jersey, Ablex Publ. Co., 1984.

Trachtenberg, Jeffrey A., "How do we confuse thee? Let us count the ways", Forbes, Mar. 21, 1988, 159-160.

Tyldesley, D. A., "Employing Usability Engineering in the Development of Office Products", The Computer Journal", 31(5):431-436 (1988).

Udagawa, K., et al; "A Parallel Two-Stage Decision Method for Statistical Character Recognition . . . "; Electronics and Communications in Japan (1965).

Vander Lugt, A., "Signal Detection By Complex Spatial Filtering", IEEE Transactions On Information Theory, IT-10, 2:139-145 (April 1964).

Vander Lugt, A., et al.; "The Use of Film Nonlinearites in Optical Spatial Filtering"; Applied Optics; 9(1):215-222 (January 1970).

Vander Lugt, A.; "Practical Considerations for the Use of Spatial Carrier-Frequency Filters"; Applied Optics; 5(11): 1760-1765 (November 1966).

Vannicola et al, "Applications of Knowledge based Systems to Surveillance", Proceedings of the 1988 IEEE National Radar Conference, 20-21 April 1988, pp. 157-164.

Verplank, William L., "Graphics in Human-Computer Communication: Principles of Graphical User-Interface Design", Xerox Office Systems.

Vitols; "Hologram Memory for Storing Digital Data"; IBM Tech. Disc. Bulletin 8(11):1581-1583 (April 1966).

Voyt, Carlton F., "PLC's Learn New Languages", Design News, Jan. 2, 1989, 78.

Wald; Sequential Analysis; Dover Publications Inc., 1947; pp. 3-43.

Wasserman, Philip D.; "Neural Computing-Theory & Practice"; 1989; pp. 128-129.

Weshsler, H. Ed., "Neural Nets For Human and Machine Perception", Academic Press, New York (1991).

Whitefield, A. "Human Factors Aspects of Pointing as an Input Technique in Interactive Computer Systems", Applied Ergonomics, June 1986, 97-104.

Wiedenbeck, Susan, Lambert, Robin, and Scholtz, Jean, "Using Protocol Analysis to Study the User Interface", Bulletin of the American Society for Information Science, June/July 1989, 25-26.

Wilke, William, "Easy Operation of Instruments by Both Man and Machine", Electro/82 Proceedings, 3/2/1-3/2/4.

Willshaw et al.; "Non-Holographic Associative Memory"; Nature; 222:960-962 (Jun. 7, 1969).

Yager, R. R., "Entropy and specificity in a mathematical theory of Evidence", Int. J. General Systems, 9:249-260 (1983).

Yamada et. al.; "Character recognition system using a neural network"; Electronics Information Communications Association Bulletin PRU 88-58, pp. 79-86.

Yamane et al.; "An Image Data Compression Method Using Two-Dimensional Extrapolative Prediction-Discrete Sine Transform"; Oct. 29-31, 1986; pp. 311-316.

Yoder, Stephen Kreider, "U.S. Inventors Thrive at Electronics Show", The Wall Street Journal, Jan. 10, 1990, B1.

Zadeh, L. A., "Fuzzy sets", Information and Control, 8:338-353 (1965).

Zadeh, L. A., "Probability measures of fuzzy events", Journal of Mathematical Analysis and Applications, 23:421-427 (1968).

Zadeh, L. A., "Fuzzy sets as a basis for a theory of possibility", Fuzzy sets and Systems 1:3-28 (1978).

Zeisel, Gunter, Tomas, Philippe, Tomaszewski, Peter, "An Interactive Menu-Driven Remote Control Unit for TV-Receivers and VC-Recorders", IEEE Transactions on Consumer Electronics, 34(3):814-818.

Zhi-Yan Xie; Brady, M., "Fractal dimension image for texture segmentation", ICARCV '92. Second International Conference on Automation, Robotics and Computer Vision, p. CV4.3/1-5 vol. 1, (1992).

Zhu, X., et al.; "Feature Detector and Application to Handwritten Character Recognition"; International Joint Conference on Neural Networks, Washington, D.C.; January 1990; pp. II-457 to II-460.

What is claimed is:

[1. A programmable control responsive to an user input and a signal received from a signal source, comprising:

a controller, operating according to a predetermined program, for receiving the user input and the signal and producing a control output, said controller producing a multivalued characterization of the signal with respect to at least one parameter;

a memory for storing data relating to an activity of the user;

a data processing system for predicting a most probable action of a user based said stored data relating to said activity of the user and said characterized signal; and a user feedback data presenting system comprising a display device for presentation of a sequence of programming options to the user, including said most probable action of the user, in a plurality of display images, each display image differing in available programming options.]

[2. The programmable control according to claim 1 being for performing an action based on user input and an information content of a signal received from a signal source, further comprising:

a user controlled direct manipulation-type input device, associated with said display device, having a device output, said device output being the user input;

a plant capable of performing a physical action, being responsive to an actuator signal; and said controller, being for receiving data from said device output of said input device and a signal received from a signal source, and displaying user feedback data on said display device, said user feedback data comprising a presentation of a sequence of programming options to the user on said display device, including said most probable action of the user, in a plurality of display images, each display image differing in available programming options, said sequence of programming options including at least one sequence of options sufficient to define an operable control program, and a presentation of additional programming options if said control program is not operable.]

[3. The system according to claim 1, being for processing a program comprising program material, in response to a viewer input, comprising:

a user input processing system for determining a viewer preference;

said controller comprises a program material processing system for characterizing the program material, as said characterized signal, based on its content;

a correlator for correlating said characterized content of the program material with said determined viewer preference to produce a correlation index; and a processor, selectively processing the program material based on said correlation index, wherein said viewer preference is an input to said data processing system, and said data processing system comprises said correlator.]

[4. The system according to claim 3, wherein said program material is encrypted, further comprising:

a decryption system for decrypting the program material if it is selected to produce unencrypted program material and optionally an associated decryption event;

a memory for storing data relating to the occurrence of said decryption event; and a central database for storing data relating to the occurrence of said decryption event in association with data relating to the viewer.]

[5. The system according to claim 3, wherein:

said user input processing system monitors a pattern of user activity and predicts a viewer preference;

said program material processing system comprises:

a processor for preprocessing the program material to produce a reduced data flow information signal substantially retaining information relating to an abstract information content of the program material and selectively eliminating data not relating to said abstract information content of the program material and for characterizing said information signal based on said abstract information content; and a comparing system for determining if said correlation index is indicative of a probable high correlation between said characterization of said information signal and said viewer preference and causing said stored program material to be processed by said processor based on said determination.]

[6. The system according to claim 3, wherein said processor comprises an image program material storage and retrieval system.]

[7. The system according to claim 3, further comprising a memory for storing a characterization of the program material; an input for receiving a feedback signal from the viewer indicating a degree of agreement with said correlation index determination, wherein said feedback signal and said stored characterization are used by said user input processing system to predict a new viewer preference.]

[8. The system according to claim 3, wherein said a program material processing system correlates and characterizes image information, further comprising:

means for storing template data;

means for storing the image data;

means for generating a plurality of addressable domains from the stored image data, each of the domains representing a different portion of the image information;

means for creating, from the stored image data, a plurality of addressable mapped ranges corresponding to different subsets of the stored image data, the creating means including means for executing, for each of the mapped ranges, a procedure upon the one of the subsets of the stored image data which corresponds to the mapped range;

means for assigning identifiers to corresponding ones of the mapped ranges, each of the identifiers specifying for the corresponding mapped range an address of the corresponding subset of stored image data;

means for selecting, for each of the domains, the one of the mapped ranges which most closely corresponds according to predetermined criteria;

means for representing at least a portion of the image information as a set of the identifiers of the selected mapped ranges; and means for selecting, from the stored templates, a template which most closely corresponds to the set of identifiers representing the image information.]

[9. The system according to claim 8 wherein said correspondence of a template and the set of identifiers is determined by a processor executing a predetermined program for executing an algorithm selected from at least one of the group consisting of algorithms for selecting a minimum Hausdorff distance between the mapped range and the domain, for selecting the highest cross-correlation of the mapped range with the domain, and for selecting the lowest mean square error of the difference between the mapped range and the domain.]

[10. The system according to claim 9 wherein said correspondence of a template and the set of identifiers is determined by selecting, for each domain, the mapped range with the minimum modified Hausdorff distance calculated as D[db,mrb]+D[1−db,I−mrb], where D is a distance calculated between a pair of sets of data each representative of an image, db is a domain, mrb is a mapped range, I−db is the inverse of a domain, and I-mrb is an inverse of a mapped range.]

[11. The system according to claim 8, wherein said means for representing further comprises means for:

(a) determining a feature of interest of the image data, (b) selecting a mapped range corresponding to the feature of interest, (c) storing the identifiers of the selected mapped range, (d) selecting a further mapped range corresponding to a portion of image data having a predetermined relationship to the feature of interest, and (e) storing the identifiers of the further mapped range.]

[12. The system according to claim 8, wherein said image data comprises data having three associated dimensions obtained by an image processor executing an algorithm selected from the group consisting of an algorithm for synthesizing a three dimensional representation based on a machine based prediction derived from two dimensional image data, an algorithm for synthesizing a three dimensional representation derived from a time series of pixel images, and an algorithm for synthesizing a three dimensional representation based on a image data representing a plurality of parallax views having at least two dimensions, said set of identifiers representing data in each of the three associated dimensions.]

[13. A method of programming a device, comprising the steps of:

providing an input for user commands and feedback;

storing information relating to the user commands and feedback in a memory;

providing a data input for external information;

predicting a subsequent user command based on the stored information relating to user commands and feedback, a status of the device, and external information from the data input;

presenting the predicted user command to the user;

accepting feedback from the user relating to the predicted subsequent user command;

modifying the predicted subsequent user command based on at least the feedback; and executing the modified predicted user command.]

[14. The method according to claim 13, further comprising the step of identifying a user and storing an user identifier with said stored information relating to the user commands;

said predicting step predicting a subsequent user command based on the stored information relating to user identifier, commands and feedback, a status of the device, and external information from the data input.]

[15. A programmable device comprising:

a user input for receiving an input variable having a path between a first input state and a second input state, said user input comprising:

path dependent user data having transitional path information between said first input state and said second input state; and path independent user data comprising information about at least one of said first state and said second state;

a filter, separating sad path dependent user data as user characterization data and said path independent user data as instructions;

a memory for storing said user characterization data;

a processor for executing said instructions; and a feedback device, presenting information relating to said instructions and said stored user characterization data.]

[16. The device according to claim 15, further comprising:

a hierarchical command structure of said processor, said command structure having commands of different function; and means for predicting a probability of execution of a plurality of commands based on said input, said feedback device presenting commands based on at least said predicted probabilities.]

[17. The programmable control according to claim 1, wherein the signal comprises image information.]

[18. The method according to claim 13, wherein said stored information comprises a set of weights of a predictive algorithm.]

[19. The method according to claim 13, herein said external information comprises a perceptual data stream.]

[20. The programmable device according to claim 15, wherein a format of information presented from said feedback device is based on said path dependent user data.]

*21. A method for receiving targeted content at a mobile device, the method comprising:*

*sending a request to receive customized information at the mobile device;*

*in response to the request, receiving the customized information at the mobile device, wherein the customized information is dependent on position information of the mobile device, as determined by a positioning system during a time period associated with sending the request, and dependent on at least one of user profile information or preferences information stored, at least in part, in a memory device of the mobile device; and*

*causing a presentation of the customized information for one or more users associated with the mobile device.*

*22. The method of claim 21, wherein the customized information is an advertisement.*

*23. The method of claim 22, wherein the advertisement concerns food.*

*24. The method of claim 22, wherein the advertisement concerns fuel.*

*25. The method of claim 22, wherein the advertisement concerns lodging.*

*26. The method of claim 21, further comprising storing, in the memory device, the at least one of the user profile information or the preferences information, wherein:*

*the positioning system is a geographic positioning system (GPS); and*

*determining further comprises determining, by the GPS, the position information of the mobile device.*

*27. The method of claim 21, wherein the positioning system is a cellular base station, and wherein determining further comprises:*

*determining, by the cellular base station, the position information of the mobile device.*

*28. The method of claim 21, wherein the preferences information includes user preferences information, and wherein receiving further comprises:*

*receiving one or more customized billboards at the mobile device dependent on demographics of the one or more users associated with the mobile device, dependent on the position information, and dependent on the user preferences information.*

*29. The method of claim 21, further comprising:*

*receiving the customized information at the mobile device dependent on an itinerary of the one or more users; and*

*causing a presentation of the customized information for the one or more users associated with the mobile device based on the itinerary.*

*30. A system for receiving targeted content at a mobile device, the system comprising:*

*a memory device of the mobile device configured to store at least one of user profile information or preferences information;*

*a positioning system configured to determine position information of the mobile device;*

*a transmitter configured to send a request to receive customized information at the mobile device;*

*a receiver configured to receive the customized information from a provider at the mobile device, wherein the customized information is dependent on the position information of the mobile device, as determined by the positioning system during a time period associated with sending the request, and dependent on at least one of the user profile information or the preferences information; and*

*a display device configured to display the customized information for one or more users associated with the mobile device.*

*31. The system of claim 30, wherein the customized information is an advertisement.*

*32. The system of claim 31, wherein the advertisement concerns food.*

*33. The system of claim 31, wherein the advertisement concerns fuel.*

*34. The system of claim 31, wherein the advertisement concerns lodging.*

*35. The system of claim 30, wherein:*

*the positioning system is a geographic positioning system (GPS); and*

*the GPS is configured to determine the position information of the mobile device.*

*36. The system of claim 30, wherein:*

*the positioning system is a cellular base station; and*

*the cellular base station is configured to determine the position information of the mobile device.*

*37. The system of claim 30, wherein:*

*the preferences information includes user preferences information; and*

*the receiver is configured to receive, from the provider, one or more customized billboards at the mobile device dependent on demographics of the one or more users associated with the mobile device, dependent on the position information, and dependent on the user preferences information.*

*38. The system of claim 30, wherein:*

*the mobile device is a cellular phone;*

*the cellular phone includes the display device; and*

*the cellular phone includes the receiver.*

*39. The system of claim 30, wherein the display device includes a touch screen.*

*40. The system of claim 30, wherein the display device includes an interactive interface configured to receive instructions from the one or more users and to display user feedback.*

*41. The system of claim 30, wherein the mobile device includes a gyroscope.*

*42. The system of claim 30, wherein the user profile information includes a demographic profile.*

*43. The system of claim 30, wherein the display device is a video display.*

*44. The system of claim 30, wherein the mobile device is configured to identify the one or more users based on a biometric.*

*45. The system of claim 44, wherein the biometric is at least one of a fingerprint, a voice sample, or a video pattern.*

*46. The system of claim 30, wherein the customized information includes an advertisement.*

*47. The system of claim 46, wherein the display device is configured to facilitate interaction between the one or more users and a service providing the advertisement.*

*48. The system of claim 30, wherein the customized information includes a plurality of advertisements.*

*49. The system of claim 30, wherein the customized information is configured to be sent via a cellular network.*

*50. The system of claim 30, wherein the display device includes a touch screen display.*

*51. The system of claim 50, wherein the touch screen display is configured to display a graphical user interface.*

*52. The system of claim 30, wherein the user profile information is based at least in part on prior actions of the one or more users.*

* * * * *